(12) United States Patent
Betlach et al.

(10) Patent No.: US 6,251,636 B1
(45) Date of Patent: Jun. 26, 2001

(54) RECOMBINANT OLEANDOLIDE POLYKETIDE SYNTHASE

(75) Inventors: Mary C. Betlach, San Francisco; Sanjay Krishnakant Shah, Concord; Robert McDaniel, Palo Alto; Li Tang, Foster City, all of CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/428,517

(22) Filed: Oct. 28, 1999

Related U.S. Application Data
(60) Provisional application No. 60/120,254, filed on Feb. 16, 1999, and provisional application No. 60/106,100, filed on Oct. 29, 1998.

(51) Int. Cl.[7] .................................................. C12P 19/62
(52) U.S. Cl. ................... 435/76; 435/320.1; 435/252.35; 435/254.2; 435/325; 435/419; 536/23.1; 536/23.2
(58) Field of Search ................................. 536/23.1, 23.2; 435/320.1, 252.35, 254.2, 325, 419, 76

(56) References Cited

PUBLICATIONS

Jacobsen et al. Precursor–Directed Biosynthesis of Erythromycin Analgos by an Engineered Polyketide Synthase. Science (Jul. 1997) 277:367–369.*
GenBank Accession No. L09654, Apr. 1996.*
Oliynyk et al. A hybrid modular polyketide synthase obtained by domain swapping. Chemistry & Biology (Oct. 1996) 6:833–839.*
Kao et al. Engineered Biosynthesis of a Complete Macrolactone in a Heterologous Host. Science (Jul. 1994) 265:509–512.*
Hu et al. Repeated polyketide synthase modules involved in the biosynthesis of a heptaene macrolide by Streptomyces sp. FR–008. Molecular Microbiology (1994) 14(1):163–172.*
Schwecke et al. The biosynthetic gene cluster for the polyketide immunosuppressant rapamycin. PNAS (Aug. 1995) 92:7839–7843.*
Kakavas et al. Identification and Characterization of the Niddamycin Polyketide Synthase Gene rom Streptomyces caelestis. J. of Bacteriology (Dec. 1997) 179(23):7515–7522.*
Xue et al. A gene cluster for macrolide antibiotic biosynthesis in Streptomyces venezuelae: Architecture of metabolic diversity. PNAS (Oct. 1998) 95:12111–12116.*

\* cited by examiner

Primary Examiner—Ponnathapu Achutamurthy
Assistant Examiner—Kathleen Kerr
(74) Attorney, Agent, or Firm—Kevin Kaster; Carolyn Favorito; Kate Murashige

(57) ABSTRACT

Recombinant DNA compounds that encode all or a portion of the oleandolide polyketide synthase are used to express recombinant polyketide synthase genes in host cells for the production of oleandolide, oleandolide derivatives, and polyketides that are useful as antibiotics and motilides.

22 Claims, 5 Drawing Sheets pKOS039-110
21.5 kb pKOS039-130
51 kb pKOS039-133
19.8 kb

SEQUENCE LISTING

<160> NUMBER OF SEQ ID NOS: 14

<210> SEQ ID NO 1
<211> LENGTH: 50937
<212> TYPE: DNA
<213> ORGANISM: Artificial Sequence
<220> FEATURE:
<223> OTHER INFORMATION: Description of Artifical Sequence:
      Recombinant DNA

<400> SEQUENCE: 1

| | | | | | |
|---|---|---|---|---|---|
| gcatgcccgc | ccgcaacacc | ggctcccgta | acggggcgag | ccggtggtca | tccatcagtt | 60 |
| tccttccgcc | cggcccgtgt | caggcccgtg | tgcgcatacc | gccgtacggc | tgcgccggtc | 120 |
| ccccgcggaa | cacctcaccg | gagtgagatc | catgacgagc | gagcaccgct | ctgcctccgt | 180 |
| gacaccccgt | cacatctcct | tcttcaacat | ccccggccac | ggccacgtga | accgtcact | 240 |
| cggcattgtc | cagggacttg | tcgcgcgcgg | ccaacgggtc | agctacggca | ttaccgacga | 300 |
| gttcggcgca | caggtcaagg | cgggccgcgc | gacggccgtt | gtgtacggct | tcattctgcc | 360 |
| ggaggagttc | aaccccgagg | agttgttggc | cgaggaccag | ggttcccgat | gggcctgttc | 420 |
| cttggcggag | gcgttccggg | tcttgccgca | gctgaggacg | gctacgccga | cgaccggccg | 480 |
| ggacctgatc | gtctacgaca | tcgcctcctg | gcccgccccg | gtgctcggcc | ggaagtggga | 540 |
| catcccttc | gtccagctct | ccccgacctc | cgtcgcctac | gagggcttcg | aggaggacgt | 600 |
| acccgcggtg | caggacccca | cggccgaccg | cggcgaggag | gccgccgccc | ccgcggggac | 660 |
| cggggacgcc | gaggagggtg | ccgaggccga | ggacggcctg | gtgcgcttct | tcacccggct | 720 |
| ctcggccttc | ctggaggagc | acggggtgga | caccccggcc | accgagttcc | tcatcgcgcc | 780 |
| caaccgctgc | atcgtcggct | gccgcgcacc | ttcccagatc | aagggcgaca | cggtcggcga | 840 |
| caactacacc | ttcgtcggtc | ccacctacgg | cgaccggtcc | caccagggca | cctgggaagg | 900 |
| ccccgggcac | gggcgtccgg | tgctgctgat | cgccctgggc | tcggcgttca | ccgaccacct | 960 |
| cgacttctac | cgcacctgcc | tgtccgccgt | cgacggcctg | gactggcacg | tggtgctctc | 1020 |
| cgtgggccgc | ttcgtcgacc | ccgcggacct | cggcgaggtc | ccgccgaacg | tcgaggtgca | 1080 |
| ccagtgggtg | ccgcagctcg | acatcctgac | caaagcctcc | gcgttcatca | cgcacgcggg | 1140 |
| catgggcagc | accatggagg | ccctgtcgaa | cgcggtgccc | atggtcgcgg | tgccgcagat | 1200 |
| cgcggagcag | acgatgaacg | ccgagcggat | cgtcgagctg | ggcctcggcc | ggcacatccc | 1260 |
| gcgggaccag | gtcacggccg | agaagctgcg | cgaggccgtg | ctcgccgtcg | cctccgaccc | 1320 |
| cggtgtcgcc | gaacggctcg | cggccgtccg | gcaggagatc | cgtgaggcgg | gcggcgcccg | 1380 |
| ggcggccgcc | gacatcctgg | agggcatcct | cgccgaagca | ggctgaccgc | cctgcctga | 1440 |
| cggtgcgcgg | gccgcccggc | ccgccgcgtg | agagtcggcc | cccgtacccg | acgacgggta | 1500 |
| cggggccga | cgcgcgcggg | cccggactca | gcaggcggcc | accgcgcccc | gtaccgcctc | 1560 |
| gatcaccgcc | ttgacggcgt | cgtcggacag | gtgcgggcct | atgggcaggc | tcagcacctc | 1620 |
| ccgggcgagc | cgctccgcca | cgggctgtgc | gcgggcggcc | tgccggctgc | cggcgtacgc | 1680 |
| ctccgaccgg | tgcaccggca | ccgggtagtg | gatcagcgtc | tcgacgccgg | ctgccgccag | 1740 |
| ccgctcccgc | agcgcggacc | ggtccgcgga | acgaatcacg | aacaggtgcc | acacgggtc | 1800 |
| cgcccacggc | gccggcctcg | gcagcacgat | ccgtccagg | ccggcgagcc | cgtcgagata | 1860 |
| gcgcgccgcc | accgcggccc | ggcgctcggg | tcccagccgt | cccaggtggg | cgagcttgac | 1920 |

-continued

```
ccgcagaacg gccgcttgca gctcgtccag ccggaagttg gtggcccgga cctcgtgccg    1980
gtacttctcc cgcgacccgt agttgcgcag cagccgcacc cgctccgcca gctccgcgtc    2040
gtccgtcacc acgcgccgc cgtcaccgaa gccgcccagg ttcttgcccg ggtagaagct     2100
gaaggcggtg gtggaccacg cgcccacccg ccggccgtac gcctgcgcac cgtgcgcctg    2160
ggcggcgtcc tccaggatcc gcacgccgtg ccgctcggcg acctcggaca cgccgccag    2220 gtccgccgga tgcccgtaca ggtgcaccgg gaggatcacc cgggtgcggg aggtgatcgc    2280
agcctcgacg cgctccgggt ccagggtgaa cgtcgcaggc tccggttcca ccgcgacggg    2340
ctccgcaccc gtcgccgaga cggcgagcca ggtcgcggcg aaggtgtgcg ccgggacgat    2400
cacctcgtca cccggcccga tgtccatggc gcgcagcgcc agttccaggg cgtcgcaccc    2460
gctgcccacc gccacgcagt gccgggcccc gcagtaggcg gcccactccg tctcgaacgc    2520
ggcgagttcg gggcccagga ggtagcgccc ggagtccagg acgcggccgg tcgcggcgtc    2580
gatgtcgtgc ttgagctcca ggtaggcggc ccggaggtcc aggaacggaa cgtccatgcg    2640
tcctccgtgg gagctgctca cggcgccgtg gcgctgagcg ggagacggcc gagggacggg    2700
cccaccatga cctgccgtcc gggtccggtc acccaggtgt gggcgccgct gtcccagttc    2760
tggagggccc tgcgctcgac gtgcagggtc agcctcctgc tctcgcccgg ccgcagctcg    2820
accttcccgt aggccgccag ggcacgcttg gcctgcgcca cccgcacgtg cggggacggc    2880
cccacgtaga cctgcgggac ctccttgccg gtgcgcgtac cggtgttgcg cagcgtgaag    2940
cagacgtcga gcccgccgtc cgccgtcgcc gtcaccttca ggtcccggta gtcgaaggag    3000
gtgtagcaca acccgtggcc gaaggagaac agcggctgga cgccctgctg ttcgtaccag    3060
cggtagccgg agtagatgcc ctcggagtag tccagttggt catcgactcc cgggtagcgc    3120
ctggcgtccc cggcgaacgg cgtctgcccc tcgtcggccg ggaaggtctg ggtcagccgg    3180
cctcctgggt cggcgtcgcc gaacagcagg gcggtggtcg cctcggcgcc ggcctggccc    3240
gggtaccaca tggtgagcac cgcggcggtc ttcctcagcc agggcatggt gagggaggag    3300
cccgtgttga gcaccaccac ggtccgtggg ttgaccgcgg ccacgcgct gatcaggtcg     3360 tcctggcggc cgggcaggga cagcgacgtg cggtccccgt cctccgagcc gtcgtcgtac    3420
gcgaagacga ccgcggtcct cgccgtccgc gcgatcgaca cggcccggtc gatcgcctcc    3480
tgggcggcct gcggagtgac ccacgtcagc tcgaaggtca tgggcgactt cgccagggcc    3540
gcgccggtga tgcgcagctt gtgcgttccg gccgccagcc gcatgggcg gctgctgacg     3600 tcgccgtaga cccagggccg acggccgaac ggctcctggc cgtcgagttc gacgtaggcg    3660
ttgccgccct gcgcgcgggc cgcgatgcgg tagctgccgg tgaccggcac ggtgatggtg    3720
ccgtcgtaga ggacaccgcc cccaccggcg gggaacacct cgcccgaggg gcggggccgc    3780
ggaagagggg cggactgcgg aacgggaacc ccgaccgtct cctcaccggt gctgtagcgc    3840
acggtgctgc cggcgccggc ccgttcgcgg atggtgtcca gaggggcgga cgcgccgtcc    3900
ggcacgatgt acgaactgcc cagcccggtc accttcggga ccttggcggt ggggccgatc    3960
acggcgatgt ccgccgccgt ctccgtggtc aggggaaggg tggcgccctc gttgcgcagc    4020
aggaccgcgc cgtcctcggc gacctggcgc gcgaccttca gccgcccgc gaggtcgcgc     4080 gccgggcggg cgggcggatc ctcgtccagc agccggaacc gggccatctg cgacacgatg    4140
cgggtgacgg cctcgtcgag ggccgactcg gggatgcgtc cctcccggat cgccgtcttg    4200
agcgggtcgc cgaagaactt gccgccgggt atcggctcgc ccggggcggg ttcgtggtcc    4260
agctcgatgc cgagttcctg gtcgagcccc ttggtgaggg cgtccgtgct ctgcgtcgcc    4320
```

-continued

```
agccagtccg aggtcaccca gccacggaac ttccactgct ccttgaggac cttgttcagc    4380
agttcgtcac tgccgcaggc cggctggccg ttgaccttgt tgtaggcgca catcaccgag    4440
ccggttccgg cagccacggc gctctcgaaa ccgggcagtt cccgctcgcg caacgtctgt    4500
tcgtcgacgt tcacgttaac gctgaaacga ttcttctcct ggttgttcgc cgcgtagtgc    4560
ttggtggcgg cgatcagccc ctgactctgg atgcccttga tctccgcggc ggccatccgc    4620
gaggtgacca gggggtcctc gctgaacgtc tcgaagttcc gcccggcgta cggcacgcgt    4680
atggagttca ccatcggcgc gaacaccacg tcctgcccga aggcgcgccc ctcccggccg    4740
atcaccgccc cgtaggaccg cgccaggccg tcgtcgaagg tggaggccag cgccacggga    4800
gcgggcagcg cgagggacgg ccggtggatc gtgattccgg cgggaccgtc ggtggcccgc    4860
atctcgggta tgccgaggcg gggaacgccc ggcaggtaca cctttgccga ctcatcgctc    4920
gtgtgatagc tccagtgcac gaacgacagc ttttcttcca gggtcatccg agccgtcaga    4980
agacgagccg tttcccacgg atcgcccgat tcggcgacgg acggaacaga ggggagcagg    5040
gcgagaccga gggccaggcc gagagtaccc gcggaggtcc gtggcgggac cggactcctg    5100
cgctgcgcac ggccgccgag acgtaaccga agtgatctca aaaggcttcc aaatcctccg    5160
cgccctcgtg ctgcgaggcg catgaaatgg gcggttgtcg cgaccacagt gcaccgtcac    5220
cgaagccgga gcaatgcccg tgaataaggt cgcgcccttc cgtggatgat ctccgcacga    5280
gatcatgccc agctcaagtg atggtcatgc acgtaccaag aaggggcttg cctgggggc    5340 gtgagctgat ctagcgttgc cgcacgacga cgagtcgtga gcgaggcgaa cgctctgccg    5400
ctcaggtggt gaacagacgg cagcccggac gttcgacgag ggtcaagcgg aacgcaggcg    5460
acaggacgcg gccaccctcc gaggcacccg tgccgaccat cctcgcaggt ccttcgccat    5520
gcccgtcgca actctccgat cgctgccgcc gatggcgaca gcccggcacc gaggcccctg    5580
gaccaggagg cgaagcgagg gccggccgcg atgcacgaat cggacccagg cgaacaccgg    5640
cacatccacc ccggcgcgtg cggtacgggc gcgcccgat gacgggcgaa cgacgaccga    5700
aaagcagacc ccttgattcg cttccatggt tgtggcagcc gcggggagcg tcggcagaga    5760
ggtgggaaac catgcatgtc cccggcgagg aaaacgggca ttccattgcc attgtcggaa    5820
ttgcgtgccg actgccgggc tctgccaccc cccaggagtt ctggagactc ctggccgact    5880
ccgcagacgc attggacgag ccccccgccg gccgtttccc gaccggctca ttatcctcgc    5940
cccccgctcc gcgcggcgga ttcctcgaca gcatcgacac tttcgacgcg gatttcttca    6000
acatctcgcc cagagaagcc ggtgtcctcg acccccagca acgcctcgcg ctggaactcg    6060
gctgggaggc gctggaagac gccggaatcg tcccgcgaca cctcagggga acccgcacct    6120
cggtcttcat gggcgccatg tgggacgact acgcgcacct ggcgcacgca cggggagaag    6180
ccgccctcac ccggcattcc ctgacgggaa cgcaccgcgg catgatcgcc aaccggctct    6240
cctacgccct gggcctccaa ggccccagcc tcaccgtcga caccggacaa tcctcctccc    6300
tcgccgccgt gcacatggcc tgcgagagcc tggcccgcgg cgaatccgac ctcgccctcg    6360
tcggcggcgt caacctcgtc ctcgatccgg ccggcacgac cggcgtcgag aggttcggag    6420
cactctcacc ggacgcagg tgctacacct tcgactcccg ggcgaacggc tacgcccgag    6480
gagagggcgg cgtcgtagtc gtcctcaagc ccacccaccg cgcgctcgcg gacggtgaca    6540
ccgtctactg cgagatcctg ggcagcgccc tcaacaacga cggcgccacg gaaggcctca    6600
ccgtccccag cgcccgcgcc caggcggacg tcctgcgaca ggcatgggaa cgggcacgcg    6660
```

-continued

```
tggccccgac ggacgtccag tacgtggaac tgcacggaac cggcacaccg gccggcgacc    6720
ccgtcgaggc cgagggcctc ggcaccgcgc tcggcaccgc acgcccggcc gaggcgccgc    6780
tcctggtcgg ctcggtcaag acgaacatcg gtcacctcga aggcgcggca ggcatcgcgg    6840
gcctcctgaa gacggtcctg agcatcaaga accggcacct cccggcaagc ctgaacttca    6900
cctcgcccaa cccccgcatc gacctcgacg ccctgcgcct cgcgtccac accgcgtacg    6960 gcccctggcc gagccccgac cggccgctgg tggcgggcgt ctcctccttc ggcatgggcg    7020
ggacgaactg ccacgtcgtc ctgtccgagt tacggaacgc gggaggcgac ggcgccggaa    7080
aagggccgta caccggcacg gaagaccggc tcggcgccac ggaggcggag aagaggccgg    7140
acccggcaac cggaaacggt cctgatcccg cccaggacac ccaccgctac cgccgctga    7200 tcctgtccgc ccgcagcgac gcggccctgc gcgcacaggc ggaacggctc cgccaccacc    7260
tggaacacag ccccggacag cgcctgcggg acaccgccta cagcctggcg acccgccgcc    7320
aggtcttcga gcggcacgcg gtggtcaccg gacacgaccg cgaggacctg ctcaacggcc    7380
tgcgtgacct ggagaacggc ctcccggccc ccaggtcct gctcgccgc acgcccaccc    7440 ccgaaccggg cggcctcgcc ttcctcttct ccgggcaggg cagccagcag cccggcatgg    7500
gcaagcgact ccaccaggtg ttccccggct tccgggacgc cctggacgag gtctgcgccg    7560
aactcgacac ccacctcggc cgactcctcg gccccgaggc cggcccgccc ctgcgcgacg    7620
tgatgttcgc cgagcggggc acggcgcaca gcgccctgct ctccgagacc cactacaccc    7680
aggccgccct cttcgccctg gaaaccgccc tcttccgcct cctggtccag tggggcctga    7740
aacccgacca cctcgcaggc cactccgtcg gcgagatcgc ggccgcccac gcagcaggca    7800
tcctcgacct gtccgacgcg gccgaactcg tggccacccg cggcgcgttg atgcgttccc    7860
tgcccggcgg cggcgtcatg ctctcggtcc aggcacccga gtccgaggtc gcacccctgc    7920
tgctcggccg tgaggcccac gtcggcctgg ccgccgtgaa cggccccgac gcggtggtcg    7980
tgtccggcga gcgcggccac gtcgccgcca tcgaacagat cctccgggac aggggccgca    8040
aaagccggta cctgcgcgtc agccacgcct tccactcccc gctcatggaa ccggtgctgg    8100
aggagttcgc cgaagccgtc gccggcctga ccttccgggc accgaccaca cccctcgtct    8160
ccaacctcac cggcgcacca gtcgacgacc ggaccatggc cacgcccgcc tactgggtcc    8220
ggcacgtccg ggaagcggtc cgcttcggcg acggcatccg ggcactcggg aaactgggca    8280
ccggcagctt cctggaagtc gggccggacg gcgtcctcac cgccatggcg cgcgcatgcg    8340
tcaccgccgc cccggagccc ggccaccgcg gcgaacaggg cgccgatgcc gacgcccaca    8400
ccgcgttgct gctgccccgcc ctgcgccgag gacgggacga ggcgcgatcg ctcaccgagg    8460
ccgtggcacg gctccacctg cacggcgtgc cgatggactg gacctccgtc ctcggcggcg    8520
acgtgagccg ggtccccctc ccgacgtacg ccttccaacg cgaatcccac tggctgccgt    8580
ccggagaggc tcacccgcga ccggcggacg acaccgaatc cggcacggga cggaccgagg    8640
cgtccccgcc gcgccgcac gacgtcctgc acctcgtgcg ctcccacgcg gcggctgtgc    8700
tcggacattc ccgggccgag cggatcgacc ccgaccgcg gttccgcgac ctcggcttcg    8760
actcgctgac ggcgctggaa ctgcgggacc ggctcgacac cgcactcggc ctccgcctgc    8820
ccagcagcgt gctcttcgac cacccgagcc ccggcgcact ggcacgcttc ctccagggcg    8880
acgacgcgag gcgccccgaa ccagggaaga cgaacggcac gcgcgccacg gagccaggcc    8940
cggacccgga cgacgagccg atcgccatcg tcggcatggc gtgccgcttc ccgggtggcg    9000
tgacctctcc ggaggacctg tggcgcctgc tcgccgcagg cgaggacgcg gtgtccggct    9060
```

```
tccccacgga ccggggctgg aacgtcactg actccgccac gcgccgcgga ggcttcctgt   9120
acgacgccgg cgagttcgat gccgccttct tcggtatctc gccgcgtgag gcgttggtga   9180
tggacccgca gcagcggttg ctgctggaga cgtcctggga ggccctcgaa cgcgcgggcg   9240
tgagccccgg cagtctgcgc ggcagcgaca cggccgtgta catcggagcc acagcgcagg   9300
actacggccc ccgactgcac gagtcggacg acgactcggg cggctacgtc ctgaccggca   9360
ataccgccag cgtggcctcc ggccgcatcg cctactccct cggtctggag gggcctgcgg   9420
tcacggtgga cacggcgtgt tcgtcgtcgc tggtggcact gcacctggcg gtgcaggcgc   9480
tgcgccgtgg cgagtgctca ctggcattgg ccggcggagc cacggtgatg ccttcgcccg   9540
gcatgttcgt ggagttctca cggcaagggg gcctctccga ggacgccgc tgcaaggcgt   9600 tcgccgcgac ggcggacggc accggctggg ccgagggtgt gggtgtgttg ttggtggagc   9660
ggttgtcgga tgcgcggcgg ttgggtcatc gggtgttggc ggtggtgcgg gggagtgcgg   9720
tcaatcagga tggtgcgtcg aatgggttga cggcgccgaa tggtccgtcg cagcagcggg   9780
tgatccgtgc ggcgttggct gacgcgggtc tggttcctgc tgatgtggat gtggtggagg   9840
cgcatggtac ggggacgcgg ttgggtgatc cgatcgaggc tcaggcgttg ttggcgacgt   9900
atgggcaggg gcgtgcgggt gggcgtccgg tggtgttggg gtcggtgaag tcgaacatcg   9960
gtcatacgca ggcggcggct ggtgtggctg gtgtgatgaa gatggtgctg cgctgggc    10020 gggtgtggt gccgaagacg ttgcatgtgg atgagccgtc tgcgcatgtg gactggtcgg   10080
ctggtgaggt ggagttggcg gttgaggcgg tgccgtggtc gcggggtggg cgggtgcggc   10140
gggctggtgt gtcgtcgttc gggatcagtg gcacgaatgc gcatgtgatc gtggaggagg   10200
cgcctgcgga gccggagccg gagccggagc ggggtccggg ctctgttgtg ggtgtggtgc   10260
cgtgggtggt gtccgggcgg gatgcggggg cgttgcgtga gcaggcggca cgcttggctg   10320
cgcacgtgtc gggtgtaagt gcggtcgatg tgggctggtc gttggtggcc acgaggtcgg   10380
tgttcgagca ccggcggtg atggtcggca gtgaactcga tgccatggcg gagtcgttgg   10440
ccggcttcgc tgcgggtggg gttgtgccgg gggtggtgtc gggtgtggct ccggctgagg   10500
gtcgtcgtgt ggtgttcgtc tttcctggtc agggttcgca gtgggtgggg atggcggctg   10560
ggttgctgga tgcgtgcccg gtgttcgcgg aggcggtggc ggagtgcgct gcggtgctgg   10620
acccgttgac cggttggtcg ctggtcgagg tgttgcgcgg tggtggtgag gctgttcttg   10680
ggcgggttga tgtggtgcag ccggcgttgt gggcggtgat ggtgtcactg gcccggacct   10740
ggcggtatta cggtgtggag cctgctgcgg ttgtggggca ttcgcagggt gagattgctg   10800
cggcttgtgt ggctgggggg ttgagtctgg ccgatggtgc gcggtggtg gtgttgcgga   10860 gccgggcgat cgcccggatc gctggtgggg gcggcatggt ctccgtcagc ctgccggccg   10920
gccgtgtccg caccatgctg gaggagttcg acggcagggt tccgttgcg gcggtcaacg   10980 gtccgtcctc gaccgtggtg tcgggtgacg tccaggccct ggatgagttg ttggccggtt   11040
gtgagcggga gggtgtccgg gctcgtcgtg tcccggtgga ctatgcctcc cactccgcgc   11100
agatggacca gttacgcgat gatctgctgg aagcgctggc gacgatcgtc cctacatcgg   11160
cgaacgtacc gttcttctcg acggtgacgg cggactggct ggacacgacc gctctggatg   11220
cggggtactg gttcacgaat ctgcgggaga cggtccggtt ccaagaagcc gtcgaagggc   11280
tcgtggctca ggggatgggc gcgttcgtcg agtgcagccc gcaccccgtc ctcgtcccgg   11340
gcatcacaga aacactcgac accttcgacg ccgacgctgt cgcactgtcg tcgctgcggc   11400
```

```
gtgacgaagg cggcctggat cggttcctca cgtccctcgc ggaagccttc gtccagggcg    11460
tcccggtcga ctggtcccgc gccttcgagg gtgcgagccc ccgcaccgtc gacctgccca    11520 cctaccccctt ccaacggcaa cgctactggc tgctcgacaa ggcggcgcaa cgggaacgcg   11580
agcggctgga ggactggcgc taccacgtcg agtggcgccc cgtcacgaca cgaccttccg    11640
cacggctgtc cggtgtctgg gccgtggcga ttccggcacg tctggcccgt gactcactgt    11700
tggtcggcgc catcgacgca ctggagcgag gcggcgcccg tgccgtgccc gtggtggtcg    11760
atgagcggga ccacgaccgg caagcgctgg tcgaggctct gcggaacggg ctgggcgacg    11820
acgacctcgc cggtgtgctc tccctttttgg ccctcgacga agccccgcac ggtgaccacc   11880
ccgacgtgcc cgtcggcatg gccgcttcgc tggcgctcgt gcaggcgatg gccgacgccg    11940
cggccgaggt gcccgtatgg ttcgcgaccc gaggcgccgt agcggcactg cccggtgagt    12000
caccggagcg acccaggcag gcgctgctct ggggactggg acgggtcgtc gccctggaac    12060
agccgcagat atgggggcggg ttggtcgacc tcccgcaaca cctggacgag gacgcgggcc   12120
gacggctggt cgatgtcgtg ggcggcctgg cggacgagga ccagcttgcc gtacgggcct    12180
cctccgtcct cgcccgacgc ctcgttcgta cgccgggtca ccgtatgtcg agccaggcgg    12240
gcgggcgcga gtggtcgccc agcggcacgg tcctggtgac cggaggcacc ggggcgctgg    12300
gcgcgcacgt cgcccgctgg ctggccggca agggcgccga gcacctggta ctcatcagcc    12360
gtcgcggagc ggacgcagcc ggggccgctg cccttcggga cagcctcacg acatggggtg    12420
tccgggtgac cctggccgcg tgcgatgcag cggaccggca cgcactggag acgctcctcg    12480
actcgctgcg cacggatccg gcgcagctga cggccgtcat ccacgccgcg ggtgctctgg    12540
acgacggcat gacgacggtg ctcacaccgg agcagatgaa caacgccctg cgagcgaaag    12600
tcacggccac cgtcaacctg cacgaactga cccgggacct cgacctctcg gccttcgtac    12660
tgttctcgtc catctccgcc accctgggaa tcccggcca ggccaactac gcgccgggaa     12720
actcgttctt ggacgccttc gcggaatggc gcagggctca ggggctcgtg cgacctcca    12780 tcgcctgggg accgtggtcc ggcggcaccg gcatggcaca tgaagggtcg gtgggcgaac    12840
ggctccagcg gcacggtgta ctcgccatgg aacccgcggc ggccatcgct gcgctcgacc    12900
acacgctggc gagcgacgaa accgcagtgg ccgtggccga catcgactgg agccggttct    12960
tcctggcgta cacagcactg cgggcacggc ccttgatcgg agagataccc gaggcacgcc    13020
gcatgctgga gtccggctca ggccccgcg acctcgagcc ggaccgtgcc gaacccgagc     13080
ttgccgtgcg tctcgcgggc ctcaccgcgg tcgagcagga acgtcttctg gtgcagctcg    13140
tgagggagca ggccgccgtc gtcctcggac attccggcgc cgaggcggtg gctccggacc    13200
gagcgttcaa ggatctcgga ttcgactcgc tgacctcggt cgaactgcgc aaccggctga    13260
acaccgccac cggcctcaga ctgccccgtga cggccgtctt cgactacgcg aggcccgcgg   13320
cgctggccgg ccatctgcgc tccaggctga tcgacgacga tggtgaccac ggtgccttgc    13380
ccggcgtgga gaagcacgcg atcgacgagc cgatcgcgat cgtgggaatg gcatgccgct    13440
tcccgggagg catcgcttcc ccggaggatc tgtgggacgt gctcaccgct ggtgaggacg    13500
ttgtctccgg actgccgcag aaccgcgggt gggacttggg gcgcctgtac gatcccgatc    13560
cggaccgggc cggtacgtca tacatgcgtg agggtgcttt cctgcacgag gcgggggagt    13620
tcgacgcggc cttcttcggt atctcgccgc gtgaggcgtt ggcgatggac ccgcagcagc    13680
ggttgctgct ggagacgtcc tgggaggccc tcgaacgggc cggcatcact ccttccaagc    13740
tggcgggcag tccgaccggt gtgttcttcg gcatgtcgaa ccaggactac gccgcccagg    13800
```

```
cgggcgacgt gccgtccgag ctggagggct acctgctcac cggctccatc tccagcgtcg    13860
cttcggggcg tgttgcttac acgttcggtc ttgaggggcc tgcggtgacg gtggatacgg    13920
cgtgttcgtc gtcgttggtg gcgttgcatc tggcggtgca ggggttgcgg cggggtgagt    13980
gttcgcttgc gttggtgggt ggggtgacgg tgatgtcgtc gccggtgacg ttgacgacgt    14040
tcagtcggca gcggggtttg tcggtggatg ggcggtgcaa ggcgttcgcg gcttcggcgg    14100
atggttttgg tgctgccgag ggtgtgggtg tgttgttggt ggagcggttg tcggatgcgc    14160
ggcggttggg tcatcgggtg ttggcggtgg tgcggggag tgcggtcaat caggatggtg    14220
cgtccaatgg tctggcggcg ccgaatggtc cgtcgcagca gcgggtgatc cgtgcggcgt    14280
tggctgacgc gggtctggct cctgccgatg tggatgtggt ggaggcgcat ggcacgggga    14340
cgcggttggg tgatccgatc gaggctcagg cgttgctggc gacgtatggg cagggtcgta    14400
ccagtgggcg tccggtgtgg ctgggtcgg tgaagtcgaa catcgggcat acgcaggcgg    14460
cggccggtgt ggctggtgtg atgaagatgg tgctggcgtt gggtcggggt gtggtgccga    14520
agacgttgca tgtggatgag ccgtcaccgc atgtggactg tcggctggt gaggtggagt    14580 tggcggttga ggcggtgccg tggtcgcggg gtgggcgggt gcggcgggct ggtgtgtcgt    14640
cgttcgggat cagcggcacg aatgcgcatg tgatcgtgga ggaggcgcct gcggagcctt    14700
cggtggagga gggtccgggc tccgttgtgg gtgtggtgcc gtgggtggtg tccgggcggg    14760
atgcgggggc gttgcgtgca caggcggcac gcttggctgc gcacgtgtcg agcacgggtg    14820
cgggtgtggt tgatgtgggc tggtcgttgg tggccacgag gtcggtgttc gagcaccggg    14880
cggtaatggt cggcactgat cttgattcca tggcggggtc gttggccggc ttcgctgcgg    14940
gtggtgttgt gccggggggtg gtgtcgggtg tggctccggc tgagggccgt cgtgtggtgt    15000
tcgtctttcc tggtcagggt tcgcagtggg tggggatggc ggctggggttg ctggatgcgt    15060 gtccggtgtt cgcggaggcg gtggcggagt gtgccgcggt gctggaccgg ttgaccggtt    15120
ggtcgctggt cgaggtgttg cgtggtggtg aggctgttct tgggcgggtt gatgtggtgc    15180
agccggcgtt gtgggcggtg atggtgtcac tggctcggac ctggcggtat tacggtgtgg    15240
agcctgctgc ggttgtgggg cattcgcagg gtgagattgc tgcggcttgt gtggctgggg    15300
ggttgagtct ggccgatggt gcgcgggtgg tggtgttgcg gagtcgggcg atcgcccgga    15360
tcgctggtgg gggcggcatg gtctcggtcg gtctttcagc tgagcgtgtc cgcaccatgc    15420
tcgacaccta cggcggcagg gtttccgtcg cggcggtcaa tggcccgtcc tcgaccgtgg    15480
tgtccggtga cgcccaggcc ctggatgagt tgttggccgg ttgtgagcgg gagggtgtcc    15540
gggctcgtcg tgtcccggtg gactatgcct cccactccgc gcagatggac cagttacgcg    15600
atgagttgct ggaggcgctg gcggacgtca ctccgcagga ctccagtgtt ccgttttttct    15660 cgacggtgac ggcggactgg ctggacacga ccgctctgga tgcggggtac tggttcacga    15720
atctgcggga gacggtccgg ttccaggaag ccgttgaagg gcttgtggct caggggatgg    15780
gcgcgttcgt cgagtgcagc ccgcaccctg tcctcgtccc gggcatcaca gaaacactcg    15840
acaccttcga cgccgacgct gtcgcactgt cgtcgctgcg gcgtgacgaa ggcggcctgg    15900
atcggttcct cacgtccctc gcggaagcct tcgtccaagg cgttcccgtc gactggaccc    15960
atgccttcga gggtggacgc ccgcgcttcg tcgacctgcc cacctatgcc ttccagcgac    16020
agcgctactg gctgcacgaa gagccgctgc aagagccggt cgatgaggcg tgggatgcca    16080
agttctggtc tgtggtcgaa cgcggcgatg ccacagccgt gtccgacttg ctgagcacgg    16140
```

```
acgccgaggc tttgcacacg gtgttgccgg ctttgtcgtc gtggcggcgg cgtcgggtgg    16200
agcatcgacg gcttcaggac tggcgttacc gggtggagtg gaagcctttc ccggccgcgc    16260
ttgatgaggt gctcggtggt ggctggttgt tcgtggtgcc gcggggcttg gcggatgatg    16320
gtgtggttgc gcgggtggtg gctgccgtca cggcgcgggg tggcgaggtc agtgtcgtgg    16380
agctcgatcc gacccgtcct gaccgccggg cttatgcgga ggctgtcgcg ggccgtggtg    16440
tgagcggggt cgtgtcgttc ttgtcctggg atgatcggcg gcactcggag cattctgttg    16500
ttcccgccgg tcttgccgcg tcgctggtgt tggcgcaggc gttggttgat cttgccgggg    16560
ttggtgaggg gccgcggttg tggctggtga cgcggggtgc ggtggttgct ggtccttcgg    16620
atgccggtgt ggtgattgat ccggtgcagg cgcaggtgtg gggtttcggg cgtgttctgg    16680
gtctggagca tcccgagttg tggggtgggc tggtggacct gccggtgggg gttgatgagg    16740
aggtgtgccg gcggttcgtg ggtgttgtgg cgtcggctgg ttttgaggat caggtggcgg    16800
tgcgtggttc gggtgtgtgg gtgcgtcgtc tggtgcgtgc tgtggtggat ggtggtgggg    16860
gtggttggcg gccgcgtggg acggtgttgg tcacgggtgg tcttggtggt ttgggtgcgc    16920
atacggcccg gtggttggtg ggtggtgggg cggatcatgt ggttcttgtg agccgtcgtg    16980
gtggcagtgc gcctggtgct gggatctgtg tgcgggagct ggaggggttg ggcgggggctc    17040 gggtgtcggt gcgggcctgt gatgtggctg atcgtgtggc gttgcgggcg ttgttgtcgg    17100
atctgggtga gccggtgacg gcggtgttcc atgcggctgg tgttcctcag tcgacgcctt    17160
tggcggagat ctctgtccag gaggcggctg atgtgatggc ggccaaggtg gcgggtgcgg    17220
tgaatctggg tgagttggtg gatccctgtg gtctggaggc gtttgtgttg ttctcctcca    17280
atgccggtgt gtggggcagt gggggggcagg cggtgtatgc ggcggcgaat gcgtttcttg    17340
atgcgttggc ggtgcgtcgt cggggtgttg gtctgccggc cacgagtgtg gcgtggggga    17400
tgtgggctgg tgaggggatg gcgtcggtgg gtggtgcggc gcgggagttg tcccgtcggg    17460
gggtgcgggc gatggatccc gagcgtgctg tggcggtgat ggctgatgcg gtgggtcgtg    17520
gtgaggcgtt cgtcgcggtc gctgatgtgg actgggaacg tttcgtcacc ggtttcgctt    17580
ctgcccgtcc ccgtccgttg atcagtgacc tgccggaggt gcgtgctgtt gtggagggcc    17640
aggtccaggg ccggggccag gggttgggct tggtcggtga ggaggagtcg tcggggtggt    17700
tgaagcggtt gtcggggttg tctcgtgtgc ggcaggagga ggagttggtg gagttggtcc    17760
gtgctcaggc tgccgttgtt ctcgggcatg gttccgcgca ggacgtcccg gctgagcggg    17820
cgttcaagga gttgggtttt gattccctca ctgctgtcga gctacgcaac gggctggccg    17880
cggccaccgg gatccggctg ccggccacca tggcattcga tcatcccacc gccaccgcca    17940
tcgcacgctt cctgcaatcc gaactcgtgg gaagtgacga cccgctgacg ctcatgcggt    18000
cggcgatcga ccagttggag accggtctgg ctctgctgga atcggacgaa gaagctcgct    18060
cggaaatcac gaagcgattg aacattcttc tgccccgctt cggaagcgga ggcagttcga    18120
gaggcaggga agcaggacaa gacgcaggcg aacatcagga tgtcgaggac gccaccatcg    18180
atgagctatt cgaggtgctc gacaacgaac tcggcaattc ctgaaaacct gtccgactgc    18240
taccgcgacc ttgaccggag aacgctgtga cgaacgacga aaagatcgtc gagtatctca    18300
agcgcgcgac cgtggacctg cgcaaggccc ggcaccgcat ctgggagctg gaggacgagc    18360
ccatcgcgat cacgtcgatg gcctgccact tcccgggcgg gatcgagagt ccggagcagc    18420
tgtgggaact cctgtccgcc ggaggcgagg tgctttccga gttccccgac gaccgcggct    18480
gggacctgga cgagatctac catcctgacc cggaacacag tgggacgagc tacgtccgtc    18540
```

```
acggcggttt cctggatcat gcgacgcagt tcgacacgga cttcttcggt atctcgccgc    18600
gtgaggcgtt ggcgatggac ccgcagcagc ggttgctgct ggagacgtcc tggcagcttt    18660
tcgagcgcgc aggagtcgat ccccatacgc tgaagggaag ccggaccgga gtattcgtcg    18720
gcgccgcaca catgggttat gcggacaggg tggacactcc gccggcgagg ccgagggct    18780 acctgctgac agggaacgcc tcggccgttg tctccgggcg tatttcctac accttcggcc    18840
ttgaggggcc tgcggtgacg gtggacacgg cgtgctcgtc gtcgctggtg gcgctgcacc    18900
tggcggtgca ggcgctgcgc cgtggcgagt gctcgctggc ggtcgtcggt ggtgtggccg    18960
tcatgtcgga cccgaaggtc ttcgtcgagt tcagccggca gcgcggactg gccagggacg    19020
gccggtccaa ggcttttgcg gcgtcagcgg atggtttcgg cttcgccgag ggagtttcgc    19080
tgctcttgct ggagcggttg tcggatgcgc ggcggttggg tcatcgggtg ttggcggtgg    19140
tgcgggggag tgcggtcaat caggatggtg cgtccaatgg tctggcggcg ccgaatggtc    19200
cgtcgcagca gcgggtgatt cgtgcggcgt tggctgacgc gggtctggct cctgccgatg    19260
tggatgtggt ggaggcgcat ggtacgggga cgcggttggg tgatccgatc gaggctcagg    19320
cgttgctggc gacgtatggg caggggcgta ccagtgggcg tccggtgtgg ctgggtcgg    19380 tgaagtcgaa catcggtcat acgcaggcgg cggccggtgt ggctggtgtg atgaagatgg    19440
tgctggctct ggagcggggt gtggtgccga agacgttgca cgtggatgag ccgtctccgc    19500
atgtggactg tcgaccggt gcggtggagt tgctgactga agagcggccg tgggagccgg    19560
aggctgagcg tcttcgtcgg gcaggcattt ccgccttcgg tgtcagtggc acgaatgcgc    19620
atgtgatcgt ggaggaggca cctgcggaac cggaaccgga gccggagccg ggaactcgtg    19680
tggttgctgc cggtgatctg gtggtgccgt gggtggtgtc cgggcgggat gcgggggcgt    19740
tgcgtgcaca ggcggcacgc ttggctgcgc atgtgtcgag cacgggtgcg ggtgtggttg    19800
atgtgggctg gtcgttggtg gccacgaggt cggtgttcga gcaccgggcg gtgatggtcg    19860
gcactgatct tgattccatg gcggggtcgt tggccgggtt tgctgcgggt ggggttgtgc    19920
cgggggtggt gtcgggtgtg gctccggctg agggtcgtcg tgtggtgttc gtctttcctg    19980 gtcaggttc gcagtgggtg gggatggcgg ctgggttgct ggatgcgtgt ccggtgttcg    20040
cggaggcggt ggcggagtgt gccgcggtgc tggacccgtt gaccggttgg tcgctggtcg    20100
aggtgttgcg cggtggtgag gctgttcttg ggcgggttga tgtggtgcag ccggcgttgt    20160
gggcggtgat ggtgtcactg gctcggacct ggcggtatta cggtgtggag cctgctgcgg    20220
ttgtggggca ttcgcaggt gagattgctg cggcttgtgt ggctgggggg ttgagtctgg    20280
ccgatggtgc gcggtggtg gtgttgcgga ccgggcgat cgcccggatc gccggtgggg    20340
gcggcatggt ctccgtcagt ctcccggccg gccgtgtccg caccatgctc gacacctacg    20400
gcggccggtt gtcggtggct gcggtcaacg gcccgtcctc gaccgtggtg tccggtgacg    20460
cccaggccct ggatgagttg ttggccggct gtgagcggga ggggtccgg gctcgtcgtg    20520 tcccggtgga ctatgcctcc cactccgcgc agatggacca gttacgcgat gagctgctgg    20580
aagcgctggc ggacatcact ccgcaacact ccagcgttcc gttcttctcg acggtgacgg    20640
cggactggct ggacacgacc gctctggatg cggggtactg gttcacgaat ctgcgggaga    20700
cggtccggtt ccaggaagcc gtcgaagggc ttgtggctca ggggatgggc gcgttcgtcg    20760
agtgcagccc acaccccgtc ctcgtccccg gtatcgagca gaccctcgac accgtggaag    20820
ccgatgctgt ggcgctgggt tcgctacggc gtgatgaggg cggcctggga cggttcctca    20880
```

```
cgtccctcgc ggaagccttc gtccagggcg tcccggtcga ctggtccgc accttcgagg    20940
gtgcgagccc ccgcaccgtc gacctgccca cctatccctt ccaacggcaa cgtttctggt    21000
tggagggatc cccggcgttg tcttcgaacg gcgtcgaggg tgaggcggac gtcgcgttct    21060
gggatgcggt cgagcgcgag gactcggcgg ttgtagccga ggagttgggg atcgacgcca    21120
aggctctgca catgacattg ccggccttgt cgtcgtggcg gcggcgtgag cggcagcgtc    21180
ggaaggtgca gcgctggcgt taccgggtgg agtggaagcg tctcccgaat tcgcgggcac    21240
aggagtcgct gcaggcggc tggttgctcg tcgtcccgca gggccgtgcc ggcgatgtcc    21300
gcgtcactca gtcggtggcg gaggtggcgg ccaagggtgg tgaagccacg gtcctggagg    21360
tcgacgccct gcatcccgac cgcgcagcat acgccgaggc cctcacccgg tggccgggtg    21420
tgcggggtgt ggtgtcgttc ctggcgtggg aggagcaggc ccttgccgaa cacccgcttc    21480
tgtctgcggg tctggcggca tcgctggcgt tgcccaggc gttgatcgat gtcggcgggt    21540
ccggtgagtc ggcgccgcgt ctgtggctgg tcacggaagc tgccgtcgtg atcggtgctg    21600
ccgacaccgg tgcggtgatc gaccccgtac acgcgcagct gtggggcttc ggccgtgtcc    21660
ttgctctgga acaccccgaa ttgtggggcg ggctgatcga cctgcccgct gtggcaggcg    21720
agcctggttc gattaccgac cacgcgcatg ccgacctact ggccacggtc ctggccacga    21780
tggtgcaggc tgctgcccga ggcgaggacc aggtcgcggt ccggacgacc ggtacttacg    21840
tacccaggct ggtgcgttca ggcggcagtg cacactcggg tgcgcggagg tggcagccgc    21900
gcgacaccgt actggtcacc ggcgggatgg gaccgctgac cgcccacatc gtccgttggc    21960
tggctgacaa cggtgccgac caggtagtac tcctgggagg tcaggagca gcggcgagg    22020
ccgaggcgct gagggccgag ttcgacgggc acacgacgaa gatcgaactc gcggacgtgg    22080
acaccgagga cagcgacgcg ctgcggtcct tgctcgaccg cacgaccggc gaacacccgc    22140
tgcgcgcggt catccatgcg ccgaccgtgg tcgagttcgc ctcggtggcc gagtcggacc    22200
tggtgcgatt cgcccgcacc atcagcagca agatcgccgg cgtcgagcag ctcgacgagg    22260
tgctgagcgg catcgacacg gcgcacgacg tggtcttctt ctcctccgtc gcgggcgtct    22320
ggggaagcgc ggggcagagc gcctacgcgg cgggcaacgc cttcctcgac gccgtcgccc    22380
agcaccgccg tctgcgcgga ctgccccgta cgtcggtggc ctggactccg tgggacgacg    22440
atcgatccct tgcctccctc ggtgactcgt acctcgaccg acgaggactg cgagcactgt    22500
ccatacccgg cgcgctcgcc tccctccagg aagtgctcga ccaggacgag gtccacgccg    22560
tggtggcgga tgtcgactgg gagcggttct acgccggctt cagtgccgtc cggcgcactt    22620
ccttcttcga cgacgtgcac gacgcccacc ggccggccct gtccacggct gcgaccaacg    22680
acggacaggc ccgggacgag gacggcggta cggaactcgt acgacgtctg cgtccgctga    22740
ccgagacgga gcaacagcga gagctcgtgt cgctcgtcca gagtgaagtc gctgccgtcc    22800
taggccactc ctccaccgac gcggtccagc cacagcgcgc gttccgagag atcgggttcg    22860
actcactgac agcggtccag ctccggaacc ggcttacggc caccacgggc atgcgccttc    22920
cgacaacgct ggtcttcgac tacccgacca ccaacggact cgccgagtac ctgcgctccg    22980
aactgttcgg tgtgtccggc gcaccagctg acctctccgt cgtccggaac gcggatgagg    23040
aggacgaccc cgtcgtcatc gtggggatgg cctgccggtt cccgggcggg atcgatacgc    23100
cggaagcctt ctggaagctg ctcgaagcgg cggcgatgt catctccgaa cttccggcca    23160
accgcggctg ggacatggag cgactcctga acccggaccc cgaggcgaag ggcaccagcg    23220
ccacacgcta cggcggtttc ctctacgacg ccggggagtt cgacgccgcc ttcttcggta    23280
```

-continued

```
tctcgccgcg tgaggcgttg gcgatggacc cgcagcaacg gctgctgctg gaaaccgtct   23340
gggagctcat cgagagcgcc ggcgtggcgc ccgactcgct ccaccggagc cggaccggca   23400
cgttcatcgg cagcaacggc cagttctacg caccgctgct gtggaactcc ggcggtgatc   23460
tggagggcta ccaaggcgtg ggcaacgccg gcagcgtcat gtccggccgc gtcgcctact   23520
ccctcggtct tgagggcct gcggtgacgg tggatacggc gtgttcgtcg tcgctggtgg   23580
cactgcacct ggcggtgcag gcgctgcgcc gtggcgagtg ctcactcgcc atagccggcg   23640
gtgtgacggt gatgtccaca ccggacagct tcgttgagtt ctcacggcaa cagggccttt   23700
ccgaggacgg ccgttgcaag gcgttcgcga gcacagccga tggtttcggc ctcgccgagg   23760
gcgtttcggc gctgttggtg gagcggttgt cggatgcgcg gcgttgggt catcgggtgt   23820
tggcggtggt gcgggggagt gcggtcaatc aggatggtgc gtcgaatggg ttgacggcgc   23880
cgaatggtcc gtcgcagcag cgggtgattc gtgcggcgtt ggctgacgcg ggtctggctc   23940
ctgctgatgt ggatgtggtg gaggcgcatg gtacgggac gcggttgggt gatccgatcg   24000
aggctcaggc gttgttggcg acgtatgggc agggtcgtgc gggtgggcgt ccggtggtgt   24060
tggggtcggt gaagtcgaac atcgggcata cgcaggcggc ggctggcgtg gctggtgtga   24120
tgaagatggt gctggcgctg gagcggggtg tggtgccgaa gacgttgcat gtggatgagc   24180
cgtcaccgca tgtggactgg tcggctggtg aggtggagtt ggcggttgag gcggtgccgt   24240
ggtcgcgggg tggcgggtg cggcgggctg gtgtgtcgtc gttcgggatc agtggcacga   24300
atgcgcatgt gattgtggag gaggcgcctg cggagccgga gccggagccg ggaactcgtg   24360
tggttgctgc tggtgatctg gtggtgccgt gggtggtgtc cgggcgggat gcgggggcgt   24420
tgcgtgagca ggcggcccgg ttggctgcgc acgtgtcgag cacgggtgcg ggtgtggttg   24480
atgtggggtg gtcgttggtg gccacgaggt cggtgttcga gcaccgggcg gtgatggtcg   24540
gcagtgaact cgattccatg gcggagtcgt tggctggctt cgctgcgggt gggttgtgc   24600
cgggggtggt gtcgggtgtg gctccggctg agggtcgtcg tgtggtgttc gtctttcctg   24660
gtcagggttc gcagtgggtg gggatggcgg ctgggttgct ggatgcgtgt ccggtgttcg   24720
cggaggcggt ggcggagtgt gccgcggtgc tggatccggt gacgggttgg tcgctggtcg   24780
aggtgttgcg cggtggtggt gaggctgttc ttgggcgggt tgatgtggtg cagccggcgt   24840
tgtgggcggt gatggtgtca ctggcccgga cctggcggta ttacggtgtg gagcctgctg   24900
cggttgtggg gcattcgcag ggtgagatcg ctgcggcttg tgtggctggg gggttgagtc   24960
tggccgatgg tgcgcgggtg gtggtgttgc ggagccgggc gatcgcccgg atcgctggtg   25020
ggggcggcat ggtctcggtc ggtctttcag ctgagcgtgt ccgcaccatg ctcgacacct   25080
acggtggccg ggtttcggtc gcggcggtca atggcccgtc ctcgaccgtc gtgtccggtg   25140
acgtccaggc cctggatgag ttgttggccg gttgtgagcg ggagggtgtc cgggctcgtc   25200
gtgtcccggt ggactatgcc tcccactccg cgcagatgga ccagttacgc gatgagctgc   25260
tggaagcgct ggcggacatc actccgcaac attccagtgt tccgttcttc tcgacggtga   25320
cggcggactg gctggacacg accgctctgg atgcgggta ctggttcacg aatctgcggg   25380
agacggtccg gttccaggaa gccgtcgaag ggctcgtggc tcagggatg ggcgcgttcg   25440
tcgagtgcag cccgcacccc gtcctcgtcc ccggtatcga gcagaccctc gacgccctcg   25500
accagaacgc cgccgtactc ggctccctgc ggcgtgacga aggcggcctg gaccgactcc   25560
tcacatccct cgcggaagcc ttcgtccaag gcgttcccgt cgactggacc cacgccttcg   25620
```

```
aaggcatgac cccccgcacc gtcgacctgc ccacctaccc cttccaacga cagcactact  25680
ggcccaagcc cgcaccggcc cccggcgcga acctgggcga cgtggcgtcc gtgggcctca  25740
ccgcggccgg ccaccccctt ctgggcgcgg tcgtggagat gcccgactcc gacgggttgg  25800
tgctcaccgg gcagatctcc ctgcggaccc atccctggct cgccgaccac gaggtgctcg  25860
gatcggtgct cctgccgggc accgcgttcg tcgagcttgc cgtccaggcc gccgaccgcg  25920
ccggttacga cgtactggac gagctgacgc tggaggcgcc cctcgtgctc cccgacaggg  25980
gcggcatcca ggtgcgtctg gccctcgggc cgtccgaggc agacgacgc cggtccctcc  26040
agctgcacag caggccggag gaggctgccg ggttccaccg ctggacgagg cacgcgagtg  26100
gattcgtcgt tcccggcggt accggggcgg cgcggcccac cgagccggcc ggcgtgtggc  26160
cgcccgcagg tgccgagccg gtcgctctcg catcggaccg gtacgcccgg ctcgtcgagc  26220
gcggctacac ctacgccccc tccttccagg ggctgcacac cgcatggcgc cacggggacg  26280
acgtgtacgc ggaagtggcg ctgccagaag gaacaccggc cgacggctac gccctgcatc  26340
cggccctgct ggacgcggcg gtccaggccg tcggactcgg ctcgttcgtc gaggatcccg  26400
gccaggtgta cctgccgttc ctctggagcg acgtgacgct gcacgcgacc ggggccacgt  26460
ccctgcgggt gagggtttca ccggccggtc ccgacaccgt tgcgctggcc ctcgccgacc  26520
cggccggggc gccggtggcc acggtgggcg ccctccgtct gcgtacgacg tccgcggcgc  26580
agctcgcccg tgcgcgcggg agcgcggaac acgcgatgtt ccgcgtggag tgggtggagg  26640
agggctcggc cgcggaccgg tgccggggcg gcgcgggcgg gacgacgtac gagggggaac  26700
gcgccgccga ggccgggggcc gccgctggta cctgggccgt actcggcccc cgggtgccgg  26760
ccgccgtccg gacgatgggc gtggatgtcg tcaccgccct cgacacgccg gaccaccccg  26820
cggacccgca gagcctcgcg gacctggcgg cgctcgggga caccgttccc gacgtggtcg  26880
tcgtgaccag cctcctgagc ctcgcctccg gagcggattc cccctaggg aaccggcccc  26940
ggccgaccgc cgccgagcag gacaccgccg ccacggtcgc cggcgtccac agcgcactcc  27000
acgcggccct ggacctggtg caggcatggc tggccgacga acgccacacc gcctcccggc  27060
tggtgctcgt cacccggcac gcgatgaccg tcgccgagtc cgaccccgag cctgacctgc  27120
tcctcgcccc ggtgtgggga ctcgtgcggt ccgcccaggc cgagaaccccc ggccgcttcg  27180
tgctcgccga catcgacggc gacgaggcat cctgggatgc tctgccccga gccgtcgcct  27240
cggccgcatc ggaggtggcg atacgggccg gcgccgtgta cgtaccgcgg ctggcccgcg  27300
ccacggacga gggactggtc gtggccgacg aggctgcggg gccctggcgg ctggacgtca  27360
cggaagcggg caccctggcg aacctcgccc tggtgccgtg cccggacgcc tcccgcccgc  27420
tgggccccga cgaggtacgg atcgccgtcc gtgccgccgg ggtcaacttc cgggacgtcc  27480
tcctggccct gggcatgtac ccggacgagg ggctcatggg cgcggaggcg gcgggcgtcg  27540
tcaccgaggt cggcgggggc gtcacgacgc tcgcgccagg tgaccgggtg atgggcctgg  27600
tgaccggtgg attcgggccg gtggccgtga cgcaccaccg gatgctcgta cggatgccgc  27660
gtggctggtc cttcgccgag gccgcgtcgg tgccggtggc gttcctgacc gcgtactacg  27720
ccctgcacga cctggcaggc ctgcgcggcg gcgagtcggt gctggtgcac tccgctgcgg  27780
gcggtgtcgg catggcggcc gtgcagttgg cacggcactg ggatgccgag gtgttcggca  27840
ccgcgagcaa gggcaagtgg gacgttctcg cggcgcaggg cctcgacgag gagcacatcg  27900
gctcgtccag gacgaccgag ttcgagcagc gcttccgcgc gaccagtggt gggcgcggga  27960
tcgatgtcgt cctgaatgcc ctctcggggtg acttcgtcga cgcctcggcg cgtctcctgc  28020
```

```
gcgagggcgg ccggttcgtc gagatgggca agaccgacat ccgtaccgac ctcggcgtcg    28080
tcggggcgga cggcgtcccg gacatccggt acgtcgcctt cgacctcgcc gaggcgggtg    28140
ccgagcggat cgggcagatg ctcgacgaga tcatggcgct cttcgacgcc ggtgtcctgc    28200
ggttgccgcc gttgcgcgcc tggccggtgc ggcgcgccca cgaggcactg aggttcgtca    28260
gccaggcacg tcatgtgggc aaggtcgtcc tcaccgtccc ggccgcgctc gacgccgagg    28320
gaaccgtgct gatcaccggg gcgggcacgc tgggagccct ggtcgcccgc cacctcgtca    28380
ccgagcacga cgtccgccgg ctgctgctgg tcagccgcag cggcgtcgcc cccgacctgg    28440
cggccgaact cggtgcgctg ggcgccgagg tcacggtggc ggcctgcgac gtcgccaacc    28500
gcaaggcgct caaggccctc ctggaggaca taccgcccga gcatccggtc acgggcatcg    28560
ttcacacggc cggcgtgctc gacgacggtg tggtgtccgg gctcacccct gaacgggtgg    28620
acaccgtcct caaacccaag gtggacgcgg ccctgaccct ggagtcagtg atcggcgaac    28680
tggacctcga cccggccctg ttcgtgatct tctcatcggc agcgagcatg ctgggcgggc    28740
ccggccaggg cagttacgcc gcggccaatc agttcctgga caccctcgcc cgacaccggg    28800
cgcgccgcgg gctcacctcc gtgtcactcg gctgggggct gtggcacgag gccagcggtc    28860
tcaccggcgc cctggccgac atcgaccgtg accggatgag ccgggcgggg atcgcgccca    28920
tgccgaccga cgaggccctg cacctgttcg acagggcaac ggaactcggc gatccggtac    28980
tcctgccgat gcgcctgaac gaggccgcgc tggaggaccg ggccgcggac ggaacactgc    29040
cgccgctgct gagtggtctg gtccgggtgc ggcacaggcc gtcggcgcgg gcaggtaccg    29100
cgaccgccgc ccccgccacc ggccccgagg cgttcgcccg ggagctggcg gcggcaccgg    29160
acccacgtcg tgccctgcgc gacctcgtcc gcggccacgt cgccctggtg ctcggacaca    29220
gtggccccga ggccatcgac gccgaacagg ccttccggga catcggtttc gactccctga    29280
ccgcagtcga actcagaaac cggctgaacg ccgagaccgg cctccgcttg cccggcacgc    29340
tcgtgttcga ctaccccaac ccgagcgcgc tcgccgatca cctgctcgaa ctcctcgctc    29400
ccgcgacaca acccaccgca gccccgctgc tcgccgaact ggaacgggtg gaacaactcc    29460
tgtctgcggc cgcgtcaccc ggcggaccgg catccgcgt ggacgaggag acgcgcacgc    29520
tcatcgccac acggctggcc acccttgcct cgcagtggac acacctcccg gtcggttcgc    29580
cgggcaacgc ggacaaccgc agcggccccg gcgagtccgg gcaggccag gaatccggag    29640 caaccgggga gcacacggcg gcgtggacgt cggacgacga tctcttcgcc ttcctcgaca    29700
agcggttgga gacgtgatgg ccgccggccg agtcagcgag tcctttcgtc cttctgctgg    29760
ggaaaacgac gcaccgggag gttttggtgg ctgaggcgga gaagctgcgc gaatacctgt    29820
ggcgcgccac gaccgaactc aaggaggtca gcgatcgact ccgcgagacc gaggaacggg    29880
cccgagagcc gatcgccatc gtgggaatga gctgccggtt ccccgcggc ggcgacgcca    29940 ccgtcaacac gcccgaacag ttctgggacc tgctgaacag cggcggtgac ggcatcgcgg    30000
gtctacccga ggaccgcggg tggacttgg ggcgcctgta cgatcccgat ccggaccggg    30060
ccggtacgtc gtacgtgcgt gagggcggtt tcctgtacga ctcggggag ttcgacgccg    30120 ccttcttcgg gatctcgccg cgtgaggcgt tggcgatgga cccgcagcag cggttgctgc    30180
tggagacgtc ctgggaggca ttcgagagcg ccggtatcaa gcgcgccgct ctgagaggca    30240 gcgacaccg cgtgtacatc ggcgcgtgga gcaccggcta tgccggcagc ccctaccgcc    30300
tggtcgaagg cctggaaggc cagctcgcca tcggcaccac actaggggcc gcttcggggc    30360
```

-continued

```
gtgttgctta cacgttcggt cttgagggc ctgcggtgac ggtggatacg gcgtgttcgt      30420
cgtcgttggt ggcgttgcat ctggcggtgc agggttgcg gcggggtgag tgttcgctgg      30480
cgttggtggg tggggtgacg gtgatgtcgt cgccggtgac gttgacgacg ttcagtcggc      30540
agcggggttt gtcggtggat gggcggtgca aggcgttccc ggcttcggcg gatggttttg      30600
gtgctgccga gggtgtgggt gtgttgttgg tggagcggtt gtcggatgcg cggcggttgg      30660
gtcatcgggt gttggcggtg gtgcggggga gtgcggtcaa tcaggatggt gcgtcgaatg      30720
ggttgacggc gccgaatggt ccgtcgcagc agcgggtgat ccgtgcggcg ttggctgacg      30780
cgggtctggc tcctgctgat gtggatgtgg tggaggcgca tggtacgggg acgcggttgg      30840
gtgatccgat cgaggctcag gcgttgttgg cgacgtatgg gcaggggcgt gcgggtgggc      30900
gtccggtgtg gctggggtcg gtgaagtcga acatcgggca tacgcaggcg gcggccggtg      30960
tggctggtgt gatgaagatg gtgctggcgc tgggcgggg tgtggtgccg aagacgttgc      31020
atgtggatga gccgtcaccg cacgtggact ggtcggccgg tgccggtgga ttgctgactg      31080
aagagcggcc gtgggagccg gaggctgagc gtcttcgtcg ggcaggcatc tccgccttcg      31140
gtgtcagtgg cacgaacgcg catgtgatcg tggaggaggc gcctgcggaa ccggagccgg      31200
agccggaac tcgtgtggtt gctgccggtg atctggtggt gccgtgggtg gtgtccgggc      31260
gggatgcgag ggcgttgcgt gcacaggcgg cacgcttggc tgcgcacgtg tcgggtgtaa      31320
gtgcggtcga tgtgggctgg tcattggtgg ccacgaggtc ggtgttcgag caccgggctg      31380
ttgcgatcgg cagtgaactc gactccatgg cgggttcgtt ggccggcttc gctgcgggtg      31440
gggtggtgcc gggggtggtg tcgggtgtgg ctccggctga gggtcgtcgt gtggtgttcg      31500
tctttcctgg tcagggttcg cagtgggtgg ggatggcggc tgggttgctg gatgcgtgtc      31560
cggtgttcgc ggaggcggtg gcggagtgcg ctgcggtgct ggatccggtg acgggttggt      31620
cgctggtcga ggtgttgcag ggcagggacg cgactgttct gggcgggtt gatgtggtgc      31680
agccggcgtt gtgggcggtg atggtgtcac tggctcggac ctggcggtat acggtgtggg      31740
agcctgctgc ggttgtgggg cattcgcagg gtgagattgc tgcggcttgt gtggctgggg      31800
ggttgagtct ggccgatggt gcgcgggtgg tggtgttgcg gagccgggcg atcgcccgga      31860
tcgctggtgg gggcggcatg gtctccgtca gcctgccggc cggccgtgtc cgcaccatgc      31920
tggaggagtt cgacggccgg ttgtcggtgg ctgcggtcaa tggcccgtcc tcgaccgtgg      31980
tgtccggtga cgtccaggcc ctggatgagt tgttggccgg ttgtgagcgg gagggtgtcc      32040
gggctcgtcg tgtcccggtg gactatgctt cccactccgc gcagatggac cagttacgcg      32100
atgagctgct ggaggcgctg gcggacatca ctccgcagga ctccagtgtt ccgttttcct      32160
cgacggtgac ggcggactgg ctgggcacga ctgccctggg tgcggggtac tggttcacga      32220
atctgcggga cacggtccgg ttccaggaag ccgtcgaagg gcttgtggct caggggatgg      32280
gcgcgttcgt cgagtgcagc ccgcacccg tcctcgtccc cggtatcgag cagaccctcg      32340
acgccctcga ccagaatgcc gccgtattcg gctcgctgcg gcgtgacgaa ggcggcctgg      32400
accggtttct cacgtccctc gcggaagcct tcgtccaggg cgttcccgtc gactggtccc      32460
gcgccttcga aggcgtgacc cctcgcaccg tcgacctgcc cacctacccc ttccaacgac      32520
agcactactg gttgatggcg gaagaggcac cggtctctca gccccctcac tcggagaaca      32580
gcttctggtc ggtagtggcc gatgcggatc ccgaggctgc tgctgaactt ctgggtgtcg      32640
atgtagaggc agtcgaggct gtaatgccgg cgttgtcttc gtggcaccgg cagagccaac      32700
ttcgtgccga agtcaaccag tggcgctacg acgttgcgtg gaagcgtctg accaccgggg      32760
```

-continued

```
cgctgcccga aaagccgggc aactggctcg tcgtgactcc agcaggaacc gacaccacgt    32820
tcgctgagtc gttggcgagg acggcagccg cagaactggg cgtatccgtc agctttgcgc    32880
aggtggacac tgctcatcct gaccggtcgc aatacgcgca tgcgctgcgt caagccctga    32940
ccggcccgga gaacgtcgat cacctcgtgt ccttgctggc cctggaccag gccactgacg    33000
acctcgccgc cgcaccttcc tgtcttgccg cgtcgctggt gttggcgcag gcgttggttg    33060
atcttggccg ggttggtgag gggccgcggt tgtggctggt gacgcggggt gcggtggttg    33120
ctggtccttc ggatgccggt gcggtgattg atccggtaca ggcgcaggtg tggggtttcg    33180
ggcgtgttct gggtctggag catcccgagt tgtggggtgg gctgatcgac ctgccggtgg    33240
gggttgatga ggaggtgtgc cggcggttcg tgggtgttgt ggcgtcggct ggttttgagg    33300
atcaggtggc ggtgcgtggt tcggtgtgt gggtgcgtcg tctggtgcgt gctgtggtgg    33360
atggtggtgg gggtggttgg cggccgcgtg ggacggtgtt ggtcacgggt ggtcttggtg    33420
gtttgggtgc gcatacggcc cggtggttgg tgggtggtgg ggcggatcat gtggttcttg    33480
tgagccgtcg tggtggcagt gcgcctggtg ctggggatct ggtgcgggag ctggaggggt    33540
tgggcggggc tcgggtgtcg gtgcgggcct gtgatgtggc tgatcgtgtg cgttgcggg    33600 cgttgttgtc ggatctgggt gagccggtga cggcggtgtt ccatgcggct ggtgttcctc    33660
agtcgacgcc tttggcggag atctctgtcc aggaggcggc tgatgtgatg gcggccaagg    33720
tggcgggtgc ggtgaatctg ggtgagttgg tggatccctg tggtctggag gcgtttgtgt    33780
tgttctcctc caatgccggt gtgtggggca gtgggggca ggcggtgtat gcggcggcga    33840
atgcgtttct tgatgcgttg gcggtgcgtc gtcgggtgt tggtctgccg gccacgagtg    33900
tggcgtgggg gatgtgggct ggtgagggga tggcgtcggt gggtggtgcg gcgcgggagt    33960
tgtcccgtcg gggggtgcgg gcgatggatc ccgagcgtgc tgtggcggtg atggctgatg    34020
cggtgggtcg tggtgaggcg ttcgtcgcgg tcgctgatgt ggactgggaa cgtttcgtca    34080
ccggtttcgc ttctgcccgt ccccgtccgt tgatcagtga cctgccggag gtgcgtgctg    34140
ttgtggaggg ccaggtccag ggccggggcc aggggttggg cttggtcggt gaggaggagt    34200 cgtcgggtg gttgaagcgg ttgtcgggt tgtctcgtgt gcggcaggag gaggagttgg    34260
tggagttggt ccgtgctcag gctgccgttg ttctcgggca tggttccgcg caggacgtcc    34320
cggctgagcg ggcgttcaag gagttgggtt ttgattccct cactgctgtc gagctacgca    34380
acgggctggc cgcggccacc gggatccggc tgccggccac catggcattc gatcatccca    34440
acgccaccgc catcgcacgc ttcctgcagt ctcagctcct tcctgacgcc gagagcgagt    34500
cggccgtgcc gtcttcaccg gaagacgagg tccgccaggc attggcgtcc ctttccctgg    34560
accagctgaa aggcgctggg cttcttgacc cactgctcgc tctgacacgc ctccgggaga    34620
tcaacagcac ggtgcagaac cctgagccga ccaccgaatc gatcgacgag atggatggcg    34680
agacgtgctg cgcctggcgc tcggcgaaat cgacggctga ccactgacc actggagctg    34740 acatgcctga ccccaccgcc aaatatgtgg aagcgctccg tgcgtcgctc aaggagaacg    34800
aacgcctgcg ccaacagaat cactcgcttc tcgccgcctc ccgtgaagcg atcgccatca    34860
cggcgatgag ctgccgtttc ggcgggggca tcgactcgcc cgaagatctc tggcgcttcc    34920
tggccgaagg ccgcgacgcg gtggcgggc ttcccgagga ccgcgggtgg gatctggatg    34980
ccttgtatca cccggacccg gagaaccccg gcaccacgta cgtccgggaa ggcgcgttcc    35040
ggtacgacgc agcccagttc gatgcggggt tcttcgggat ttcgccgcgt gaggcgttgg    35100
```

-continued

```
cgatggaccc gcagcagcgg ttgctgctgg agacatcctg ggagcttttc gagcgtgccg   35160
atatcgatcc gtacacagtc aggggaacgg cgacggggat attcatcgga gccggacatc   35220
agggctatgg tcccgacccc aagagggctc cggagagcgt ggcgggttac ctgctgacgg   35280
gaacggcatc ggccgtgctg tccgggcgta tttcctacac gttcggtctt gagggggcctg  35340 cggtcacggt ggacacggcg tgttcgtcat cgctggtggc actgcacctg gcggtgcagg   35400
cgctgcgccg gggcgagtgc tcactcgcca tagccggcgg tgtggccgtc atgtcgaccc   35460
cggatgcctt cgtggagttc agccgccaac agggcatggc aagagacggc cgatgtaagg   35520
cattcgccgc ggcagcggac ggtatgggat ggggcgaggg agtttcgctg ctcttgctgg   35580
agcggttgtc ggatgcgcgg cggttgggtc atcgggtgtt ggcggtggtg cggggggagtg  35640 cggtcaatca ggatggtgcg tcgaatggcc tggcggcgcc gaatggtccg tcgcagcagc   35700
gggtgattcg tgcggcgttg gctgacgcgg gtctggctcc tgccgatgtg gatgtggtgg   35760
aggcgcatgg tacggggacg cggttgggtg atccgatcga ggctcaggcg ttgctggcga   35820
cgtatgggca ggggcgtgcg ggtgggcgtc cggtgtggct ggggtcggtg aagtcgaaca   35880
tcgggcatac gcaggcggcg gctggtgtgg ctggtgtgat gaagatggtg ctggcgttgg   35940
ggcggggtgt ggtgccgaag acgttgcatg tggatgagcc gtcaccgcac gtggactggt   36000
cggccggtgc ggtggagttg ctgactgaag agcggccgtg ggagccggag gctgagcgtc   36060
ttcgtcgggc aggcatctcc gccttcggtg tcagtggcac gaacgcgcat gtgatcgtgg   36120
aggaggcgcc tgcggaaccg gagccggagc cgggaactcg tgtggttgct gccggtgatc   36180
tggtggtgcc gtgggtggtg tccgggcggg atgtgggggc gttgcgtgag caggcggcac   36240
gcttggctgc gcacgtgtcg agcacggggtg cgggtgtggt tgatgtgggc tggtcgttgg   36300
tggccacgag gtcggtgttc gagcaccggg cggtgatggt cggcactgat cttgattcca   36360 tggcgggggtc gttggccggg tttgctgcgg gtggtgtcgt ccccgggggtg gtgtcgggtg   36420 tggcgccggc tgagggtcgt cgtgtggtgt tcgtcttcc tggtcagggt tcgcagtggg   36480
tggggatggc ggctggggtgtg ctggatgcgt gcccggtgtt cgcggaggcg gtggcggagt   36540
gtgccgcggt gctggatccg gtgacgggtt ggtcgctggt cgaggtgttg cagggcaggg   36600
acgcgactgt tcttgggcgg gttgatgtgg tgcagccggc gttgtgggcg gtgatggtgt   36660
cactggctcg gacctggcgg tattacggtg tggagcctgc tgcggttgtg gggcattcgc   36720
agggtgagat tgctgcggct tgtgtggctg gggggttgag tctggccgat ggtgcgcggg   36780
tggtggtgtt gcggagccgg gcgatcgccc ggatcgctgg tggggcggc atggtctccg   36840 tcagtctccc ggccggccgt gtccgcacca tgctcgacac ctacgcggc cgggtttcgg   36900 tcgcggcggt caacggtccg tcctcgaccg tggtgtccgg tgacgtccag gcccttgatg   36960
agttgttggc cggttgtgag cgggagggtg tccgggctcg tcgtgtcccg gtggactatg   37020
cctcccactc cgcgcagatg gaccagttac gcgatgagct gctggaggcg ctggcggaca   37080
tcactccgca ggactccagt gttccgttct tctcgacggt gacggcggac tggctggaca   37140
cgaccgctct ggatgcgggg tactggttca cgaatctgcg ggagacggtc cggttccagg   37200
aagccgtcga agggcttgtg gctcagggga tgggcgcgtt cgtcgagtgc agcccgcacc   37260
ccgtcctcgt ccccggtatc gagcagaccc tcgacgccct cgaccagaat gccgccgtac   37320
tcggctcgct gcggcgtgac gaaggcggcc tggaccgact tctcacatcc ctcgcggaag   37380
ccttcgtcca aggcgttccc gtcgattgga cccacgcctt cgagggcgtg accctcgca   37440 ccgtcgacct gcccaccctac cccttccaac ggcaacgttt ctggttggac ggttcgccgg   37500
```

```
catcgtctgc gaatggcgtt gacggtgagg cggacgccat gatctgggac gcggtcgagc   37560
gtgaggactc ggtcgctgta gccgaggagt tggggatcga cgccgaggct ttgcacacgg   37620
tgttgccggc cttgtcgtcg tggcggcggc gtcggtgga gcatcgacgg cttcaggact    37680
ggcgttaccg ggtggagtgg aagccttttcc cggccgcgct tgatgagtg ctcggtggtg   37740 gctggttgtt cgtggtgccg cggggcttgg cggatgatgg tgtggttgcg cgggtggtgg   37800
ctgccgtcac ggcgcggggt ggcgaggtca gtgtcgtgga gctcgatccg acccgtcctg   37860
accgccgggc ttatgcggag gctgtcgcgg gccgtggtgt gagcgggtc gtgtcgttct    37920 tgtcctggga tgatcggcgg cactcggagc atcctgttgt tcccgccggt cttgccgcgt   37980
cgctggtgtt ggcgcaggcg ttggttgatc ttggccgggt tggtgagggg ccgcggttgt   38040
ggctggtgac gcgggatgcg gtggtcgctg gtccttcgga tgccggtgcg gtgattgatc   38100
cggtacaggc gcaggtgtgg ggtttcggc gtgttctggg tctggagcat cccgagttgt    38160
ggggtgggct gatcgacctg ccggtggagg cgcccgaacc tggctcgacg tgcgaccaca   38220
cgtatgccga cctgctcgcc acggttgtgg cgtcggctgg ttttgaggat caggtggcg    38280 tgcgtggttc gggtgtgtgg gtgcgtcgtc tggtgcgtgc tgtggtggat ggtggtgggg   38340
gtggttggcg gccgcgtggg acggtgttgg tcacgggtgg tcttggtggt ttgggtgcgc   38400
atacggcccg gtggttggtg ggtggtgggg cggatcatgt ggtgcttgtg agccgtcgtg   38460
gtggcagtgc gcctggtgct ggggatctgg tgcgggagct ggagggtgtt ggcggggctc   38520
gggtgtcggt gcgggcctgt gatgtggctg atcgtgtggc gttgcgggcg ttgttgtcgg   38580
atctgggtga gccggtgacg gcggtgttcc atgcggctgg tgttcctcag tcgacgcctt   38640
tggcggagat ctctgtccag gaggcggctg atgtgatggc ggccaaggtg gcgggtgcgg   38700
tgaatctggg tgagttggtg gatccctgtg gtctggaggc gtttgtgttg ttctcctcca   38760
atgccggtgt gtggggcagt ggggggcagg cggtgtatgc ggcggcgaat gcgtttcttg   38820
atgcgttggc ggtgcgtcgt cggggtgttg gtctgccggc gacgagtgtg gcgtgggga   38880 tgtgggctgg tgaggggatg gcgtcggtgg gtggtgcggc gcgggagttg tcccgtcggg   38940
gggtgcgggc gatggatccc gagcgtgctg tggcggtgat ggctgatgcg gtggggcgtg   39000
gtgaggcgtt cgtcgcggtc gccgatgtgg actgggaacg tttcgtcacc ggtttcgcct   39060
ctgcccgtcc ccgtccgttg atcagcgacc tcccggaggt ccgtaccgcc ctgcggaacc   39120
aggagcagga gcaactccac gcccccgtcc ccgaggaccg atcggcacag cttctgcggc   39180
ggctgtccat gctgtctccc gccggacggg aagccgaact ggtgaagctc gtccgtaccg   39240
aggcagccgc tgttctgggg cacggctccg cgcaggacgt cccggccgag cggcgttca    39300 aggagctggg cttcgactcc ctcaccgctg ttcagctacg caacagactg gccgccgcca   39360
ccggcaccag gctccccgcc agcgccgtct tcgaccaccc ccacgctgcg gctctcgcca   39420
ggtggctgct cgcggggatg cggcatgccg acggtggaca cggtggtggg cacgccggtg   39480
gacccgggcc ggacgccgac gaaggtcggt cggccgcgc tggtcacagc ggaatgctgg    39540
ccgatctgta ccggcgttcc gccgagttgg gccggagccg ggagttcatc gggctgctgg   39600 ccgacaccg ggccttccgc ccggtgttcc acgggccggc ggacctcgac gcgccgttgg    39660
aggccgttcc gctggcggac ggggtgcgca aaccgcagtt gatctgttgc agcgggaccg   39720
cgccggtcgg cgggccgcac gagttcgcgc gcctggcttc gttcttccgc ggcactcgtg   39780
cggtctcggc gcttccgctg cccggctacc tgcccggtga gcagttgccc gcggaacctcg  39840
```

-continued

```
acgccgtgct cgccgcgcag gccgaggcgg tcgagaagca gaccgggggt gcgccgttcg  39900
tcctggtcgg ctactcggcg ggcggactga tggcccacgc actggcctgc cacctggccg  39960
ggcgcggcac accgccgagc ggtgaggtgc tggtggacct ctatccgccg ggccggcagg  40020
aaccggtgtt cggctggcag aaggagctca ccgagggcat gttcgcccag gacttcgtgc  40080
ccatggacga tacgcggctg acggccctcg gcacgtacga ccgtctcatg ggcgagtggc  40140
ggccggcgcc ctccggactg cccaccctcc tgatccgggc caccgaaccc atggcggagt  40200
ggaccggggc catcgactgg cgggcctcct gggagtacga ccacaccgcc gtcgacatgc  40260
cggggaacca cttcacgatc atgcgcgagc acgcggagga cgcggcccgg cacatcgacg  40320
tctggctgaa ggggctcacc ccctgacacc tgcccgcacc ctgtgactcc tgcccgtacc  40380
ggcgtcccgg tcctcccgac ccgcgtgcgc aacggacgag tcgctcagga ggtccccatc  40440
ggcatgcccc gctttcctcc ccctctccga acgcatcgac gacccgatcc ccctcaggga  40500
ccggtgaagg agcgtgttgc actcatgcag gacatgcaag gcgtacagcc cgaaccagcc  40560
agtgtcgaac acgcggcgga cgcagctcga acagagcgaa cggcgcacgg aagccgccca  40620
ggagatggag gacagcgaac tggggcgccg cctgcagatg ctccgcggca tgcagtgggt  40680
cttcggcgcc aacggcgatc cgtacgcccg gctgctgtgt ggcatggagg atgacccgtc  40740
acctttctac gacgcgatac ggaccctggg cgagctgcac cggagcagga ccggagcctg  40800
ggtcaccgcc gaccccgggc tcggggccgc catcctcgcc gaccggaagg ctcggtgccc  40860
ggaaggctcg tggccggtgc gggcgaagac cgacgggctg gagcagtacg tgctgcccgg  40920
gcaccaggcg ttcctgcggc tggagcgcga ggaggccgag cgactgcggg aggtcgcggc  40980
gccggtgctg ggggccgcgg cggtcgacgc gtggcgcccg ctgatcgacg aggtctgcgc  41040
ggggctcgcg aaggggctgc cggacacgtt cgacctggtc gaggagtacg cggggctggt  41100
gccggtcgag gtgctggcgc ggatctgggg cgtcccggag gaggaccgcg cccggttcgg  41160
gcgtgactgc cgggcgctcg ctcccgcgct ggacagcctc ctgtgtcccc agcagttggc  41220
gctgagcaag gacatggcgt ccgccctgga ggacctgcgt ctcctcttcg acggcctcga  41280
cgcgacgccg cgcctcgccg gccccgccga cggtgacgga acggccgtgg ccatgctcac  41340
cgttctgctc tgcacggagc cggtgaccac ggcgatcggg aacaccgtgc tcgggctcct  41400
tcccgggcag tggcccgtgc cctgcaccgg ccgggtggct gccgggcagg ttgccgggca  41460
ggcgctgcac cgggcggtgt cgtaccgtat cgcgacgcgc ttcgcccggg aggacctgga  41520
gttggcgggc tgcgaggtca gtccggtgga cgaggtggtg gtcctggccg gagcgatcgg  41580
ccggaacgga ccgtccgcag ccgccccgcc tgccccaccg ggcccagcgg cccgcccgc  41640
cccgtcggtc ttcggtgccg ccgccttcga gaacgcgctg gccgaacccc tcgtccgggc  41700
tgtgacggga gcgccctcc aggccctcgc ggaggggccc cccggctga cggcggcggg  41760
accgtcgta cgacggcggc gttcccctgt cgtcggcggg ctgcaccggg ctccggtggc  41820
cgccgcatga gcatcgcgtc gaacggcgcg cgctcggccc ccgccggcc cctgcgcgtg  41880
atgatgacca ccttcgcggc caacacgcac ttccagccgc tggttcccct ggcctgggca  41940
ctgcggacag ccgggcacga ggtgcgcgtg gtgagccagc cctcgctgag cgacgtggtg  42000
acgcaggcgg ggctcacctc ggtcccggtg ggcaccgagg ctccggtcga gcagttcgcg  42060
gcgacctggg gcgacgatgc ctacatcggc gtcaacagca tcgacttcac cggcaacgac  42120
cccggcctgt ggacgtggcc gtacctcctg ggcatggaga ccatgctggt gccggccttc  42180
tacgagttgc tgaacaacga gtccttcgtg gacggcgtag tcgagttcgc ccgtgactgg  42240
```

-continued

```
cggcccgacc tggtgatctg ggagccgctg acgttcgccg gcgcggtggc ggcgcgcgtc    42300
accggcgcgg cccacgcccg gctgccgtgg gggcaggaga tcaccctgcg cgggcggcag    42360
gcgttcctcg ccgagcgtgc cctgcaaccg ttcgagcacc gggaggatcc cacggccgag    42420
tggctgggcc gcatgctcga ccggtacggc tgctcgttcg acgaggagat ggtcaccggg    42480
cagtggacca tcgacacgct gccgcgcagc atgcggctgg agctgtccga ggagctgcgc    42540
accctggaca tgcggtacgt gccgtacaac ggaccggcgg tcgtaccccc ctgggtgtgg    42600
gaaccgtgcg agcggcccg ggtctgtctg acgatcggca cctcccagcg tgactccggc    42660
cgggaccatg tccccctcga ccacctgctc gactccctcg ccgacgtgga cgcggagatc    42720
gtggccacgc tcgacaccac ccagcaggag cgcctgcggg gcgcggcccc cggcaacgtc    42780
cggctggtgg acttcgtccc gctgcacgcg ctgatgccga cctgctcggc gatcgtgcac    42840
cacggtggtc cgggcacgtg gtcgacggcg gcgctccacg gcgtcccgca gatcatcctg    42900
gacacctcgt gggacacacc ggtgcgggcg cagcgcatgc agcaactcgg ggcgggcctg    42960
tcgatgccgg tgggggaact gggcgtcgag gcgctgcggg accgggtcct gcggctgctg    43020
ggggagccgg agttccgcgc gggcgccgag cggatccggg ccgagatgct cgcgatgccc    43080 gccccccggtg acgtcgtacc ggacctggaa cgactcaccg cggagcatgc caccggcgcg    43140
atggcgggaa ggcggtgaga cgatgcgcgt actgctgacc tgcttcgcca acgacaccca    43200
cttccacggg ctggtgccgc tggcgtgggc gctgcgggcc gccgggcacg aagtccgcgt    43260
ggccagtcag cccgccctgt ccgacacgat cacccaagcg ggactgaccg cggtgcccgt    43320
gggccgggac accgccttcc tggagctgat ggggagatc ggcgcggacg tccagaagta    43380
ctccaccggc atcgacctgg gcgtccgcgc ggagctgacg agctgggagt acctgctcgg    43440
catgcacacg accctggtgc ccacgttcta ctcgctggtc aacgacgagc cgttcgtcga    43500
cgggctcgtc gcgctgaccc gggcctggcg gcccgacctc atcctgtggg agcacttcag    43560
cttcgccggg gcgttggcgg cgcgggccac cggcacgccc cacgcccgcg tgctgtgggg    43620
gtcggacctc atcgtccggt tccgccggga cttcctcgcg gagcgggcga accggcccgc    43680
cgagcaccgc gaggacccca tggcggagtg gctgggctgg gcggccgaac ggctgggctc    43740
caccttcgac gaggagctgg tgaccgggca gtggacgatc gacccgctgc cgcggagcat    43800
gcggctgccc accgggacga cgacggtgcc gatgcggtac gtgccgtaca acgggcgggc    43860
cgtggtcccc gcatgggtcc ggcagcgtgc gcggcggccc cggatctgcc tgacgctcgg    43920
tgtgtcggcc cggcagaccc tgggcgacgg cgtgtcgctg gcggaggtgc tggccgcgct    43980
gggcgacgtg gacgcggaga tcgtggccac gctggacgcc tcccagcgca agctcctggg    44040
gccggtgccg gacaacgtcc ggctggtgga cttcgtgccc ctgcacgccc tgatgccgac    44100
ctgttcggcg atcgtgcacc acggcggcgc cggtacctgg ctgacggccg ccgtccacgg    44160
cgtcccgcag atcgtcctcg gtgacctctg ggacaacctg ctgcgcgccc ggcagacaca    44220
ggccgcgggc gcgggcctgt tcatccatcc gtccgaggtc accgcggccg ggctcggtga    44280
gggcgtgcgc cgggtgctga cggacccttc catccgggcc gccgcacagc gcgtccggga    44340
cgagatgaat gcagagccga cgccgggcga ggtcgtcacg gtgctggagc ggctcgcgc    44400 gagcggcgga cgcggacgag gaggcgggaa ccatgcgggc tgacacggag ccgaccaccg    44460
ggtacgagga cgagttcgcc gagatctacg acgccgtgta ccggggccgg ggcaaggact    44520
acgccggcga ggcgaaggac gtggcggacc tcgtgcgcga ccgggtgccg gacgcgtcct    44580
```

```
ccctcctgga cgtggcctgc ggcacgggcg cgcacctgcg gcacttcgcc acgtctcttcg  44640
acgacgcccg cggtctcgaa ctgtccgcga gcatgctgga catcgcccgc tcccgcatgc  44700
cgggcgtgcc gctgcaccaa ggggacatgc gatccttcga cctggggcca cgcgtctccg  44760
cggtcacctg catgttcagc tccgtcggcc acctggccac caccgccgaa ctcgacgcga  44820
cgctgcggtg cttcgcccgg cacacccggc ccggcggcgt ggccgtcatc gaaccgtggt  44880
ggttcccgga gaccttcacc gacggctacg tggcgggtga catcgtacgc gtcgacggcc  44940
ggaccatctc ccgggtgtcc cactcggtac gggacggcgg cgccacccgc atggagatcc  45000
actacgtgat cgccgacgcc gagcacggtc cccggcacct ggtcgagcac caccgcatca  45060
cgctgttccc gcggcatgcg tacacggccg cgtacgagaa ggcgggctac accgtcgagt  45120
acctcgacgg cgggccctcg ggccgggggc tgttcgtcgg cacccggacg tgaacccgcc  45180
cgcgcaccgc ccgatcaccc tgctcaacgc cgttcacacg gatcaccgga ccacgcgaag  45240
gacctttcac atgtcgtacg acgaccacgc ggtgctggaa gcgatactgc ggtgcgccgg  45300
aggtgacgag cgcttcctgc tgaacaccgt cgaggaatgg ggagccgccg agatcaccgc  45360
ggcgctcgtg gacgagttgc tgttccgctg cgagatcccg caggtgggcg gtgaggcgtt  45420
catcggcctg gacgtcctgc acggcgccga ccggatcagc catgtgctgc aggtgacgga  45480
cggcaagccg gtcacgtcgg cggaaccggc cggccaggaa ctgggcggcc gtacctggag  45540
ttcacgctca gcgaccctcc tgcgggagct gttcggcccg ccgtccggcc gcaccgcggg  45600
gggcttcggc gtctccttcc tgcccgacct gcgcggcccg cggaccatgg agggcgcggc  45660
cctggccgcc cgcgccacca acgtggtgct gcacgcgacg accaacgaga cgccccccact  45720
ggaccggctg gccctgcgct acgagtccga caagtggggc ggcgtccact ggttcaccgg  45780
ccactacgac cggcacctgc gggccgtgcg cgaccaggcg gtgcggatcc tggagatcgg  45840
catcggcggc tacgacgacc tgctgccgag cggcgcctca ctgaagatgt ggaagcgcta  45900
cttcccgcgc ggcctggtct tcggcgtgga catcttcgac agtcggcgtg cgaccagccg  45960
cgtgtcaaga cgctccgcgg cccggcagga cgacccggag ttcatgcgcc gcgtcgccga  46020
ggagcacggg ccgttcgacg tcatcatcga cgacggcagc cacatcaacg cacacatgcg  46080
gacgtcgttc tcggtgatgt tcccccacct gcgcaacggc ggcttctacg tcatcgagga  46140
caccttcacc tcctactggc ccgggtacgg agggccatcc ggagcccggt gcccgtccgg  46200
aacaaccgcc ctggagatgg tcaagggact gatcgactcg gtgcactacg aggagcggcc  46260
ggacggcgcg gccacggccg actacatcgc caggaacctc gtcgggctgc acgcctacca  46320
aacgacctcg tcttcctcga gaagggcgat caacaaggag ggcggcatcc cccacaccgt  46380
gccccgggag ccgttctgga acgacaacta gccacggccg caaccagagc cggaaaccgc  46440
accactgtcc gcgccacctc ggaaccacct ccagcaaagg acacaccgct gtgaccgata  46500
cgcacaccgg accgacaccg gccgacgcgg tacccgccta cccgttcagc ctgccgcacg  46560
ccctggacct cgaccgcac tacgccgaac tccgccgcga cgaacccgtc tccagggtgc  46620
gcctgcccta cggcgagggc acggcctggc tggtcacccg catgtccgac gcccgtatcg  46680
ttctgggcga ctcccgcttc agcaccgcgg ccgccaccga tcccgccacc ccccggatgt  46740
tccccacccc gcccgagccg gacggcgtcc tgcccagga cccgccggac cacacccggc  46800
tgcggcggct ggtgggcaag gccttcacgg cacgccgggt ggaggagatg cggccccgtg  46860
tccgctccct cgtcgactcc ctgctcgacg acatggtggc gcacgttca cccgccgacc  46920
tggtcgagtt cctcgccgtt cccttccccg tcgcggtcat ctgcgaactg ctcggcgtgc  46980
```

```
ccttggagga ccgcgacctg ttccggacct tctccgacgc catgctctcc tcgacccggc   47040
tcaccgccgc ggagatacag cgggtccagc aggacttcat ggtctacatg gacggcctgg   47100
tcgcccagcg ccgcgacgcc cccaccgagg acctgctcgg cgccctcgcc ctcgccaccg   47160
acaacgacga ccacctgacc aagggcgaga tcgtcaacat gggggtgagc ctgctcatcg   47220
cgggccacga gacgtcggtc aaccagatca ccaacctcgt ccacctcctg ctgaccgagc   47280
gcaagcgcta cgagtcgctg gtcgccgacc cggccctcgt gcccgcggcg gtggaggaga   47340
tgctgcggta cacaccgctg gtgtccgccg gcagcttcgt ccgcgtggcc accgaggacg   47400
tggagctgag caccgtgacc gtgcgggccg gggagccctg cgtcgtccac ttcgcgtcgg   47460
ccaaccggga cgaggaggtc ttcgaccacg ccgacgagct ggacttccac cgtgagcgca   47520
acccgcacat agcgttcggg cacggagcgc accactgcat cggcgcccaa ctgggccgac   47580
tggaactcca ggaggccctg tccgccctcg tccggcgctt ccccaccctc gatctggccg   47640
agccggtcgc gggactgaag tggaagcagg gcatgctgat ccgcggactg aacgccaga   47700
tcgtctcctg gtgacggccg gccgcccggc cgcccgccgg caccggcgc caccagggca   47760
ccggccggga ccgcagaccc ggccggtgcc cctcgcccga ggccgcctca ctccacgaag   47820
cggccaccct ccatgtgcat gcggcgaccg gtgaaccgct cgcgcaacat gcggtcgtgg   47880
gagaccacga ccagtgcgcc ccggtagtgc gccagcgcct cctccaggtc ctccacgagc   47940
gcgggcgaca ggtggttcgt cggctcgtcg agcagcagca ggtccgccgg gtcgcgcagc   48000
agacgggcca gggccagccg cctcaactgc ccggtggaca ggtctcccac cgcggtgccc   48060
agcgccgagg gccggaagag cccgaatccc aggagcgcgc cccggtgttc ctccgcgatg   48120
ccgggcagcc ccgccgcgaa ggccgccagc aggctctgct gccggtcggt gatctccgtc   48180
tcctgcggca gccagccgat gcgctccggg cgctcgcact cgccctgatc gggcgccagg   48240
tcaccggcca gcacgcgcag cagggtgctc ttgcccgcgc cgttgtgccc cgtgatcagg   48300
atcgctcac cggggtcgac ggtgaaggac gggacgtcga gccgcgtgcc gacggtgacc   48360
ttgtacagct cggcgagtgc cccgccgcgc ccgaccgtgc cgccaccctc cacccgggcc   48420
cggaaacgca tgggttgagg gggccgcggc accgggttct cctccagccg gcggacccgc   48480
tccttggcgt tgcggacccg cgcggagatc tgcttctcca cgttgcgctg gtggcgctgg   48540
ttcgaccgct cggtgttgcg ccgcgggccg gtgccaggt ggtcggcggc gctgcgggcc   48600
agttcccgct ggcgtgccag gtcctccagc cagtcctggt aagcctgctc ccagcggcgc   48660
cgcgcggccg ccttggcttg caggtatccc gcgtaaccgc cgccgtgccg gttgacggtg   48720
cgccgctcgc cgtccacctc ccacagggcg gtggccacgc gctccaggaa gacccggtcg   48780
tgcgagacga ccagcacgct gccgcggtgg gcccgcaggc gctcctccag ccactccagc   48840
gccccgacgt cgaggtggtt ggtgggttcg tcgagcagca tcagctgcgg ggacgcgcc   48900
agcaggcagg ccaggttgag acgcgcctgc tcacctccgg agaggctgcc gagccgccgg   48960
tcgcccgtga tgcccgccag accgaggccg tgcatcgccg cgtcgacacg ggcgtccgcc   49020
gcgtagccgt cgcgggcctc gaacgcctcc agcaggtcgc cgtaggcgcc gagcaggccc   49080
tccagctcct cgggctccgc cccggccagc gcctgctccg cctcacgcaa cccccgctcc   49140
agggagcgca gttcggcgag ggcgtggtcg atggcgtcct gaacggtgtc ctccgggggc   49200
aggtccggtg tctgggggag gtagccgcag ccgccgggag cccggacgag gacctggcca   49260
ccgtccgggc ggtccacgcc ggcgagcatg cggagcaggg tcgacttgcc cgatccgttc   49320
```

-continued

```
tcaccgatga tgccgacgcg ctcgccgagt gccaccgact ggttgacgcc gtccaacagc    49380
ggccgtccgc cgggtgcccg gacgacgtcg tcgaggacga cctggaagga accggtctca    49440
ggttgcgtgg gaaggagctt ttccggcgtg ccggtgagcg ccgcggcgcc ggtatcggaa    49500
cggtgtgcgt tctgcatggg tgatccgcca ttcggagaaa aagaggcagt gtggccaaaa    49560
gggagcggcc cacggcagac ggcggaagaa gagaacgcct cggcgaacgc ggcgcacccg    49620
acggtgcgca gcgcgaaaaa agggaggcga agaagcgagc cggaggcgtc gcgatcagcg    49680
gcgggagaag ccgcgtcacc gtcctgccgg gaaccctcga cggcgccgga gcggcaaccg    49740
cgtacgcggt gctcctcggc gcccggactc ccgtggcggt atcagaggaa gtagtaactg    49800
accacgtcgg cacgatagca gagcagacgg agccggcagg gggtcgcgag gtgcgatggc    49860
tgaatgtgtg ccacgcttcg gattttttgc tcgcgggacg acgaggccgt gtgcgaacgt    49920
gtcccgggca gtcgttcgtc agcgggaggt tcatatgcag gacaaccagg gtggatccgg    49980
agccgagtcc gagaccggga ccgagagcga cgtcaagcgg aagttccggg aggcactgga    50040
gcgcaagaag ctcctcagcc gggaacgccg ggcgcacgag gacgctcgtt ccaaggtgaa    50100
cggaacgtcc cgcaatggcg ccaggaaggc gaatttccgc cgcaaggccg ggtgacaccg    50160
accgctgcgc acaccgtgcc cccacagctc gactccgctg cgacaggggc ctgcccgcgc    50220
cggggaaccg gcccgggcag gtgtagggtg gcgggcatgt atccaggtgt cggttccctg    50280
aagctccgcc gccgcgcctg acggtgcggc cctgaactct cgtttcgcgt gcccaccgtc    50340
gcggtgtcag tgccgggcgg ctgtttcgtg ctgcccggtt ccggagcgaa cctgtggagc    50400
acaccgtggg cgcattcccc gcaaggccgg cctgaggccg cgaccgatac acgagttcac    50460
cgatgcgagc gagggccgcc gccgcgccgg tggcgacgac caccccttcc gcaccggccc    50520
cgacgccctc tcgccggcgc cgctcccggc cccggccggc ggcgccaccc gggtacgccg    50580
ctcccgcggc cccggcggcg cgtgccgcgc acaggccgta ccggccggcc gttcggccgg    50640
tggacctctg cgccctgccg tccccgcggc aacgtcgccg gacacggaca ccgcccctcg    50700
gccgccggcc gccgtcacca ccccggggcg ccggcgtctc gccgctctcg cgccggcccc    50760
gtccacgacc gctcccgtgc ctgccggaag ggccgactca tgaccgagcg cacctccccc    50820
gccgtcctcg cgccctcgg ccggccggcc taccgccgcc tcttcgccgc catggtcctc    50880
gccctcttcg ggtacggcgg gtggaccatc tacctcgcgc tccaggcgct ggagctc       50937
```

<210> SEQ ID NO 2
<211> LENGTH: 4150
<212> TYPE: PRT
<213> ORGANISM: Artificial Sequence
<220> FEATURE:
<223> OTHER INFORMATION: Description of Artificial Sequence:
      Recombinant Oleandolide PKS

<400> SEQUENCE: 2

```
Met His Val Pro Gly Glu Glu Asn Gly His Ser Ile Ala Ile Val Gly
  1               5                  10                  15

Ile Ala Cys Arg Leu Pro Gly Ser Ala Thr Pro Gln Glu Phe Trp Arg
                 20                  25                  30

Leu Leu Ala Asp Ser Ala Asp Ala Leu Asp Glu Pro Pro Ala Gly Arg
             35                  40                  45

Phe Pro Thr Gly Ser Leu Ser Ser Pro Ala Pro Arg Gly Gly Phe
         50                  55                  60

Leu Asp Ser Ile Asp Thr Phe Asp Ala Asp Phe Phe Asn Ile Ser Pro
 65                  70                  75                  80
```

-continued

```
Arg Glu Ala Gly Val Leu Asp Pro Gln Gln Arg Leu Ala Leu Glu Leu
                 85                  90                  95

Gly Trp Glu Ala Leu Glu Asp Ala Gly Ile Val Pro Arg His Leu Arg
            100                 105                 110

Gly Thr Arg Thr Ser Val Phe Met Gly Ala Met Trp Asp Asp Tyr Ala
            115                 120                 125

His Leu Ala His Ala Arg Gly Glu Ala Leu Thr Arg His Ser Leu
        130                 135                 140

Thr Gly Thr His Arg Gly Met Ile Ala Asn Arg Leu Ser Tyr Ala Leu
145                 150                 155                 160

Gly Leu Gln Gly Pro Ser Leu Thr Val Asp Thr Gly Gln Ser Ser Ser
                165                 170                 175

Leu Ala Ala Val His Met Ala Cys Glu Ser Leu Ala Arg Gly Glu Ser
                180                 185                 190

Asp Leu Ala Leu Val Gly Gly Val Asn Leu Val Leu Asp Pro Ala Gly
                195                 200                 205

Thr Thr Gly Val Glu Arg Phe Gly Ala Leu Ser Pro Asp Gly Arg Cys
                210                 215                 220

Tyr Thr Phe Asp Ser Arg Ala Asn Gly Tyr Ala Arg Gly Glu Gly Gly
225                 230                 235                 240

Val Val Val Val Leu Lys Pro Thr His Arg Ala Leu Ala Asp Gly Asp
                245                 250                 255

Thr Val Tyr Cys Glu Ile Leu Gly Ser Ala Leu Asn Asn Asp Gly Ala
                260                 265                 270

Thr Glu Gly Leu Thr Val Pro Ser Ala Arg Ala Gln Ala Asp Val Leu
                275                 280                 285

Arg Gln Ala Trp Glu Arg Ala Arg Val Ala Pro Thr Asp Val Gln Tyr
290                 295                 300

Val Glu Leu His Gly Thr Gly Thr Pro Ala Gly Asp Pro Val Glu Ala
305                 310                 315                 320

Glu Gly Leu Gly Thr Ala Leu Gly Thr Ala Arg Pro Ala Glu Ala Pro
                325                 330                 335

Leu Leu Val Gly Ser Val Lys Thr Asn Ile Gly His Leu Glu Gly Ala
                340                 345                 350

Ala Gly Ile Ala Gly Leu Leu Lys Thr Val Leu Ser Ile Lys Asn Arg
            355                 360                 365

His Leu Pro Ala Ser Leu Asn Phe Thr Ser Pro Asn Pro Arg Ile Asp
        370                 375                 380

Leu Asp Ala Leu Arg Leu Arg Val His Thr Ala Tyr Gly Pro Trp Pro
385                 390                 395                 400

Ser Pro Asp Arg Pro Leu Val Ala Gly Val Ser Ser Phe Gly Met Gly
                405                 410                 415

Gly Thr Asn Cys His Val Val Leu Ser Glu Leu Arg Asn Ala Gly Gly
                420                 425                 430

Asp Gly Ala Gly Lys Gly Pro Tyr Thr Gly Thr Glu Asp Arg Leu Gly
            435                 440                 445

Ala Thr Glu Ala Glu Lys Arg Pro Asp Pro Ala Thr Gly Asn Gly Pro
450                 455                 460

Asp Pro Ala Gln Asp Thr His Arg Tyr Pro Pro Leu Ile Leu Ser Ala
465                 470                 475                 480

Arg Ser Asp Ala Ala Leu Arg Ala Gln Ala Glu Arg Leu Arg His His
                485                 490                 495
```

```
Leu Glu His Ser Pro Gly Gln Arg Leu Arg Asp Thr Ala Tyr Ser Leu
            500                 505                 510

Ala Thr Arg Arg Gln Val Phe Glu Arg His Ala Val Thr Gly His
        515                 520                 525

Asp Arg Glu Asp Leu Leu Asn Gly Leu Arg Asp Leu Glu Asn Gly Leu
            530                 535                 540

Pro Ala Pro Gln Val Leu Leu Gly Arg Thr Pro Thr Pro Glu Pro Gly
545                 550                 555                 560

Gly Leu Ala Phe Leu Phe Ser Gly Gln Gly Ser Gln Gln Pro Gly Met
                565                 570                 575

Gly Lys Arg Leu His Gln Val Phe Pro Gly Phe Arg Asp Ala Leu Asp
            580                 585                 590

Glu Val Cys Ala Glu Leu Asp Thr His Leu Gly Arg Leu Leu Gly Pro
            595                 600                 605

Glu Ala Gly Pro Pro Leu Arg Asp Val Met Phe Ala Glu Arg Gly Thr
            610                 615                 620

Ala His Ser Ala Leu Leu Ser Glu Thr His Tyr Thr Gln Ala Ala Leu
625                 630                 635                 640

Phe Ala Leu Glu Thr Ala Leu Phe Arg Leu Leu Val Gln Trp Gly Leu
                645                 650                 655

Lys Pro Asp His Leu Ala Gly His Ser Val Gly Glu Ile Ala Ala Ala
            660                 665                 670

His Ala Ala Gly Ile Leu Asp Leu Ser Asp Ala Ala Glu Leu Val Ala
        675                 680                 685

Thr Arg Gly Ala Leu Met Arg Ser Leu Pro Gly Gly Gly Val Met Leu
    690                 695                 700

Ser Val Gln Ala Pro Glu Ser Glu Val Ala Pro Leu Leu Leu Gly Arg
705                 710                 715                 720

Glu Ala His Val Gly Leu Ala Ala Val Asn Gly Pro Asp Ala Val Val
                725                 730                 735

Val Ser Gly Glu Arg Gly His Val Ala Ala Ile Glu Gln Ile Leu Arg
            740                 745                 750

Asp Arg Gly Arg Lys Ser Arg Tyr Leu Arg Val Ser His Ala Phe His
            755                 760                 765

Ser Pro Leu Met Glu Pro Val Leu Glu Glu Phe Ala Glu Ala Val Ala
        770                 775                 780

Gly Leu Thr Phe Arg Ala Pro Thr Thr Pro Leu Val Ser Asn Leu Thr
785                 790                 795                 800

Gly Ala Pro Val Asp Asp Arg Thr Met Ala Thr Pro Ala Tyr Trp Val
                805                 810                 815

Arg His Val Arg Glu Ala Val Arg Phe Gly Asp Gly Ile Arg Ala Leu
            820                 825                 830

Gly Lys Leu Gly Thr Gly Ser Phe Leu Glu Val Gly Pro Asp Gly Val
            835                 840                 845

Leu Thr Ala Met Ala Arg Ala Cys Val Thr Ala Ala Pro Glu Pro Gly
    850                 855                 860

His Arg Gly Glu Gln Gly Ala Asp Ala Asp Ala His Thr Ala Leu Leu
865                 870                 875                 880

Leu Pro Ala Leu Arg Arg Gly Arg Asp Glu Ala Arg Ser Leu Thr Glu
                885                 890                 895

Ala Val Ala Arg Leu His Leu His Gly Val Pro Met Asp Trp Thr Ser
            900                 905                 910

Val Leu Gly Gly Asp Val Ser Arg Val Pro Leu Pro Thr Tyr Ala Phe
```

-continued

```
                915                 920                 925
Gln Arg Glu Ser His Trp Leu Pro Ser Gly Glu Ala His Pro Arg Pro
930                 935                 940
Ala Asp Asp Thr Glu Ser Gly Thr Gly Arg Thr Glu Ala Ser Pro Pro
945                 950                 955                 960
Arg Pro His Asp Val Leu His Leu Val Arg Ser His Ala Ala Ala Val
                965                 970                 975
Leu Gly His Ser Arg Ala Glu Arg Ile Asp Pro Asp Arg Ala Phe Arg
                980                 985                 990
Asp Leu Gly Phe Asp Ser Leu Thr Ala Leu Glu Leu Arg Asp Arg Leu
                995                 1000                1005
Asp Thr Ala Leu Gly Leu Arg Leu Pro Ser Ser Val Leu Phe Asp His
    1010                1015                1020
Pro Ser Pro Gly Ala Leu Ala Arg Phe Leu Gln Gly Asp Asp Thr Arg
1025                1030                1035                1040
Arg Pro Glu Pro Gly Lys Thr Asn Gly Thr Arg Ala Thr Glu Pro Gly
                1045                1050                1055
Pro Asp Pro Asp Asp Glu Pro Ile Ala Ile Val Gly Met Ala Cys Arg
                1060                1065                1070
Phe Pro Gly Gly Val Thr Ser Pro Glu Asp Leu Trp Arg Leu Leu Ala
                1075                1080                1085
Ala Gly Glu Asp Ala Val Ser Gly Phe Pro Thr Asp Arg Gly Trp Asn
                1090                1095                1100
Val Thr Asp Ser Ala Thr Arg Arg Gly Gly Phe Leu Tyr Asp Ala Gly
1105                1110                1115                1120
Glu Phe Asp Ala Ala Phe Phe Gly Ile Ser Pro Arg Glu Ala Leu Val
                1125                1130                1135
Met Asp Pro Gln Gln Arg Leu Leu Leu Glu Thr Ser Trp Glu Ala Leu
                1140                1145                1150
Glu Arg Ala Gly Val Ser Pro Gly Ser Leu Arg Gly Ser Asp Thr Ala
                1155                1160                1165
Val Tyr Ile Gly Ala Thr Ala Gln Asp Tyr Gly Pro Arg Leu His Glu
    1170                1175                1180
Ser Asp Asp Asp Ser Gly Gly Tyr Val Leu Thr Gly Asn Thr Ala Ser
1185                1190                1195                1200
Val Ala Ser Gly Arg Ile Ala Tyr Ser Leu Gly Leu Glu Gly Pro Ala
                1205                1210                1215
Val Thr Val Asp Thr Ala Cys Ser Ser Ser Leu Val Ala Leu His Leu
                1220                1225                1230
Ala Val Gln Ala Leu Arg Arg Gly Glu Cys Ser Leu Ala Leu Ala Gly
                1235                1240                1245
Gly Ala Thr Val Met Pro Ser Pro Gly Met Phe Val Glu Phe Ser Arg
    1250                1255                1260
Gln Gly Gly Leu Ser Glu Asp Gly Arg Cys Lys Ala Phe Ala Ala Thr
1265                1270                1275                1280
Ala Asp Gly Thr Gly Trp Ala Glu Gly Val Gly Val Leu Leu Val Glu
                1285                1290                1295
Arg Leu Ser Asp Ala Arg Arg Leu Gly His Arg Val Leu Ala Val Val
                1300                1305                1310
Arg Gly Ser Ala Val Asn Gln Asp Gly Ala Ser Asn Gly Leu Thr Ala
                1315                1320                1325
Pro Asn Gly Pro Ser Gln Gln Arg Val Ile Arg Ala Ala Leu Ala Asp
    1330                1335                1340
```

-continued

```
Ala Gly Leu Val Pro Ala Asp Val Asp Val Glu Ala His Gly Thr
1345                1350                1355                1360

Gly Thr Arg Leu Gly Asp Pro Ile Glu Ala Gln Ala Leu Leu Ala Thr
            1365                1370                1375

Tyr Gly Gln Gly Arg Ala Gly Gly Arg Pro Val Val Leu Gly Ser Val
        1380                1385                1390

Lys Ser Asn Ile Gly His Thr Gln Ala Ala Gly Val Ala Gly Val
    1395                1400                1405

Met Lys Met Val Leu Ala Leu Gly Arg Gly Val Val Pro Lys Thr Leu
    1410                1415                1420

His Val Asp Glu Pro Ser Ala His Val Asp Trp Ser Ala Gly Glu Val
1425                1430                1435                1440

Glu Leu Ala Val Glu Ala Val Pro Trp Ser Arg Gly Gly Arg Val Arg
            1445                1450                1455

Arg Ala Gly Val Ser Ser Phe Gly Ile Ser Gly Thr Asn Ala His Val
            1460                1465                1470

Ile Val Glu Glu Ala Pro Ala Glu Pro Glu Pro Glu Pro Glu Arg Gly
        1475                1480                1485

Pro Gly Ser Val Val Gly Val Val Pro Trp Val Val Ser Gly Arg Asp
    1490                1495                1500

Ala Gly Ala Leu Arg Glu Gln Ala Ala Arg Leu Ala Ala His Val Ser
1505                1510                1515                1520

Gly Val Ser Ala Val Asp Val Gly Trp Ser Leu Val Ala Thr Arg Ser
            1525                1530                1535

Val Phe Glu His Arg Ala Val Met Val Gly Ser Glu Leu Asp Ala Met
        1540                1545                1550

Ala Glu Ser Leu Ala Gly Phe Ala Ala Gly Gly Val Val Pro Gly Val
    1555                1560                1565

Val Ser Gly Val Ala Pro Ala Glu Gly Arg Arg Val Val Phe Val Phe
    1570                1575                1580

Pro Gly Gln Gly Ser Gln Trp Val Gly Met Ala Ala Gly Leu Leu Asp
1585                1590                1595                1600

Ala Cys Pro Val Phe Ala Glu Ala Val Ala Glu Cys Ala Ala Val Leu
            1605                1610                1615

Asp Pro Leu Thr Gly Trp Ser Leu Val Glu Val Leu Arg Gly Gly Gly
            1620                1625                1630

Glu Ala Val Leu Gly Arg Val Asp Val Val Gln Pro Ala Leu Trp Ala
        1635                1640                1645

Val Met Val Ser Leu Ala Arg Thr Trp Arg Tyr Tyr Gly Val Glu Pro
    1650                1655                1660

Ala Ala Val Val Gly His Ser Gln Gly Glu Ile Ala Ala Ala Cys Val
1665                1670                1675                1680

Ala Gly Gly Leu Ser Leu Ala Asp Gly Ala Arg Val Val Val Leu Arg
            1685                1690                1695

Ser Arg Ala Ile Ala Arg Ile Ala Gly Gly Gly Met Val Ser Val
            1700                1705                1710

Ser Leu Pro Ala Gly Arg Val Arg Thr Met Leu Glu Glu Phe Asp Gly
        1715                1720                1725

Arg Val Ser Val Ala Ala Val Asn Gly Pro Ser Ser Thr Val Val Ser
    1730                1735                1740

Gly Asp Val Gln Ala Leu Asp Glu Leu Leu Ala Gly Cys Glu Arg Glu
1745                1750                1755                1760
```

-continued

```
Gly Val Arg Ala Arg Arg Val Pro Val Asp Tyr Ala Ser His Ser Ala
            1765                1770                1775

Gln Met Asp Gln Leu Arg Asp Asp Leu Leu Glu Ala Leu Ala Thr Ile
            1780                1785                1790

Val Pro Thr Ser Ala Asn Val Pro Phe Phe Ser Thr Val Thr Ala Asp
            1795                1800                1805

Trp Leu Asp Thr Thr Ala Leu Asp Ala Gly Tyr Trp Phe Thr Asn Leu
        1810                1815                1820

Arg Glu Thr Val Arg Phe Gln Glu Ala Val Glu Gly Leu Val Ala Gln
1825                1830                1835                1840

Gly Met Gly Ala Phe Val Glu Cys Ser Pro His Pro Val Leu Val Pro
            1845                1850                1855

Gly Ile Thr Glu Thr Leu Asp Thr Phe Asp Ala Asp Ala Val Ala Leu
            1860                1865                1870

Ser Ser Leu Arg Arg Asp Glu Gly Gly Leu Asp Arg Phe Leu Thr Ser
            1875                1880                1885

Leu Ala Glu Ala Phe Val Gln Gly Val Pro Val Asp Trp Ser Arg Ala
            1890                1895                1900

Phe Glu Gly Ala Ser Pro Arg Thr Val Asp Leu Pro Thr Tyr Pro Phe
1905                1910                1915                1920

Gln Arg Gln Arg Tyr Trp Leu Leu Asp Lys Ala Ala Gln Arg Glu Arg
            1925                1930                1935

Glu Arg Leu Glu Asp Trp Arg Tyr His Val Glu Trp Arg Pro Val Thr
            1940                1945                1950

Thr Arg Pro Ser Ala Arg Leu Ser Gly Val Trp Ala Val Ala Ile Pro
            1955                1960                1965

Ala Arg Leu Ala Arg Asp Ser Leu Leu Val Gly Ala Ile Asp Ala Leu
        1970                1975                1980

Glu Arg Gly Gly Ala Arg Ala Val Pro Val Val Val Asp Glu Arg Asp
1985                1990                1995                2000

His Asp Arg Gln Ala Leu Val Glu Ala Leu Arg Asn Gly Leu Gly Asp
            2005                2010                2015

Asp Asp Leu Ala Gly Val Leu Ser Leu Leu Ala Leu Asp Glu Ala Pro
            2020                2025                2030

His Gly Asp His Pro Asp Val Pro Val Gly Met Ala Ala Ser Leu Ala
            2035                2040                2045

Leu Val Gln Ala Met Ala Asp Ala Ala Ala Glu Val Pro Val Trp Phe
        2050                2055                2060

Ala Thr Arg Gly Ala Val Ala Ala Leu Pro Gly Glu Ser Pro Glu Arg
2065                2070                2075                2080

Pro Arg Gln Ala Leu Leu Trp Gly Leu Gly Arg Val Val Ala Leu Glu
            2085                2090                2095

Gln Pro Gln Ile Trp Gly Gly Leu Val Asp Leu Pro Gln His Leu Asp
            2100                2105                2110

Glu Asp Ala Gly Arg Arg Leu Val Asp Val Gly Gly Leu Ala Asp
            2115                2120                2125

Glu Asp Gln Leu Ala Val Arg Ala Ser Ser Val Leu Ala Arg Arg Leu
            2130                2135                2140

Val Arg Thr Pro Gly His Arg Met Ser Ser Gln Ala Gly Gly Arg Glu
2145                2150                2155                2160

Trp Ser Pro Ser Gly Thr Val Leu Val Thr Gly Gly Thr Gly Ala Leu
            2165                2170                2175

Gly Ala His Val Ala Arg Trp Leu Ala Gly Lys Gly Ala Glu His Leu
```

-continued

```
              2180                2185                2190
Val Leu Ile Ser Arg Arg Gly Ala Asp Ala Gly Ala Ala Ala Leu
              2195                2200                2205
Arg Asp Ser Leu Thr Asp Met Gly Val Arg Val Thr Leu Ala Ala Cys
2210                2215                2220
Asp Ala Ala Asp Arg His Ala Leu Glu Thr Leu Leu Asp Ser Leu Arg
2225                2230                2235                2240
Thr Asp Pro Ala Gln Leu Thr Ala Val Ile His Ala Ala Gly Ala Leu
              2245                2250                2255
Asp Asp Gly Met Thr Thr Val Leu Thr Pro Glu Gln Met Asn Asn Ala
              2260                2265                2270
Leu Arg Ala Lys Val Thr Ala Thr Val Asn Leu His Glu Leu Thr Arg
              2275                2280                2285
Asp Leu Asp Leu Ser Ala Phe Val Leu Phe Ser Ser Ile Ser Ala Thr
              2290                2295                2300
Leu Gly Ile Pro Gly Gln Ala Asn Tyr Ala Pro Gly Asn Ser Phe Leu
2305                2310                2315                2320
Asp Ala Phe Ala Glu Trp Arg Arg Ala Gln Gly Leu Val Ala Thr Ser
              2325                2330                2335
Ile Ala Trp Gly Pro Trp Ser Gly Gly Thr Gly Met Ala His Glu Gly
              2340                2345                2350
Ser Val Gly Glu Arg Leu Gln Arg His Gly Val Leu Ala Met Glu Pro
              2355                2360                2365
Ala Ala Ala Ile Ala Ala Leu Asp His Thr Leu Ala Ser Asp Glu Thr
              2370                2375                2380
Ala Val Ala Val Ala Asp Ile Asp Trp Ser Arg Phe Phe Leu Ala Tyr
2385                2390                2395                2400
Thr Ala Leu Arg Ala Arg Pro Leu Ile Gly Glu Ile Pro Glu Ala Arg
              2405                2410                2415
Arg Met Leu Glu Ser Gly Ser Gly Pro Gly Asp Leu Glu Pro Asp Arg
              2420                2425                2430
Ala Glu Pro Glu Leu Ala Val Arg Leu Ala Gly Leu Thr Ala Val Glu
              2435                2440                2445
Gln Glu Arg Leu Leu Val Gln Leu Val Arg Glu Gln Ala Ala Val Val
              2450                2455                2460
Leu Gly His Ser Gly Ala Glu Ala Val Ala Pro Asp Arg Ala Phe Lys
2465                2470                2475                2480
Asp Leu Gly Phe Asp Ser Leu Thr Ser Val Glu Leu Arg Asn Arg Leu
              2485                2490                2495
Asn Thr Ala Thr Gly Leu Arg Leu Pro Val Thr Ala Val Phe Asp Tyr
              2500                2505                2510
Ala Arg Pro Ala Ala Leu Ala Gly His Leu Arg Ser Arg Leu Ile Asp
              2515                2520                2525
Asp Asp Gly Asp His Gly Ala Leu Pro Gly Val Glu Lys His Ala Ile
              2530                2535                2540
Asp Glu Pro Ile Ala Ile Val Gly Met Ala Cys Arg Phe Pro Gly Gly
2545                2550                2555                2560
Ile Ala Ser Pro Glu Asp Leu Trp Asp Val Leu Thr Ala Gly Glu Asp
              2565                2570                2575
Val Val Ser Gly Leu Pro Gln Asn Arg Gly Trp Asp Leu Gly Arg Leu
              2580                2585                2590
Tyr Asp Pro Asp Pro Asp Arg Ala Gly Thr Ser Tyr Met Arg Glu Gly
              2595                2600                2605
```

-continued

```
Ala Phe Leu His Glu Ala Gly Glu Phe Asp Ala Ala Phe Phe Gly Ile
    2610                2615                2620
Ser Pro Arg Glu Ala Leu Ala Met Asp Pro Gln Gln Arg Leu Leu Leu
2625                2630                2635                2640
Glu Thr Ser Trp Glu Ala Leu Glu Arg Ala Gly Ile Thr Pro Ser Lys
                2645                2650                2655
Leu Ala Gly Ser Pro Thr Gly Val Phe Phe Gly Met Ser Asn Gln Asp
            2660                2665                2670
Tyr Ala Ala Gln Ala Gly Asp Val Pro Ser Glu Leu Glu Gly Tyr Leu
        2675                2680                2685
Leu Thr Gly Ser Ile Ser Ser Val Ala Ser Gly Arg Val Ala Tyr Thr
    2690                2695                2700
Phe Gly Leu Glu Gly Pro Ala Val Thr Val Asp Thr Ala Cys Ser Ser
2705                2710                2715                2720
Ser Leu Val Ala Leu His Leu Ala Val Gln Gly Leu Arg Arg Gly Glu
                2725                2730                2735
Cys Ser Leu Ala Leu Val Gly Gly Val Thr Val Met Ser Ser Pro Val
            2740                2745                2750
Thr Leu Thr Thr Phe Ser Arg Gln Arg Gly Leu Ser Val Asp Gly Arg
        2755                2760                2765
Cys Lys Ala Phe Ala Ala Ser Ala Asp Gly Phe Gly Ala Ala Glu Gly
    2770                2775                2780
Val Gly Val Leu Leu Val Glu Arg Leu Ser Asp Ala Arg Arg Leu Gly
2785                2790                2795                2800
His Arg Val Leu Ala Val Val Arg Gly Ser Ala Val Asn Gln Asp Gly
                2805                2810                2815
Ala Ser Asn Gly Leu Ala Ala Pro Asn Gly Pro Ser Gln Gln Arg Val
            2820                2825                2830
Ile Arg Ala Ala Leu Ala Asp Ala Gly Leu Ala Pro Ala Asp Val Asp
        2835                2840                2845
Val Val Glu Ala His Gly Thr Gly Thr Arg Leu Gly Asp Pro Ile Glu
    2850                2855                2860
Ala Gln Ala Leu Leu Ala Thr Tyr Gly Gln Gly Arg Thr Ser Gly Arg
2865                2870                2875                2880
Pro Val Trp Leu Gly Ser Val Lys Ser Asn Ile Gly His Thr Gln Ala
                2885                2890                2895
Ala Ala Gly Val Ala Gly Val Met Lys Met Val Leu Ala Leu Gly Arg
            2900                2905                2910
Gly Val Val Pro Lys Thr Leu His Val Asp Glu Pro Ser Pro His Val
        2915                2920                2925
Asp Trp Ser Ala Gly Glu Val Glu Leu Ala Val Glu Ala Val Pro Trp
    2930                2935                2940
Ser Arg Gly Gly Arg Val Arg Arg Ala Gly Val Ser Ser Phe Gly Ile
2945                2950                2955                2960
Ser Gly Thr Asn Ala His Val Ile Val Glu Glu Ala Pro Ala Glu Pro
                2965                2970                2975
Ser Val Glu Glu Gly Pro Gly Ser Val Val Gly Val Val Pro Trp Val
            2980                2985                2990
Val Ser Gly Arg Asp Ala Gly Ala Leu Arg Ala Gln Ala Ala Arg Leu
        2995                3000                3005
Ala Ala His Val Ser Ser Thr Gly Ala Gly Val Val Asp Val Gly Trp
    3010                3015                3020
```

-continued

```
Ser Leu Val Ala Thr Arg Ser Val Phe Glu His Arg Ala Val Met Val
3025                3030                3035                3040

Gly Thr Asp Leu Asp Ser Met Ala Gly Ser Leu Ala Gly Phe Ala Ala
            3045                3050                3055

Gly Gly Val Val Pro Gly Val Ser Gly Val Ala Pro Ala Glu Gly
            3060                3065                3070

Arg Arg Val Val Phe Val Phe Pro Gly Gln Gly Ser Gln Trp Val Gly
        3075                3080                3085

Met Ala Ala Gly Leu Leu Asp Ala Cys Pro Val Phe Ala Glu Ala Val
3090                3095                3100

Ala Glu Cys Ala Ala Val Leu Asp Arg Leu Thr Gly Trp Ser Leu Val
3105                3110                3115                3120

Glu Val Leu Arg Gly Gly Glu Ala Val Leu Gly Arg Val Asp Val Val
            3125                3130                3135

Gln Pro Ala Leu Trp Ala Val Met Val Ser Leu Ala Arg Thr Trp Arg
        3140                3145                3150

Tyr Tyr Gly Val Glu Pro Ala Ala Val Val Gly His Ser Gln Gly Glu
        3155                3160                3165

Ile Ala Ala Ala Cys Val Ala Gly Gly Leu Ser Leu Ala Asp Gly Ala
        3170                3175                3180

Arg Val Val Leu Arg Ser Arg Ala Ile Ala Arg Ile Ala Gly Gly
3185                3190                3195                3200

Gly Gly Met Val Ser Val Gly Leu Ser Ala Glu Arg Val Arg Thr Met
            3205                3210                3215

Leu Asp Thr Tyr Gly Gly Arg Val Ser Val Ala Ala Val Asn Gly Pro
            3220                3225                3230

Ser Ser Thr Val Val Ser Gly Asp Ala Gln Ala Leu Asp Glu Leu Leu
        3235                3240                3245

Ala Gly Cys Glu Arg Glu Gly Val Arg Ala Arg Arg Val Pro Val Asp
        3250                3255                3260

Tyr Ala Ser His Ser Ala Gln Met Asp Gln Leu Arg Asp Glu Leu Leu
3265                3270                3275                3280

Glu Ala Leu Ala Asp Val Thr Pro Gln Asp Ser Ser Val Pro Phe Phe
            3285                3290                3295

Ser Thr Val Thr Ala Asp Trp Leu Asp Thr Thr Ala Leu Asp Ala Gly
            3300                3305                3310

Tyr Trp Phe Thr Asn Leu Arg Glu Thr Val Arg Phe Gln Glu Ala Val
        3315                3320                3325

Glu Gly Leu Val Ala Gln Gly Met Gly Ala Phe Val Glu Cys Ser Pro
3330                3335                3340

His Pro Val Leu Val Pro Gly Ile Thr Glu Thr Leu Asp Thr Phe Asp
3345                3350                3355                3360

Ala Asp Ala Val Ala Leu Ser Ser Leu Arg Arg Asp Glu Gly Gly Leu
            3365                3370                3375

Asp Arg Phe Leu Thr Ser Leu Ala Glu Ala Phe Val Gln Gly Val Pro
        3380                3385                3390

Val Asp Trp Thr His Ala Phe Glu Gly Gly Arg Pro Arg Phe Val Asp
        3395                3400                3405

Leu Pro Thr Tyr Ala Phe Gln Arg Gln Arg Tyr Trp Leu His Glu Glu
        3410                3415                3420

Pro Leu Gln Glu Pro Val Asp Glu Ala Trp Asp Ala Glu Phe Trp Ser
3425                3430                3435                3440

Val Val Glu Arg Gly Asp Ala Thr Ala Val Ser Asp Leu Leu Ser Thr
```

-continued

```
                    3445                3450                3455

Asp Ala Glu Ala Leu His Thr Val Leu Pro Ala Leu Ser Ser Trp Arg
                3460                3465                3470

Arg Arg Arg Val Glu His Arg Arg Leu Gln Asp Trp Arg Tyr Arg Val
            3475                3480                3485

Glu Trp Lys Pro Phe Pro Ala Ala Leu Asp Glu Val Leu Gly Gly Gly
        3490                3495                3500

Trp Leu Phe Val Val Pro Arg Gly Leu Ala Asp Asp Gly Val Val Ala
3505                3510                3515                3520

Arg Val Val Ala Ala Val Thr Ala Arg Gly Gly Glu Val Ser Val Val
            3525                3530                3535

Glu Leu Asp Pro Thr Arg Pro Asp Arg Arg Ala Tyr Ala Glu Ala Val
        3540                3545                3550

Ala Gly Arg Gly Val Ser Gly Val Val Ser Phe Leu Ser Trp Asp Asp
        3555                3560                3565

Arg Arg His Ser Glu His Ser Val Pro Ala Gly Leu Ala Ala Ser
        3570                3575                3580

Leu Val Leu Ala Gln Ala Leu Val Asp Leu Gly Arg Val Gly Glu Gly
3585                3590                3595                3600

Pro Arg Leu Trp Leu Val Thr Arg Gly Ala Val Val Ala Gly Pro Ser
            3605                3610                3615

Asp Ala Gly Val Val Ile Asp Pro Val Gln Ala Gln Val Trp Gly Phe
            3620                3625                3630

Gly Arg Val Leu Gly Leu Glu His Pro Glu Leu Trp Gly Gly Leu Val
            3635                3640                3645

Asp Leu Pro Val Gly Val Asp Glu Glu Val Cys Arg Arg Phe Val Gly
        3650                3655                3660

Val Val Ala Ser Ala Gly Phe Glu Asp Gln Val Ala Val Arg Gly Ser
3665                3670                3675                3680

Gly Val Trp Val Arg Arg Leu Val Arg Ala Val Val Asp Gly Gly Gly
            3685                3690                3695

Gly Gly Trp Arg Pro Arg Gly Thr Val Leu Val Thr Gly Gly Leu Gly
        3700                3705                3710

Gly Leu Gly Ala His Thr Ala Arg Trp Leu Val Gly Gly Gly Ala Asp
        3715                3720                3725

His Val Val Leu Val Ser Arg Arg Gly Gly Ser Ala Pro Gly Ala Gly
        3730                3735                3740

Asp Leu Val Arg Glu Leu Glu Gly Leu Gly Gly Ala Arg Val Ser Val
3745                3750                3755                3760

Arg Ala Cys Asp Val Ala Asp Arg Val Ala Leu Arg Ala Leu Leu Ser
            3765                3770                3775

Asp Leu Gly Glu Pro Val Thr Ala Val Phe His Ala Ala Gly Val Pro
            3780                3785                3790

Gln Ser Thr Pro Leu Ala Glu Ile Ser Val Gln Glu Ala Ala Asp Val
        3795                3800                3805

Met Ala Ala Lys Val Ala Gly Ala Val Asn Leu Gly Glu Leu Val Asp
        3810                3815                3820

Pro Cys Gly Leu Glu Ala Phe Val Leu Phe Ser Ser Asn Ala Gly Val
3825                3830                3835                3840

Trp Gly Ser Gly Gly Gln Ala Val Tyr Ala Ala Ala Asn Ala Phe Leu
            3845                3850                3855

Asp Ala Leu Ala Val Arg Arg Arg Gly Val Gly Leu Pro Ala Thr Ser
            3860                3865                3870
```

-continued

```
Val Ala Trp Gly Met Trp Ala Gly Glu Gly Met Ala Ser Val Gly Gly
    3875                3880                3885

Ala Ala Arg Glu Leu Ser Arg Arg Gly Val Arg Ala Met Asp Pro Glu
    3890                3895                3900

Arg Ala Val Ala Val Met Ala Asp Ala Val Gly Arg Gly Glu Ala Phe
3905                3910                3915                3920

Val Ala Val Ala Asp Val Asp Trp Glu Arg Phe Val Thr Gly Phe Ala
                3925                3930                3935

Ser Ala Arg Pro Arg Pro Leu Ile Ser Asp Leu Pro Glu Val Arg Ala
    3940                3945                3950

Val Val Glu Gly Gln Val Gln Gly Arg Gly Gln Gly Leu Gly Leu Val
    3955                3960                3965

Gly Glu Glu Glu Ser Ser Gly Trp Leu Lys Arg Leu Ser Gly Leu Ser
    3970                3975                3980

Arg Val Arg Gln Glu Glu Glu Leu Val Glu Leu Val Arg Ala Gln Ala
3985                3990                3995                4000

Ala Val Val Leu Gly His Gly Ser Ala Gln Asp Val Pro Ala Glu Arg
                4005                4010                4015

Ala Phe Lys Glu Leu Gly Phe Asp Ser Leu Thr Ala Val Glu Leu Arg
                4020                4025                4030

Asn Gly Leu Ala Ala Ala Thr Gly Ile Arg Leu Pro Ala Thr Met Ala
    4035                4040                4045

Phe Asp His Pro Thr Ala Thr Ala Ile Ala Arg Phe Leu Gln Ser Glu
    4050                4055                4060

Leu Val Gly Ser Asp Asp Pro Leu Thr Leu Met Arg Ser Ala Ile Asp
4065                4070                4075                4080

Gln Leu Glu Thr Gly Leu Ala Leu Leu Glu Ser Asp Glu Glu Ala Arg
                4085                4090                4095

Ser Glu Ile Thr Lys Arg Leu Asn Ile Leu Leu Pro Arg Phe Gly Ser
                4100                4105                4110

Gly Gly Ser Ser Arg Gly Arg Glu Ala Gly Gln Asp Ala Gly Glu His
    4115                4120                4125

Gln Asp Val Glu Asp Ala Thr Ile Asp Glu Leu Phe Glu Val Leu Asp
    4130                4135                4140

Asn Glu Leu Gly Asn Ser
4145                4150

<210> SEQ ID NO 3
<211> LENGTH: 3816
<212> TYPE: PRT
<213> ORGANISM: Artificial Sequence
<220> FEATURE:
<223> OTHER INFORMATION: Description of Artificial Sequence:
      Recombinant Oleandolide PKS

<400> SEQUENCE: 3

Val Thr Asn Asp Glu Lys Ile Val Glu Tyr Leu Lys Arg Ala Thr Val
1               5                   10                  15

Asp Leu Arg Lys Ala Arg His Arg Ile Trp Glu Leu Glu Asp Glu Pro
                20                  25                  30

Ile Ala Ile Thr Ser Met Ala Cys His Phe Pro Gly Gly Ile Glu Ser
            35                  40                  45

Pro Glu Gln Leu Trp Glu Leu Leu Ser Ala Gly Gly Glu Val Leu Ser
        50                  55                  60

Glu Phe Pro Asp Asp Arg Gly Trp Asp Leu Asp Glu Ile Tyr His Pro
```

-continued

```
             65                  70                  75                  80
Asp Pro Glu His Ser Gly Thr Ser Tyr Val Arg His Gly Gly Phe Leu
                     85                  90                  95
Asp His Ala Thr Gln Phe Asp Thr Asp Phe Phe Gly Ile Ser Pro Arg
                100                 105                 110
Glu Ala Leu Ala Met Asp Pro Gln Gln Arg Leu Leu Leu Glu Thr Ser
                115                 120                 125
Trp Gln Leu Phe Glu Arg Ala Gly Val Asp Pro His Thr Leu Lys Gly
            130                 135                 140
Ser Arg Thr Gly Val Phe Val Gly Ala Ala His Met Gly Tyr Ala Asp
145                 150                 155                 160
Arg Val Asp Thr Pro Pro Ala Glu Ala Glu Gly Tyr Leu Leu Thr Gly
                165                 170                 175
Asn Ala Ser Ala Val Val Ser Gly Arg Ile Ser Tyr Thr Phe Gly Leu
                180                 185                 190
Glu Gly Pro Ala Val Thr Val Asp Thr Ala Cys Ser Ser Ser Leu Val
            195                 200                 205
Ala Leu His Leu Ala Val Gln Ala Leu Arg Arg Gly Glu Cys Ser Leu
        210                 215                 220
Ala Val Val Gly Gly Val Ala Val Met Ser Asp Pro Lys Val Phe Val
225                 230                 235                 240
Glu Phe Ser Arg Gln Arg Gly Leu Ala Arg Asp Gly Arg Ser Lys Ala
                245                 250                 255
Phe Ala Ala Ser Ala Asp Gly Phe Gly Phe Ala Glu Gly Val Ser Leu
                260                 265                 270
Leu Leu Leu Glu Arg Leu Ser Asp Ala Arg Arg Leu Gly His Arg Val
            275                 280                 285
Leu Ala Val Val Arg Gly Ser Ala Val Asn Gln Asp Gly Ala Ser Asn
        290                 295                 300
Gly Leu Ala Ala Pro Asn Gly Pro Ser Gln Gln Arg Val Ile Arg Ala
305                 310                 315                 320
Ala Leu Ala Asp Ala Gly Leu Ala Pro Ala Asp Val Asp Val Val Glu
                325                 330                 335
Ala His Gly Thr Gly Thr Arg Leu Gly Asp Pro Ile Glu Ala Gln Ala
            340                 345                 350
Leu Leu Ala Thr Tyr Gly Gln Gly Arg Thr Ser Gly Arg Pro Val Trp
        355                 360                 365
Leu Gly Ser Val Lys Ser Asn Ile Gly His Thr Gln Ala Ala Ala Gly
        370                 375                 380
Val Ala Gly Val Met Lys Met Val Leu Ala Leu Glu Arg Gly Val Val
385                 390                 395                 400
Pro Lys Thr Leu His Val Asp Glu Pro Ser Pro His Val Asp Trp Ser
                405                 410                 415
Thr Gly Ala Val Glu Leu Leu Thr Glu Glu Arg Pro Trp Glu Pro Glu
                420                 425                 430
Ala Glu Arg Leu Arg Arg Ala Gly Ile Ser Ala Phe Gly Val Ser Gly
            435                 440                 445
Thr Asn Ala His Val Ile Val Glu Glu Ala Pro Ala Glu Pro Glu Pro
        450                 455                 460
Glu Pro Glu Pro Gly Thr Arg Val Val Ala Ala Gly Asp Leu Val Val
465                 470                 475                 480
Pro Trp Val Val Ser Gly Arg Asp Ala Gly Ala Leu Arg Ala Gln Ala
                485                 490                 495
```

-continued

```
Ala Arg Leu Ala Ala His Val Ser Ser Thr Gly Ala Gly Val Val Asp
            500                 505                 510

Val Gly Trp Ser Leu Val Ala Thr Arg Ser Val Phe Glu His Arg Ala
            515                 520                 525

Val Met Val Gly Thr Asp Leu Asp Ser Met Ala Gly Ser Leu Ala Gly
            530                 535                 540

Phe Ala Ala Gly Gly Val Val Pro Gly Val Val Ser Gly Val Ala Pro
545                 550                 555                 560

Ala Glu Gly Arg Arg Val Val Phe Val Phe Pro Gly Gln Gly Ser Gln
                565                 570                 575

Trp Val Gly Met Ala Ala Gly Leu Leu Asp Ala Cys Pro Val Phe Ala
            580                 585                 590

Glu Ala Val Ala Glu Cys Ala Ala Val Leu Asp Pro Leu Thr Gly Trp
            595                 600                 605

Ser Leu Val Glu Val Leu Arg Gly Gly Glu Ala Val Leu Gly Arg Val
            610                 615                 620

Asp Val Val Gln Pro Ala Leu Trp Ala Val Met Val Ser Leu Ala Arg
625                 630                 635                 640

Thr Trp Arg Tyr Tyr Gly Val Glu Pro Ala Ala Val Val Gly His Ser
                645                 650                 655

Gln Gly Glu Ile Ala Ala Ala Cys Val Ala Gly Gly Leu Ser Leu Ala
            660                 665                 670

Asp Gly Ala Arg Val Val Leu Arg Ser Arg Ala Ile Ala Arg Ile
            675                 680                 685

Ala Gly Gly Gly Gly Met Val Ser Val Ser Leu Pro Ala Gly Arg Val
            690                 695                 700

Arg Thr Met Leu Asp Thr Tyr Gly Gly Arg Leu Ser Val Ala Ala Val
705                 710                 715                 720

Asn Gly Pro Ser Ser Thr Val Val Ser Gly Asp Ala Gln Ala Leu Asp
                725                 730                 735

Glu Leu Leu Ala Gly Cys Glu Arg Glu Gly Val Arg Ala Arg Arg Val
            740                 745                 750

Pro Val Asp Tyr Ala Ser His Ser Ala Gln Met Asp Gln Leu Arg Asp
            755                 760                 765

Glu Leu Leu Glu Ala Leu Ala Asp Ile Thr Pro Gln His Ser Ser Val
770                 775                 780

Pro Phe Phe Ser Thr Val Thr Ala Asp Trp Leu Asp Thr Thr Ala Leu
785                 790                 795                 800

Asp Ala Gly Tyr Trp Phe Thr Asn Leu Arg Glu Thr Val Arg Phe Gln
                805                 810                 815

Glu Ala Val Glu Gly Leu Val Ala Gln Gly Met Gly Ala Phe Val Glu
            820                 825                 830

Cys Ser Pro His Pro Val Leu Val Pro Gly Ile Glu Gln Thr Leu Asp
            835                 840                 845

Thr Val Glu Ala Asp Ala Val Ala Leu Gly Ser Leu Arg Arg Asp Glu
            850                 855                 860

Gly Gly Leu Gly Arg Phe Leu Thr Ser Leu Ala Glu Ala Phe Val Gln
865                 870                 875                 880

Gly Val Pro Val Asp Trp Ser Arg Thr Phe Glu Gly Ala Ser Pro Arg
                885                 890                 895

Thr Val Asp Leu Pro Thr Tyr Pro Phe Gln Arg Gln Arg Phe Trp Leu
            900                 905                 910
```

```
Glu Gly Ser Pro Ala Leu Ser Ser Asn Gly Val Glu Gly Glu Ala Asp
        915                 920                 925

Val Ala Phe Trp Asp Ala Val Glu Arg Glu Asp Ser Ala Val Val Ala
        930                 935                 940

Glu Glu Leu Gly Ile Asp Ala Lys Ala Leu His Met Thr Leu Pro Ala
945                 950                 955                 960

Leu Ser Ser Trp Arg Arg Arg Gly Arg Gln Arg Arg Lys Val Gln Arg
        965                 970                 975

Trp Arg Tyr Arg Val Glu Trp Lys Arg Leu Pro Asn Ser Arg Ala Gln
        980                 985                 990

Glu Ser Leu Gln Gly Gly Trp Leu Val Val Pro Gln Gly Arg Ala
        995                 1000                1005

Gly Asp Val Arg Val Thr Gln Ser Val Ala Glu Val Ala Ala Lys Gly
1010                1015                1020

Gly Glu Ala Thr Val Leu Glu Val Asp Ala Leu His Pro Asp Arg Ala
1025                1030                1035                1040

Ala Tyr Ala Glu Ala Leu Thr Arg Trp Pro Gly Val Arg Gly Val Val
                1045                1050                1055

Ser Phe Leu Ala Trp Glu Glu Gln Ala Leu Ala Glu His Pro Val Leu
                1060                1065                1070

Ser Ala Gly Leu Ala Ala Ser Leu Ala Leu Ala Gln Ala Leu Ile Asp
        1075                1080                1085

Val Gly Gly Ser Gly Glu Ser Ala Pro Arg Leu Trp Leu Val Thr Glu
        1090                1095                1100

Ala Ala Val Val Ile Gly Ala Ala Asp Thr Gly Ala Val Ile Asp Pro
1105                1110                1115                1120

Val His Ala Gln Leu Trp Gly Phe Gly Arg Val Leu Ala Leu Glu His
                1125                1130                1135

Pro Glu Leu Trp Gly Gly Leu Ile Asp Leu Pro Ala Val Ala Gly Glu
                1140                1145                1150

Pro Gly Ser Ile Thr Asp His Ala His Ala Asp Leu Leu Ala Thr Val
        1155                1160                1165

Leu Ala Thr Met Val Gln Ala Ala Ala Arg Gly Glu Asp Gln Val Ala
        1170                1175                1180

Val Arg Thr Thr Gly Thr Tyr Val Pro Arg Leu Val Arg Ser Gly Gly
1185                1190                1195                1200

Ser Ala His Ser Gly Ala Arg Arg Trp Gln Pro Arg Asp Thr Val Leu
                1205                1210                1215

Val Thr Gly Gly Met Gly Pro Leu Thr Ala His Ile Val Arg Trp Leu
        1220                1225                1230

Ala Asp Asn Gly Ala Asp Gln Val Val Leu Gly Gly Gln Gly Ala
        1235                1240                1245

Asp Gly Glu Ala Glu Ala Leu Arg Ala Glu Phe Asp Gly His Thr Thr
        1250                1255                1260

Lys Ile Glu Leu Ala Asp Val Asp Thr Glu Asp Ser Asp Ala Leu Arg
1265                1270                1275                1280

Ser Leu Leu Asp Arg Thr Thr Gly Glu His Pro Leu Arg Ala Val Ile
                1285                1290                1295

His Ala Pro Thr Val Val Glu Phe Ala Ser Val Ala Glu Ser Asp Leu
                1300                1305                1310

Val Arg Phe Ala Arg Thr Ile Ser Ser Lys Ile Ala Gly Val Glu Gln
        1315                1320                1325

Leu Asp Glu Val Leu Ser Gly Ile Asp Thr Ala His Asp Val Val Phe
```

-continued

```
               1330                1335                1340

Phe Ser Ser Val Ala Gly Val Trp Gly Ser Ala Gly Gln Ser Ala Tyr
1345                1350                1355                1360

Ala Ala Gly Asn Ala Phe Leu Asp Ala Val Ala Gln His Arg Arg Leu
               1365                1370                1375

Arg Gly Leu Pro Gly Thr Ser Val Ala Trp Thr Pro Trp Asp Asp Asp
          1380                1385                1390

Arg Ser Leu Ala Ser Leu Gly Asp Ser Tyr Leu Asp Arg Arg Gly Leu
          1395                1400                1405

Arg Ala Leu Ser Ile Pro Gly Ala Leu Ala Ser Leu Gln Glu Val Leu
     1410                1415                1420

Asp Gln Asp Glu Val His Ala Val Val Ala Asp Val Asp Trp Glu Arg
1425                1430                1435                1440

Phe Tyr Ala Gly Phe Ser Ala Val Arg Arg Thr Ser Phe Phe Asp Asp
               1445                1450                1455

Val His Asp Ala His Arg Pro Ala Leu Ser Thr Ala Ala Thr Asn Asp
          1460                1465                1470

Gly Gln Ala Arg Asp Glu Asp Gly Gly Thr Glu Leu Val Arg Arg Leu
          1475                1480                1485

Arg Pro Leu Thr Glu Thr Glu Gln Gln Arg Glu Leu Val Ser Leu Val
     1490                1495                1500

Gln Ser Glu Val Ala Ala Val Leu Gly His Ser Ser Thr Asp Ala Val
1505                1510                1515                1520

Gln Pro Gln Arg Ala Phe Arg Glu Ile Gly Phe Asp Ser Leu Thr Ala
               1525                1530                1535

Val Gln Leu Arg Asn Arg Leu Thr Ala Thr Thr Gly Met Arg Leu Pro
          1540                1545                1550

Thr Thr Leu Val Phe Asp Tyr Pro Thr Thr Asn Gly Leu Ala Glu Tyr
     1555                1560                1565

Leu Arg Ser Glu Leu Phe Gly Val Ser Gly Ala Pro Ala Asp Leu Ser
     1570                1575                1580

Val Val Arg Asn Ala Asp Glu Glu Asp Asp Pro Val Val Ile Val Gly
1585                1590                1595                1600

Met Ala Cys Arg Phe Pro Gly Gly Ile Asp Thr Pro Glu Ala Phe Trp
               1605                1610                1615

Lys Leu Leu Glu Ala Gly Gly Asp Val Ile Ser Glu Leu Pro Ala Asn
          1620                1625                1630

Arg Gly Trp Asp Met Glu Arg Leu Leu Asn Pro Asp Pro Glu Ala Lys
     1635                1640                1645

Gly Thr Ser Ala Thr Arg Tyr Gly Gly Phe Leu Tyr Asp Ala Gly Glu
     1650                1655                1660

Phe Asp Ala Ala Phe Phe Gly Ile Ser Pro Arg Glu Ala Leu Ala Met
1665                1670                1675                1680

Asp Pro Gln Gln Arg Leu Leu Leu Glu Thr Val Trp Glu Leu Ile Glu
               1685                1690                1695

Ser Ala Gly Val Ala Pro Asp Ser Leu His Arg Ser Arg Thr Gly Thr
          1700                1705                1710

Phe Ile Gly Ser Asn Gly Gln Phe Tyr Ala Pro Leu Leu Trp Asn Ser
     1715                1720                1725

Gly Gly Asp Leu Glu Gly Tyr Gln Gly Val Gly Asn Ala Gly Ser Val
     1730                1735                1740

Met Ser Gly Arg Val Ala Tyr Ser Leu Gly Leu Glu Gly Pro Ala Val
1745                1750                1755                1760
```

-continued

```
Thr Val Asp Thr Ala Cys Ser Ser Leu Val Ala Leu His Leu Ala
            1765                1770                1775
Val Gln Ala Leu Arg Arg Gly Glu Cys Ser Leu Ala Ile Ala Gly Gly
        1780                1785                1790
Val Thr Val Met Ser Thr Pro Asp Ser Phe Val Glu Phe Ser Arg Gln
        1795                1800                1805
Gln Gly Leu Ser Glu Asp Gly Arg Cys Lys Ala Phe Ala Ser Thr Ala
        1810                1815                1820
Asp Gly Phe Gly Leu Ala Glu Gly Val Ser Ala Leu Leu Val Glu Arg
1825                1830                1835                1840
Leu Ser Asp Ala Arg Arg Leu Gly His Arg Val Leu Ala Val Val Arg
            1845                1850                1855
Gly Ser Ala Val Asn Gln Asp Gly Ala Ser Asn Gly Leu Thr Ala Pro
            1860                1865                1870
Asn Gly Pro Ser Gln Gln Arg Val Ile Arg Ala Ala Leu Ala Asp Ala
            1875                1880                1885
Gly Leu Ala Pro Ala Asp Val Asp Val Val Glu Ala His Gly Thr Gly
            1890                1895                1900
Thr Arg Leu Gly Asp Pro Ile Glu Ala Gln Ala Leu Leu Ala Thr Tyr
1905                1910                1915                1920
Gly Gln Gly Arg Ala Gly Gly Arg Pro Val Val Leu Gly Ser Val Lys
            1925                1930                1935
Ser Asn Ile Gly His Thr Gln Ala Ala Ala Gly Val Ala Gly Val Met
            1940                1945                1950
Lys Met Val Leu Ala Leu Glu Arg Gly Val Val Pro Lys Thr Leu His
        1955                1960                1965
Val Asp Glu Pro Ser Pro His Val Asp Trp Ser Ala Gly Glu Val Glu
    1970                1975                1980
Leu Ala Val Glu Ala Val Pro Trp Ser Arg Gly Arg Val Arg Arg
1985                1990                1995                2000
Ala Gly Val Ser Ser Phe Gly Ile Ser Gly Thr Asn Ala His Val Ile
            2005                2010                2015
Val Glu Glu Ala Pro Ala Glu Pro Glu Pro Glu Pro Gly Thr Arg Val
            2020                2025                2030
Val Ala Ala Gly Asp Leu Val Val Pro Trp Val Val Ser Gly Arg Asp
            2035                2040                2045
Ala Gly Ala Leu Arg Glu Gln Ala Ala Arg Leu Ala Ala His Val Ser
        2050                2055                2060
Ser Thr Gly Ala Gly Val Val Asp Val Gly Trp Ser Leu Val Ala Thr
2065                2070                2075                2080
Arg Ser Val Phe Glu His Arg Ala Val Met Val Gly Ser Glu Leu Asp
            2085                2090                2095
Ser Met Ala Glu Ser Leu Ala Gly Phe Ala Ala Gly Val Val Pro
            2100                2105                2110
Gly Val Val Ser Gly Val Ala Pro Ala Glu Gly Arg Arg Val Val Phe
        2115                2120                2125
Val Phe Pro Gly Gln Gly Ser Gln Trp Val Gly Met Ala Ala Gly Leu
    2130                2135                2140
Leu Asp Ala Cys Pro Val Phe Ala Glu Ala Val Ala Glu Cys Ala Ala
2145                2150                2155                2160
Val Leu Asp Pro Val Thr Gly Trp Ser Leu Val Glu Val Leu Arg Gly
            2165                2170                2175
```

```
Gly Gly Glu Ala Val Leu Gly Arg Val Asp Val Val Gln Pro Ala Leu
        2180                2185                2190

Trp Ala Val Met Val Ser Leu Ala Arg Thr Trp Arg Tyr Tyr Gly Val
        2195                2200                2205

Glu Pro Ala Ala Val Val Gly His Ser Gln Gly Glu Ile Ala Ala Ala
        2210                2215                2220

Cys Val Ala Gly Gly Leu Ser Leu Ala Asp Gly Ala Arg Val Val Val
2225                2230                2235                2240

Leu Arg Ser Arg Ala Ile Ala Arg Ile Ala Gly Gly Gly Met Val
        2245                2250                2255

Ser Val Gly Leu Ser Ala Glu Arg Val Arg Thr Met Leu Asp Thr Tyr
        2260                2265                2270

Gly Gly Arg Val Ser Val Ala Ala Val Asn Gly Pro Ser Ser Thr Val
        2275                2280                2285

Val Ser Gly Asp Val Gln Ala Leu Asp Glu Leu Leu Ala Gly Cys Glu
        2290                2295                2300

Arg Glu Gly Val Arg Ala Arg Arg Val Pro Val Asp Tyr Ala Ser His
2305                2310                2315                2320

Ser Ala Gln Met Asp Gln Leu Arg Asp Glu Leu Leu Glu Ala Leu Ala
        2325                2330                2335

Asp Ile Thr Pro Gln His Ser Ser Val Pro Phe Phe Ser Thr Val Thr
        2340                2345                2350

Ala Asp Trp Leu Asp Thr Thr Ala Leu Asp Ala Gly Tyr Trp Phe Thr
        2355                2360                2365

Asn Leu Arg Glu Thr Val Arg Phe Gln Glu Ala Val Glu Gly Leu Val
        2370                2375                2380

Ala Gln Gly Met Gly Ala Phe Val Glu Cys Ser Pro His Pro Val Leu
2385                2390                2395                2400

Val Pro Gly Ile Glu Gln Thr Leu Asp Ala Leu Asp Gln Asn Ala Ala
        2405                2410                2415

Val Leu Gly Ser Leu Arg Arg Asp Glu Gly Gly Leu Asp Arg Leu Leu
        2420                2425                2430

Thr Ser Leu Ala Glu Ala Phe Val Gln Gly Val Pro Val Asp Trp Thr
        2435                2440                2445

His Ala Phe Glu Gly Met Thr Pro Arg Thr Val Asp Leu Pro Thr Tyr
        2450                2455                2460

Pro Phe Gln Arg Gln His Tyr Trp Pro Lys Pro Ala Pro Ala Pro Gly
2465                2470                2475                2480

Ala Asn Leu Gly Asp Val Ala Ser Val Gly Leu Thr Ala Ala Gly His
        2485                2490                2495

Pro Leu Leu Gly Ala Val Val Glu Met Pro Asp Ser Asp Gly Leu Val
        2500                2505                2510

Leu Thr Gly Gln Ile Ser Leu Arg Thr His Pro Trp Leu Ala Asp His
        2515                2520                2525

Glu Val Leu Gly Ser Val Leu Leu Pro Gly Thr Ala Phe Val Glu Leu
        2530                2535                2540

Ala Val Gln Ala Ala Asp Arg Ala Gly Tyr Asp Val Leu Asp Glu Leu
2545                2550                2555                2560

Thr Leu Glu Ala Pro Leu Val Leu Pro Asp Arg Gly Gly Ile Gln Val
        2565                2570                2575

Arg Leu Ala Leu Gly Pro Ser Glu Ala Asp Gly Arg Arg Ser Leu Gln
        2580                2585                2590

Leu His Ser Arg Pro Glu Glu Ala Ala Gly Phe His Arg Trp Thr Arg
```

```
                    2595                2600                2605
His Ala Ser Gly Phe Val Val Pro Gly Gly Thr Gly Ala Ala Arg Pro
    2610                2615                2620
Thr Glu Pro Ala Gly Val Trp Pro Pro Ala Gly Ala Glu Pro Val Ala
2625                2630                2635                2640
Leu Ala Ser Asp Arg Tyr Ala Arg Leu Val Glu Arg Gly Tyr Thr Tyr
                2645                2650                2655
Gly Pro Ser Phe Gln Gly Leu His Thr Ala Trp Arg His Gly Asp Asp
            2660                2665                2670
Val Tyr Ala Glu Val Ala Leu Pro Glu Gly Thr Pro Ala Asp Gly Tyr
        2675                2680                2685
Ala Leu His Pro Ala Leu Leu Asp Ala Ala Val Gln Ala Val Gly Leu
    2690                2695                2700
Gly Ser Phe Val Glu Asp Pro Gly Gln Val Tyr Leu Pro Phe Leu Trp
2705                2710                2715                2720
Ser Asp Val Thr Leu His Ala Thr Gly Ala Thr Ser Leu Arg Val Arg
                2725                2730                2735
Val Ser Pro Ala Gly Pro Asp Thr Val Ala Leu Ala Leu Ala Asp Pro
            2740                2745                2750
Ala Gly Ala Pro Val Ala Thr Val Gly Ala Leu Arg Leu Arg Thr Thr
        2755                2760                2765
Ser Ala Ala Gln Leu Ala Arg Ala Arg Gly Ser Ala Glu His Ala Met
    2770                2775                2780
Phe Arg Val Glu Trp Val Glu Glu Gly Ser Ala Ala Asp Arg Cys Arg
2785                2790                2795                2800
Gly Gly Ala Gly Gly Thr Thr Tyr Glu Gly Glu Arg Ala Ala Glu Ala
                2805                2810                2815
Gly Ala Ala Ala Gly Thr Trp Ala Val Leu Gly Pro Arg Val Pro Ala
            2820                2825                2830
Ala Val Arg Thr Met Gly Val Asp Val Val Thr Ala Leu Asp Thr Pro
        2835                2840                2845
Asp His Pro Ala Asp Pro Gln Ser Leu Ala Asp Leu Ala Ala Leu Gly
    2850                2855                2860
Asp Thr Val Pro Asp Val Val Val Thr Ser Leu Leu Ser Leu Ala
2865                2870                2875                2880
Ser Gly Ala Asp Ser Pro Leu Gly Asn Arg Pro Arg Pro Thr Ala Ala
                2885                2890                2895
Glu Gln Asp Thr Ala Ala Thr Val Ala Gly Val His Ser Ala Leu His
            2900                2905                2910
Ala Ala Leu Asp Leu Val Gln Ala Trp Leu Ala Asp Glu Arg His Thr
        2915                2920                2925
Ala Ser Arg Leu Val Leu Val Thr Arg His Ala Met Thr Val Ala Glu
    2930                2935                2940
Ser Asp Pro Glu Pro Asp Leu Leu Leu Ala Pro Val Trp Gly Leu Val
2945                2950                2955                2960
Arg Ser Ala Gln Ala Glu Asn Pro Gly Arg Phe Val Leu Ala Asp Ile
                2965                2970                2975
Asp Gly Asp Glu Ala Ser Trp Asp Ala Leu Pro Arg Ala Val Ala Ser
            2980                2985                2990
Ala Ala Ser Glu Val Ala Ile Arg Ala Gly Ala Val Tyr Val Pro Arg
        2995                3000                3005
Leu Ala Arg Ala Thr Asp Glu Gly Leu Val Val Ala Asp Glu Ala Ala
    3010                3015                3020
```

-continued

```
Gly Pro Trp Arg Leu Asp Val Thr Glu Ala Gly Thr Leu Ala Asn Leu
3025                3030                3035                3040

Ala Leu Val Pro Cys Pro Asp Ala Ser Arg Pro Leu Gly Pro Asp Glu
            3045                3050                3055

Val Arg Ile Ala Val Arg Ala Ala Gly Val Asn Phe Arg Asp Val Leu
        3060                3065                3070

Leu Ala Leu Gly Met Tyr Pro Asp Glu Gly Leu Met Gly Ala Glu Ala
    3075                3080                3085

Ala Gly Val Val Thr Glu Val Gly Gly Val Thr Thr Leu Ala Pro
3090                3095                3100

Gly Asp Arg Val Met Gly Leu Val Thr Gly Gly Phe Gly Pro Val Ala
3105                3110                3115                3120

Val Thr His His Arg Met Leu Val Arg Met Pro Arg Gly Trp Ser Phe
            3125                3130                3135

Ala Glu Ala Ala Ser Val Pro Val Ala Phe Leu Thr Ala Tyr Tyr Ala
            3140                3145                3150

Leu His Asp Leu Ala Gly Leu Arg Gly Gly Glu Ser Val Leu Val His
        3155                3160                3165

Ser Ala Ala Gly Gly Val Gly Met Ala Ala Val Gln Leu Ala Arg His
    3170                3175                3180

Trp Asp Ala Glu Val Phe Gly Thr Ala Ser Lys Gly Lys Trp Asp Val
3185                3190                3195                3200

Leu Ala Ala Gln Gly Leu Asp Glu Glu His Ile Gly Ser Ser Arg Thr
            3205                3210                3215

Thr Glu Phe Glu Gln Arg Phe Arg Ala Thr Ser Gly Gly Arg Gly Ile
        3220                3225                3230

Asp Val Val Leu Asn Ala Leu Ser Gly Asp Phe Val Asp Ala Ser Ala
            3235                3240                3245

Arg Leu Leu Arg Glu Gly Gly Arg Phe Val Glu Met Gly Lys Thr Asp
    3250                3255                3260

Ile Arg Thr Asp Leu Gly Val Val Gly Ala Asp Gly Val Pro Asp Ile
3265                3270                3275                3280

Arg Tyr Val Ala Phe Asp Leu Ala Glu Ala Gly Ala Glu Arg Ile Gly
            3285                3290                3295

Gln Met Leu Asp Glu Ile Met Ala Leu Phe Asp Ala Gly Val Leu Arg
        3300                3305                3310

Leu Pro Pro Leu Arg Ala Trp Pro Val Arg Arg Ala His Glu Ala Leu
    3315                3320                3325

Arg Phe Val Ser Gln Ala Arg His Val Gly Lys Val Val Leu Thr Val
    3330                3335                3340

Pro Ala Ala Leu Asp Ala Glu Gly Thr Val Leu Ile Thr Gly Ala Gly
3345                3350                3355                3360

Thr Leu Gly Ala Leu Val Ala Arg His Leu Val Thr Glu His Asp Val
            3365                3370                3375

Arg Arg Leu Leu Leu Val Ser Arg Ser Gly Val Ala Pro Asp Leu Ala
        3380                3385                3390

Ala Glu Leu Gly Ala Leu Gly Ala Glu Val Thr Val Ala Ala Cys Asp
    3395                3400                3405

Val Ala Asn Arg Lys Ala Leu Lys Ala Leu Leu Glu Asp Ile Pro Pro
    3410                3415                3420

Glu His Pro Val Thr Gly Ile Val His Thr Ala Gly Val Leu Asp Asp
3425                3430                3435                3440
```

-continued

```
Gly Val Val Ser Gly Leu Thr Pro Glu Arg Val Asp Thr Val Leu Lys
            3445                3450                3455

Pro Lys Val Asp Ala Ala Leu Thr Leu Glu Ser Val Ile Gly Glu Leu
            3460                3465                3470

Asp Leu Asp Pro Ala Leu Phe Val Ile Phe Ser Ser Ala Ala Ser Met
            3475                3480                3485

Leu Gly Gly Pro Gly Gln Gly Ser Tyr Ala Ala Ala Asn Gln Phe Leu
            3490                3495                3500

Asp Thr Leu Ala Arg His Arg Ala Arg Arg Gly Leu Thr Ser Val Ser
3505                3510                3515                3520

Leu Gly Trp Gly Leu Trp His Glu Ala Ser Gly Leu Thr Gly Gly Leu
            3525                3530                3535

Ala Asp Ile Asp Arg Asp Arg Met Ser Arg Ala Gly Ile Ala Pro Met
            3540                3545                3550

Pro Thr Asp Glu Ala Leu His Leu Phe Asp Arg Ala Thr Glu Leu Gly
            3555                3560                3565

Asp Pro Val Leu Leu Pro Met Arg Leu Asn Glu Ala Ala Leu Glu Asp
            3570                3575                3580

Arg Ala Ala Asp Gly Thr Leu Pro Pro Leu Leu Ser Gly Leu Val Arg
3585                3590                3595                3600

Val Arg His Arg Pro Ser Ala Arg Ala Gly Thr Ala Thr Ala Ala Pro
            3605                3610                3615

Ala Thr Gly Pro Glu Ala Phe Ala Arg Glu Leu Ala Ala Ala Pro Asp
            3620                3625                3630

Pro Arg Arg Ala Leu Arg Asp Leu Val Arg Gly His Val Ala Leu Val
            3635                3640                3645

Leu Gly His Ser Gly Pro Glu Ala Ile Asp Ala Glu Gln Ala Phe Arg
            3650                3655                3660

Asp Ile Gly Phe Asp Ser Leu Thr Ala Val Glu Leu Arg Asn Arg Leu
3665                3670                3675                3680

Asn Ala Glu Thr Gly Leu Arg Leu Pro Gly Thr Leu Val Phe Asp Tyr
            3685                3690                3695

Pro Asn Pro Ser Ala Leu Ala Asp His Leu Leu Glu Leu Leu Ala Pro
            3700                3705                3710

Ala Thr Gln Pro Thr Ala Ala Pro Leu Leu Ala Glu Leu Glu Arg Val
            3715                3720                3725

Glu Gln Leu Leu Ser Ala Ala Ser Pro Gly Gly Pro Ala Ser Ala
            3730                3735                3740

Val Asp Glu Glu Thr Arg Thr Leu Ile Ala Thr Arg Leu Ala Thr Leu
3745                3750                3755                3760

Ala Ser Gln Trp Thr His Leu Pro Val Gly Ser Pro Gly Asn Ala Asp
            3765                3770                3775

Asn Arg Ser Gly Pro Gly Glu Ser Gly Gln Ala Gln Glu Ser Gly Ala
            3780                3785                3790

Thr Gly Glu His Thr Ala Ala Trp Thr Ser Asp Asp Leu Phe Ala
            3795                3800                3805

Phe Leu Asp Lys Arg Leu Glu Thr
   3810                3815

<210> SEQ ID NO 4
<211> LENGTH: 3519
<212> TYPE: PRT
<213> ORGANISM: Artificial Sequence
<220> FEATURE:
<223> OTHER INFORMATION: Description of Artificial Sequence:
```

-continued

Recombinant Oleandolide PKS

<400> SEQUENCE: 4

```
Val Ala Glu Ala Glu Lys Leu Arg Glu Tyr Leu Trp Arg Ala Thr Thr
  1               5                  10                  15

Glu Leu Lys Glu Val Ser Asp Arg Leu Arg Glu Thr Glu Glu Arg Ala
             20                  25                  30

Arg Glu Pro Ile Ala Ile Val Gly Met Ser Cys Arg Phe Pro Gly Gly
         35                  40                  45

Gly Asp Ala Thr Val Asn Thr Pro Glu Gln Phe Trp Asp Leu Leu Asn
     50                  55                  60

Ser Gly Gly Asp Gly Ile Ala Gly Leu Pro Glu Asp Arg Gly Trp Asp
 65                  70                  75                  80

Leu Gly Arg Leu Tyr Asp Pro Asp Pro Asp Arg Ala Gly Thr Ser Tyr
                 85                  90                  95

Val Arg Glu Gly Gly Phe Leu Tyr Asp Ser Gly Glu Phe Asp Ala Ala
            100                 105                 110

Phe Phe Gly Ile Ser Pro Arg Glu Ala Leu Ala Met Asp Pro Gln Gln
        115                 120                 125

Arg Leu Leu Leu Glu Thr Ser Trp Glu Ala Phe Glu Ser Ala Gly Ile
    130                 135                 140

Lys Arg Ala Ala Leu Arg Gly Ser Asp Thr Gly Val Tyr Ile Gly Ala
145                 150                 155                 160

Trp Ser Thr Gly Tyr Ala Gly Ser Pro Tyr Arg Leu Val Glu Gly Leu
                165                 170                 175

Glu Gly Gln Leu Ala Ile Gly Thr Thr Leu Gly Ala Ala Ser Gly Arg
            180                 185                 190

Val Ala Tyr Thr Phe Gly Leu Glu Gly Pro Ala Val Thr Val Asp Thr
        195                 200                 205

Ala Cys Ser Ser Ser Leu Val Ala Leu His Leu Ala Val Gln Gly Leu
    210                 215                 220

Arg Arg Gly Glu Cys Ser Leu Ala Leu Val Gly Gly Val Thr Val Met
225                 230                 235                 240

Ser Ser Pro Val Thr Leu Thr Thr Phe Ser Arg Gln Arg Gly Leu Ser
                245                 250                 255

Val Asp Gly Arg Cys Lys Ala Phe Pro Ala Ser Ala Asp Gly Phe Gly
            260                 265                 270

Ala Ala Glu Gly Val Gly Val Leu Leu Val Glu Arg Leu Ser Asp Ala
        275                 280                 285

Arg Arg Leu Gly His Arg Val Leu Ala Val Val Arg Gly Ser Ala Val
    290                 295                 300

Asn Gln Asp Gly Ala Ser Asn Gly Leu Thr Ala Pro Asn Gly Pro Ser
305                 310                 315                 320

Gln Gln Arg Val Ile Arg Ala Ala Leu Ala Asp Ala Gly Leu Ala Pro
                325                 330                 335

Ala Asp Val Asp Val Val Glu Ala His Gly Thr Gly Thr Arg Leu Gly
            340                 345                 350

Asp Pro Ile Glu Ala Gln Ala Leu Leu Ala Thr Tyr Gly Gln Gly Arg
        355                 360                 365

Ala Gly Gly Arg Pro Val Trp Leu Gly Ser Val Lys Ser Asn Ile Gly
    370                 375                 380

His Thr Gln Ala Ala Ala Gly Val Ala Gly Val Met Lys Met Val Leu
385                 390                 395                 400
```

```
Ala Leu Gly Arg Gly Val Val Pro Lys Thr Leu His Val Asp Glu Pro
                405                 410                 415

Ser Pro His Val Asp Trp Ser Gly Ala Val Glu Leu Leu Thr Glu
            420                 425                 430

Glu Arg Pro Trp Glu Pro Glu Ala Glu Arg Leu Arg Arg Ala Gly Ile
            435                 440                 445

Ser Ala Phe Gly Val Ser Gly Thr Asn Ala His Val Ile Val Glu Glu
    450                 455                 460

Ala Pro Ala Glu Pro Glu Pro Glu Pro Gly Thr Arg Val Val Ala Ala
465                 470                 475                 480

Gly Asp Leu Val Val Pro Trp Val Val Ser Gly Arg Asp Ala Arg Ala
                485                 490                 495

Leu Arg Ala Gln Ala Ala Arg Leu Ala Ala His Val Ser Gly Val Ser
                500                 505                 510

Ala Val Asp Val Gly Trp Ser Leu Val Ala Thr Arg Ser Val Phe Glu
            515                 520                 525

His Arg Ala Val Ala Ile Gly Ser Glu Leu Asp Ser Met Ala Gly Ser
    530                 535                 540

Leu Ala Gly Phe Ala Ala Gly Gly Val Val Pro Gly Val Val Ser Gly
545                 550                 555                 560

Val Ala Pro Ala Glu Gly Arg Arg Val Val Phe Val Phe Pro Gly Gln
                565                 570                 575

Gly Ser Gln Trp Val Gly Met Ala Ala Gly Leu Leu Asp Ala Cys Pro
            580                 585                 590

Val Phe Ala Glu Ala Val Ala Glu Cys Ala Ala Val Leu Asp Pro Val
    595                 600                 605

Thr Gly Trp Ser Leu Val Glu Val Leu Gln Gly Arg Asp Ala Thr Val
610                 615                 620

Leu Gly Arg Val Asp Val Val Gln Pro Ala Leu Trp Ala Val Met Val
625                 630                 635                 640

Ser Leu Ala Arg Thr Trp Arg Tyr Tyr Gly Val Glu Pro Ala Ala Val
                645                 650                 655

Val Gly His Ser Gln Gly Glu Ile Ala Ala Ala Cys Val Ala Gly Gly
                660                 665                 670

Leu Ser Leu Ala Asp Gly Ala Arg Val Val Leu Arg Ser Arg Ala
    675                 680                 685

Ile Ala Arg Ile Ala Gly Gly Gly Met Val Ser Val Ser Leu Pro
    690                 695                 700

Ala Gly Arg Val Arg Thr Met Leu Glu Glu Phe Asp Gly Arg Leu Ser
705                 710                 715                 720

Val Ala Ala Val Asn Gly Pro Ser Ser Thr Val Val Ser Gly Asp Val
                725                 730                 735

Gln Ala Leu Asp Glu Leu Leu Ala Gly Cys Glu Arg Glu Gly Val Arg
            740                 745                 750

Ala Arg Arg Val Pro Val Asp Tyr Ala Ser His Ser Ala Gln Met Asp
            755                 760                 765

Gln Leu Arg Asp Glu Leu Leu Glu Ala Leu Ala Asp Ile Thr Pro Gln
    770                 775                 780

Asp Ser Ser Val Pro Phe Phe Ser Thr Val Thr Ala Asp Trp Leu Gly
785                 790                 795                 800

Thr Thr Ala Leu Gly Ala Gly Tyr Trp Phe Thr Asn Leu Arg Glu Thr
                805                 810                 815

Val Arg Phe Gln Glu Ala Val Glu Gly Leu Val Ala Gln Gly Met Gly
```

-continued

```
              820                 825                 830
Ala Phe Val Glu Cys Ser Pro His Pro Val Leu Val Pro Gly Ile Glu
            835                 840                 845
Gln Thr Leu Asp Ala Leu Asp Gln Asn Ala Ala Val Phe Gly Ser Leu
        850                 855                 860
Arg Arg Asp Glu Gly Gly Leu Asp Arg Phe Leu Thr Ser Leu Ala Glu
865                 870                 875                 880
Ala Phe Val Gln Gly Val Pro Val Asp Trp Ser Arg Ala Phe Glu Gly
                885                 890                 895
Val Thr Pro Arg Thr Val Asp Leu Pro Thr Tyr Pro Phe Gln Arg Gln
            900                 905                 910
His Tyr Trp Leu Met Ala Glu Glu Ala Pro Val Ser Gln Pro Pro His
        915                 920                 925
Ser Glu Asn Ser Phe Trp Ser Val Val Ala Asp Ala Asp Ala Glu Ala
    930                 935                 940
Ala Ala Glu Leu Leu Gly Val Asp Val Glu Ala Val Glu Ala Val Met
945                 950                 955                 960
Pro Ala Leu Ser Ser Trp His Arg Gln Ser Gln Leu Arg Ala Glu Val
                965                 970                 975
Asn Gln Trp Arg Tyr Asp Val Ala Trp Lys Arg Leu Thr Thr Gly Ala
            980                 985                 990
Leu Pro Glu Lys Pro Gly Asn Trp Leu Val Val Thr Pro Ala Gly Thr
        995                 1000                1005
Asp Thr Thr Phe Ala Glu Ser Leu Ala Arg Thr Ala Ala Ala Glu Leu
    1010                1015                1020
Gly Val Ser Val Ser Phe Ala Gln Val Asp Thr Ala His Pro Asp Arg
1025                1030                1035                1040
Ser Gln Tyr Ala His Ala Leu Arg Gln Ala Leu Thr Gly Pro Glu Asn
                1045                1050                1055
Val Asp His Leu Val Ser Leu Leu Ala Leu Asp Gln Ala Thr Asp Asp
            1060                1065                1070
Leu Ala Ala Ala Pro Ser Cys Leu Ala Ala Ser Leu Val Leu Ala Gln
        1075                1080                1085
Ala Leu Val Asp Leu Gly Arg Val Gly Glu Gly Pro Arg Leu Trp Leu
    1090                1095                1100
Val Thr Arg Gly Ala Val Val Ala Gly Pro Ser Asp Ala Gly Ala Val
1105                1110                1115                1120
Ile Asp Pro Val Gln Ala Gln Val Trp Gly Phe Gly Arg Val Leu Gly
                1125                1130                1135
Leu Glu His Pro Glu Leu Trp Gly Gly Leu Ile Asp Leu Pro Val Gly
            1140                1145                1150
Val Asp Glu Glu Val Cys Arg Arg Phe Val Gly Val Val Ala Ser Ala
        1155                1160                1165
Gly Phe Glu Asp Gln Val Ala Val Arg Gly Ser Gly Val Trp Val Arg
    1170                1175                1180
Arg Leu Val Arg Ala Val Val Asp Gly Gly Gly Gly Trp Arg Pro
1185                1190                1195                1200
Arg Gly Thr Val Leu Val Thr Gly Gly Leu Gly Gly Leu Gly Ala His
                1205                1210                1215
Thr Ala Arg Trp Leu Val Gly Gly Ala Asp His Val Val Leu Val
            1220                1225                1230
Ser Arg Arg Gly Gly Ser Ala Pro Gly Ala Gly Asp Leu Val Arg Glu
        1235                1240                1245
```

-continued

```
Leu Glu Gly Leu Gly Gly Ala Arg Val Ser Val Arg Ala Cys Asp Val
    1250                1255                1260
Ala Asp Arg Val Ala Leu Arg Ala Leu Leu Ser Asp Leu Gly Glu Pro
1265                1270                1275                1280
Val Thr Ala Val Phe His Ala Ala Gly Val Pro Gln Ser Thr Pro Leu
            1285                1290                1295
Ala Glu Ile Ser Val Gln Glu Ala Ala Asp Val Met Ala Ala Lys Val
            1300                1305                1310
Ala Gly Ala Val Asn Leu Gly Glu Leu Val Asp Pro Cys Gly Leu Glu
            1315                1320                1325
Ala Phe Val Leu Phe Ser Ser Asn Ala Gly Val Trp Gly Ser Gly Gly
            1330                1335                1340
Gln Ala Val Tyr Ala Ala Ala Asn Ala Phe Leu Asp Ala Leu Ala Val
1345                1350                1355                1360
Arg Arg Arg Gly Val Gly Leu Pro Ala Thr Ser Val Ala Trp Gly Met
            1365                1370                1375
Trp Ala Gly Glu Gly Met Ala Ser Val Gly Gly Ala Ala Arg Glu Leu
            1380                1385                1390
Ser Arg Arg Gly Val Arg Ala Met Asp Pro Glu Arg Ala Val Ala Val
            1395                1400                1405
Met Ala Asp Ala Val Gly Arg Gly Glu Ala Phe Val Ala Val Ala Asp
    1410                1415                1420
Val Asp Trp Glu Arg Phe Val Thr Gly Phe Ala Ser Ala Arg Pro Arg
1425                1430                1435                1440
Pro Leu Ile Ser Asp Leu Pro Glu Val Arg Ala Val Val Glu Gly Gln
            1445                1450                1455
Val Gln Gly Arg Gly Gln Gly Leu Gly Leu Val Gly Glu Glu Glu Ser
            1460                1465                1470
Ser Gly Trp Leu Lys Arg Leu Ser Gly Leu Ser Arg Val Arg Gln Glu
            1475                1480                1485
Glu Glu Leu Val Glu Leu Val Arg Ala Gln Ala Ala Val Val Leu Gly
    1490                1495                1500
His Gly Ser Ala Gln Asp Val Pro Ala Glu Arg Ala Phe Lys Glu Leu
1505                1510                1515                1520
Gly Phe Asp Ser Leu Thr Ala Val Glu Leu Arg Asn Gly Leu Ala Ala
            1525                1530                1535
Ala Thr Gly Ile Arg Leu Pro Ala Thr Met Ala Phe Asp His Pro Asn
            1540                1545                1550
Ala Thr Ala Ile Ala Arg Phe Leu Gln Ser Gln Leu Leu Pro Asp Ala
            1555                1560                1565
Glu Ser Glu Ser Ala Val Pro Ser Ser Pro Glu Asp Glu Val Arg Gln
    1570                1575                1580
Ala Leu Ala Ser Leu Ser Leu Asp Gln Leu Lys Gly Ala Gly Leu Leu
1585                1590                1595                1600
Asp Pro Leu Leu Ala Leu Thr Arg Leu Arg Glu Ile Asn Ser Thr Val
            1605                1610                1615
Gln Asn Pro Glu Pro Thr Thr Glu Ser Ile Asp Glu Met Asp Gly Glu
            1620                1625                1630
Thr Cys Cys Ala Trp Arg Ser Ala Lys Ser Thr Ala Glu Pro Leu Thr
    1635                1640                1645
Thr Gly Ala Asp Met Pro Asp Pro Thr Ala Lys Tyr Val Glu Ala Leu
    1650                1655                1660
```

```
Arg Ala Ser Leu Lys Glu Asn Glu Arg Leu Arg Gln Gln Asn His Ser
1665                1670                1675                1680

Leu Leu Ala Ala Ser Arg Glu Ala Ile Ala Ile Thr Ala Met Ser Cys
            1685                1690                1695

Arg Phe Gly Gly Gly Ile Asp Ser Pro Glu Asp Leu Trp Arg Phe Leu
        1700                1705                1710

Ala Glu Gly Arg Asp Ala Val Ala Gly Leu Pro Glu Asp Arg Gly Trp
    1715                1720                1725

Asp Leu Asp Ala Leu Tyr His Pro Asp Pro Glu Asn Pro Gly Thr Thr
    1730                1735                1740

Tyr Val Arg Glu Gly Ala Phe Arg Tyr Asp Ala Ala Gln Phe Asp Ala
1745                1750                1755                1760

Gly Phe Phe Gly Ile Ser Pro Arg Glu Ala Leu Ala Met Asp Pro Gln
        1765                1770                1775

Gln Arg Leu Leu Leu Glu Thr Ser Trp Glu Leu Phe Glu Arg Ala Asp
    1780                1785                1790

Ile Asp Pro Tyr Thr Val Arg Gly Thr Ala Thr Gly Ile Phe Ile Gly
        1795                1800                1805

Ala Gly His Gln Gly Tyr Gly Pro Asp Pro Lys Arg Ala Pro Glu Ser
    1810                1815                1820

Val Ala Gly Tyr Leu Leu Thr Gly Thr Ala Ser Ala Val Leu Ser Gly
1825                1830                1835                1840

Arg Ile Ser Tyr Thr Phe Gly Leu Glu Gly Pro Ala Val Thr Val Asp
        1845                1850                1855

Thr Ala Cys Ser Ser Ser Leu Val Ala Leu His Leu Ala Val Gln Ala
        1860                1865                1870

Leu Arg Arg Gly Glu Cys Ser Leu Ala Ile Ala Gly Gly Val Ala Val
    1875                1880                1885

Met Ser Thr Pro Asp Ala Phe Val Glu Phe Ser Arg Gln Gln Gly Met
    1890                1895                1900

Ala Arg Asp Gly Arg Cys Lys Ala Phe Ala Ala Ala Ala Asp Gly Met
1905                1910                1915                1920

Gly Trp Gly Glu Gly Val Ser Leu Leu Leu Leu Glu Arg Leu Ser Asp
        1925                1930                1935

Ala Arg Arg Leu Gly His Arg Val Leu Ala Val Val Arg Gly Ser Ala
        1940                1945                1950

Val Asn Gln Asp Gly Ala Ser Asn Gly Leu Ala Ala Pro Asn Gly Pro
    1955                1960                1965

Ser Gln Gln Arg Val Ile Arg Ala Ala Leu Ala Asp Ala Gly Leu Ala
    1970                1975                1980

Pro Ala Asp Val Asp Val Val Glu Ala His Gly Thr Gly Thr Arg Leu
1985                1990                1995                2000

Gly Asp Pro Ile Glu Ala Gln Ala Leu Leu Ala Thr Tyr Gly Gln Gly
            2005                2010                2015

Arg Ala Gly Gly Arg Pro Val Trp Leu Gly Ser Val Lys Ser Asn Ile
        2020                2025                2030

Gly His Thr Gln Ala Ala Ala Gly Val Ala Gly Val Met Lys Met Val
        2035                2040                2045

Leu Ala Leu Gly Arg Gly Val Val Pro Lys Thr Leu His Val Asp Glu
    2050                2055                2060

Pro Ser Pro His Val Asp Trp Ser Ala Gly Ala Val Glu Leu Leu Thr
2065                2070                2075                2080

Glu Glu Arg Pro Trp Glu Pro Glu Ala Glu Arg Leu Arg Arg Ala Gly
```

-continued

```
                    2085                2090                2095
Ile Ser Ala Phe Gly Val Ser Gly Thr Asn Ala His Val Ile Val Glu
            2100                2105                2110
Glu Ala Pro Ala Glu Pro Glu Pro Glu Pro Gly Thr Arg Val Val Ala
            2115                2120                2125
Ala Gly Asp Leu Val Val Pro Trp Val Ser Gly Arg Asp Val Gly
            2130                2135                2140
Ala Leu Arg Glu Gln Ala Ala Arg Leu Ala Ala His Val Ser Ser Thr
2145                2150                2155                2160
Gly Ala Gly Val Val Asp Val Gly Trp Ser Leu Val Ala Thr Arg Ser
            2165                2170                2175
Val Phe Glu His Arg Ala Val Met Val Gly Thr Asp Leu Asp Ser Met
            2180                2185                2190
Ala Gly Ser Leu Ala Gly Phe Ala Ala Gly Val Val Pro Gly Val
            2195                2200                2205
Val Ser Gly Val Ala Pro Ala Glu Gly Arg Arg Val Val Phe Val Phe
            2210                2215                2220
Pro Gly Gln Gly Ser Gln Trp Val Gly Met Ala Ala Gly Leu Leu Asp
2225                2230                2235                2240
Ala Cys Pro Val Phe Ala Glu Ala Val Ala Glu Cys Ala Ala Val Leu
            2245                2250                2255
Asp Pro Val Thr Gly Trp Ser Leu Val Glu Val Leu Gln Gly Arg Asp
            2260                2265                2270
Ala Thr Val Leu Gly Arg Val Asp Val Val Gln Pro Ala Leu Trp Ala
            2275                2280                2285
Val Met Val Ser Leu Ala Arg Thr Trp Arg Tyr Tyr Gly Val Glu Pro
            2290                2295                2300
Ala Ala Val Val Gly His Ser Gln Gly Glu Ile Ala Ala Ala Cys Val
2305                2310                2315                2320
Ala Gly Gly Leu Ser Leu Ala Asp Gly Ala Arg Val Val Leu Arg
            2325                2330                2335
Ser Arg Ala Ile Ala Arg Ile Ala Gly Gly Gly Met Val Ser Val
            2340                2345                2350
Ser Leu Pro Ala Gly Arg Val Arg Thr Met Leu Asp Thr Tyr Gly Gly
            2355                2360                2365
Arg Val Ser Val Ala Ala Val Asn Gly Pro Ser Ser Thr Val Val Ser
            2370                2375                2380
Gly Asp Val Gln Ala Leu Asp Glu Leu Leu Ala Gly Cys Glu Arg Glu
2385                2390                2395                2400
Gly Val Arg Ala Arg Arg Val Pro Val Asp Tyr Ala Ser His Ser Ala
            2405                2410                2415
Gln Met Asp Gln Leu Arg Asp Glu Leu Leu Glu Ala Leu Ala Asp Ile
            2420                2425                2430
Thr Pro Gln Asp Ser Ser Val Pro Phe Phe Ser Thr Val Thr Ala Asp
            2435                2440                2445
Trp Leu Asp Thr Thr Ala Leu Asp Ala Gly Tyr Trp Phe Thr Asn Leu
            2450                2455                2460
Arg Glu Thr Val Arg Phe Gln Glu Ala Val Glu Gly Leu Val Ala Gln
2465                2470                2475                2480
Gly Met Gly Ala Phe Val Glu Cys Ser Pro His Pro Val Leu Val Pro
            2485                2490                2495
Gly Ile Glu Gln Thr Leu Asp Ala Leu Asp Gln Asn Ala Ala Val Leu
            2500                2505                2510
```

```
Gly Ser Leu Arg Arg Asp Glu Gly Gly Leu Asp Arg Leu Leu Thr Ser
    2515                2520                2525
Leu Ala Glu Ala Phe Val Gln Gly Val Pro Val Asp Trp Thr His Ala
    2530                2535                2540
Phe Glu Gly Val Thr Pro Arg Thr Val Asp Leu Pro Thr Tyr Pro Phe
2545                2550                2555                2560
Gln Arg Gln Arg Phe Trp Leu Asp Gly Ser Pro Ala Ser Ser Ala Asn
            2565                2570                2575
Gly Val Asp Gly Glu Ala Asp Ala Met Ile Trp Asp Ala Val Glu Arg
        2580                2585                2590
Glu Asp Ser Val Ala Val Ala Glu Glu Leu Gly Ile Asp Ala Glu Ala
        2595                2600                2605
Leu His Thr Val Leu Pro Ala Leu Ser Ser Trp Arg Arg Arg Val
    2610                2615                2620
Glu His Arg Arg Leu Gln Asp Trp Arg Tyr Arg Val Glu Trp Lys Pro
2625                2630                2635                2640
Phe Pro Ala Ala Leu Asp Glu Val Leu Gly Gly Gly Trp Leu Phe Val
            2645                2650                2655
Val Pro Arg Gly Leu Ala Asp Asp Gly Val Val Ala Arg Val Val Ala
        2660                2665                2670
Ala Val Thr Ala Arg Gly Gly Glu Val Ser Val Val Glu Leu Asp Pro
    2675                2680                2685
Thr Arg Pro Asp Arg Arg Ala Tyr Ala Glu Ala Val Ala Gly Arg Gly
    2690                2695                2700
Val Ser Gly Val Val Ser Phe Leu Ser Trp Asp Asp Arg Arg His Ser
2705                2710                2715                2720
Glu His Pro Val Val Pro Ala Gly Leu Ala Ala Ser Leu Val Leu Ala
            2725                2730                2735
Gln Ala Leu Val Asp Leu Gly Arg Val Gly Glu Gly Pro Arg Leu Trp
        2740                2745                2750
Leu Val Thr Arg Asp Ala Val Val Ala Gly Pro Ser Asp Ala Gly Ala
        2755                2760                2765
Val Ile Asp Pro Val Gln Ala Gln Val Trp Gly Phe Gly Arg Val Leu
    2770                2775                2780
Gly Leu Glu His Pro Glu Leu Trp Gly Gly Leu Ile Asp Leu Pro Val
2785                2790                2795                2800
Glu Ala Pro Glu Pro Gly Ser Thr Cys Asp His Thr Tyr Ala Asp Leu
            2805                2810                2815
Leu Ala Thr Val Val Ala Ser Ala Gly Phe Glu Asp Gln Val Ala Val
        2820                2825                2830
Arg Gly Ser Gly Val Trp Val Arg Arg Leu Val Arg Ala Val Val Asp
        2835                2840                2845
Gly Gly Gly Gly Gly Trp Arg Pro Arg Gly Thr Val Leu Val Thr Gly
2850                2855                2860
Gly Leu Gly Gly Leu Gly Ala His Thr Ala Arg Trp Leu Val Gly Gly
2865                2870                2875                2880
Gly Ala Asp His Val Val Leu Val Ser Arg Arg Gly Gly Ser Ala Pro
        2885                2890                2895
Gly Ala Gly Asp Leu Val Arg Glu Leu Glu Gly Leu Gly Gly Ala Arg
            2900                2905                2910
Val Ser Val Arg Ala Cys Asp Val Ala Asp Arg Val Ala Leu Arg Ala
2915                2920                2925
```

-continued

```
Leu Leu Ser Asp Leu Gly Glu Pro Val Thr Ala Val Phe His Ala Ala
    2930                2935                2940

Gly Val Pro Gln Ser Thr Pro Leu Ala Glu Ile Ser Val Gln Glu Ala
2945                2950                2955                2960

Ala Asp Val Met Ala Ala Lys Val Ala Gly Ala Val Asn Leu Gly Glu
                2965                2970                2975

Leu Val Asp Pro Cys Gly Leu Glu Ala Phe Val Leu Phe Ser Ser Asn
            2980                2985                2990

Ala Gly Val Trp Gly Ser Gly Gly Gln Ala Val Tyr Ala Ala Ala Asn
        2995                3000                3005

Ala Phe Leu Asp Ala Leu Ala Val Arg Arg Arg Gly Val Gly Leu Pro
    3010                3015                3020

Ala Thr Ser Val Ala Trp Gly Met Trp Ala Gly Glu Gly Met Ala Ser
3025                3030                3035                3040

Val Gly Gly Ala Ala Arg Glu Leu Ser Arg Arg Gly Val Arg Ala Met
                3045                3050                3055

Asp Pro Glu Arg Ala Val Ala Val Met Ala Asp Ala Val Gly Arg Gly
            3060                3065                3070

Glu Ala Phe Val Ala Val Ala Asp Val Asp Trp Glu Arg Phe Val Thr
        3075                3080                3085

Gly Phe Ala Ser Ala Arg Pro Arg Pro Leu Ile Ser Asp Leu Pro Glu
    3090                3095                3100

Val Arg Thr Ala Leu Arg Asn Gln Glu Gln Glu Gln Leu His Ala Pro
3105                3110                3115                3120

Val Pro Glu Asp Arg Ser Ala Gln Leu Leu Arg Arg Leu Ser Met Leu
                3125                3130                3135

Ser Pro Ala Gly Arg Glu Ala Glu Leu Val Lys Leu Val Arg Thr Glu
            3140                3145                3150

Ala Ala Ala Val Leu Gly His Gly Ser Ala Gln Asp Val Pro Ala Glu
        3155                3160                3165

Arg Ala Phe Lys Glu Leu Gly Phe Asp Ser Leu Thr Ala Val Gln Leu
    3170                3175                3180

Arg Asn Arg Leu Ala Ala Ala Thr Gly Thr Arg Leu Pro Ala Ser Ala
3185                3190                3195                3200

Val Phe Asp His Pro His Ala Ala Leu Ala Arg Trp Leu Leu Ala
                3205                3210                3215

Gly Met Arg His Ala Asp Gly Gly His Gly Gly Gly His Ala Gly Gly
            3220                3225                3230

Pro Gly Pro Asp Ala Asp Glu Gly Arg Ser Ala Gly Ala Gly His Ser
        3235                3240                3245

Gly Met Leu Ala Asp Leu Tyr Arg Arg Ser Ala Glu Leu Gly Arg Ser
    3250                3255                3260

Arg Glu Phe Ile Gly Leu Leu Ala Asp Thr Ala Ala Phe Arg Pro Val
3265                3270                3275                3280

Phe His Gly Pro Ala Asp Leu Asp Ala Pro Leu Glu Ala Val Pro Leu
                3285                3290                3295

Ala Asp Gly Val Arg Lys Pro Gln Leu Ile Cys Cys Ser Gly Thr Ala
            3300                3305                3310

Pro Val Gly Gly Pro His Glu Phe Ala Arg Leu Ala Ser Phe Phe Arg
        3315                3320                3325

Gly Thr Arg Ala Val Ser Ala Leu Pro Leu Pro Gly Tyr Leu Pro Gly
    3330                3335                3340

Glu Gln Leu Pro Ala Asp Leu Asp Ala Val Leu Ala Ala Gln Ala Glu
```

```
                3345                3350                3355                3360
Ala Val Glu Lys Gln Thr Gly Gly Ala Pro Phe Val Leu Val Gly Tyr
                3365                3370                3375

Ser Ala Gly Gly Leu Met Ala His Ala Leu Ala Cys His Leu Ala Gly
                3380                3385                3390

Arg Gly Thr Pro Pro Ser Gly Glu Val Leu Val Asp Val Tyr Pro Pro
    3395                3400                3405

Gly Arg Gln Glu Pro Val Phe Gly Trp Gln Lys Glu Leu Thr Glu Gly
    3410                3415                3420

Met Phe Ala Gln Asp Phe Val Pro Met Asp Asp Thr Arg Leu Thr Ala
3425                3430                3435                3440

Leu Gly Thr Tyr Asp Arg Leu Met Gly Glu Trp Arg Pro Ala Pro Ser
        3445                3450                3455

Gly Leu Pro Thr Leu Leu Ile Arg Ala Thr Glu Pro Met Ala Glu Trp
            3460                3465                3470

Thr Gly Ala Ile Asp Trp Arg Ala Ser Trp Glu Tyr Asp His Thr Ala
        3475                3480                3485

Val Asp Met Pro Gly Asn His Phe Thr Ile Met Arg Glu His Ala Glu
    3490                3495                3500

Asp Ala Ala Arg His Ile Asp Val Trp Leu Lys Gly Leu Thr Pro
3505                3510                3515
```

```
<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 5
taaggaggac catatgcatc gctcgagtct agacctagg                        39

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 6
aattcctagg tctagactcg agcgatgcat atggtcctcc                       40

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 7
ttcctaggct agcccgaccc gagcacgcgc cggca                            35

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 8
ccttaattaa ggatcctacc aaccggcacg attgtgcc                         38
```

```
<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 9
gcgaattccc gggtggcgtg acctct                                              26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
gagctagccg ccgtgtccac cgtgacc                                             27

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 11
cggctagctc gtcgctggtg gcactgcac                                           29

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
cgaagcttga ccaggaaaga cgaacacc                                            28

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 13
aattcatatg gctgaggcgg agaagctgcg cgaatacctg tgg                           43

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 14
cgcgccacag gtattcgcgc agcttctccg cctcagccat atg                           43
```

RECOMBINANT OLEANDOLIDE POLYKETIDE SYNTHASE

CROSS-REFERENCE TO RELATED APPLICATIONS

This application claims priority under 35 U.S.C. §19(e) to U.S. provisional application Ser. Nos. 60/120,254, filed Feb. 16, 1999; and 60/106,100, filed Oct. 29, 1998, each of which is incorporated herein by reference.

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; and 5,712,146; Fu et al., 1994, Biochemistry 33: 9321–9326; McDaniel et al., 1993, Science 262: 1546–1550; and Rohr, 1995, Angew. Chem. Int. Ed Engl. 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. Two major types of PKS enzymes are known; these differ in their composition and mode of synthesis. These two major types of PKS enzymes are commonly referred to as Type I or "modular" and Type II "iterative" PKS enzymes.

Modular PKSs are responsible for producing a large number of 12-, 14-, and 16-membered macrolide antibiotics including erythromycin, methymycin, narbomycin, oleandomycin, picromycin, and tylosin. Modular PKS enzymes for 14-membered polyketides are encoded by PKS genes that often consist of three or more open reading frames (ORFs). Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. The polyketide metabolites; E. Horwood: New York, 1991, incorporated herein by reference).

During the past half decade, the study of modular PKS function and specificity has been greatly facilitated by the plasmid-based Streptomyces coelicolor expression system developed with the 6-deoxyerythronolide B (6-dEB) synthase (DEBS) genes (see Kao et al., 1994, Science, 265: 509–512, McDaniel et al., 1993, Science 262: 1546–1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, Saccharopolyspora erythraea, allows more facile construction of recombinant PKSs, and reduces the complexity of PKS analysis by providing a "clean" host background. This system also expedited construction of the first combinatorial modular polyketide library in Streptomyces (see PCT publication No. WO 98/49315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, Curr. Opin. Microbiol. 1: 319–329; Carreras and Santi, 1998, Curr. Opin. Biotech. 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

Oleandomycin is an antibacterial polyketide (described in U.S. Pat. No. 2,757,123, incorporated herein by reference) produced by a modular PKS in Streptomyces antibioticus. Oleandomycin has the structure shown below, with the conventional numbering scheme and stereochemical representation.

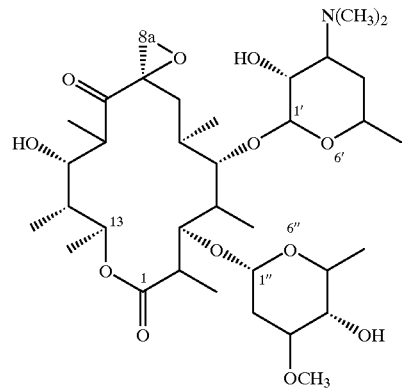

As is the case for certain other macrolide antibiotics, the macrolide product of the PKS, 8,8a-deoxyoleandolide, also referred to herein simply as oleandolide (although oleandolide in other contexts refers to the epoxidated aglycone), is further modified by epoxidation (at C-8 and C-8a) and glycosylation (an oleandrose at C-3 and a desosamine at C-5) to yield oleandomycin.

The reference Swan et al., 1994, entitled "Characterisation of a *Streptomyces antibioticus* gene encoding a type I polyketide synthase which has an unusual coding sequence," *Mol. Gen. Genet.* 242: 358–362, incorporated herein by reference, describes the DNA sequence of the coding region of a gene designated ORFB hypothesized to encode modules 5 and 6 and a fragment of a gene designated ORFA hypothesized to contain the ACP domain of module 4 of the oleandolide PKS. The reference Quiros et al., 1998, entitled "Two glycosyltransferases and a glycosidase are involved in oleandomycin modification during its biosynthesis by *Streptomyces antibioticus*," *Mol. Microbiol.* 28(6): 1177–1185, incorporated herein by reference, describes genes and gene products involved in oleandomycin modification during its biosynthesis. In particular, the reference describes a glycosyltransferase involved in rendering oleandomycin non-toxic to the producer cell and a glycosidase that reactivates oleandomycin after the glycosylated form is excreted from the cell. See also Olano et al., August 1998, "Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308, and PCT patent publication No. 99/05283, incorporated herein by reference. While a number of semi-synthetic oleandomycin derivatives have been described, see U.S. Pat. Nos. 4,085,119; 4,090,017; 4,125,705; 4,133,950; 4,140,848; 4,166,901; 4,336,368; and 5,268,462, incorporated herein by reference, the number and diversity of such derivatives have been limited due to the inability to manipulate the PKS genes.

Genetic systems that allow rapid engineering of the oleandolide PKS would be valuable for creating novel compounds for pharmaceutical, agricultural, and veterinary applications. The production of such compounds could be accomplished if the heterologous expression of the oleandolide PKS in *Streptomyces coelicolor* and *S. lividans* and other host cells were possible. The present invention meets these and other needs.

SUMMARY OF THE INVENTION

The present invention provides recombinant methods and materials for expressing PKS enzymes derived in whole and in part from the oleandolide PKS in recombinant host cells. The invention also provides the polyketides produced by such PKS enzymes. The invention provides in recombinant form all of the genes for the proteins that constitute the complete PKS that ultimately results, in *Streptomyces antibioticus*, in the production of oleandolide, which is further glycosylated and epoxidated to form oleandomycin. Thus, in one embodiment, the invention is directed to recombinant materials comprising nucleic acids with nucleotide sequences encoding at least one domain, module, or protein encoded by an oleandolide PKS gene. In one preferred embodiment of the invention, the DNA compounds of the invention comprise a coding sequence for at least one and preferably two or more of the domains of the loading module and extender modules 1 through 4, inclusive, of 8,8a-deoxyoleandolide synthase.

In one embodiment, the invention provides a recombinant expression vector that comprises a heterologous promoter positioned to drive expression of one or more of the oleandolide PKS genes. In a preferred embodiment, the promoter is derived from another PKS gene. In a related embodiment, the invention provides recombinant host cells comprising the vector that produces oleandolide. In a preferred embodiment, the host cell is *Streptomyces lividans* or *S. coelicolor*.

In another embodiment, the invention provides a recombinant expression vector that comprises a promoter positioned to drive expression of a hybrid PKS comprising all or part of the oleandolide PKS and at least a part of a second PKS. In a related embodiment, the invention provides recombinant host cells comprising the vector that produces the hybrid PKS and its corresponding polyketide. In a preferred embodiment, the host cell is *Streptomyces lividans* or *S. coelicolor*.

In a related embodiment, the invention provides recombinant materials for the production of libraries of polyketides wherein the polyketide members of the library are synthesized by hybrid PKS enzymes of the invention. The resulting polyketides can be further modified to convert them to other useful compounds, such as antibiotics, typically through hydroxylation and/or glycosylation. Modified macrolides provided by the invention that are useful intermediates in the preparation of antibiotics are of particular benefit.

In another related embodiment, the invention provides a method to prepare a nucleic acid that encodes a modified PKS, which method comprises using the oleandolide PKS encoding sequence as a scaffold and modifying the portions of the nucleotide sequence that encode enzymatic activities, either by mutagenesis, inactivation, deletion, insertion, or replacement. The thus modified oleandolide PKS encoding nucleotide sequence can then be expressed in a suitable host cell and the cell employed to produce a polyketide different from that produced by the oleandolide PKS. In addition, portions of the oleandolide PKS coding sequence can be inserted into other PKS coding sequences to modify the products thereof.

In another related embodiment, the invention is directed to a multiplicity of cell colonies, constituting a library of colonies, wherein each colony of the library contains an expression vector for the production of a modular PKS derived in whole or in part from the oleandolide PKS. Thus, at least a portion of the modular PKS is identical to that found in the PKS that produces oleandolide and is identifiable as such. The derived portion can be prepared synthetically or directly from DNA derived from organisms that produce oleandolide. In addition, the invention provides methods to screen the resulting polyketide and antibiotic libraries.

The invention also provides novel polyketides, motilides, antibiotics, and other useful compounds derived therefrom. The compounds of the invention can also be used in the manufacture of another compound. In a preferred embodiment, the compounds of the invention are formulated as antibiotics in a mixture or solution for administration to an animal or human.

These and other embodiments of the invention are described in more detail in the following description, the examples, and claims set forth below.

DETAILED DESCRIPTION OF THE INVENTION

Figure 1:
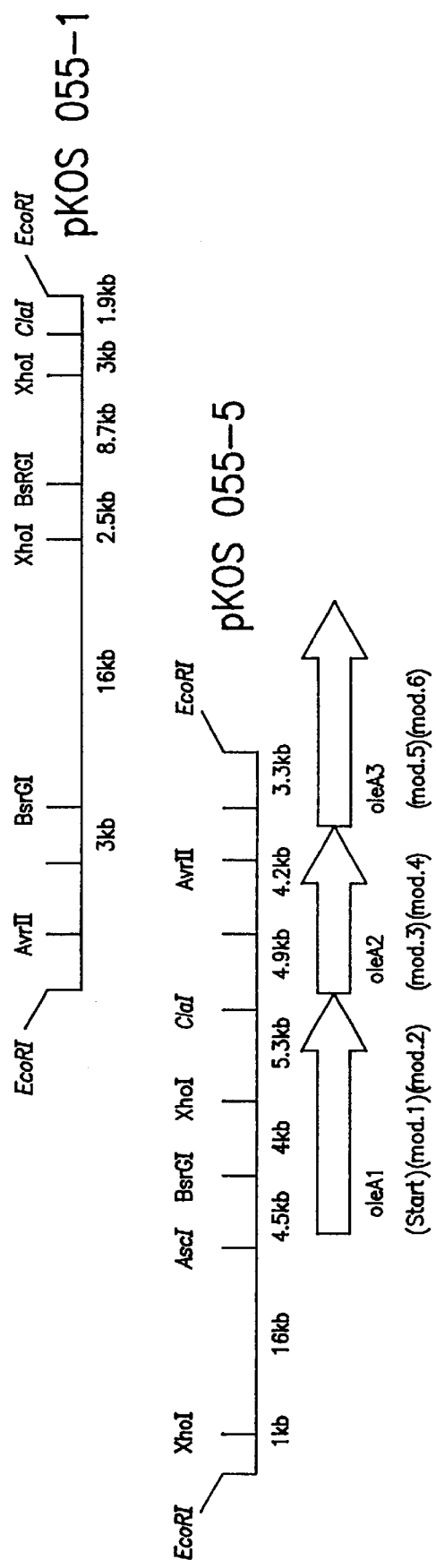
FIG. 1 shows restriction site and function maps of the insert DNA in cosmids pKOS055-1 and pKOS055-5 of the invention. Various restriction sites (XhoI, ClaI, EcoRI) are also shown. Italicized restriction sites in the Figure indicate that not all of such sites are shown; the EcoRI sites shown are derived from the cosmid DNA into which the PKS gene segments were inserted. The location of the coding sequences for modules 1–6 of oleandolide PKS is indicated by brackets with labels underneath the brackets (i.e., mod. 2 is module 2). The sizes (in kilobase (kb) pairs) of various portions of the inserts are also shown. The open reading frames for the oleAI (oleA1), oleAII (oleA2), and oleAIII (oleA3) genes are shown as arrows pointing in the direction of transcription.

The present invention provides useful compounds and methods for producing polyketides in recombinant host cells. As used herein, the term recombinant refers to a compound or composition produced by human intervention. The invention provides recombinant DNA compounds encoding all or a portion of the oleandolide PKS. The invention provides recombinant expression vectors useful in producing the oleandolide PKS and hybrid PKSs composed of a portion of the oleandolide PKS in recombinant host cells. The invention provides the polyketides produced by the recombinant PKS as well as those derived therefrom by chemical processes and/or by treatment with polyketide modification enzymes.

To appreciate the many and diverse benefits and applications of the invention, the description of the invention below is organized as follows. In Section I, the recombinant oleandolide PKS provided by the invention is described. In Section II, methods for heterologous expression of the oleandolide PKS and oleandolide modification enzymes provided by the invention are described. In Section III, the hybrid PKS genes provided by the invention and the polyketides produced thereby are described. In Section IV, the polyketide compounds provided by the invention and pharmaceutical compositions of those compounds are described. The detailed description is followed by a variety of working examples illustrating the invention.

The oleandolide synthase gene, like other PKS genes, is composed of coding sequences organized in a loading module, a number of extender modules, and a thioesterase domain. As described more fully below, each of these domains and modules is a polypeptide with one or more specific functions. Generally, the loading module is responsible for binding the first building block used to synthesize the polyketide and transferring it to the first extender module. The building blocks used to form complex polyketides are typically acylthioesters, most commonly acetyl, propionyl, malonyl, 2-hydroxymalonyl, 2-methylmalonyl, and 2-ethylmalonyl CoA. Other building blocks include amino acid like acylthioesters. PKSs catalyze the biosynthesis of polyketides through repeated, decarboxylative Claisen condensations between the acylthioester building blocks. Each module is responsible for binding a building block, performing one or more functions, and transferring the resulting compound to the next module. The next module, in turn, is responsible for attaching the next building block and transferring the growing compound to the next module until synthesis is complete. At that point, an enzymatic thioesterase activity cleaves the polyketide from the PKS.

Such modular organization is characteristic of the class of PKS enzymes that synthesize complex polyketides and is well known in the art. The polyketide known as 6-deoxyerythronolide B (6-dEB) is a classic example of this type of complex polyketide. The genes, known as eryAI, eryAII, and eryAIII (also referred to herein as the DEBS genes, for the proteins, known as DEBS1, DEBS2, and DEBS3, that comprise the 6-dEB synthase), that code for the multi-subunit protein known as DEBS that synthesizes 6-dEB are described in U.S. Pat. No. 5,824,513, incorporated herein by reference. Recombinant methods for manipulating modular PKS genes are described in U.S. Pat. Nos. 5,672,491; 5,843,718; 5,830,750; and 5,712,146; and in PCT publication Nos. 98/49315 and 97/02358, each of which is incorporated herein by reference.

The loading module of DEBS consists of two domains, an acyl-transferase (AT) domain and an acyl carrier protein (ACP) domain. Each extender module of DEBS, like those of other modular PKS enzymes, contains a ketosynthase (KS), AT, and ACP domains, and zero, one, two, or three domains for enzymatic activities that modify the beta-carbon of the growing polyketide chain. A module can also contain domains for other enzymatic activities, such as, for example, a methyltransferase activity. Finally, the releasing domain contains a thioesterase and, often, a cyclase activity.

The AT domain of the loading module recognizes a particular acyl-CoA (for DEBS this is usually propionyl but sometimes butyryl or acetyl) and transfers it as a thiol ester to the ACP of the loading module. Concurrently, the AT on each of the extender modules recognizes a particular extender-CoA (malonyl or alpha-substituted malonyl, i.e., methylmalonyl, ethylmalonyl, and 2-hydroxymalonyl) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS and a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a polyketone, from which the name polyketide arises. Most commonly, however, additional enzymatic activities modify the beta keto group of each two-carbon unit just after it has been added to the growing polyketide chain but before it is transferred to the next module. Thus, in addition to the minimal module containing KS, AT, and ACP domains necessary to form the carbon-carbon bond, modules may contain a ketoreductase (KR) that reduces the keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring or polyketide modification enzymes; these enzymes add carbohydrate groups or methyl groups, or make other modifications, i.e., oxidation or reduction, on the polyketide core molecule.

While the above description applies generally to modular PKS enzymes, there are a number of variations that exist in nature. For example, some polyketides, such as epothilone, incorporate a building block that is derived from an amino acid. PKS enzymes for such polyketides include an activity that functions as an amino acid ligase or as a non-ribosomal peptide synthetase (NRPS). Another example of a variation, which is actually found more often than the two domain loading module construct found in DEBS, occurs when the loading module of the PKS is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. For example, the oleandolide PKS loading module contains a $KS^Q$. Yet another example of a variation has been mentioned above in the context of modules that include a methyltransferase activity; modules can also include an epimerase activity. The components of a PKS are described further below in specific reference to the oleandolide PKS and the various recombinant and hybrid PKSs provided by the invention.

Section I: The Oleandolide PKS

The oleandolide PKS was isolated and cloned by the following procedure. Genomic DNA was isolated from an oleandomycin producing strain of *Streptomyces antibioticus* (ATCC 11891), partially digested with a restriction enzyme, and cloned into a commercially available cosmid vector to produce a genomic library. This library was then introduced into *E. coli* and probed with a DNA fragment generated from *S. antibioticus* DNA using primers complementary to sequences of KS domains encoding extender modules 5 and 6 of the oleandolide PKS. Several colonies that hybridized to the probe were pooled, replated, and probed again, resulting in the identification of a set of cosmids. These latter cosmids were isolated and transformed into a commercially available *E. coli* strain. Plasmid DNA was isolated and analyzed by DNA sequence analysis and restriction enzyme digestion, which revealed that the desired DNA had been isolated and that the entire PKS gene cluster was contained in overlapping segments on two of the cosmids identified.

Further analysis of these cosmids and subclones prepared from the cosmids facilitated the identification of the location of various oleandolide PKS genes and ORFs, as well as the modules and domains in the PKS proteins encoded by those ORFs. The location of these genes and modules is shown on FIGS. 1 and 2. FIG. 1 shows that the complete oleandolide PKS gene cluster is contained within the insert DNA of cosmids pKOS055-1 (insert size of ~43 kb) and pKOS055-5 (insert size of ~47 kb). Each of these cosmids has been deposited with the American Type Culture Collection in accordance with the terms of the Budapest Treaty (cosmid pKOS055-1 is available under accession no. ATCC 203798; cosmid pKOS055-5 is available under accession no. ATCC 203799). Various additional reagents of the invention can be isolated from these cosmids. DNA sequence analysis was also performed on the various subclones of the invention, as described herein.

Those of skill in the art will recognize that, due to the degenerate nature of the genetic code, a variety of DNA compounds differing in their nucleotide sequences can be used to encode a given amino acid sequence of the invention. The native DNA sequence encoding the oleandolide PKS of *Streptomyces antibioticus* is shown herein merely to illustrate a preferred embodiment of the invention, and the invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences encoded by the DNA sequences shown herein merely illustrate preferred embodiments of the invention.

The recombinant nucleic acids, proteins, and peptides of the invention are many and diverse. To facilitate an understanding of the invention and the diverse compounds and methods provided thereby, the following description of the various regions of the oleandolide PKS and corresponding coding sequences is provided. To facilitate description of the invention, reference to a PKS, protein, module, or domain herein can also refer to DNA compounds comprising coding sequences therefor and vice versa. Also, unless otherwise indicated, reference to a heterologous PKS refers to a PKS or DNA compounds comprising coding sequences therefor from an organism other than *Streptomyces antibioticus*. In addition, reference to a PKS or its coding sequence includes reference to any portion thereof.

Thus, the invention provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form. These DNA molecules comprise one or more sequences that encode one or more domains (or fragments of such domains) of one or more modules in one or more of the ORFs of the oleandolide PKS gene cluster. Examples of such domains include the KS, AT, DH, KR, ER, ACP, and TE domains of at least one of the 6 extender modules and loading module encoded by the 3 ORFs of the oleandomycin PKS genes.

In one embodiment, the DNA molecule comprises an ORF other than or in addition to the ORFB described in Swan et al., supra; which corresponds to the oleAIII gene ORF herein, the module is a module other than or in addition to extender module 5 and/or module 6 of ORFB; and the domain is a domain other than or in addition to a domain of module 5 and/or module 6 of ORFB or the ACP domain of module 4 of ORFA. In an especially preferred embodiment, the DNA molecule is a recombinant DNA expression vector or plasmid. Such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions).

Figure 2:
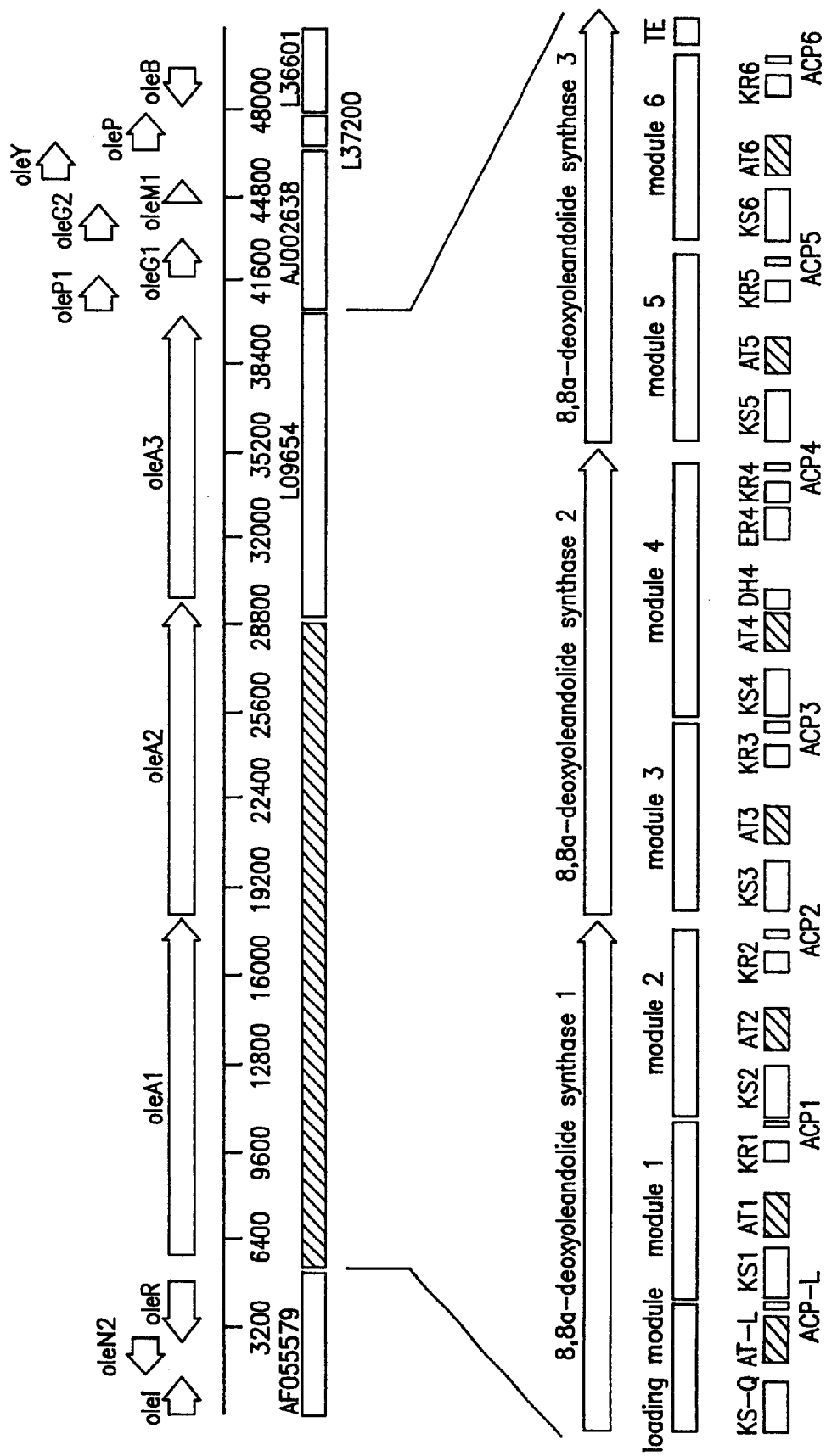
FIG. 2 shows a function map of the oleandomycin gene cluster. In the top half of the Figure, the various open reading frames of the genes (oleI, oleN2, oleR, oleAI, etc.) are shown as arrows pointing in the direction of transcription. Directly beneath, a line indicates the size in base pairs (bp) of the gene cluster. The bar with alphanumeric identifiers under the size indicator line references Genbank accession numbers providing the nucleotide sequence of the indicated region, which sequence information is incorporated herein by reference. The cross-hatched portion of this bar indicates the region of the gene cluster for which sequence information is provided herein. In the bottom half of the Figure, the oleandolide PKS proteins are shown as arrow bars, with the location of the modules of the PKS shown below, and with the various domains of the modules shown below the modules.

The oleandolide PKS, also known as 8,8a-deoxyoleandolide synthase, is encoded by three ORFs (oleAI, oleAII, and oleAIII). Each ORF encodes 2 extender modules of the PKS; the first ORF also encodes the loading module. Each module is composed of at least a KS, an AT, and an ACP domain. The locations of the various encoding regions of these ORFs are shown in FIG. 2 and described with reference to the sequence information below.

ORF1 encodes 8,8a-deoxyoleandolide synthase I and begins at nucleotide 5772 and ends at nucleotide 18224 in the sequence below. ORF1 encodes a loading module (encoded by nucleotides 5799–8873), composed of a $KS^Q$ domain (encoded by nucleotides 5799–7055), a malonyl-specific AT domain (encoded by nucleotides 7458–8563), and an ACP domain (encoded by nucleotides 8634–8873). ORF1 also encodes extender module 1 (encoded by nucleotides 8955–13349), composed of a KS domain (KS1, encoded by nucleotides 8955–10205), an AT domain (AT1, encoded by nucleotides 10512–11549), a KR domain (KR1, encoded by nucleotides 12258–12818), and an ACP domain (ACP1, encoded by nucleotides 13092–13349), and extender module 2 (encoded by nucleotides 13407–17966), composed of a KS domain (KS2, encoded by nucleotides 13407–14690), an AT domain (AT2, encoded by nucleotides 14997–16031), a KR domain (KR2, encoded by nucleotides 16872–17423), and an ACP domain (ACP2, encoded by nucleotides 17709–17996).

ORF2 encodes 8,8a-deoxyoleandolide synthase 2 and begins at nucleotide 18267 and ends at nucleotide 29717 in the sequence below. ORF2 encodes extender module 3 (encoded by nucleotides 18357–22985), composed of a KS domain (KS3, encoded by nucleotides 18357–19643), an AT domain (AT3, encoded by nucleotides 19965–20999), an inactive KR domain (KR3, encoded by nucleotides 21897–22449), and an ACP domain (ACP3, encoded by nucleotides 22728–22985), and extender module 4 (encoded by nucleotides 23046–29396), composed of a KS domain (KS4, encoded by nucleotides 23046–24329), an AT domain (AT4, encoded by nucleotides 24645–25682), a DH domain (DH4, encoded by nucleotides 25719–26256), an ER domain (ER4, encoded by nucleotides 27429–28301), a KR domain (KR4, encoded by nucleotides 28314–28862), and an ACP domain (ACP4, encoded by nucleotides 29147–29396).

ORF3 encodes 8,8a-deoxyoleandolide synthase 3 and begins at nucleotide 29787 and ends at nucleotide 40346 in the sequence below. This sequence has been previously reported by Swan et al., supra. ORF3 encodes extender module 5 (encoded by nucleotides 29886–34478), composed of a KS domain (KS5, encoded by nucleotides 29886–31184), an AT domain (AT5, encoded by nucleotides 31494–32531), a KR domain (KR5, encoded by nucleotides 33384–33935), and an ACP domain (ACP5, encoded by nucleotides 34221–34478), and extender module 6 (encoded by nucleotides 34845–39440), composed of a KS domain (KS6, encoded by nucleotides 34845–36131), an AT domain (AT6, encoded by nucleotides 36447–37484), a KR domain (KR6, encoded by nucleotides 38352–38903), and an ACP domain (ACP6, encoded by nucleotides 39183–39440). ORF3 also encodes a TE domain at nucleotides 39657–40343.

The DNA sequence below also includes the sequences of a number of the tailoring enzyme genes in the oleandomycin gene cluster, including oleI (nucleotides 152–1426), oleN2 (nucleotides 1528–2637), oleR (nucleotides 2658–4967), oleP1 (nucleotides 40625–41830), oleG1 (nucleotides 41878–43158), oleG2 (nucleotides 43163–44443), oleM1 (nucleotides 44433–45173), oleY (nucleotides 45251–46411), oleP (nucleotides 46491–47714), and oleB (nucleotides 47808–49517).

```
The sequence of the portion of the oleandomycin gene cluster
described above follows: (SEQ ID NO:1)
    1  GCATGCCCGC CCGCAACACC GGCTCCCGTA ACGGGGCGAG CCGGTGGTCA TCCATCAGTT

61  TCCTTCCGCC CGGCCCGTGT CAGGCCCGTG TGCGCATACC GCCGTACGGC TGCGCCGGTC

121  CCCCGCGGAA CACCTCACCG GAGTGAGATC CATGACGAGC GAGCACCGCT CTGCCTCCGT

181  GACACCCCGT CACATCTCCT TCTTCAACAT CCCCGGCCAC GGCCACGTGA ACCCGTCACT

241  CGGCATTGTC CAGGGACTTG TCGCGCGCGG CCAACGGGTC AGCTACGGCA TTACCGACGA

301  GTTCGGCGCA CAGGTCAAGG CGGGCCGCGC GACGGCCGTT GTGTACGGCT TCATTCTGCC

361  GGAGGAGTTC AACCCCGAGG AGTTGTTGGC CGAGGACCAG GGTTCCCGAT GGGCCTGTTC

421  CTTGGCGGAG GCGTTCCGGG TCTTGCCGCA GCTGAGGACG GCTACGCCGA CGACCGGCCG

481  GGACCTGATC GTCTACGACA TCGCCTCCTG GCCCGCCCCG GTGCTCGGCC GGAAGTGGGA

541  CATCCCCTTC GTCCAGCTCT CCCCGACCTC CGTCGCCTAC GAGGGCTTCG AGGAGGACGT

601  ACCCGCGGTG CAGGACCCCA CGGCCGACCG CGGCGAGGAG GCCGCCGCCC CCGCGGGGAC
```

-continued

```
 661 CGGGGACGCC GAGGAGGGTG CCGAGGCCGA GGACGGCCTG GTGCGCTTCT TCACCCGGCT
 721 CTCGGCCTTC CTGGAGGAGC ACGGGGTGGA CACCCCGGCC ACCGAGTTCC TCATCGCGCC
 781 CAACCGCTGC ATCGTCGGCT GCCGCGCACC TTCCCAGATC AAGGGCGACA CGGTCGGCGA
 841 CAACTACACC TTCGTCGGTC CCACCTACGG CGACCGGTCC CACCAGGGCA CCTGGGAAGG
 901 CCCCGGGCAC GGGCGTCCGG TGCTGCTGAT CGCCCTGGGC TCGGCGTTCA CCGACCACCT
 961 CGACTTCTAC CGCACCTGCC TGTCCGCCGT CGACGGCCTG GACTGGCACG TGGTGCTCTC
1021 CGTGGGCCGC TTCGTCGACC CCGCGGACCT CGGCGAGGTC CCGCCGAACG TCGAGGTGCA
1081 CCAGTGGGTG CCGCAGCTCG ACATCCTGAC CAAAGCCTCC GCGTTCATCA CGCACGCGGG
1141 CATGGGCAGC ACCATGGAGG CCCTGTCGAA CGCGGTGCCC ATGGTCGCGG TGCCGCAGAT
1201 CGCGGAGCAG ACGATGAACG CCGAGCGGAT CGTCGAGCTG GGCCTCGGCC GGCACATCCC
1261 GCGGGACCAG GTCACGGCCG AGAAGCTGCG CGAGGCCGTG CTCGCCGTCG CCTCCGACCC
1321 CGGTGTCGCC GAACGGCTCG CGGCCGTCCG GCAGGAGATC CGTGAGGCGG GCGGCGCCCG
1381 GGCGGCCGCC GACATCCTGG AGGGCATCCT CGCCGAAGCA GGCTGACCGC CCCTGCCTGA
1441 CGGTGCGCGG GCCGCCCGGC CCGCCGCGTG AGAGTCGGCC CCCGTACCCG ACGACGGGTA
1501 CGGGGGCCGA CGCGCGCGGG CCCGGACTCA GCAGGCGGCC ACCGCGCCCC GTACCGCCTC
1561 GATCACCGCC TTGACGGCGT CGTCGGACAG GTGCGGGCCT ATGGGCAGGC TCAGCACCTC
1621 CCGGGCGAGC CGCTCCGCCA CGGGCTGTGC GCGGCGGCC TGCCGGCTGC CGGCGTACGC
1681 CTCCGACCGG TGCACCGGCA CCGGGTAGTG GATCAGCGTC TCGACGCCGG CTGCCGCCAG
1741 CCGCTCCCGC AGCGCGGACC GGTCCGCGGA ACGAATCACG AACAGGTGCC ACACGGGGTC
1801 CGCCCACGGC GCCGGCCTCG GCAGCACGAT CCCGTCCAGG CCGGCGAGCC CGTCGAGATA
1861 GCGCGCCGCC ACCGCGGCCC GGCGCTCGGG TCCCAGCCGT CCCAGGTGGG CGAGCTTGAC
1921 CCGCAGAACG GCCGCTTGCA GCTCGTCCAG CCGGAAGTTG GTGGCCCGGA CCTCGTGCCG
1981 GTACTTCTCC CGCGACCCGT AGTTGCGCAG CAGCCGCACC CGCTCCGCCA GCTCCGCGTC
2041 GTCCGTCACC ACGGCGCCGC CGTCACCGAA GCCGCCCAGG TTCTTGCCCG GGTAGAAGCT
2101 GAAGGCGGTG GTGGACCACG CGCCCACCCG CCGGCCGTAC GCCTGCGCAC CGTGCGCCTG
2161 GGCGGCGTCC TCCAGGATCC GCACGCCGTG CCGCTCGGCG ACCTCGGACA CGCCGCCAG
2221 GTCCGCCGGA TGCCCGTACA GGTGCACCGG GAGGATCACC CGGGTGCGGG AGGTGATCGC
2281 AGCCTCGACG CGCTCCGGGT CCAGGGTGAA CGTCGCAGGC TCCGGTTCCA CCGCGACGGG
2341 CTCCGCACCC GTCGCCGAGA CGGCGAGCCA GGTCGCGGCG AAGGTGTGCG CCGGGACGAT
2401 CACCTCGTCA CCCGGCCCGA TGTCCATGGC GCGCAGCGCC AGTTCCAGGG CGTCGCACCC
2461 GCTGCCCACC GCCACGCAGT GCCGGGCCCC GCAGTAGGCG CCCACTCCG TCTCGAACGC
2521 GGCGAGTTCG GGCCCAGGA GGTAGCGCCC GGAGTCCAGG ACGCGGCCGG TCGCGGCGTC
2581 GATGTCGTGC TTGAGCTCCA GGTAGGCGGC CCGGAGGTCC AGGAACGGAA CGTCCATGCG
2641 TCCTCCGTGG GAGCTGCTCA CGGCGCCGTG GCGCTGAGCG GGAGACGGCC GAGGGACGGG
2701 CCCACCATGA CCTGCCGTCC GGGTCCGGTC ACCCAGGTGT GGGCGCCGCT GTCCCAGTTC
2761 TGGAGGGCCC TGCGCTCGAC GTGCAGGGTC AGCCTCCTGC TCTCGCCCGG CCGCAGCTCG
2821 ACCTTCCCGT AGGCCGCCAG GGCACGCTTG CCTGCGCCA CCCGCACGTG CGGGGACGGC
2881 CCCACGTAGA CCTGCGGGAC CTCCTTGCCG GTGCGCGTAC CGGTGTTGCG CAGCGTGAAG
2941 CAGACGTCGA GCCCGCCGTC CGCCGTCGCC GTCACCTTCA GGTCCCGGTA GTCGAAGGAG
3001 GTGTAGCACA ACCCGTGGCC GAAGGAGAAC AGCGGCTGGA CGCCCTGCTG TTCGTACCAG
```

-continued

```
3061  CGGTAGCCGG AGTAGATGCC CTCGGAGTAG TCCAGTTGGT CATCGACTCC CGGGTAGCGC
3121  CTGGCGTCCC CGGCGAACGG CGTCTGCCCC TCGTCGGCCG GGAAGGTCTG GGTCAGCCGG
3181  CCTCCTGGGT CGGCGTCGCC GAACAGCAGG GCGGTGGTCG CCTCGGCGCC GGCCTGGCCC
3241  GGGTACCACA TGGTGAGCAC CGCGGCGGTC TTCCTCAGCC AGGGCATGGT GAGGGAGGAG
3301  CCCGTGTTGA GCACCACCAC GGTCCGTGGG TTGACCGCGG CCACGGCGCT GATCAGGTCG
3361  TCCTGGCGGC CGGGCAGGGA CAGCGACGTG CGGTCCCCGT CCTCCGAGCC GTCGTCGTAC
3421  GCGAAGACGA CCGCGGTCCT CGCCGTCCGC GCGATCGACA CGGCCCGGTC GATCGCCTCC
3481  TGGGCGGCCT GCGGAGTGAC CCACGTCAGC TCGAAGGTCA TGGGCGACTT CGCCAGGGCC
3541  GCGCCGGTGA TGCGCAGCTT GTGCGTTCCG CCGCCAGCC GCATGGGCG GCTGCTGACG
3601  TCGCCGTAGA CCCAGGGCCG ACGGCCGAAC GGCTCCTGGC CGTCGAGTTC GACGTAGGCG
3661  TTGCCGCCCT GCGCGCGGGC CGCGATGCGG TAGCTGCCGG TGACCGGCAC GGTGATGGTG
3721  CCGTCGTAGA GGACACCGCC CCCACCGGCG GGAACACCT CGCCCGAGGG GCGGGGCCGC
3781  GGAAGAGGGG CGGACTGCGG AACGGGAACC CCGACCGTCT CCTCACCGGT GCTGTAGCGC
3841  ACGGTGCTGC CGGCGCCGGC CCGTTCGCGG ATGGTGTCCA GAGGGGCGGA CGCGCCGTCC
3901  GGCACGATGT ACGAACTGCC CAGCCCGGTC ACCTTCGGGA CCTTGGCGGT GGGGCCGATC
3961  ACGGCGATGT CCGCCGCCGT CTCCGTGGTC AGGGGAAGGG TGGCGCCCTC GTTGCGCAGC
4021  AGGACCGCGC CGTCCTCGGC GACCTGGCGC GCGACCTTCA AGCCGCCCGC GAGGTCGCGC
4081  GCCGGGCGGG CGGGCGGATC CTCGTCCAGC AGCCGGAACC GGGCCATCTG CGACACGATG
4141  CGGGTGACGG CCTCGTCGAG GGCCGACTCG GGATGCGTC CCTCCCGGAT CGCCGTCTTG
4201  AGCGGGTCGC CGAAGAACTT GCCGCCGGGT ATCGGCTCGC CCGGGGCGGG TTCGTGGTCC
4261  AGCTCGATGC CGAGTTCCTG GTCGAGCCCC TTGGTGAGGG CGTCCGTGCT CTGCGTCGCC
4321  AGCCAGTCCG AGGTCACCCA GCCACGGAAC TTCCACTGCT CCTTGAGGAC CTTGTTCAGC
4381  AGTTCGTCAC TGCCGCAGGC CGGCTGGCCG TTGACCTTGT TGTAGGCGCA CATCACCGAG
4441  CCGGTTCCGG CAGCCACGGC GCTCTCGAAA CCGGGCAGTT CCCGCTCGCG CAACGTCTGT
4501  TCGTCGACGT TCACGTTAAC GCTGAAACGA TTCTTCTCCT GGTTGTTCGC CGCGTAGTGC
4561  TTGGTGGCGG CGATCAGCCC CTGACTCTGG ATGCCCTTGA TCTCCGCGGC GGCCATCCGC
4621  GAGGTGACCA GGGGGTCCTC GCTGAACGTC TCGAAGTTCC GCCCGGCGTA CGGCACGCGT
4681  ATGGAGTTCA CCATCGGCGC GAACACCACG TCCTGCCCGA AGGCGCGCCC CTCCCGGCCG
4741  ATCACCGCCC CGTAGGACCG CGCCAGGCCG TCGTCGAAGG TGGAGGCCAG CGCCACGGGA
4801  GCGGGCAGCG CGAGGGACGG CCGGTGGATC GTGATTCCGG CGGGACCGTC GGTGGCCCGC
4861  ATCTCGGGTA TGCCGAGGCG GGGAACGCCC GGCAGGTACA CCTTTGCCGA CTCATCGCTC
4921  GTGTGATAGC TCCAGTGCAC GAACGACAGC TTTTCTTCCA GGGTCATCCG AGCCGTCAGA
4981  AGACGAGCCG TTTCCCACGG ATCGCCCGAT TCGGCGACGG ACGGAACAGA GGGGAGCAGG
5041  GCGAGACCGA GGGCCAGGCC GAGAGTACCC GCGGAGGTCC GTGGCGGGAC CGGACTCCTG
5101  CGCTGCGCAC GGCCGCCGAG ACGTAACCGA AGTGATCTCA AAAGGCTTCC AAATCCTCCG
5161  CGCCCTCGTG CTGCGAGGCG CATGAAATGG GCGGTTGTCG CGACCACAGT GCACCGTCAC
5221  CGAAGCCGGA GCAATGCCCG TGAATAAGGT CGCGCCCTTC CGTGGATGAT CTCCGCACGA
5281  GATCATGCCC AGCTCAAGTG ATGGTCATGC ACGTACCAAG AAGGGGCTTG CCTGGGGGGC
5341  GTGAGCTGAT CTAGCGTTGC CGCACGACGA CGAGTCGTGA GCGAGGCGAA CGCTCTGCCG
5401  CTCAGGGGGT GAACAGACGG CAGCCCGGAC GTTCGACGAG GGTCAAGCGG AACGCAGGCG
```

```
-continued

5461  ACAGGACGCG GCCACCCTCC GAGGCACCCG TGCCGACCAT CCTCGCAGGT CCTTCGCCAT
5521  GCCCGTCGCA ACTCTCCGAT CGCTGCCGCC GATGGCGACA GCCCGGCACC GAGGCCCCTG
5581  GACCAGGAGG CGAAGCGAGG GCCGGCCGCG ATGCACGAAT CGGACCCAGG CGAACACCGG
5641  CACATCCACC CCGGCGCGTG CGGTACGGGC CGCGCCCGAT GACGGGCGAA CGACGACCGA
5701  AAAGCAGACC CCTTGATTCG CTTCCATGGT TGTGGCAGCC GCGGGGAGCG TCGGCAGAGA
5761  GGTGGGAAAC CATGCATGTC CCCGGCGAGG AAAACGGGCA TTCCATTGCC ATTGTCGGAA
5821  TTGCGTGCCG ACTGCCGGGC TCTGCCACCC CCCAGGAGTT CTGGAGACTC CTGGCCGACT
5881  CCGCAGACGC ATTGGACGAG CCCCCCGCCG GCCGTTTCCC GACCGGCTCA TTATCCTCGC
5941  CCCCCGCTCC GCGCGGCGGA TTCCTCGACA GCATCGACAC TTTCGACGCG GATTTCTTCA
6001  ACATCTCGCC CAGAGAAGCC GGTGTCCTCG ACCCCCAGCA ACGCCTCGCG CTGGAACTCG
6061  GCTGGGAGGC GCTGGAAGAC GCCGGAATCG TCCCGCGACA CCTCAGGGGA ACCCGCACCT
6121  CGGTCTTCAT GGGCGCCATG TGGGACGACT ACGCGCACCT GGCGCACGCA CGGGGAGAAG
6181  CCGCCCTCAC CCGGCATTCC CTGACGGGAA CGCACCGCGG CATGATCGCC AACCGGCTCT
6241  CCTACGCCCT GGGCCTCCAA GGCCCCAGCC TCACCGTCGA CACCGGACAA TCCTCCTCCC
6301  TCGCCGCCGT GCACATGGCC TGCGAGAGCC TGGCCCGCGG CGAATCCGAC CTCGCCCTCG
6361  TCGGCGGCGT CAACCTCGTC CTCGATCCGG CCGGCACGAC CGGCGTCGAG AGGTTCGGAG
6421  CACTCTCACC GGACGGCAGG TGCTACACCT TCGACTCCCG GGCGAACGGC TACGCCCGAG
6481  GAGAGGGCGG CGTCGTAGTC GTCCTCAAGC CCACCCACCG CGCGCTCGCG GACGGTGACA
6541  CCGTCTACTG CGAGATCCTG GGCAGCGCCC TCAACAACGA CGGCGCCACG GAAGGCCTCA
6601  CCGTCCCCAG CGCCCGCCCC CAGGCGGACG TCCTGCGACA GGCATGGGAA CGGGCACGCG
6661  TGGCCCCGAC GGACGTCCAG TACGTGGAAC TGCACGGAAC CGGCACACCG GCCGGCGACC
6721  CCGTCGAGGC CGAGGGCCTC GGCACCGCGC TCGGCACCGC ACGCCCGGCC GAGGCGCCGC
6781  TCCTGGTCGG CTCGGTCAAG ACGAACATCG GTCACCTCGA AGGCGCGGCA GGCATCGCGG
6841  GCCTCCTGAA GACGGTCCTG AGCATCAAGA ACCGGCACCT CCCGGCAAGC CTGAACTTCA
6901  CCTCGCCCAA CCCCCGCATC GACCTCGACG CCCTGCGCCT GCGCGTCCAC ACCGCGTACG
6961  GCCCCTGGCC GAGCCCCGAC CGGCCGCTGG TGGCGGGCGT CTCCTCCTTC GGCATGGGCG
7021  GGACGAACTG CCACGTCGTC CTGTCCGAGT TACGGAACGC GGGAGGCGAC GGCGCCGGAA
7081  AAGGGCCGTA CACCGGCACG GAAGACCGGC TCGGCGCCAC GGAGGCGGAA AAGAGGCCGG
7141  ACCCGGCAAC CGGAAACGGT CCTGATCCCG CCCAGGACAC CCACCGCTAC CCGCCGCTGA
7201  TCCTGTCCGC CCGCAGCGAC GCGGCCCTGC GCGCACAGGC GGAACGGCTC CGCCACCACC
7261  TGGAACACAG CCCCGGACAG CGCCTGCGGG ACACCGCCTA CAGCCTGGCG ACCCGCCGCC
7321  AGGTCTTCGA GCGGCACGCG GTGGTCACCG GACACGACCG CGAGGACCTG CTCAACGGCC
7381  TGCGTGACCT GGAGAACGGC CTCCCGGCCC CCCAGGTCCT GCTCGGCCGC ACGCCCACCC
7441  CCGAACCGGG CGGCCTCGCC TTCCTCTTCT CCGGGCAGGG CAGCCAGCAG CCCGGCATGG
7501  GCAAGCGACT CCACCAGGTG TTCCCCGGCT TCCGGACGCC CTGGACGAG GTCTGCGCCG
7561  AACTCGACAC CCACCTCGGC CGACTCCTCG GCCCCGAGGC CGGCCCGCCC CTGCGCGACG
7621  TGATGTTCGC CGAGCGGGGC ACGGCGCACA GCGCCCTGCT CTCCGAGACC CACTACACCC
7681  AGGCCGCCCT CTTCGCCCTG GAAACCGCCC TCTTCCGCCT CCTGGTCCAG TGGGGCCTGA
7741  AACCCGACCA CCTCGCAGGC CACTCCGTCG GCGAGATCGC GGCCGCCCAC GCAGCAGGCA
7801  TCCTCGACCT GTCCGACGCG GCCGAACTCG TGGCCACCCG CGGCGCGTTG ATGCGTTCCC
```

-continued

```
 7861 TGCCCGGCGG CGGCGTCATG CTCTCGGTCC AGGCACCCGA GTCCGAGGTC GCACCCCTGC
 7921 TGCTCGGCCG TGAGGCCCAC GTCGGCCTGG CCGCCGTGAA CGGCCCCGAC GCGGTGGTCG
 7981 TGTCCGGCGA GCGCGGCCAC GTCGCCGCCA TCGAACAGAT CCTCCGGGAC AGGGGCCGCA
 8041 AAAGCCGGTA CCTGCGCGTC AGCCACGCCT TCCACTCCCC GCTCATGGAA CCGGTGCTGG
 8101 AGGAGTTCGC CGAAGCCGTC GCCGGCCTGA CCTTCCGGGC ACCGACCACA CCCCTCGTCT
 8161 CCAACCTCAC CGGCGCACCA GTCGACGACC GGACCATGGC CACGCCCGCC TACTGGGTCC
 8221 GGCACGTCCG GGAAGCGGTC CGCTTCGGCG ACGGCATCCG GGCACTCGGG AAACTGGGCA
 8281 CCGGCAGCTT CCTGGAAGTC GGGCCGGACG GCGTCCTCAC CGCCATGGCG CGCGCATGCG
 8341 TCACCGCCGC CCCGGAGCCC GGCCACCGCG GCGAACAGGG CGCCGATGCC GACGCCCACA
 8401 CCGCGTTGCT GCTGCCCGCC CTGCGCCGAG GACGGGACGA GGCGCGATCG CTCACCGAGG
 8461 CCGTGGCACG GCTCCACCTG CACGGCGTGC CGATGGACTG GACCTCCGTC CTCGGCGGCG
 8521 ACGTGAGCCG GGTCCCCCTC CCGACGTACG CCTTCCAACG CGAATCCCAC TGGCTGCCGT
 8581 CCGGAGAGGC TCACCCGCGA CCGGCGGACG ACACCGAATC CGGCACGGGA CGGACCGAGG
 8641 CGTCCCCGCC GCGGCCGCAC GACGTCCTGC ACCTCGTGCG CTCCCACGCG GCGGCTGTGC
 8701 TCGGACATTC CCGGGCCGAG CGGATCGACC CCGACCGCGC GTTCCGCGAC CTCGGCTTCG
 8761 ACTCGCTGAC GGCGCTGGAA CTGCGGGACC GGCTCGACAC CGCACTCGGC CTCCGCCTGC
 8821 CCAGCAGCGT GCTCTTCGAC CACCCGAGCC CCGGCGCACT GGCACGCTTC CTCCAGGGCG
 8881 ACGACACGAG GCGCCCCGAA CCAGGGAAGA CGAACGGCAC GCGCGCCACG GAGCCAGGCC
 8941 CGGACCCGGA CGACGAGCCG ATCGCCATCG TCGGCATGGC GTGCCGCTTC CCGGGTGGCG
 9001 TGACCTCTCC GGAGGACCTG TGGCGCCTGC TCGCCGCAGG CGAGGACGCG GTGTCCGGCT
 9061 TCCCCACGCA CCGGGGCTGG AACGTCACTG ACTCCGCCAC GCGCCGCGGA GGCTTCCTGT
 9121 ACGACGCCGG CGAGTTCGAT GCCGCCTTCT TCGGTATCTC GCCGCGTGAG GCGTTGGTGA
 9181 TGGACCCGCA GCAGCGGTTG CTGCTGGAGA CGTCCTGGGA GGCCCTCGAA CGCGCGGGCG
 9241 TGAGCCCCGG CAGTCTGCGC GGCAGCGACA CGGCCGTGTA CATCGGAGCC ACAGCGCAGG
 9301 ACTACGGCCC CCGACTGCAC GAGTCGGACG ACGACTCGGG CGGCTACGTC CTGACCGGCA
 9361 ATACCGCCAG CGTGGCCTCC GGCCGCATCG CCTACTCCCT CGGTCTGGAG GGGCCTGCGG
 9421 TCACGGTGGA CACGGCGTGT TCGTCGTCGC TGGTGGCACT GCACCTGGCG GTGCAGGCGC
 9481 TGCGCCGTGG CGAGTGCTCA CTGGCATTGG CCGGCGGAGC ACGGTGATGG CCTTCGCCCG
 9541 GCATGTTCGT GGAGTTCTCA CGGCAAGGGG GCCTCTCCGA GGACGGCCGC TGCAAGGCGT
 9601 TCGCCGCGAC GGCGGACGGC ACCGGCTGGG CCGAGGGTGT GGGTGTGTTG TTGGTGGAGC
 9661 GGTTGTCGGA TGCGCGGCGG TTGGGTCATC GGGTGTTGGC GGTGGTGCGG GGGAGTGCGG
 9721 TCAATCAGGA TGGTGCGTCG AATGGGTTGA CGGCGCCGAA TGGTCCGTCG CAGCAGCGGG
 9781 TGATCCGTGC GGCGTTGGCT GACGCGGGTC TGGTTCCTGC TGATGTGGAT GTGGTGGAGG
 9841 CGCATGGTAC GGGGACGCGC TTGGGTGATC CGATCGAGGC TCAGGCGTTG TTGGCGACGT
 9901 ATGGGCAGGG GCGTGCGGGT GGGCGTCCGG TGGTGTTGGG GTCGGTGAAG TCGAACATCG
 9961 GTCATACGCA GGCGGCGGCT GGTGTGGCTG GTGTGATGAA GATGGTGCTG GCGCTGGGGC
10021 GGGGTGTGGT GCCGAAGACG TTGCATGTGG ATGAGCCGTC TGCGCATGTG GACTGGTCGG
10081 CTGGTGAGGT GGAGTTGGCG GTTGAGGCGG TGCCGTGGTC GCGGGGTGGG CGGGTGCGGC
10141 GGGCTGGTGT GTCGTCGTTC GGGATCAGTG GCACGAATGC GCATGTGATC GTGGAGGAGG
10201 CGCCTGCGGA GCCGGAGCCG GAGCCGGAGC GGGGTCCGGG CTCTGTTGTG GGTGTGGTGC
```

-continued

```
10261 CGTGGGTGGT GTCCGGGCGG GATGCGGGGG CGTTGCGTGA GCAGGCGGCA CGCTTGGCTG
10321 CGCACGTGTC GGGTGTAAGT GCGGTCGATG TGGGCTGGTC GTTGGTGGCC ACGAGGTCGG
10381 TGTTCGAGCA CCGGGCGGTG ATGGTCGGCA GTGAACTCGA TGCCATGGCG GAGTCGTTGG
10441 CCGGCTTCGC TGCGGGTGGG GTTGTGCCGG GGTGGTGTC  GGGTGTGGCT CCGGCTGAGG
10501 GTCGTCGTGT GGTGTTCGTC TTTCCTGGTC AGGGTTCGCA GTGGGTGGGG ATGGCGGCTG
10561 GGTTGCTGGA TGCGTGCCCG GTGTTCGCGG AGGCGGTGGC GGAGTGCGCT GCGGTGCTGG
10621 ACCCGTTGAC CGGTTGGTCG CTGGTCGAGG TGTTGCGCGG TGGTGGTGAG GCTGTTCTTG
10681 GGCGGGTTGA TGTGGTGCAG CCGGCGTTGT GGGCGGTGAT GGTGTCACTG GCCCGGACCT
10741 GGCGGTATTA CGGTGTGGAG CCTGCTGCGG TTGTGGGGCA TTCGCAGGGT GAGATTGCTG
10801 CGGCTTGTGT GGCTGGGGGG TTGAGTCTGG CCGATGGTGC GCGGGTGGTG GTGTTGCGGA
10861 GCCGGGCGAT CGCCCGGATC GCTGGTGGGG GCGGCATGGT CTCCGTCAGC CTGCCGGCCG
10921 GCCGTGTCCG CACCATGCTG GAGGAGTTCG ACGGCAGGGT TTCCGTTGCG GCGGTCAACG
10981 GTCCGTCCTC GACCGTGGTG TCGGGTGACG TCCAGGCCCT GGATGAGTTG TTGGCCGGTT
11041 GTGAGCGGGA GGGTGTCCGG GCTCGTCGTG TCCCGGTGGA CTATGCCTCC CACTCCGCGC
11101 AGATGGACCA GTTACGCGAT GATCTGCTGG AAGCGCTGGC GACGATCGTC CCTACATCGG
11161 CGAACGTACC GTTCTTCTCG ACGGTGACGG CGGACTGGCT GGACACGACC GCTCTGGATG
11221 CGGGGTACTG GTTCACGAAT CTGCGGGAGA CGGTCCGGTT CCAAGAAGCC GTCGAAGGGC
11281 TCGTGGCTCA GGGGATGGGC GCGTTCGTCG AGTGCAGCCC GCACCCCGTC CTCGTCCCGG
11341 GCATCACAGA AACACTCGAC ACCTTCGACG CCGACGCTGT CGCACTGTCG TCGCTGCGGC
11401 GTGACGAAGG CGGCCTGGAT CGGTTCCTCA CGTCCCTCGC GGAAGCCTTC GTCCAGGGCG
11461 TCCCGGTCGA CTGGTCCCGC GCCTTCGAGG GTGCGAGCCC CCGCACCGTC GACCTGCCCA
11521 CCTACCCCTT CCAACGGCAA CGCTACTGGC TGCTCGACAA GGCGGCGCAA CGGGAACGCG
11581 AGCGGCTGGA GGACTGGCGC TACCACGTCG AGTGGCGCCC CGTCACGACA CGACCTTCCG
11641 CACGGCTGTC CGGTGTCTGG GCCGTGGCGA TTCCGGCACG TCTGGCCCGT GACTCACTGT
11701 TGGTCGGCGC CATCGACGCA CTGGAGCGAG GCGGCGCCCG TGCCGTGCCC GTGGTGGTCG
11761 ATGAGCGGGA CCACGACCGG CAAGCGCTGG TCGAGGCTCT GCGGAACGGG CTGGGCGACG
11821 ACGACCTCGC CGGTGTGCTC TCCCTTTTGG CCCTCGACGA AGCCCCGCAC GGTGACCACC
11881 CCGACGTGCC CGTCGGCATG GCCGCTTCGC TGGCGCTCGT GCAGGCGATG GCCGACGCCG
11941 CGGCCGAGGT GCCCGTATGG TTCGCGACCC GAGGCGCCGT AGCGGCACTG CCCGGTGAGT
12001 CACCGGAGCG ACCCAGGCAG GCGCTGCTCT GGGGACTGGG ACGGGTCGTC GCCCTGGAAC
12061 AGCCGCAGAT ATGGGGCGGG TTGGTCGACC TCCCGCAACA CCTGGACGAG GACGCGGGCC
12121 GACGGCTGGT CGATGTCGTG GGCGGCCTGG CGGACGAGGA CCAGCTTGCC GTACGGGCCT
12181 CCTCCGTCCT CGCCCGACGC CTCGTTCGTA CGCCGGGTCA CCGTATGTCG AGCCAGGCGG
12241 GCGGGCGCGA GTGGTCGCCC AGCGGCACGG TCCTGGTGAC CGGAGGCACC GGGGCGCTGG
12301 GCGCGCACGT CGCCCGCTGG CTGGCCGGCA AGGGCGCCGA GCACCTGGTA CTCATCAGCC
12361 GTCGCGGAGC GGACGCAGCC GGGGCCGCTG CCCTTCGGGA CAGCCTCACG GACATGGGTG
12421 TCCGGGTGAC CCTGGCCGCG TGCGATGCAG CGGACCGGCA CGCACTGGAG ACGCTCCTCG
12481 ACTCGCTGCG CACGGATCCG GCGCAGCTGA CGGCCGTCAT CCACGCCGCG GGTGCTCTGG
12541 ACGACGGCAT GACGACGGTG CTCACACCGG AGCAGATGAA CAACGCCCTG CGAGCGAAAG
12601 TCACGGCCAC CGTCAACCTG CACGAACTGA CCCGGGACCT CGACCTCTCG GCCTTCGTAC
```

-continued

```
12661  TGTTCTCGTC CATCTCCGCC ACCCTGGGAA TCCCCGGGCA GGCCAACTAC GCGCCGGGAA
12721  ACTCGTTCTT GGACGCCTTC GCGGAATGGC GCAGGGCTCA GGGGCTCGTG GCGACCTCCA
12781  TCGCCTGGGG ACCGTGGTCC GGCGGCACCG GCATGGCACA TGAAGGGTCG GTGGGCGAAC
12841  GGCTCCAGCG GCACGGTGTA CTCGCCATGG AACCCGCGGC GGCCATCGCT GCGCTCGACC
12901  ACACGCTGGC GAGCGACGAA ACCGCAGTGG CCGTGGCCGA CATCGACTGG AGCCGGTTCT
12961  TCCTGGCGTA CACAGCACTG CGGGCACGGC CCTTGATCGG AGAGATACCC GAGGCACGCC
13021  GCATGCTGGA GTCCGGCTCA GGCCCCGGCG ACCTCGAGCC GGACCGTGCC GAACCCGAGC
13081  TTGCCGTGCG TCTCGCGGGC CTCACCGCGG TCGAGCAGGA ACGTCTTCTG GTGCAGCTCG
13141  TGAGGGAGCA GGCCGCCGTC GTCCTCGGAC ATTCCGGCGC CGAGGCGGTG GCTCCGGACC
13201  GAGCGTTCAA GGATCTCGGA TTCGACTCGC TGACCTCGGT CGAACTGCGC AACCGGCTGA
13261  ACACCGCCAC CGGCCTCAGA CTGCCCGTGA CGGCCGTCTT CGACTACGCG AGGCCCGCGG
13321  CGCTGGCCGG CCATCTGCGC TCCAGGCTGA TCGACGACGA TGGTGACCAC GGTGCCTTGC
13381  CCGGCGTGGA GAAGCACGCG ATCGACGAGC CGATCGCGAT CGTGGGAATG GCATGCCGCT
13441  TCCCGGGAGG CATCGCTTCC CCGGAGGATC TGTGGGACGT GCTCACCGCT GGTGAGGACG
13501  TTGTCTCCGG ACTGCCGCAG AACCGCGGGT GGGACTTGGG GCGCCTGTAC GATCCCGATC
13561  CGGACCGGGC CGGTACGTCA TACATGCGTG AGGGTGCTTT CCTGCACGAG GCGGGGGAGT
13621  TCGACGCGGC CTTCTTCGGT ATCTCGCCGC GTGAGGCGTT GGCGATGGAC CCGCAGCAGC
13681  GGTTGCTGCT GGAGACGTCC TGGGAGGCCC TCGAACGGGC CGGCATCACT CCTTCCAAGC
13741  TGGCGGGCAG TCCGACCGGT GTGTTCTTCG GCATGTCGAA CCAGGACTAC GCCGCCCAGG
13801  CGGGCGACGT GCCGTCCGAG CTGGAGGGCT ACCTGCTCAC CGGCTCCATC TCCAGCGTCG
13861  CTTCGGGGCG TGTTGCTTAC ACGTTCGGTC TTGAGGGGCC TGCGGTGACG GTGGATACGG
13921  CGTGTTCGTC GTCGTTGGTG GCGTTGCATC TGGCGGTGCA GGGGTTGCGG CGGGGTGAGT
13981  GTTCGCTTGC GTTGGTGGGT GGGGTGACGG TGATGTCGTC GCCGGTGACG TTGACGACGT
14041  TCAGTCGGCA GCGGGGTTTG TCGGTGGATG GGCGGTGCAA GGCGTTCGCG GCTTCGGCGG
14101  ATGGTTTTGG TGCTGCCGAG GGTGTGGGTG TGTTGTTGGT GGAGCGGTTG TCGGATGCGC
14161  GGCGGTTGGG TCATCGGGTG TTGGCGGTGG TGCGGGGGAG TGCGGTCAAT CAGGATGGTG
14221  CGTCCAATGG TCTGCGGCGC CCGAATGGTC CGTCGCAGCA GCGGGTGATC CGTGCGGCGT
14281  TGGCTGACGC GGGTCTGGCT CCTGCCGATG TGGATGTGGT GGAGGCGCAT GGCACGGGGA
14341  CGCGGTTGGG TGATCCGATC GAGGCTCAGG CGTTGCTGGC GACGTATGGG CAGGGTCGTA
14401  CCAGTGGGCG TCCGGTGTGG CTGGGGTCGG TGAAGTCGAA CATCGGGCAT ACGCAGGCGG
14461  CGGCCGGTGT GGCTGGTGTG ATGAAGATGG TGCTGGCGTT GGGTCGGGGT GTGGTGCCGA
14521  AGACGTTGCA TGTGGATGAG CCGTCACCGC ATGTGGACTG GTCGGCTGGT GAGGTGGAGT
14581  TGGCGGTTGA GGCGGTGCCG TGGTCGCGGG GTGGGCGGGT GCGGCGGGCT GGTGTGTCGT
14641  CGTTCGGGAT CAGCGGCACG AATGCGCATG TGATCGTGGA GGAGGCGCCT GCGGAGCCTT
14701  CGGTGGAGGA GGGTCCGGGC TCCGTTGTGG GTGTGGTGCC GTGGGTGGTG TCCGGGCGGG
14761  ATGCGGGGGC GTTGCGTGCA CAGGCGGCAC GCTTGGCTGC GCACGTGTCG AGCACGGGTG
14821  CGGGTGTGGT TGATGTGGGC TGGTCGTTGG TGGCCACGAG GTCGGTGTTC GAGCACCGGG
14881  CGGTAATGGT CGGCACTGAT CTTGATTCCA TGGCGGGGTC GTTGGCCGGC TTCGCTGCGG
14941  GTGGTGTTGT GCCGGGGGTG GTGTCGGGTG TGGCTCCGGC TGAGGGCCGT CGTGTGGTGT
15001  TCGTCTTTCC TGGTCAGGGT TCGCAGTGGG TGGGGATGGC GGCTGGGTTG CTGGATGCGT
```

-continued

```
15061  GTCCGGTGTT CGCGGAGGCG GTGGCGGAGT GTGCCGCGGT GCTGGACCGG TTGACCGGTT
15121  GGTCGCTGGT CGAGGTGTTG CGTGGTGGTG AGGCTGTTCT TGGGCGGGTT GATGTGGTGC
15181  AGCCGGCGTT GTGGGCGGTG ATGGTGTCAC TGGCTCGGAC CTGGCGGTAT TACGGTGTGG
15241  AGCCTGCTGC GGTTGTGGGG CATTCGCAGG GTGAGATTGC TGCGGCTTGT GTGGCTGGGG
15301  GGTTGAGTCT GGCCGATGGT GCGCGGGTGG TGGTGTTGCG GAGTCGGGCG ATCGCCCGGA
15361  TCGCTGGTGG GGGCGGCATG GTCTCGGTCG GTCTTTCAGC TGAGCGTGTC CGCACCATGC
15421  TCGACACCTA CGGCGGCAGG GTTTCCGTCG CGGCGGTCAA TGGCCCGTCC TCGACCGTGG
15481  TGTCCGGTGA CGCCCAGGCC CTGGATGAGT TGTTGGCCGG TTGTGAGCGG GAGGGTGTCC
15541  GGGCTCGTCG TGTCCCGGTG GACTATGCCT CCCACTCCGC GCAGATGGAC CAGTTACGCG
15601  ATGAGTTGCT GGAGGCGCTG GCGGACGTCA CTCCGCAGGA CTCCAGTGTT CCGTTTTTCT
15661  CGACGGTGAC GGCGGACTGG CTGGACACGA CCGCTCTGGA TGCGGGGTAC TGGTTCACGA
15721  ATCTGCGGGA GACGGTCCGG TTCCAGGAAG CCGTTGAAGG GCTTGTGGCT CAGGGGATGG
15781  GCGCGTTCGT CGAGTGCAGC CCGCACCCTG TCCTCGTCCC GGGCATCACA GAAACACTCG
15841  ACACCTTCGA CGCCGACGCT GTCGCACTGT CGTCGCTGCG GCGTGACGAA GGCGGCCTGG
15901  ATCGGTTCCT CACGTCCCTC GCGGAAGCCT TCGTCCAAGG CGTTCCCGTC GACTGGACCC
15961  ATGCCTTCGA GGGTGGACGC CCGCGCTTCG TCGACCTGCC CACCTATGCC TTCCAGCGAC
16021  AGCGCTACTG GCTGCACGAA GAGCCGCTGC AAGAGCCGGT CGATGAGGCG TGGGATGCCG
16081  AGTTCTGGTC TGTGGTCGAA CGCGGCGATG CCACAGCCGT GTCCGACTTG CTGAGCACGG
16141  ACGCCGAGGC TTTGCACACG GTGTTGCCGG CTTTGTCGTC GTGGCGGCGG CGTCGGGTGG
16201  AGCATCGACG GCTTCAGGAC TGGCGTTACC GGGTGGAGTG GAAGCCTTTC CCGGCCGCGC
16261  TTGATGAGGT GCTCGGTGGT GGCTGGTTGT TCGTGGTGCC GCGGGGCTTG GCGGATGATG
16321  GTGTGGTTGC GCGGGTGGTG GCTGCCGTCA CGGCGCGGGG TGGCGAGGTC AGTGTCGTGG
16381  AGCTCGATCC GACCCGTCCT GACCGCCGGG CTTATGCGGA GGCTGTCGCG GGCCGTGGTG
16441  TGAGCGGGGT CGTGTCGTTC TTGTCCTGGG ATGATCGGCG GCACTCGGAG CATTCTGTTG
16501  TTCCCGCCGG TCTTGCCGCG TCGCTGGTGT TGGCGCAGGC GTTGGTTGAT CTTGGCCGGG
16561  TTGGTGAGGG GCCGCGGTTG TGGCTGGTGA CGCGGGGTGC GGTGGTTGCT GGTCCTTCGG
16621  ATGCCGGTGT GGTGATTGAT CCGGTGCAGG CGCAGGTGTG GGGTTTCGGG CGTGTTCTGG
16681  GTCTGGAGCA TCCCGAGTTG TGGGGTGGGC TGGTGGACCT GCCGGTGGGG GTTGATGAGG
16741  AGGTGTGCCG GCGGTTCGTG GGTGTTGTGG CGTCGGCTGG TTTTGAGGAT CAGGTGGCGG
16801  TGCGTGGTTC GGGTGTGTGG GTGCGTCGTC TGGTGCGTGC TGTGGTGGAT GGTGGTGGGG
16861  GTGGTTGGCG GCCGCGTGGG ACGGTGTTGG TCACGGGTGG TCTTGGTGGT TTGGGTGCGC
16921  ATACGGCCCG GTGGTTGGTG GGTGGTGGGG CGGATCATGT GGTTCTTGTG AGCCGTCGTG
16981  GTGGCAGTGC GCCTGGTGCT GGGGATCTGG TGCGGGAGCT GGAGGGGTTG GGCGGGGCTC
17041  GGGTGTCGGT GCGGGCCTGT GATGTGGCTG ATCGTGTGGC GTTGCGGGCG TTGTTGTCGG
17101  ATCTGGGTGA GCCGGTGACG GCGGTGTTCC ATGCGGCTGG TGTTCCTCAG TCGACGCCTT
17161  TGGCGGAGAT CTCTGTCCAG GAGGCGGCTG ATGTGATGGC GGCCAAGGTG GCGGGTGCGG
17221  TGAATCTGGG TGAGTTGGTG GATCCCTGTG GTCTGGAGGC GTTTGTGTTG TTCTCCTCCA
17281  ATGCCGGTGT GTGGGGCAGT GGGGGGCAGG CGGTGTATGC GGCGGCGAAT GCGTTTCTTG
17341  ATGCGTTGGC GGTGCGTCGT CGGGGTGTTG GTCTGCCGGC CACGAGTGTG GCGTGGGGGA
17401  TGTGGGCTGG TGAGGGGATG GCGTCGGTGG GTGGTGCGGC GCGGGAGTTG TCCCGTCGGG
```

-continued

```
17461  GGGTGCGGGC GATGGATCCC GAGCGTGCTG TGGCGGTGAT GGCTGATGCG GTGGGTCGTG

17521  GTGAGGCGTT CGTCGCGGTC GCTGATGTGG ACTGGGAACG TTTCGTCACC GGTTTCGCTT

17581  CTGCCCGTCC CCGTCCGTTG ATCAGTGACC TGCCGGAGGT GCGTGCTGTT GTGGAGGGCC

17641  AGGTCCAGGG CCGGGGCCAG GGGTTGGGCT TGGTCGGTGA GGAGGAGTCG TCGGGGTGGT

17701  TGAAGCGGTT GTCGGGGTTG TCTCGTGTGC GGCAGGAGGA GGAGTTGGTG GAGTTGGTCC

17761  GTGCTCAGGC TGCCGTTGTT CTCGGGCATG GTTCCGCGCA GGACGTCCCG GCTGAGCGGG

17821  CGTTCAAGGA GTTGGGTTTT GATTCCCTCA CTGCTGTCGA GCTACGCAAC GGGCTGGCCG

17881  CGGCCACCGG GATCCGGCTG CCGGCCACCA TGGCATTCGA TCATCCCACC GCCACCGCCA

17941  TCGCACGCTT CCTGCAATCC GAACTCGTGG GAAGTGACGA CCCGCTGACG CTCATGCGGT

18001  CGGCGATCGA CCAGTTGGAG ACCGGTCTGG CTCTGCTGGA ATCGGACGAA GAAGCTCGCT

18061  CGGAAATCAC GAAGCGATTG AACATTCTTC TGCCCCGCTT CGGAAGCGGA GGCAGTTCGA

18121  GAGGCAGGGA AGCAGGACAA GACGCAGGCG AACATCAGGA TGTCGAGGAC GCCACCATCG

18181  ATGAGCTATT CGAGGTGCTC GACAACGAAC TCGGCAATTC CTGAAAACCT GTCCGACTGC

18241  TACCGCGACC TTGACCGGAG AACGCTGTGA CGAACGACGA AAAGATCGTC GAGTATCTCA

18301  AGCGCGCGAC CGTGGACCTG CGCAAGGCCC GGCACCGCAT CTGGGAGCTG GAGGACGAGC

18361  CCATCGCGAT CACGTCGATG GCCTGCCACT TCCCGGGCGG GATCGAGAGT CCGGAGCAGC

18421  TGTGGGAACT CCTGTCCGCC GGAGGCGAGG TGCTTTCCGA GTTCCCCGAC GACCGCGGCT

18481  GGGACCTGGA CGAGATCTAC CATCCTGACC CGGAACACAG TGGGACGAGC TACGTCCGTC

18541  ACGGCGGTTT CCTGGATCAT GCGACGCAGT TCGACACGGA CTTCTTCGGT ATCTCGCCGC

18601  GTGAGGCGTT GGCGATGGAC CCGCAGCAGC GGTTGCTGCT GGAGACGTCC TGGCAGCTTT

18661  TCGAGCGCGC AGGAGTCGAT CCCCATACGC TGAAGGGAAG CCGGACCGGA GTATTCGTCG

18721  GCGCCGCACA CATGGGTTAT GCGGACAGGG TGGACACTCC GCCGGCGGAG GCCGAGGGCT

18781  ACCTGCTGAC AGGGAACGCC TCGGCCGTTG TCTCCGGGCG TATTTCCTAC ACCTTCGGCC

18841  TTGAGGGGCC TGCGGTGACG GTGGACACGG CGTGCTCGTC GTCGCTGGTG GCGCTGCACC

18901  TGGCGGTGCA GGCGCTGCGC CGTGGCGAGT GCTCGCTGGC GGTCGTCGGT GGTGTGGCCG

18961  TCATGTCGGA CCCGAAGGTC TTCGTCGAGT TCAGCCGGCA GCGCGGACTG GCCAGGGACG

19021  GCCGGTCCAA GGCTTTTGCG GCGTCAGCGG ATGGTTTCGG CTTCGCCGAG GGAGTTTCGC

19081  TGCTCTTGCT GGAGCGGTTG TCGGATGCGC GGCGGTTGGG TCATCGGGTG TTGGCGGTGG

19141  TGCGGGGGAG TGCGGTCAAT CAGGATGGTG CGTCCAATGG TCTGGCGGCG CCGAATGGTC

19201  CGTCGCAGCA GCGGGTGATT CGTGCGGCGT TGGCTGACGC GGGTCTGGCT CCTGCCGATG

19261  TGGATGTGGT GGAGGCGCAT GGTACGGGGA CGCGGTTGGG TGATCCGATC GAGGCTCAGG

19321  CGTTGCTGGC GACGTATGGG CAGGGGCGTA CCAGTGGGCG TCCGGTGTGG CTGGGGTCGG

19381  TGAAGTCGAA CATCGGTCAT ACGCAGGCGG CGGCCGGTGT GGCTGGTGTG ATGAAGATGG

19441  TGCTGGCTCT GGAGCGGGGT GTGGTGCCGA AGACGTTGCA CGTGGATGAG CCGTCTCCGC

19501  ATGTGGACTG GTCGACCGGT GCGGTGGAGT TGCTGACTGA AGAGCGGCCG TGGGAGCCGG

19561  AGGCTGAGCG TCTTCGTCGG GCAGGCATTT CCGCCTTCGG TGTCAGTGGC ACGAATGCGC

19621  ATGTGATCGT GGAGGAGGCA CCTGCGGAAC CGGAACCGGA GCCGGAGCCG GAACTCGTG

19681  TGGTTGCTGC CGGTGATCTG GTGGTGCCGT GGGTGGTGTC CGGGCGGGAT GCGGGGGCGT

19741  TGCGTGCACA GGCGGCACGC TTGGCTGCGC ATGTGTCGAG CACGGGTGCG GGTGTGGTTG

19801  ATGTGGGCTG GTCGTTGGTG GCCACGAGGT CGGTGTTCGA GCACCGGGCG GTGATGGTCG
```

-continued

```
19861  GCACTGATCT TGATTCCATG GCGGGTCGT TGGCCGGGTT TGCTGCGGGT GGGGTTGTGC
19921  CGGGGGTGGT GTCGGGTGTG GCTCCGGCTG AGGGTCGTCG TGTGGTGTTC GTCTTTCCTG
19981  GTCAGGGTTC GCAGTGGGTG GGGATGGCGG CTGGGTTGCT GGATGCGTGT CCGGTGTTCG
20041  CGGAGGCGGT GGCGGAGTGT GCCGCGGTGC TGGACCCGTT GACCGGTTGG TCGCTGGTCG
20101  AGGTGTTGCG CGGTGGTGAG GCTGTTCTTG GCGGGGTTGA TGTGGTGCAG CCGGCGTTGT
20161  GGGCGGTGAT GGTGTCACTG GCTCGGACCT GGCGGTATTA CGGTGTGGAG CCTGCTGCGG
20221  TTGTGGGGCA TTCGCAGGGT GAGATTGCTG CGGCTTGTGT GGCTGGGGGG TTGAGTCTGG
20281  CCGATGGTGC GCGGGTGGTG GTGTTGCGGA GCCGGGCGAT CGCCCGGATC GCCGGTGGGG
20341  GCGGCATGGT CTCCGTCAGT CTCCCGGCCG GCCGTGTCCG CACCATGCTC GACACCTACG
20401  GCGGCCGGTT GTCGGTGGCT GCGGTCAACG GCCCGTCCTC GACCGTGGTG TCCGGTGACG
20461  CCCAGGCCCT GGATGAGTTG TTGGCCGGCT GTGAGCGGGA GGGGGTCCGG GCTCGTCGTG
20521  TCCCGGTGGA CTATGCCTCC CACTCCGCGC AGATGGACCA GTTACGCGAT GAGCTGCTGG
20581  AAGCGCTGGC GGACATCACT CCGCAACACT CCAGCGTTCC GTTCTTCTCG ACGGTGACGG
20641  CGGACTGGCT GGACACGACC GCTCTGGATG CGGGGTACTG GTTCACGAAT CTGCGGGAGA
20701  CGGTCCGGTT CCAGGAAGCC GTCGAAGGGC TTGTGGCTCA GGGGATGGGC GCGTTCGTCG
20761  AGTGCAGCCC ACACCCCGTC CTCGTCCCCG GTATCGAGCA GACCCTCGAC ACCGTGGAAG
20821  CCGATGCTGT GGCGCTGGGT TCGCTACGGC GTGATGAGGG CGGCCTGGGA CGGTTCCTCA
20881  CGTCCCTCGC GGAAGCCTTC GTCCAGGGCG TCCCGGTCGA CTGGTCCCGC ACCTTCGAGG
20941  GTGCGAGCCC CCGCACCGTC GACCTGCCCA CCTATCCCTT CCAACGGCAA CGTTTCTGGT
21001  TGGAGGGATC CCCGGCGTTG TCTTCGAACG GCGTCGAGGG TGAGGCGGAC GTCGCGTTCT
21061  GGGATGCGGT CGAGCGCGAG GACTCGGCGG TTGTAGCCGA GGAGTTGGGG ATCGACGCCA
21121  AGGCTCTGCA CATGACATTG CCGGCCTTGT CGTCGTGGCG GCGGCGTGAG CGGCAGCGTC
21181  GGAAGGTGCA GCGCTGGCGT TACCGGGTGG AGTGGAAGCG TCTCCCGAAT TCGCGGGCAC
21241  AGGAGTCGCT GCAGGGCGGC TGGTTGCTCG TCGTCCCGCA GGGCCGTGCC GGCGATGTCC
21301  GCGTCACTCA GTCGGTGGCG GAGGTGGCGG CCAAGGGTGG TGAAGCCACG GTCCTGGAGG
21361  TCGACGCCCT GCATCCCGAC CGCGCAGCAT ACGCCGAGGC CCTCACCCGG TGGCCGGGTG
21421  TGCGGGGTGT GGTGTCGTTC CTGGCGTGGG AGGAGCAGGC CCTTGCCGAA CACCCCGTTC
21481  TGTCTGCGGG TCTGGCGGCA TCGCTGGCGT TGGCCCAGGC GTTGATCGAT GTCGGCGGGT
21541  CCGGTGAGTC GGCGCCGCGT CTGTGGCTGG TCACGGAAGC TGCCGTCGTG ATCGGTGCTG
21601  CCGACACCGG TGCGGTGATC GACCCCGTAC ACGCGCAGCT GTGGGGCTTC GGCCGTGTCC
21661  TTGCTCTGGA ACACCCCGAA TTGTGGGGCG GGCTGATCGA CCTGCCCGCT GTGGCAGGCG
21721  AGCCTGGTTC GATTACCGAC CACGCGCATG CCGACCTACT GGCCACGGTC CTGGCCACGA
21781  TGGTGCAGGC TGCTGCCCGA GGCGAGGACC AGGTCGCGGT CCGGACGACC GGTACTTACG
21841  TACCCAGGCT GGTGCGTTCA GGCGGCAGTG CACACTCGGG TGCGCGGAGG TGGCAGCCGC
21901  GCGACACCGT ACTGGTCACC GGCGGGATGG GACCGCTGAC CGCCCACATC GTCCGTTGGC
21961  TGGCTGACAA CGGTGCCGAC CAGGTAGTAC TCCTGGGAGG TCAGGGAGCA GACGGCGAGG
22021  CCGAGGCGCT GAGGGCCGAG TTCGACGGGC ACACGACGAA GATCGAACTC GCGGACGTGG
22081  ACACCGAGGA CAGCGACGCG CTGCGGTCCT TGCTCGACCG CACGACCGGC GAACACCCGC
22141  TGCGCGCGGT CATCCATGCG CCGACCGTGG TCGAGTTCGC CTCGGTGGCC GAGTCGGACC
22201  TGGTGCGATT CGCCCGCACC ATCAGCAGCA AGATCGCCGG CGTCGAGCAG CTCGACGAGG
```

-continued

```
22261  TGCTGAGCGG CATCGACACG GCGCACGACG TGGTCTTCTT CTCCTCCGTC GCGGGCGTCT
22321  GGGGAAGCGC GGGGCAGAGC GCCTACGCGG CGGGCAACGC CTTCCTCGAC GCCGTCGCCC
22381  AGCACCGCCG TCTGCGCGGA CTGCCCGGTA CGTCGGTGGC CTGGACTCCG TGGGACGACG
22441  ATCGATCCCT TGCCTCCCTC GGTGACTCGT ACCTCGACCG ACGAGGACTG CGAGCACTGT
22501  CCATACCCGG CGCGCTCGCC TCCCTCCAGG AAGTGCTCGA CCAGCACGAG GTCCACGCCG
22561  TGGTGGCGGA TGTCGACTGG GAGCGGTTCT ACGCCGGCTT CAGTGCCGTC CGGCGCACTT
22621  CCTTCTTCGA CGACGTGCAC GACGCCCACC GGCCGGCCCT GTCCACGGCT GCGACCAACG
22681  ACGGACAGGC CCGGGACGAG GACGGCGGTA CGGAACTCGT ACGACGTCTG CGTCCGCTGA
22741  CCGAGACGGA GCAACAGCGA GAGCTCGTGT CGCTCGTCCA GAGTGAAGTC GCTGCCGTCC
22801  TAGGCCACTC CTCCACCGAC GCGGTCCAGC ACAGCGCGC GTTCCGAGAG ATCGGGTTCG
22861  ACTCACTGAC AGCGGTCCAG CTCCGGAACC GGCTTACGGC CACCACGGGC ATGCGCCTTC
22921  CGACAACGCT GGTCTTCGAC TACCCGACCA CCAACGGACT CGCCGAGTAC CTGCGCTCCG
22981  AACTGTTCGG TGTGTCCGGC GCACCAGCTG ACCTCTCCGT CGTCCGGAAC GCGGATGAGG
23041  AGGACGACCC CGTCGTCATC GTGGGGATGG CCTGCCGGTT CCCGGGCGGG ATCGATACGC
23101  CGGAAGCCTT CTGGAAGCTG CTCGAAGCGG GCGGCGATGT CATCTCCGAA CTTCCGGCCA
23161  ACCGCGGCTG GGACATGGAG CGACTCCTGA ACCCGGACCC CGAGGCGAAG GGCACCAGCG
23221  CCACACGCTA CGGCGGTTTC CTCTACGACG CCGGGGAGTT CGACGCCGCC TTCTTCGGTA
23281  TCTCGCCGCG TGAGGCGTTG GCGATGGACC CGCAGCAACG GCTGCTGCTG GAAACCGTCT
23341  GGGAGCTCAT CGAGAGCGCC GGCGTGGCGC CCGACTCGCT CCACCGGAGC CGGACCGGCA
23401  CGTTCATCGG CAGCAACGGC CAGTTCTACG CACCGCTGCT GTGGAACTCC GGCGGTGATC
23461  TGGAGGGCTA CCAAGGCGTG GGCAACGCCG GCAGCGTCAT GTCCGGCCGC GTCGCCTACT
23521  CCCTCGGTCT TGAGGGGCCT GCGGTGACGG TGGATACGGC GTGTTCGTCG TCGCTGGTGG
23581  CACTGCACCT GGCGGTGCAG GCGCTGCGCC GTGGCGAGTG CTCACTCGCC ATAGCCGGCG
23641  GTGTGACGGT GATGTCCACA CCGGACAGCT TCGTTGAGTT CTCACGGCAA CAGGGCCTTT
23701  CCGAGGACGG CCGTTGCAAG GCGTTCGCGA GCACAGCCGA TGGTTTCGGC CTCGCCGAGG
23761  GCGTTTCGGC GCTGTTGGTG GAGCGGTTGT CGGATGCGCG GCGGTTGGGT CATCGGGTGT
23821  TGGCGGTGGT GCGGGGGAGT GCGGTCAATC AGGATGGTGC GTCGAATGGG TTGACGGCGC
23881  CGAATGGTCC GTCGCAGCAG CGGGTGATTC GTGCGGCGTT GGCTGACGCG GGTCTGGCTC
23941  CTGCTGATGT GGATGTGGTG GAGGCGCATG GTACGGGGAC GCGGTTGGGT GATCCGATCG
24001  AGGCTCAGGC GTTGTTGGCG ACGTATGGGC AGGGTCGTGC GGGTGGGCGT CCGGTGGTGT
24061  TGGGGTCGGT GAAGTCGAAC ATCGGGCATA CGCAGGCGGC GGCTGGCGTG GCTGGTGTGA
24121  TGAAGATGGT GCTGGCGCTG GAGCGGGGTG TGGTGCCGAA GACGTTGCAT GTGGATGAGC
24181  CGTCACCGCA TGTGGACTGG TCGGCTGGTG AGGTGGAGTT GGCGGTTGAG GCGGTGCCGT
24241  GGTCGCGGGG TGGGCGGGTG CGGCGGCTG GTGTGTCGTC GTTCGGATC AGTGGCACGA
24301  ATGCGCATGT GATTGTGGAG GAGGCGCCTG CGGAGCCGGA GCCGGAGCCG GAACTCGTG
24361  TGGTTGCTGC TGGTGATCTG GTGGTGCCGT GGGTGGTGTC CGGGCGGGAT GCGGGGGCGT
24421  TGCGTGAGCA GGCGGCCCGG TTGGCTGCGC ACGTGTCGAG CACGGGTGCG GGTGTGGTTG
24481  ATGTGGGGTG GTCGTTGGTG GCCACGAGGT CGGTGTTCGA GCACCGGGCG GTGATGGTCG
24541  GCAGTGAACT CGATTCCATG GCGGAGTCGT TGGCTGGCTT CGCTGCGGGT GGGGTTGTGC
24601  CGGGGGTGGT GTCGGGTGTG GCTCCGGCTG AGGGTCGTCG TGTGGTGTTC GTCTTTCCTG
```

-continued

```
24661  GTCAGGGTTC GCAGTGGGTG GGGATGGCGG CTGGGTTGCT GGATGCGTGT CCGGTGTTCG
24721  CGGAGGCGGT GGCGGAGTGT GCCGCGGTGC TGGATCCGGT GACGGGTTGG TCGCTGGTCG
24781  AGGTGTTGCG CGGTGGTGGT GAGGCTGTTC TTGGGCGGGT TGATGTGGTG CAGCCGGCGT
24841  TGTGGGCGGT GATGGTGTCA CTGGCCCGGA CCTGGCGGTA TTACGGTGTG GAGCCTGCTG
24901  CGGTTGTGGG GCATTCGCAG GGTGAGATCG CTGCGGCTTG TGTGGCTGGG GGGTTGAGTC
24961  TGGCCGATGG TGCGCGGGTG GTGGTGTTGC GGAGCCGGGC GATCGCCCGG ATCGCTGGTG
25021  GGGGCGGCAT GGTCTCGGTC GGTCTTTCAG CTGAGCGTGT CCGCACCATG CTCGACACCT
25081  ACGGTGGCCG GGTTTCGGTC GCGGCGGTCA ATGGCCCGTC CTCGACCGTC GTGTCCGGTG
25141  ACGTCCAGGC CCTGGATGAG TTGTTGGCCG GTTGTGAGCG GGAGGGTGTC CGGGCTCGTC
25201  GTGTCCCGGT GGACTATGCC TCCCACTCCG CGCAGATGGA CCAGTTACGC GATGAGCTGC
25261  TGGAAGCGCT GGCGGACATC ACTCCGCAAC ATTCCAGTGT TCCGTTCTTC TCGACGGTGA
25321  CGGCGGACTG GCTGGACACG ACCGCTCTGG ATGCGGGGTA CTGGTTCACG AATCTGCGGG
25381  AGACGGTCCG GTTCCAGGAA GCCGTCGAAG GGCTCGTGGC TCAGGGGATG GGCGCGTTCG
25441  TCGAGTGCAG CCCGCACCCC GTCCTCGTCC CCGGTATCGA GCAGACCCTC GACGCCCTCG
25501  ACCAGAACGC CGCCGTACTC GGCTCCCTGC GGCGTGACGA AGGCGGCCTG GACCGACTCC
25561  TCACATCCCT CGCGGAAGCC TTCGTCCAAG GCGTTCCCGT CGACTGGACC CACGCCTTCG
25621  AAGGCATGAC CCCCCGCACC GTCGACCTGC CCACCTACCC CTTCCAACGA CAGCACTACT
25681  GGCCCAAGCC CGCACCGGCC CCCGGCGCGA ACCTGGGCGA CGTGGCGTCC GTGGGCCTCA
25741  CCGCGGCCGG CCACCCCCTT CTGGGCGCGG TCGTGGAGAT GCCCGACTCC GACGGGTTGG
25801  TGCTCACCGG GCAGATCTCC CTGCGGACCC ATCCCTGGCT CGCCGACCAC GAGGTGCTCG
25861  GATCGGTGCT CCTGCCGGGC ACCGCGTTCG TCGAGCTTGC CGTCCAGGCC GCCGACCGCG
25921  CCGGTTACGA CGTACTGGAC GAGCTGACGC TGGAGGCGCC CCTCGTGCTC CCCGACAGGG
25981  GCGGCATCCA GGTGCGTCTG GCCCTCGGGC CGTCCGAGGC AGACGGACGC CGGTCCCTCC
26041  AGCTGCACAG CAGGCCGGAG GAGGCTGCCG GGTTCCACCG CTGGACGAGG CACGCGAGTG
26101  GATTCGTCGT TCCCGGCGGT ACCGGGGCGG CGCGGCCCAC CGAGCCGGCC GGCGTGTGGC
26161  CGCCCGCAGG TGCCGAGCCG GTCGCTCTCG CATCGGACCG GTACGCCCGG CTCGTCGAGC
26221  GCGGCTACAC CTACGGCCCC TCCTTCCAGG GGCTGCACAC CGCATGGCGC CACGGGGACG
26281  ACGTGTACGC GGAAGTGGCG CTGCCAGAAG GAACACCGGC CGACGGCTAC GCCCTGCATC
26341  CGGCCCTGCT GGACGCGGCG GTCCAGGCCG TCGGACTCGG CTCGTTCGTC GAGGATCCCG
26401  GCCAGGTGTA CCTGCCGTTC CTCTGGAGCG ACGTGACGCT GCACGCGACC GGGGCCACGT
26461  CCCTGCGGGT GAGGGTTTCA CCGGCCGGTC CCGACACCGT TGCGCTGGCC CTCGCCGACC
26521  CGGCCGGGGC GCCGGTGGCC ACGGTGGGCG CCCTCCGTCT GCGTACGACG TCCGCGGCGC
26581  AGCTCGCCCG TGCGCGCGGG AGCGCGGAAC ACGCGATGTT CCGCGTGGAG TGGGTGGAGG
26641  AGGGCTCGGC CGCGGACCGG TGCCGGGGCG CGCGCGGCGG GACGACGTAC GAGGGGGAAC
26701  GCGCCGCCGA GGCCGGGGCC GCCGCTGGTA CCTGGGCCGT ACTCGGCCCC CGGGTGCCGG
26761  CCGCCGTCCG GACGATGGGC GTGGATGTCG TCACCGCCCT CGACACGCCG GACCACCCCG
26821  CGGACCCGCA GAGCCTCGCG GACCTGGCGG CGCTCGGGGA CACCGTTCCC GACGTGGTCG
26881  TCGTGACCAG CCTCCTGAGC CTCGCCTCCG GAGCGGATTC CCCCTAGGG AACCGGCCCC
26941  GGCCGACCGC CGCCGAGCAG GACACCGCCG CCACGGTCGC CGGCGTCCAC AGCGCACTCC
27001  ACGCGGCCCT GGACCTGGTG CAGGCATGGC TGGCCGACGA ACGCCACACC GCCTCCCGGC
```

-continued

```
27061  TGGTGCTCGT CACCCGGCAC GCGATGACCG TCGCCGAGTC CGACCCCGAG CCTGACCTGC
27121  TCCTCGCCCC GGTGTGGGGA CTCGTGCGGT CCGCCCAGGC CGAGAACCCC GGCCGCTTCG
27181  TGCTCGCCGA CATCGACGGC GACGAGGCAT CCTGGGATGC TCTGCCCCGA GCCGTCGCCT
27241  CGGCCGCATC GGAGGTGGCG ATACGGGCCG GCGCCGTGTA CGTACCGCGG CTGGCCCGCG
27301  CCACGGACGA GGGACTGGTC GTGGCCGACG AGGCTGCGGG GCCCTGGCGG CTGGACGTCA
27361  CGGAAGCGGG CACCCTGGCG AACCTCGCCC TGGTGCCGTG CCCGGACGCC TCCCGCCCGC
27421  TGGGCCCCGA CGAGGTACGG ATCGCCGTCC GTGCCGCCGG GGTCAACTTC CGGGACGTCC
27481  TCCTGGCCCT GGGCATGTAC CCGGACGAGG GGCTCATGGG CGCGGAGGCG GCGGGCGTCG
27541  TCACCGAGGT CGGCGGGGGC GTCACGACGC TCGCGCCAGG TGACCGGGTG ATGGGCCTGG
27601  TGACCGGTGG ATTCGGGCCG GTGGCCGTGA CGCACCACCG GATGCTCGTA CGGATGCCGC
27661  GTGGCTGGTC CTTCGCCGAG GCCGCGTCGG TGCCGGTGGC GTTCCTGACC GCGTACTACG
27721  CCCTGCACGA CCTGGCAGGC CTGCGCGGCG GCGAGTCGGT GCTGGTGCAC TCCGCTGCGG
27781  GCGGTGTCGG CATGGCGGCC GTGCAGTTGG CACGGCACTG GGATGCCGAG GTGTTCGGCA
27841  CCGCGAGCAA GGGCAAGTGG GACGTTCTCG CGGCGCAGGG CCTCGACGAG GAGCACATCG
27901  GCTCGTCCAG GACGACCGAG TTCGAGCAGC GCTTCCGCGC GACCAGTGGT GGGCGCGGGA
27961  TCGATGTCGT CCTGAATGCC CTCTCGGGTG ACTTCGTCGA CGCCTCGGCG CGTCTCCTGC
28021  GCGAGGGCGG CCGGTTCGTC GAGATGGGCA AGACCGACAT CCGTACCGAC CTCGGCGTCG
28081  TCGGGCGGA CGGCGTCCCG GACATCCGGT ACGTCGCCTT CGACCTCGCC GAGGCGGGTG
28141  CCGAGCGGAT CGGGCAGATG CTCGACGAGA TCATGGCGCT CTTCGACGCC GGTGTCCTGC
28201  GGTTGCCGCC GTTGCGCGCC TGGCCGGTGC GGCGCGCCCA CGAGGCACTG AGGTTCGTCA
28261  GCCAGGCACG TCATGTGGGC AAGGTCGTCC TCACCGTCCC GGCCGCGCTC GACGCCGAGG
28321  CAACCGTGCT GATCACCGGG GCGGGCACGC TGGGAGCCCT GGTCGCCCGC CACCTCGTCA
28381  CCGAGCACGA CGTCCGCCGG CTGCTGCTGG TCAGCCGCAG CGGCGTCGCC CCCGACCTGG
28441  CGGCCGAACT CGGTGCGCTG GGCGCCGAGG TCACGGTGGC GGCCTGCGAC GTCGCCAACC
28501  GCAAGGCGCT CAAGGCCCTC CTGGAGGACA TACCGCCCGA GCATCCGGTC ACGGGCATCG
28561  TTCACACGGC CGGCGTGCTC GACGACGGTG TGGTGTCCGG GCTCACCCCT GAACGGGTGG
28621  ACACCGTCCT CAAACCCAAG GTGGACGCGG CCCTGACCCT GGAGTCAGTG ATCGGCGAAC
28681  TGGACCTCGA CCCGGCCCTG TTCGTGATCT CTCTCATCGG AGCGAGCATG CTGGGCGGGC
28741  CCGGCCAGGG CAGTTACGCC GCGGCCAATC AGTTCCTGGA CACCCTCGCC CGACACCGGG
28801  CGCGCCGCGG GCTCACCTCC GTGTCACTCG GCTGGGGGCT GTGGCACGAG GCCAGCGGTC
28861  TCACCGGCGG CCTGGCCGAC ATCGACCGTG ACCGGATGAG CCGGGCGGGG ATCGCGCCCA
28921  TGCCGACCGA CGAGGCCCTG CACCTGTTCG ACAGGGCAAC GGAACTCGGC GATCCGGTAC
28981  TCCTGCCGAT GCGCCTGAAC GAGGCCGCGC TGGAGGACCG GGCCGCGGAC GGAACACTGC
29041  CGCCGCTGCT GAGTGGTCTG GTCCGGGTGC GGCACAGGCC GTCGGCGCGG GCAGGTACCG
29101  CGACCGCCGC CCCCGCCACC GGCCCCGAGG CGTTCGCCCG GGAGCTGGCG GCGGCACCGG
29161  ACCCACGTCG TGCCCTGCGC GACCTCGTCC GCGGCCACGT CGCCCTGGTG CTCGGACACA
29221  GTGGCCCCGA GGCCATCGAC GCCGAACAGG CCTTCCGGGA CATCGGTTTC GACTCCCTGA
29281  CCGCAGTCGA ACTCAGAAAC CGGCTGAACG CCGAGACCGG CCTCCGCTTG CCCGGCACGC
29341  TCGTGTTCGA CTACCCCAAC CCGAGCGCGC TCGCCGATCA CCTGCTCGAA CTCCTCGCTC
29401  CCGCGACACA ACCCACCGCA GCCCCGCTGC TCGCCGAACT GGAACGGGTG GAACAACTCC
```

-continued

```
29461  TGTCTGCGGC CGCGTCACCC GGCGGACCGG CATCCGCGGT GGACGAGGAG ACGCGCACGC
29521  TCATCGCCAC ACGGCTGGCC ACCCTTGCCT CGCAGTGGAC ACACCTCCCG GTCGGTTCGC
29581  CGGGCAACGC GGACAACCGC AGCGGCCCCG GCGAGTCCGG GCAGGCCCAG GAATCCGGAG
29641  CAACCGGGGA GCACACGGCG GCGTGGACGT CGGACGACGA TCTCTTCGCC TTCCTCGACA
29701  AGCGGTTGGA GACGTGATGG CCGCCGGCCG AGTCAGCGAG TCCTTTCGTC CTTCTGCTGG
29761  GGAAAACGAC GCACCGGGAG GTTTTGGTGG CTGAGGCGGA GAAGCTGCGC GAATACCTGT
29821  GGCGCGCCAC GACCGAACTC AAGGAGGTCA GCGATCGACT CCGCGAGACC GAGGAACGGG
29881  CCCGAGAGCC GATCGCCATC GTGGGAATGA GCTGCCGGTT CCCCGGCGGC GGCGACGCCA
29941  CCGTCAACAC GCCCGAACAG TTCTGGGACC TGCTGAACAG CGGCGGTGAC GGCATCGCGG
30001  GTCTACCCGA GGACCGCGGG TGGGACTTGG GGCGCCTGTA CGATCCCGAT CCGGACCGGG
30061  CCGGTACGTC GTACGTGCGT GAGGGCGGTT TCCTGTACGA CTCGGGGGAG TTCGACGCCG
30121  CCTTCTTCGG GATCTCGCCG CGTGAGGCGT TGGCGATGGA CCCGCAGCAG CGGTTGCTGC
30181  TGGAGACGTC CTGGGAGGCA TTCGAGAGCG CCGGTATCAA GCGCGCCGCT CTGAGAGGCA
30241  GCGACACCGG CGTGTACATC GGCGCGTGGA GCACCGGCTA TGCCGGCAGC CCCTACCGCC
30301  TGGTCGAAGG CCTGGAAGGC CAGCTCGCCA TCGGCACCAC ACTAGGGGCC GCTTCGGGGC
30361  GTGTTGCTTA CACGTTCGGT CTTGAGGGGC CTGCGGTGAC GGTGGATACG GCGTGTTCGT
30421  CGTCGTTGGT GGCGTTGCAT CTGGCGGTGC AGGGGTTGCG GCGGGGTGAG TGTTCGCTGG
30481  CGTTGGTGGG TGGGGTGACG GTGATGTCGT CGCCGGTGAC GTTGACGACG TTCAGTCGGC
30541  AGCGGGGTTT GTCGGTGGAT GGGCGGTGCA AGGCGTTCCC GGCTTCGGCG GATGGTTTTG
30601  GTGCTGCCGA GGGTGTGGGT GTGTTGTTGG TGGAGCGGTT GTCGGATGCG CGGCGGTTGG
30661  GTCATCGGGT GTTGGCGGTG GTGCGGGGGA GTGCGGTCAA TCAGGATGGT GCGTCGAATG
30721  GGTTGACGGC GCCGAATGGT CCGTCGCAGC AGCGGGTGAT CCGTGCGGCG TTGGCTGACG
30781  CGGGTCTGGC TCCTGCTGAT GTGGATGTGG TGGAGGCGCA TGGTACGGGG ACGCGGTTGG
30841  GTGATCCGAT CGAGGCTCAG GCGTTGTTGG CGACGTATGG CAGGGGCGT GCGGGTGGGC
30901  GTCCGGTGTG GCTGGGGTCG GTGAAGTCGA ACATCGGGCA TACGCAGGCG GCGGCCGGTG
30961  TGGCTGGTGT GATGAAGATG GTGCTGGCGC TGGGGCGGGG TGTGGTGCCG AAGACGTTGC
31021  ATGTGGATGA GCCGTCACCG CACGTGGACT GGTCGGCCGG TGCGGTGGAG TTGCTGACTG
31081  AAGAGCGGCC GTGGGAGCCG GAGGCTGAGC GTCTTCGTCG GGCAGGCATC TCCGCCTTCG
31141  GTGTCAGTGG CACGAACGCG CATGTGATCG TGGAGGAGGC GCCTGCGGAA CCGGAGCCGG
31201  AGCCGGGAAC TCGTGTGGTT GCTGCCGGTG ATCTGGTGGT GCCGTGGGTG GTGTCCGGGC
31261  GGGATGCGAG GGCGTTGCGT GCACAGGCGG CACGCTTGGC TGCGCACGTG TCGGGTGTAA
31321  GTGCGGTCGA TGTGGGCTGG TCATTGGTGG CCACGAGGTC GGTGTTCGAG CACCGGGCTG
31381  TTGCGATCGG CAGTGAACTC GACTCCATGG CGGGTTCGTT GGCCGGCTTC GCTGCGGGTG
31441  GGGTGGTGCC GGGGGTGGTG TCGGGTGTGG CTCCGGCTGA GGGTCGTCGT GTGGTGTTCG
31501  TCTTTCCTGG TCAGGGTTCG CAGTGGGTGG GGATGGCGGC TGGGTTGCTG GATGCGTGTC
31561  CGGTGTTCGC GGAGGCGGTG GCGGAGTGCG CTGCGGTGCT GGATCCGGTG ACGGGTTGGT
31621  CGCTGGTCGA GGTGTTGCAG GGCAGGGACG CGACTGTTCT TGGGCGGGTT GATGTGGTGC
31681  AGCCGGCGTT GTGGGCGGTG ATGGTGTCAC TGGCTCGGAC CTGGCGGTAT TACGGTGTGG
31741  AGCCTGCTGC GGTTGTGGGG CATTCGCAGG GTGAGATTGC TGCGGCTTGT GTGGCTGGGG
31801  GGTTGAGTCT GGCCGATGGT GCGCGGGTGG TGGTGTTGCG GAGCCGGGCG ATCGCCCGGA
```

```
31861  TCGCTGGTGG GGGCGGCATG GTCTCCGTCA GCCTGCCGGC CGGCCGTGTC CGCACCATGC
31921  TGGAGGAGTT CGACGGCCGG TTGTCGGTGG CTGCGGTCAA TGGCCCGTCC TCGACCGTGG
31981  TGTCCGGTGA CGTCCAGGCC CTGGATGAGT TGTTGGCCGG TTGTGAGCGG GAGGGTGTCC
32041  GGGCTCGTCG TGTCCCGGTG GACTATGCTT CCCACTCCGC GCAGATGGAC CAGTTACGCG
32101  ATGAGCTGCT GGAGGCGCTG GCGGACATCA CTCCGCAGGA CTCCAGTGTT CCGTTTTTCT
32161  CGACGGTGAC GGCGGACTGG CTGGGCACGA CTGCCCTGGG TGCGGGGTAC TGGTTCACGA
32221  ATCTGCGGGA GACGGTCCGG TTCCAGGAAG CCGTCGAAGG GCTTGTGGCT CAGGGGATGG
32281  GCGCGTTCGT CGAGTGCAGC CCGCACCCCG TCCTCGTCCC CGGTATCGAG CAGACCCTCG
32341  ACGCCCTCGA CCAGAATGCC GCCGTATTCG GCTCGCTGCG GCGTGACGAA GGCGGCCTGG
32401  ACCGGTTTCT CACGTCCCTC GCGGAAGCCT TCGTCCAGGG CGTTCCCGTC GACTGGTCCC
32461  GCGCCTTCGA AGGCGTGACC CCTCGCACCG TCGACCTGCC CACCTACCCC TTCCAACGAC
32521  AGCACTACTG GTTGATGGCG GAAGAGGCAC CGGTCTCTCA GCCCCCTCAC TCGGAGAACA
32581  GCTTCTGGTC GGTAGTGGCC GATGCGGATG CCGAGGCTGC TGCTGAACTT CTGGGTGTCG
32641  ATGTAGAGGC AGTCGAGGCT GTAATGCCGG CGTTGTCTTC GTGGCACCGG CAGAGCCAAC
32701  TTCGTGCCGA AGTCAACCAG TGGCGCTACG ACGTTGCGTG GAAGCGTCTG ACCACCGGGG
32761  CGCTGCCCGA AAAGCCGGGC AACTGGCTCG TCGTGACTCC AGCAGGAACC GACACCACGT
32821  TCGCTGAGTC GTTGGCGAGG ACGGCAGCCG CAGAACTGGG CGTATCCGTC AGCTTTGCGC
32881  AGGTGGACAC TGCTCATCCT GACCGGTCGC AATACGCGCA TGCGCTGCGT CAAGCCCTGA
32941  CCGGCCCGGA GAACGTCGAT CACCTCGTGT CCTTGCTGGC CCTGGACCAG GCCACTGACG
33001  ACCTCGCCGC CGCACCTTCC TGTCTTGCCG CGTCGCTGGT GTTGGCGCAG GCGTTGGTTG
33061  ATCTTGGCCG GGTTGGTGAG GGGCCGCGGT TGTGGCTGGT GACGCGGGGT GCGGTGGTTG
33121  CTGGTCCTTC GGATGCCGGT GCGGTGATTG ATCCGGTACA GGCGCAGGTG TGGGGTTTCG
33181  GGCGTGTTCT GGGTCTGGAG CATCCCGAGT TGTGGGGTGG GCTGATCGAC CTGCCGGTGG
33241  GGGTTGATGA GGAGGTGTGC CGGCGGTTCG TGGGTGTTGT GGCGTCGGCT GGTTTTGAGG
33301  ATCAGGTGGC GGTGCGTGGT TCGGGTGTGT GGGTGCGTCG TCTGGTGCGT GCTGTGGTGG
33361  ATGGTGGTGG GGGTGGTTGG CGGCCGCGTG GGACGGTGTT GGTCACGGGT GGTCTTGGTG
33421  GTTTGGGTGC GCATACGGCC CGGTGGTTGG TGGGTGGTGG GGCGGATCAT GTGGTTCTTG
33481  TGAGCCGTCG TGGTGGCAGT GCGCCTGGTG CTGGGGATCT GGTGCGGGAG CTGGAGGGGT
33541  TGGGCGGGGC TCGGGTGTCG GTGCGGGCCT GTGATGTGGC TGATCGTGTG GCGTTGCGGG
33601  CGTTGTTGTC GGATCTGGGT GAGCCGGTGA CGGCGGTGTT CCATGCGGCT GGTGTTCCTC
33661  AGTCGACGCC TTTGGCGGAG ATCTCTGTCC AGGAGGCGGC TGATGTGATG GCGGCCAAGG
33721  TGGCGGGTGC GGTGAATCTG GGTGAGTTGG TGGATCCCTG TGGTCTGGAG GCGTTTGTGT
33781  TGTTCTCCTC CAATGCCGGT GTGTGGGGCA GTGGGGGGCA GGCGGTGTAT GCGGCGGCGA
33841  ATGCGTTTCT TGATGCGTTG GCGGTGCGTC GTCGGGGTGT TGGTCTGCCG GCCACGAGTG
33901  TGGCGTGGGG GATGTGGGCT GGTGAGGGGA TGGCGTCGGT GGGTGGTGCG GCGCGGGAGT
33961  TGTCCCGTCG GGGGGTGCGG GCGATGGATC CCGAGCGTGC TGTGGCGGTG ATGGCTGATG
34021  CGGTGGGTCG TGGTGAGGCG TTCGTCGCGG TCGCTGATGT GGACTGGGAA CGTTTCGTCA
34081  CCGGTTTCGC TTCTGCCCGT CCCCGTCCGT TGATCAGTGA CCTGCCGGAG GTGCGTGCTG
34141  TTGTGGAGGG CCAGGTCCAG GGCCGGGGCC AGGGGTTGGG CTTGGTCGGT GAGGAGGAGT
34201  CGTCGGGGTG GTTGAAGCGG TTGTCGGGGT TGTCTCGTGT GCGGCAGGAG GAGGAGTTGG
```

-continued

```
34261 TGGAGTTGGT CCGTGCTCAG GCTGCCGTTG TTCTCGGGCA TGGTTCCGCG CAGGACGTCC
34321 CGGCTGAGCG GGCGTTCAAG GAGTTGGGTT TTGATTCCCT CACTGCTGTC GAGCTACGCA
34381 ACGGGCTGGC CGCGGCCACC GGGATCCGGC TGCCGGCCAC CATGGCATTC GATCATCCCA
34441 ACGCCACCGC CATCGCACGC TTCCTGCAGT CTCAGCTCCT TCCTGACGCC GAGAGCGAGT
34501 CGGCCGTGCC GTCTTCACCG GAAGACGAGG TCCGCCAGGC ATTGGCGTCC CTTTCCCTGG
34561 ACCAGCTGAA AGGCGCTGGG CTTCTTGACC CACTGCTCGC TCTGACACGC CTCCGGGAGA
34621 TCAACAGCAC GGTGCAGAAC CCTGAGCCGA CCACCGAATC GATCGACGAG ATGGATGGCG
34681 AGACGTGCTG CGCCTGGCGC TCGGCGAAAT CGACGGCTGA GCCACTGACC ACTGGAGCTG
34741 ACATGCCTGA CCCCACCGCC AAATATGTGG AAGCGCTCCG TGCGTCGCTC AAGGAGAACG
34801 AACGCCTGCG CCAACAGAAT CACTCGCTTC TCGCCGCCTC CCGTGAAGCG ATCGCCATCA
34861 CGGCGATGAG CTGCCGTTTC GGCGGGGGCA TCGACTCGCC CGAAGATCTC TGGCGCTTCC
34921 TGGCCGAAGG CCCGCGACGCG GTGGCGGGGC TTCCCGAGGA CCGCGGGTGG GATCTGGATG
34981 CCTTGTATCA CCCCGACCCG GAGAACCCCG GCACCACGTA CGTCCGGGAA GGCGCGTTCC
35041 GGTACGACGC AGCCCAGTTC GATGCGGGGT TCTTCGGGAT TTCGCCGCGT GAGGCGTTGG
35101 CGATGGACCC GCAGCAGCGG TTGCTGCTGG AGACATCCTG GGAGCTTTTC GAGCGTGCCG
35161 ATATCGATCC GTACACAGTC AGGGGAACGG CGACGGGGAT ATTCATCGGA GCCGGACATC
35221 AGGGCTATGG TCCCGACCCC AAGAGGGCTC CGGAGAGCGT GGCGGGTTAC CTGCTGACGG
35281 GAACGGCATC GGCCGTGCTG TCCGGGCGTA TTTCCTACAC GTTCGGTCTT GAGGGGCCTG
35341 CGGTCACGGT GGACACGGCG TGTTCGTCAT CGCTGGTGGC ACTGCACCTG GCGGTGCAGG
35401 CGCTGCGCCG GGGCGAGTGC TCACTCGCCA TAGCCGGCGG TGTGGCCGTC ATGTCGACCC
35461 CGGATGCCTT CGTGGAGTTC AGCCGCCAAC AGGGCATGGC AAGAGACGGC CGATGTAAGG
35521 CATTCGCCGC GGCAGCGGAC GGTATGGGAT GGGGCGAGGG AGTTTCGCTG CTCTTGCTGG
35581 AGCGGTTGTC GGATGCGCGG CGGTTGGGTC ATCGGGTGTT GGCGGTGGTG CGGGGGAGTG
35641 CGGTCAATCA GGATGGTGCG TCGAATGGCC TGGCGGCGCC GAATGGTCCG TCGCAGCAGC
35701 GGGTGATTCG TGCGGCGTTG GCTGACGCGG GTCTGGCTCC TGCCGATGTG GATGTGGTGG
35761 AGGCGCATGG TACGGGGACG CGGTTGGGTG ATCCGATCGA GGCTCAGGCG TTGCTGGCGA
35821 CGTATGGGCA GGGGCGTGCG GGTGGGCGTC CGGTGTGGCT GGGGTCGGTG AAGTCGAACA
35881 TCGGGCATAC GCAGGCGGCG GCTGGTGTGG CTGGTGTGAT GAAGATGGTG CTGGCGTTGG
35941 GGCGGGGTGT GGTGCCGAAG ACGTTGCATG TGGATGAGCC GTCACCGCAC GTGGACTGGT
36001 CGGCCGGTGC GGTGGAGTTG CTGACTGAAG AGCGGCCGTG GGAGCCGGAG GCTGAGCGTC
36061 TTCGTCGGGC AGGCATCTCC GCCTTCGGTG TCAGTGGCAC GAACGCGCAT GTGATCGTGG
36121 AGGAGGCGCC TGCGGAACCG GAGCCGGAGC CGGGAACTCG TGTGGTTGCT GCCGGTGATC
36181 TGGTGGTGCC GTGGGTGGTG TCCGGGCGGG ATGTGGGGGC GTTGCGTGAG CAGGCGGCAC
36241 GCTTGGCTGC GCACGTGTCG AGCACGGGTG CGGGTGTGGT TGATGTGGGC TGGTCGTTGG
36301 TGGCCACGAG GTCGGTGTTC GAGCACCGGG CGGTGATGGT CGGCACTGAT CTTGATTCCA
36361 TGGCGGGGTC GTTGGCCGGG TTTGCTGCGG GTGGTGTCGT CCCCGGGGTG GTGTCGGGTG
36421 TGGCGCCGGC TGAGGGTCGT CGTGTGGTGT TCGTCTTTCC TGGTCAGGGT TCGCAGTGGG
36481 TGGGGATGGC GGCTGGGTTG CTGGATGCGT GCCCGGTGTT CGCGGAGGCG GTGGCGGAGT
36541 GTGCCGCGGT GCTGGATCCG GTGACGGGTT GGTCGCTGGT CGAGGTGTTG CAGGGCAGGG
36601 ACGCGACTGT TCTTGGGCGG GTTGATGTGG TGCAGCCGGC GTTGTGGGCG GTGATGGTGT
```

```
36661  CACTGGCTCG GACCTGGCGG TATTACGGTG TGGAGCCTGC TGCGGTTGTG GGGCATTCGC

36721  AGGGTGAGAT TGCTGCGGCT TGTGTGGCTG GGGGGTTGAG TCTGGCCGAT GGTGCGCGGG

36781  TGGTGGTGTT GCGGAGCCGG GCGATCGCCC GGATCGCTGG TGGGGCGGC ATGGTCTCCG

36841  TCAGTCTCCC GGCCGGCCGT GTCCGCACCA TGCTCGACAC CTACGGCGGC CGGGTTTCGG

36901  TCGCGGCGGT CAACGGTCCG TCCTCGACCG TGGTGTCCGG TGACGTCCAG GCCCTTGATG

36961  AGTTGTTGGC CGGTTGTGAG CGGGAGGGTG TCCGGGCTCG TCGTGTCCCG GTGGACTATG

37021  CCTCCCACTC CGCGCAGATG GACCAGTTAC GCGATGAGCT GCTGGAGGCG CTGGCGGACA

37081  TCACTCCGCA GGACTCCAGT GTTCCGTTCT TCTCGACGGT GACGGCGGAC TGGCTGGACA

37141  CGACCGCTCT GGATGCGGGG TACTGGTTCA CGAATCTGCG GGAGACGGTC CGGTTCCAGG

37201  AAGCCGTCGA AGGGCTTGTG GCTCAGGGGA TGGGCGCGTT CGTCGAGTGC AGCCCGCACC

37261  CCGTCCTCGT CCCCGGTATC GAGCAGACCC TCGACGCCCT CGACCAGAAT GCCGCCGTAC

37321  TCGGCTCGCT GCGGCGTGAC GAAGGCGGCC TGGACCGACT TCTCACATCC CTCGCGGAAG

37381  CCTTCGTCCA AGGCGTTCCC GTCGATTGGA CCCACGCCTT CGAGGGCGTG ACCCCTCGCA

37441  CCGTCGACCT GCCCACCTAC CCCTTCCAAC GGCAACGTTT CTGGTTGGAC GGTTCGCCGG

37501  CATCGTCTGC GAATGGCGTT GACGGTGAGG CGGACGCCAT GATCTGGGAC GCGGTCGAGC

37561  GTGAGGACTC GGTCGCTGTA GCCGAGGAGT TGGGGATCGA CGCCGAGGCT TTGCACACGG

37621  TGTTGCCGGC CTTGTCGTCG TGGCGGCGGC GTCGGGTGGA GCATCGACGG CTTCAGGACT

37681  GGCGTTACCG GGTGGAGTGG AAGCCTTTCC CGGCCGCGCT TGATGAGGTG CTCGGTGGTG

37741  GCTGGTTGTT CGTGGTGCCG CGGGGCTTGG CGGATGATGG TGTGGTTGCG CGGGTGGTGG

37801  CTGCCGTCAC GGCGCGGGGT GGCGAGGTCA GTGTCGTGGA GCTCGATCCG ACCCGTCCTG

37861  ACCGCCGGGC TTATGCGGAG GCTGTCGCGG GCCGTGGTGT GAGCGGGGTC GTGTCGTTCT

37921  TGTCCTGGGA TGATCGGCGG CACTCGGAGC ATCCTGTTGT TCCCGCCGGT CTTGCCGCGT

37981  CGCTGGTGTT GGCGCAGGCG TTGGTTGATC TTGGCCGGGT TGGTGAGGGG CCGCGGTTGT

38041  GGCTGGTGAC GCGGGATGCG GTGGTCGCTG GTCCTTCGGA TGCCGGTGCG GTGATTGATC

38101  CGGTACAGGC GCAGGTGTGG GGTTTCGGGC GTGTTCTGGG TCTGGAGCAT CCCGAGTTGT

38161  GGGGTGGGCT GATCGACCTG CCGGTGGAGG CGCCCGAACC TGGCTCGACG TGCGACCACA

38221  CGTATGCCGA CCTGCTCGCC ACGGTTGTGG CGTCGGCTGG TTTTGAGGAT CAGGTGGCGG

38281  TGCGTGGTTC GGGTGTGTGG GTGCGTCGTC TGGTGCGTGC TGTGGTGGAT GGTGGTGGGG

38341  GTGGTTGGCG GCCGCGTGGG ACGGTGTTGG TCACGGGTGG TCTTGGTGGT TTGGGTGCGC

38401  ATACGGCCCG GTGGTTGGTG GGTGGTGGGG CGGATCATGT GGTGCTTGTG AGCCGTCGTG

38461  GTGGCAGTGC GCCTGGTGCT GGGGATCTGG TGCGGAGCT GGAGGGGTTG GGCGGGGCTC

38521  GGGTGTCGGT GCGGGCCTGT GATGTGGCTG ATCGTGTGGC GTTGCGGGCG TTGTTGTCGG

38581  ATCTGGGTGA GCCGGTGACG GCGGTGTTCC ATGCGGCTGG TGTTCCTCAG TCGACGCCTT

38641  TGGCGGAGAT CTCTGTCCAG GAGGCGGCTG ATGTGATGGC GGCCAAGGTG GCGGGTGCGG

38701  TGAATCTGGG TGAGTTGGTG GATCCCTGTG GTCTGGAGGC GTTTGTGTTG TTCTCCTCCA

38761  ATGCCGGTGT GTGGGGCAGT GGGGGGCAGG CGGTGTATGC GGCGGCGAAT GCGTTTCTTG

38821  ATGCGTTGGC GGTGCGTCGT CGGGGTGTTG GTCTGCCGGC GACGAGTGTG GCGTGGGGGA

38881  TGTGGGCTGG TGAGGGGATG GCGTCGGTGG GTGGTGCGGC GCGGGAGTTG TCCCGTCGGG

38941  GGGTGCGGGC GATGGATCCC GAGCGTGCTG TGGCGGTGAT GGCTGATGCG GTGGGGCGTG

39001  GTGAGGCGTT CGTCGCGGTC GCCGATGTGG ACTGGGAACG TTTCGTCACC GGTTTCGCCT
```

-continued

```
39061 CTGCCCGTCC CCGTCCGTTG ATCAGCGACC TCCCGGAGGT CCGTACCGCC CTGCGGAACC
39121 AGGAGCAGGA GCAACTCCAC GCCCCCGTCC CCGAGGACCG ATCGGCACAG CTTCTGCGGC
39181 GGCTGTCCAT GCTGTCTCCC GCCGGACGGG AAGCCGAACT GGTGAAGCTC GTCCGTACCG
39241 AGGCAGCCGC TGTTCTGGGG CACGGCTCCG CGCAGGACGT CCCGGCCGAG CGGGCGTTCA
39301 AGGAGCTGGG CTTCGACTCC CTCACCGCTG TTCAGCTACG CAACAGACTG GCCGCCGCCA
39361 CCGGCACCAG GCTCCCCGCC AGCGCCGTCT TCGACCACCC CCACGCTGCG GCTCTCGCCA
39421 GGTGGCTGCT CGCGGGGATG CGGCATGCCG ACGGTGGACA CGGTGGTGGG CACGCCGGTG
39481 GACCCGGGCC GGACGCCGAC GAAGGTCGGT CGGCCGGCGC TGGTCACAGC GGAATGCTGG
39541 CCGATCTGTA CCGGCGTTCC GCCGAGTTGG GCCGGAGCCG GGAGTTCATC GGGCTGCTGG
39601 CCGACACCGC GGCCTTCCGC CCGGTGTTCC ACGGGCCGGC GGACCTCGAC GCGCCGTTGG
39661 AGGCCGTTCC GCTGGCGGAC GGGGTGCGCA AACCGCAGTT GATCTGTTGC AGCGGGACCG
39721 CGCCGGTCGG CGGGCCGCAC GAGTTCGCGC GCCTGGCTTC GTTCTTCCGC GGCACTCGTG
39781 CGGTCTCGGC GCTTCCGCTG CCCGGCTACC TGCCCGGTGA GCAGTTGCCC GCGGACCTCG
39841 ACGCCGTGCT CGCCGCGCAG GCCGAGGCGG TCGAGAAGCA GACCGGGGGT GCGCCGTTCG
39901 TCCTGGTCGG CTACTCGGCG GCGGACTGA TGGCCCACGC ACTGGCCTGC CACCTGGCCG
39961 GGCGCGGCAC ACCGCCGAGC GGTGAGGTGC TGGTGGACGT CTATCCGCCG GGCCGGCAGG
40021 AACCGGTGTT CGGCTGGCAG AAGGAGCTCA CCGAGGGCAT GTTCGCCCAG GACTTCGTGC
40081 CCATGGACGA TACGCGGCTG ACGGCCCTCG GCACGTACGA CCGTCTCATG GGCGAGTGGC
40141 GGCCGGCGCC CTCCGGACTG CCCACCCTCC TGATCCGGGC CACCGAACCC ATGGCGGAGT
40201 GGACCGGGGC CATCGACTGG CGGGCCTCCT GGGAGTACGA CCACACCGCC GTCGACATGC
40261 CGGGGAACCA CTTCACGATC ATGCGCGAGC ACGCGGAGGA CGCGGCCCGG CACATCGACG
40321 TCTGGCTGAA GGGGCTCACC CCCTGACACC TGCCCGCACC CTGTGACTCC TGCCCGTACC
40381 GGCGTCCCGG TCCTCCCGAC CCGCGTGCGC AACGGACGAG TCGCTCAGGA GGTCCCCATC
40441 GGCATGCCCC GCTTTCCTCC CCCTCTCCGA ACGCATCGAC GACCCGATCC CCCTCAGGGA
40501 CCGGTGAAGG AGCGTGTTGC ACTCATGCAG GACATGCAAG GCGTACAGCC CGAACCAGCC
40561 AGTGTCGAAC ACGCGGCGGA CGCAGCTCGA ACAGAGCGAA CGGCGCACGG AAGCCGCCCA
40621 GGAGATGGAG GACAGCGAAC TGGGGCGCCG CCTGCAGATG CTCCGCGGCA TGCAGTGGGT
40681 CTTCGGCGCC AACGGCGATC CGTACGCCCG GCTGCTGTGT GGCATGGAGG ATGACCCGTC
40741 ACCTTTCTAC GACGCGATAC GGACCCTGGG CGAGCTGCAC CGGAGCAGGA CCGGAGCCTG
40801 GGTCACCGCC GACCCCGGGC TCGGGGCCG CATCCTCGCC GACCGGAAGG CTCGGTGCCC
40861 GGAAGGCTCG TGGCCGGTGC GGGCGAAGAC CGACGGGCTG GAGCAGTACG TGCTGCCCGG
40921 GCACCAGGCG TTCCTGCGGC TGGAGCGCGA GGAGGCCGAG CGACTGCGGG AGGTCGCGGC
40981 GCCGGTGCTG GGGGCCGCGG CGGTCGACGC GTGGCGCCCG CTGATCGACG AGGTCTGCGC
41041 GGGGCTCGCG AAGGGGCTGC CGGACACGTT CGACCTGGTC GAGGAGTACG CGGGGCTGGT
41101 GCCGGTCGAG GTGCTGGCGC GGATCTGGGG CGTCCGGAG GAGGACCGCG CCCGGTTCGG
41161 GCGTGACTGC CGGGCGCTCG CTCCCGCGCT GGACAGCCTC CTGTGTCCCC AGCAGTTGGC
41221 GCTGAGCAAG GACATGGCGT CCGCCCTGGA GGACCTGCGT CTCCTCTTCG ACGGCCTCGA
41281 CGCGACGCCG CGCCTCGCCG GCCCCGCCGA CGGTGACGGA ACGGCCGTGG CCATGCTCAC
41341 CGTTCTGCTC TGCACGGAGC CGGTGACCAC GGCGATCGGG AACACCGTGC TCGGGCTCCT
41401 TCCCGGGCAG TGGCCCGTGC CCTGCACCGG CCGGGTGGCT GCCGGGCAGG TTGCCGGGCA
```

-continued

```
41461  GGCGCTGCAC CGGGCGGTGT CGTACCGTAT CGCGACGCGG TTCGCCCGGG AGGACCTGGA
41521  GTTGGCGGGC TGCGAGGTCA AGTCCGGTGA CGAGGTGGTG GTCCTGGCCG GAGCGATCGG
41581  CCGGAACGGA CCGTCCGCAG CCGCCCCGCC TGCCCCACCG GGCCCAGCGG CCCCGCCCGC
41641  CCCGTCGGTC TTCGGTGCCG CCGCCTTCGA GAACGCGCTG GCCGAACCCC TCGTCCGGGC
41701  TGTGACGGGA GCGGCCCTCC AGGCCCTCGC GGAGGGGCCC CCCCGGCTGA CGGCGGCGGG
41761  ACCCGTCGTA CGACGGCGGC GTTCCCCTGT CGTCGGCGGG CTGCACCGGG CTCCGGTGGC
41821  CGCCGCATGA GCATCGCGTC GAACGGCGCG CGCTCGGCCC CCGCCGGCC CCTGCGCGTG
41881  ATGATGACCA CCTTCGCGGC CAACACGCAC TTCCAGCCGC TGGTTCCCCT GGCCTGGGCA
41941  CTGCGGACAG CCGGGCACGA GGTGCGCGTG GTGAGCCAGC CCTCGCTGAG CGACGTGGTG
42001  ACGCAGGCGG GGCTCACCTC GGTCCCGGTG GGCACCGAGG CTCCGGTCGA GCAGTTCGCG
42061  GCGACCTGGG GCGACGATGC CTACATCGGC GTCAACAGCA TCGACTTCAC CGGCAACGAC
42121  CCCGGCCTGT GGACGTGGCC GTACCTCCTG GGCATGGAGA CCATGCTGGT GCCGGCCTTC
42181  TACGAGTTGC TGAACAACGA GTCCTTCGTG GACGGCGTAG TCGAGTTCGC CCGTGACTGG
42241  CGGCCCGACC TGGTGATCTG GGAGCCGCTG ACGTTCGCCG GCGCGGTGGC GGCGCGCGTC
42301  ACCGGCGCGG CCCACGCCCG GCTGCCGTGG GGGCAGGAGA TCACCCTGCG CGGGCGGCAG
42361  GCGTTCCTCG CCGAGCGTGC CCTGCAACCG TTCGAGCACC GGGAGGATCC CACGGCCGAG
42421  TGGCTGGGCC GCATGCTCGA CCGGTACGGC TGCTCGTTCG ACGAGGAGAT GGTCACCGGG
42481  CAGTGGACCA TCGACACGCT GCCGCGCAGC ATGCGGCTGG AGCTGTCCGA GGAGCTGCGC
42541  ACCCTGGACA TGCGGTACGT GCCGTACAAC GGACCGGCGG TCGTACCCCC CTGGGTGTGG
42601  GAACCGTGCG AGCGGCCCCG GGTCTGTCTG ACGATCGGCA CCTCCCAGCG TGACTCCGGC
42661  CGGGACCATG TCCCCCTCGA CCACCTGCTC GACTCCCTCG CCGACGTGGA CGCGGAGATC
42721  GTGGCCACGC TCGACACCAC CCAGCAGGAG CGCCTGCGGG GCGCGGCCCC CGGCAACGTC
42781  CGGCTGGTGG ACTTCGTCCC GCTGCACGCG CTGATGCCGA CCTGCTCGGC GATCGTGCAC
42841  CACGGTGGTC CGGGCACGTG GTCGACGGCG GCGCTCCACG GCGTCCCGCA GATCATCCTG
42901  GACACCTCGT GGGACACACC GGTGCGGGCG CAGCGCATGC AGCAACTCGG GGCGGGCCTG
42961  TCGATGCCGG TGGGGAACT GGGCGTCGAG GCGCTGCGGG ACCGGGTCCT GCGGCTGCTG
43021  GGGGAGCCGG AGTTCCGCGC GGGCGCCGAG CGGATCCGGG CCGAGATGCT CGCGATGCCC
43081  GCCCCGGTG ACGTCGTACC GGACCTGGAA CGACTCACCG CGGAGCATGC CACCGGCGCG
43141  ATGGCGGGAA GGCGGTGAGA CGATGCGCGT ACTGCTGACC TGCTTCGCCA ACGACACCCA
43201  CTTCCACGGG CTGGTGCCGC TGGCGTGGGC GCTGCGGGCC GCCGGGCACG AAGTCCGCGT
43261  GGCCAGTCAG CCCGCCCTGT CCGACACGAT CACCCAAGCG GGACTGACCG CGGTGCCCGT
43321  GGGCCGGGAC ACCGCCTTCC TGGAGCTGAT GGGGGAGATC GGCGCGGACG TCCAGAAGTA
43381  CTCCACCGGC ATCGACCTGG GCGTCCGCGC GGAGCTGACG AGCTGGGAGT ACCTGCTCGG
43441  CATGCACACG ACCCTGGTGC CCACGTTCTA CTCGCTGGTC AACGACGAGC CGTTCGTCGA
43501  CGGGCTCGTC GCGCTGACCC GGGCCTGGCG GCCCGACCTC ATCCTGTGGG AGCACTTCAG
43561  CTTCGCCGGG GCGTTGGCGG CGCGGGCCAC CGGCACGCCC ACGCCCGCG TGCTGTGGGG
43621  GTCGGACCTC ATCGTCCGGT TCCGCCGGGA CTTCCTCGCG GAGCGGGCGA ACCGGCCCGC
43681  CGAGCACCGC GAGGACCCCA TGGCGGAGTG GCTGGGCTGG GCGGCCGAAC GGCTGGGCTC
43741  CACCTTCGAC GAGGAGCTGG TGACCGGGCA GTGGACGATC GACCCGCTGC CGCGGAGCAT
43801  GCGGCTGCCC ACCGGGACGA CGACGGTGCC GATGCGGTAC GTGCCGTACA ACGGGCGGGC
```

-continued

```
43861  CGTGGTCCCC GCATGGGTCC GGCAGCGTGC GCGGCGGCCC CGGATCTGCC TGACGCTCGG
43921  TGTGTCGGCC CGGCAGACCC TGGGCGACGG CGTGTCGCTG GCGGAGGTGC TGGCCGCGCT
43981  GGGCGACGTG GACGCGGAGA TCGTGGCCAC GCTGGACGCC TCCCAGCGCA AGCTCCTGGG
44041  GCCGGTGCCG GACAACGTCC GGCTGGTGGA CTTCGTGCCC CTGCACGCCC TGATGCCGAC
44101  CTGTTCGGCG ATCGTGCACC ACGGCGGCGC CGGTACCTGG CTGACGGCCG CCGTCCACGG
44161  CGTCCCGCAG ATCGTCCTCG GTGACCTCTG GACAACCTG CTGCGCGCCC GGCAGACACA
44221  GGCCGCGGGC GCGGGCCTGT TCATCCATCC GTCCGAGGTC ACCGCGGCCG GGCTCGGTGA
44281  GGGCGTGCGC CGGGTGCTGA CGGACCCTTC CATCCGGGCC GCCGCACAGC GCGTCCGGGA
44341  CGAGATGAAT GCAGAGCCGA CGCCGGGCGA GGTCGTCACG GTGCTGGAGC GGCTCGCCGC
44401  GAGCGGCGGA CGCGGACGAG GAGGCGGGAA CCATGCGGGC TGACACGGAG CCGACCACCG
44461  GGTACGAGGA CGAGTTCGCC GAGATCTACG ACGCCGTGTA CCGGGGCCGG GGCAAGGACT
44521  ACGCCGGCGA GGCGAAGGAC GTGGCGGACC TCGTGCGCGA CCGGGTGCCG GACGCGTCCT
44581  CCCTCCTGGA CGTGGCCTGC GGCACGGGCG CGCACCTGCG GCACTTCGCC ACGCTCTTCG
44641  ACGACGCCCG CGGTCTCGAA CTGTCCGCGA GCATGCTGGA CATCGCCCGC TCCCGCATGC
44701  CGGGCGTGCC GCTGCACCAA GGGGACATGC GATCCTTCGA CCTGGGGCCA CGCGTCTCCG
44761  CGGTCACCTG CATGTTCAGC TCCGTCGGCC ACCTGGCCAC CACCGCCGAA CTCGACGCGA
44821  CGCTGCGGTG CTTCGCCCGG CACACCCGGC CCGGCGGCGT GGCCGTCATC GAACCGTGGT
44881  GGTTCCCGGA GACCTTCACC GACGGCTACG TGGCGGGTGA CATCGTACGC GTCGACGGCC
44941  GGACCATCTC CCGGGTGTCC CACTCGGTAC GGGACGGCGG CGCCACCCGC ATGGAGATCC
45001  ACTACGTGAT CGCCGACGCC GAGCACGGTC CCCGGCACCT GGTCGAGCAC CACCGCATCA
45061  CGCTGTTCCC GCGGCATGCG TACACGGCCG CGTACGAGAA GGCGGGCTAC ACCGTCGAGT
45121  ACCTCGACGG CGGGCCCTCG GGCCGGGGGC TGTTCGTCGG CACCCGGACG TGAACCCGCC
45181  CGCGCACCGC CCGATCACCC TGCTCAACGC CGTTCACACG GATCACCGGA CCACGCGAAG
45241  GACCTTTCAC ATGTCGTACG ACGACCACGC GGTGCTGAA GCGATACTGC GGTGCGCCGG
45301  AGGTGACGAG CGCTTCCTGC TGAACACCGT CGAGGAATGG GGAGCCGCCG AGATCACCGC
45361  GGCGCTCGTG GACGAGTTGC TGTTCCGCTG CGAGATCCCG CAGGTGGGCG GTGAGGCGTT
45421  CATCGGCCTG GACGTCCTGC ACGGCGCCGA CCGGATCAGC CATGTGCTGC AGGTGACGGA
45481  CGGCAAGCCG GTCACGTCGG CGGAACCGGC CGGCCAGGAA CTGGGCGGCC GTACCTGGAG
45541  TTCACGCTCA GCGACCCTCC TGCGGGAGCT GTTCGGCCCG CCGTCCGGCC GCACCGCGGG
45601  GGGCTTCGGC GTCTCCTTCC TGCCCGACCT GCGCGGCCCG CGGACCATGG AGGGCGCGGC
45661  CCTGGCCGCC CGCGCCACCA ACGTGGTGCT GCACGCGACG ACCAACGAGA CGCCCCCACT
45721  GGACCGGCTG GCCCTGCGCT ACGAGTCCGA CAAGTGGGGC GGCGTCCACT GGTTCACCGG
45781  CCACTACGAC CGGCACCTGC GGGCCGTGCG CGACCAGGCG GTGCGGATCC TGGAGATCGG
45841  CATCGGCGGC TACGACGACC TGCTGCCGAG CGGCGCCCTCA CTGAAGATGT GGAAGCGCTA
45901  CTTCCCGCGC GGCCTGGTCT TCGGCGTGGA CATCTTCGAC AGTCGGCGTG CGACCAGCCG
45961  CGTGTCAAGA CGCTCCGCGG CCCGGCAGGA CGACCCGGAG TTCATGCGCC GCGTCGCCGA
46021  GGAGCACGGG CCGTTCGACG TCATCATCGA CGACGGCAGC CACATCAACG CACACATGCG
46081  GACGTCGTTC TCGGTGATGT TCCCCCACCT GCGCAACGGC GGCTTCTACG TCATCGAGGA
46141  CACCTTCACC TCCTACTGGC CCGGGTACGG AGGGCCATCC GGAGCCCGGT GCCCGTCCGG
46201  AACAACCGCG CTGGAGATGG TCAAGGGACT GATCGACTCG GTGCACTACG AGGAGCGGCC
```

-continued

```
46261  GGACGGCGCG GCCACGGCCG ACTACATCGC CAGGAACCTC GTCGGGCTGC ACGCCTACCA
46321  AACGACCTCG TCTTCCTCGA GAAGGGCGAT CAACAAGGAG GGCGGCATCC CCCACACCGT
46381  GCCCCGGGAG CCGTTCTGGA ACGACAACTA GCCACGGCCG CAACCAGAGC CGGAAACCGC
46441  ACCACTGTCC GCGCCACCTC GGAACCACCT CCAGCAAAGG ACACACCGCT GTGACCGATA
46501  CGCACACCGG ACCGACACCG GCCGACGCGG TACCCGCCTA CCCGTTCAGC CTGCCGCACG
46561  CCCTGGACCT CGACCCGCAC TACGCCGAAC TCCGCCGCGA CGAACCCGTC TCCAGGGTGC
46621  GCCTGCCCTA CGGCGAGGGC ACGGCCTGGC TGGTCACCCG CATGTCCGAC GCCCGTATCG
46681  TTCTGGGCGA CTCCCGCTTC AGCACCGCGG CCGCCACCGA TCCCGCCACC CCCCGGATGT
46741  TCCCCACCCC GCCCGAGCCG GACGGCGTCC TCGCCCAGGA CCCGCCGGAC CACACCCGGC
46801  TGCGGCGGCT GGTGGGCAAG GCCTTCACGG CACGCCGGGT GGAGGAGATG CGGCCCCGTG
46861  TCCGCTCCCT CGTCGACTCC CTGCTCGACG ACATGGTGGC CACGGTTCA CCCGCCGACC
46921  TGGTCGAGTT CCTCGCCGTT CCCTTCCCCG TCGCGGTCAT CTGCGAACTG CTCGGCGTGC
46981  CCTTGGAGGA CCGCGACCTG TTCCGGACCT TCTCCGACGC CATGCTCTCC TCGACCCGGC
47041  TCACCGCCGC GGAGATACAG CGGGTCCAGC AGGACTTCAT GGTCTACATG GACGGCCTGG
47101  TCGCCCAGCG CCGCGACGCC CCCACCGAGG ACCTGCTCGG CGCCCTCGCC CTCGCCACCG
47161  ACAACGACGA CCACCTGACC AAGGGCGAGA TCGTCAACAT GGGGGTGAGC CTGCTCATCG
47221  CGGGCCACGA CGTCGGTC AACCAGATCA CCAACCTCGT CCACCTCCTG CTGACCGAGC
47281  GCAAGCGCTA CGAGTCGCTG GTCGCCGACC CGGCCCTCGT GCCCGCGGCG GTGGAGGAGA
47341  TGCTGCGGTA CACACCGCTG GTGTCCGCCG GCAGCTTCGT CCGCGTGGCC ACCGAGGACG
47401  TGGAGCTGAG CACCGTGACC GTGCGGGCCG GGGAGCCCTG CGTCGTCCAC TTCGCGTCGG
47461  CCAACCGGGA CGAGGAGGTC TTCGACCACG CCGACGAGCT GGACTTCCAC CGTGAGCGCA
47521  ACCCGCACAT AGCGTTCGGG CACGGAGCGC ACCACTGCAT CGGCGCCCAA CTGGGCCGAC
47581  TGGAACTCCA GGAGGCCCTG TCCGCCCTCG TCCGGCGCTT CCCCACCCTC GATCTGGCCG
47641  AGCCGGTCGC GGGACTGAAG TGGAAGCAGG GCATGCTGAT CCGCGGACTG GAACGCCAGA
47701  TCGTCTCCTG GTGACGGCCG GCCGCCCGGC CGCCCGCCGG GCACCGGCGC CACCAGGGCA
47761  CCGGCCGGGA CCGCAGACCC GGCCGGTGCC CCTCGCCCGA GGCCGCCTCA CTCCACGAAG
47821  CGGCCACCCT CCATGTGCAT GCGGCGACCG GTGAACCGCT GCGCGAACAT GCGGTCGTGG
47881  GAGACCACGA CCAGTGCGCC CCGGTAGTGC GCCAGCGCCT CCTCCAGGTC CTCCACGAGC
47941  GCGGGCGACA GGTGGTTCGT CGGCTCGTCG AGCAGCAGCA GGTCCGCCGG GTCGCGCAGC
48001  AGACGGGCCA GGGCCAGCCG CCTCAACTGC CGGTGGACA GGTCTCCCAC CGCGGTGCCC
48061  AGCGCCGAGG GCCGGAAGAG CCCGAATCCC AGGAGCGCGC CCCGGTGTTC CTCCGCGATG
48121  CCGGGCAGCC CCGCCGCGAA GGCCGCCAGC AGGCTCTGCT GCCGGTCGGT GATCTCCGTC
48181  TCCTGCGGCA GCCAGCCGAT GCGCTCCGGG CGCTCGCACT CGCCCTGATC GGGCGCCAGG
48241  TCACCGGCCA GCACGCGCAG CAGGGTGCTC TTGCCCGCGC CGTTGTGCCC CGTGATCAGG
48301  ATGCGCTCAC CGGGGTCGAC GGTGAAGGAC GGGACGTCGA GCCGCGTGCC GACGGTGACC
48361  TTGTACAGCT CGGCGAGTGC CCCGCCGCGC CCGACCGTGC CGCCACCCTC CACCCGGGCC
48421  CGGAAACGCA TGGGTTGAGG GGGCCGCGGC ACCGGGTTCT CCTCCAGCCG GCGGACCCGC
48481  TCCTTGGCGT TGCCGACCCG CGCGGAGATC TGCTTCTCCA CGTTGCGCTG GTGGCGCTGG
48541  TTCGACCGCT CGGTGTTGCG CCGCGGGCCG GTGGCCAGGT GGTCGGCGGC GCTGCGGGCC
48601  AGTTCCCGCT GGCGTGCCAG GTCCTCCAGC CAGTCCTGGT AAGCCTGCTC CCAGCGGCGC
```

-continued

```
48661  CGCGCGGCCG CCTTGGCTTG CAGGTATCCC GCGTAACCGC CGCCGTGCCG GTTGACGGTG

48721  CGCCGCTCGC CGTCCACCTC CCACAGGGCG GTGGCCACGC GCTCCAGGAA GACCCGGTCG

48781  TGCGAGACGA CCAGCACGCT GCCGCGGTGG GCCCGCAGGC GCTCCTCCAG CCACTCCAGC

48841  GCCCCGACGT CGAGGTGGTT GGTGGGTTCG TCGAGCAGCA TCAGCTGCGG GGACGCGGCC

48901  AGCAGGCAGG CCAGGTTGAG ACGCGCCTGC TCACCTCCGG AGAGGCTGCC GAGCCGCCGG

48961  TCGCCCGTGA TGCCCGCCAG ACCGAGGCCG TGCATCGCCG CGTCGACACG GGCGTCCGCC

49021  GCGTAGCCGT CGCGGGCCTC GAACGCCTCC AGCAGGTCGC CGTAGGCGCC GAGCAGGCCC

49081  TCCAGCTCCT CGGGCTCCGC CCCGGCCAGC GCCTGCTCCG CCTCACGCAA CCCCCGCTCC

49141  AGGGAGCGCA GTTCGGCGAG GGCGTGGTCG ATGGCGTCCT GAACGGTGTC CTCCGGGGGC

49201  AGGTCCGGTG TCTGGGGGAG GTAGCCGCAG CCGCCGGGAG CCCGGACGAG GACCTGGCCA

49261  CCGTCCGGGC GGTCCACGCC GGCGAGCATG CGGAGCAGGG TCGACTTGCC CGATCCGTTC

49321  TCACCGATGA TGCCGACGCG CTCGCCGAGT GCCACCGACT GGTTGACGCC GTCCAACAGC

49381  GGCCGTCCGC CGGGTGCCCG GACGACGTCG TCGAGGACGA CCTGGAAGGA ACCGGTCTCA

49441  GGTTGCGTGG GAAGGAGCTT TTCCGGCGTG CCGGTGSGCG CCGCGGCGCC GGTATCGGAA

49501  CGGTGTGCGT TCTGCATGGG TGATCCGCCA TTCGGAGAAA AAGAGGCAGT GTGGCCAAAA

49561  GGGAGCGGCC CACGGCAGAC GGCGGAAGAA GAGAACGCCT CGGCGAACGC GGCGCACCCG

49621  ACGGTGCGCA GCGCGAAAAA AGGGAGGCGA AGAAGCGAGC CGGAGGCGTC GCGATCAGCG

49681  GCGGGAGAAG CCGCGTCACC GTCCTGCCGG GAACCCTCGA CGGCGCCGGA GCGGCAACCG

49741  CGTACGCGGT GCTCCTCGGC GCCCGGACTC CCGTGGCGGT ATCAGAGGAA GTAGTAACTG

49801  ACCACGTCGG CACGATAGCA GAGCAGACGG AGCCGGCAGG GGGTCGCGAG GTGCGATGGC

49861  TGAATGTGTG CCACGCTTCG GATTTTTTGC TCGCGGGACG ACGAGGCCGT GTGCGAACGT

49921  GTCCCGGGCA GTCGTTCGTC AGCGGGAGGT TCATATGCAG GACAACCAGG GTGGATCCGG

49981  AGCCGAGTCC GAGACCGGGA CCGAGAGCGA CGTCAAGCGG AAGTTCCGGG AGGCACTGGA

50041  GCGCAAGAAG CTCCTCAGCC GGGAACGCCG GGCGCACGAG GACGCTCGTT CCAAGGTGAA

50101  CGGAACGTCC CGCAATGGCG CCAGGAAGGC GAATTTCCGC CGCAAGGCCG GGTGACACCG

50161  ACCGCTGCGC ACACCCGTGC CCCACAGCTC GACTCCGCTG CGACAGGGGC CTGCCCGCGC

50221  CGGGGAACCG GCCCGGGCAG GTGTAGGGTG GCGGGCATGT ATCCAGGTGT CGGTTCCCTG

50281  AAGCTCCGCC GCCGCGCCTG ACGGTGCGGC CCTGAACTCT CGTTTCGCGT GCCCACCGTC

50341  GCGGTGTCAG TGCCGGGCGG CTGTTTCGTG CTGCCCGGTT CCGGAGCGAA CCTGTGGAGC

50401  ACACCGTGGG CGCATTCCCC GCAAGGCCGG CCTGAGGCCG CGACCGATAC ACGAGTTCAC

50461  CGATGCGAGC GAGGGCCGCC GCCGCGCCGG TGGCGACGAC CACCCCTTCC GCACCGGCCC

50521  CGACGCCCTC TCGCCGGCGC CGCTCCCGGC CCCGGCCGGC GGCGCCACCC GGGTACGCCG

50581  CTCCCGCGGC CCCGGCGGCG CGTGCCGCGC ACAGGCCGTA CCGGCCGGCC GTTCGGCCGG

50641  TGGACCTCTG CGCCCTGCCG TCCCCGCGGC AACGTCGCCG GACACGGACA CCGCCCCTCG

50701  GCCGCCGGCC GCCGTCACCA CCCCGGGGCG CCGGCGTCTC GCCGCTCTCG CGCCGGCCCC

50761  GTCCACGACC GCTCCCGTGC CTGCCGGAAG GGCCGACTCA TGACCGAGCG ACACCTCCCC

50821  GCCGTCCTCG CGCCCCTCGG CCGGCCGGGC TACCGCCGCC TCTTCGCCGC CATGGTCCTC

50881  GCCCTCTTCG GGTACGGCGG GTGGACCATC TACCTCGCGC TCCAGGCGCT GGAGCTC
```

The above DNA sequence encodes the following 8,8a-deoxyoleandolide synthase proteins:
8,8a-deoxyoleandolide synthase 1: (SEQ ID NO:2)

```
8,8a-deoxyoleandolide synthase 1:
                                                             (SEQ ID NO:2)
   1 MPVPGEENGH SIAIVGIACR LPGSATPQEF WRLLADSADA LDEPPAGRFP TGSLSSPPAP

61 RGGFLDSIDT FDADFFNISP REAGVLDPQQ RLALELGWEA LEDAGIVPRH LRGTRTSVFM

121 GAMWDDYAHL AHARGEAALT RHSLTGTHRG MIANRLSYAL GLQGPSLTVD TGQSSSLAAV

181 HMACESLARG ESDLALVGGV NLVLDPAGTT GVERFGALSP DGRCYTFDSR ANGYARGEGG

241 VVVVLKPTHR ALADGDTVYC EILGSALNND GATEGLTVPS ARAQADVLRQ AWERARVAPT

301 DVQYVELHGT GTPAGDPVEA EGLGTALGTA RPAEAPLLVG SVKTNIGHLE GAAGIAGLLK

361 TVLSIKNRHL PASLNFTSPN PRIDLDALRL RVHTAYGPWP SPDRPLVAGV SSFGMGGTNC

421 HVVLSELRNA GGDGAGKGPY TGTEDRLGAT EAEKRPDPAT GNGPDPAQDT HRYPPLILSA

481 RSDAALRAQA ERLRHHLEHS PGQRLRDTAY SLATRRQVFE RHAVVTGHDR EDLLNGLRDL

541 ENGLPAPQVL LGRTPTPEPG GLAFLFSGQG SQQPGMGKRL HQVFPGFRDA LDEVCAELDT

601 HLGRLLGPEA GPPLRDVMFA ERGTAHSALL SETHYTQAAL FALETALFRL LVQWGLKPDH

661 LAGHSVGEIA AAHAAGILDL SDAAELVATR GALMRSLPGG GVMLSVQAPE SEVAPLLLGR

721 EAHVGLAAVN GPDAVVVSGE RGHVAAIEQI LRDRGRKSRY LRVSHAFHSP LMEPVLEEFA

781 EAVAGLTFRA PTTPLVSNLT GAPVDDRTMA TPAYWVRHVR EAVRFGDGIR ALGKLGTGSF

841 LEVGPDGVLT AMARACVTAA PEPGHRGEQG ADADAHTALL LPALRRGRDE ARSLTEAVAR

901 LHLHGVPMDW TSVLGGDVSR VPLPTYAFQR ESHWLPSGEA HPRPADDTES GTGRTEASPP

961 RPHDVLHLVR SHAAAVLGHS RAERIDPDRA FRDLGFDSLT ALELRDRLDT ALGLRLPSSV

1021 LFDHPSPGAL ARFLQGDDTR RPEPGKTNGT RATEPGPDPD DEPIAIVGMA CRFPGGVTSP

1081 EDLWRLLAAG EDAVSGFPTD RGWNVTDSAT RRGGFLYDAG EFDAAFFGIS PREALVMDPQ

1141 QRLLLETSWE ALERAGVSPG SLRGSDTAVY IGATAQDYGP RLHESDDDSG GYVLTGNTAS

1201 VASGRIAYSL GLEGPAVTVD TACSSSLVAL HLAVQALRRG ECSLALAGGA TVMPSPGMFV

1261 EFSRQGGLSE DGRCKAFAAT ADGTGWAEGV GVLLVERLSD ARRLGHRVLA VVRGSAVNQD

1321 GASNGLTAPN GPSQQRVIRA ALADAGLVPA DVDVVEAHGT GTRLGDPIEA QALLATYGQG

1381 RAGGRPVVLG SVKSNIGHTQ AAAGVAGVMK MVLALGRGVV PKTLHVDEPS AHVDWSAGEV

1441 ELAVEAVPWS RGGRVRRAGV SSFGISGTNA HVIVEEAPAE PEPEPERGPG SVVGVVPWVV

1501 SGRDAGALRE QAARLAAHVS GVSAVDVGWS LVATRSVFEH RAVMVGSELD AMAESLAGFA

1561 AGGVVPGVVS GVAPAEGRRV VFVFPGQGSQ WVGMAAGLLD ACPVFAEAVA ECAAVLDPLT

1621 GWSLVEVLRG GGEAVLGRVD VVQPALWAVM VSLARTWRYY GVEPAAVVGH SQGEIAAACV

1681 AGGLSLADGA RVVVLRSRAI ARIAGGGGMV SVSLPAGRVR TMLEEFDGRV SVAAVNGPSS

1741 TVVSGDVQAL DELLAGCERE GVRARRVPVD YASHSAQMDQ LRDDLLEALA TIVPTSANVP

1801 FFSTVTADWL DTTALDAGYW FTNLRETVRF QEAVEGLVAQ GMGATVECSP HPVLVPGITE

1861 TLDTFDADAV ALSSLRRDEG GLDRFLTSLA EAFVQGVPVD WSRAFEGASP RTVDLPTYPF

1921 QRQRYWLLDK AAQRERERLE DWRYHVEWRP VTTRPSARLS GVWAVAIPAR LARDSLLVGA

1981 IDALERGGAR AVPVVVDERD HDRQALVEAL RNGLGDDDLA GVLSLLALDE APHGDHPDVP

2041 VGMAASLALV QAMADAAAEV PVWFATRGAV AALPGESPER PRQALLWGLG RVVALEQPQI

2101 WGGLVDLPQH LDEDAGRRLV DVVGGLADED QLAVRASSVL ARRLVRTPGH RMSSQAGGRE

2161 WSPSGTVLVT GGTGALGAHV ARWLAGKGAE HLVLISRRGA DAAGAAALRD SLTDMGVRVT
```

-continued

```
2221 LAACDAADRH ALETLLDSLR TDPAQLTAVI HAAGALDDGM TTVLTPEQMN NALRAKVTAT

2281 VNLHELTRDL DLSAFVLFSS ISATLGIPGQ ANYAPGNSFL DAFAEWRRAQ GLVATSIAWG

2341 PWSGGTGMAH EGSVGERLQR HGVLAMEPAA AIAALDHTLA SDETAVAVAD IDWSRFFLAY

2401 TALRARPLIG EIPEARRMLE SGSGPGDLEP DRAEPELAVR LAGLTAVEQE RLLVQLVREQ

2461 AAVVLGHSGA EAVAPDRAFK DLGFDSLTSV ELRNRLNTAT GLRLPVTAVF DYARPAALAG

2521 HLRSRLIDDD GDHGALPGVE KHAIDEPIAI VGMACRFPGG IASPEDLWDV LTAGEDVVSG

2581 LPQNRGWDLG RLYDPDPDRA GTSYMREGAF LHEAGEFDAA FFGISPREAL AMDPQQRLLL

2641 ETSWEALERA GITPSKLAGS PTGVFFGMSN QDYAAQAGDV PSELEGYLLT GSISSVASGR

2701 VAYTFGLEGP AVTVDTACSS SLVALHLAVQ GLRRGECSLA LVGGVTVMSS PVTLTTFSRQ

2761 RGLSVDGRCK AFAASADGFG AAEGVGVLLV ERLSDARRLG HRVLAVVRGS AVNQDGASNG

2821 LAAPNGPSQQ RVIRAALADA GLAPADVDVV EAHGTGTRLG DPIEAQALLA TYGQGRTSGR

2881 PVWLGSVKSN IGHTQAAAGV AGVMKMVLAL GRGVVPKTLH VDEPSPHVDW SAGEVELAVE

2941 AVPWSRGGRV RRAGVSSFGI SGTNAHVIVE EAPAEPSVEE GPGSVVGVVP WVVSGRDAGA

3001 LRAQAARLAA HVSSTGAGVV DVGWSLVATR SVFEHRAVMV GTDLDSMAGS LAGFAAGGVV

3061 PGVVSGVAPA EGRRVVFVFP GQGSQWVGMA AGLLDACPVF AEAVAECAAV LDRLTGWSLV

3121 EVLRGGEAVL GRVDVVQPAL WAVMVSLART WRYYGVEPAA VVGHSQGEIA AACVAGGLSL

3181 ADGARVVVLR SRAIARIAGG GGMVSVGLSA ERVRTMLDTY GGRVSVAAVN GPSSTVVSGD

3241 AQALDELLAG CEREGVRARR VPVDYASHSA QMDQLRDELL EALADVTPQD SSVPFFSTVT

3301 ADWLDTTALD AGYWFTNLRE TVRFQEAVEG LVAQGMGAFV ECSPHPVLVP GITETLDTFD

3361 ADAVALSSLR RDEGGLDRFL TSLAEAFVQG VPVDWTHAFE GGRPRFVDLP TYAFQRQRYW

3421 LHEEPLQEPV DEAWDAEFWS VVERGDATAV SDLLSTDAEA LHTVLPALSS WRRRRVEHRR

3481 LQDWRYRVEW KPFPAALDEV LGGGWLFVVP RGLADDGVVA RVVAAVTARG GEVSVVELDP

3541 TRPDRRAYAE AVAGRGVSGV VSFLSWDDRR HSEHSVVPAG LAASLVLAQA LVDLGRVGEG

3601 PRLWLVTRGA VVAGPSDAGV VIDPVQAQVW GFGRVLGLEH PELWGGLVDL PVGVDEEVCR

3661 RFVGVVASAG FEDQVAVRGS GVWVRRLVRA VVDGGGGGWR PRGTVLVTGG LGGLGAHTAR

3721 WLVGGGADHV VLVSRRGGSA PGAGDLVREL EGLGGARVSV RACDVADRVA LRALLSDLGE

3781 PVTAVFHAAG VPQSTPLAEI SVQEAADVMA AKVAGAVNLG ELVDPCGLEA FVLFSSNAGV

3841 WGSGGQAVYA AANAFLDALA VRRRGVGLPA TSVAWGMWAG EGMASVGGAA RELSRRGVRA

3901 MDPERAVAVM ADAVGRGEAF VAVADVDWER FVTGFASARP RPLISDLPEV RAVVEGQVQG

3961 RGQGLGLVGE EESSGWLKRL SGLSRVRQEE ELVELVRAQA AVVLGHGSAQ DVPAERAFKE

4021 LGFDSLTAVE LRNGLAAATG IRLPATMAFD HPTATAIARF LQSELVGSDD PLTLMRSAID

4081 QLETGLALLE SDEEARSEIT KRLNILLPRF GSGGSSRGRE AGQDAGEHQD VEDATIDELF

4141 EVLDNELGNS
                                                    55
```

8,8a-deoxyoleandolide synthase 2: (SEQ ID NO:3)

```
8,8a-deoxyoleandolide synthase 2:
                                                    (SEQ ID NO:3)
   1 VTNDEKIVEY LKRATVDLRK ARHRIWELED EPIAITSMAC HFPGGIESPE QLWELLSAGG

61 EVLSEFPDDR GWDLDEIYHP DPEHSGTSYV RHGGFLDHAT QFDTDFFGIS PREALAMDPQ

121 QRLLLETSWQ LFERAGVDPH TLKGSRTGVF VGAAHMGYAD RVDTPPAEAE GYLLTGNASA
```

-continued

```
 181 VVSGRISYTF GLEGPAVTVD TACSSSLVAL HLAVQALRRG ECSLAVVGGV AVMSDPKVFV
 241 EFSRQRGLAR DGRSKAFAAS ADGFGFAEGV SLLLLERLSD ARRLGHRVLA VVRGSAVNQD
 301 GASNGLAAPN GPSQQRVIRA ALADAGLAPA DVDVVEAHGT GTRLGDPIEA QALLATYGQG
 361 RTSGRPVWLG SVKSNIGHTQ AAAGVAGMMK MVLALERGVV PKTLHVDEPS PHVDWSTGAV
 421 ELLTEERPWE PEAERLRRAG ISAFGVSGTN AHVIVEEEAPA EPEPEPEPGT RVVAAGDLVV
 481 PWVVSGRDAG ALRAQAARLA AHVSSTGAGV VDVGWSLVAT RSVFEHRAVM VGTDLDSMAG
 541 SLAGFAAGGV VPGVVSGVAP AEGRRVVFVF PGQGSQWVGM AAGLLDACPV FAEAVAECAA
 601 VLDPLTGWSL VEVLRGGEAV LGRVDVVQPA LWAVMVSLAR TWRYYGVEPA AVVGHSQGEI
 661 AAACVAGGLS LADGARVVVL RSRAIARIAG GGGMVSVSLP AGRVRTMLDT YGGRLSVAAV
 721 NGPSSTVVSG DAQALDELLA GCEREGVRAR RVPVDYASHS AQMDQLRDEL LEALADITPQ
 781 HSSVPFFSTV TADWLDTTAL DAGYWFTNLR ETVRFQEAVE GLVAQGMGAF VECSPHPVLV
 841 PGIEQTLDTV EADAVALGSL RRDEGGLGRF LTSLAEAFVQ GVPVDWSRTF EGASPRTVDL
 901 PTYPFQRQRF WLEGSPALSS NGVEGEADVA FWDAVEREDS AVVAEELGID AKALHMTLPA
 961 LSSWRRRERQ RRKVQRWRYR VEWKRLPNSR AQESLQGGWL LVVPQGRAGD VRVTQSVAEV
1021 AAKGGEATVL EVDALHPDRA AYAEALTRWP GVRGVVSFLA WEEQALAEHP VLSAGLAASL
1081 ALAQALIDVG GSGESAPRLW LVTEAAVVIG AADTGAVIDP VHAQLWGFGR VLALEHPELW
1141 GGLIDLPAVA GEPGSITDHA HADLLATVLA TMVQAAARGE DQVAVRTTGT YVPRLVRSGG
1201 SAHSGARRWQ PRDTVLVTGG MGPLTAHIVR WLADNGADQV VLLGGQGADG EAAALRAEFD
1261 GHTTKIELAD VDTEDSDALR SLLDRTTGEH PLRAVIHAPT VVEFASVAES DLVRFARTIS
1321 SKIAGVEQLD EVLSGIDTAH DVVFFSSVAG VWGSAGQSAY AAGNAFLDAV AQHRRLRGLP
1381 GTSVAWTPWD DDRSLASLGD SYLDRRGLRA LSIPGALASL QEVLDQDEVH AVVADVDWER
1441 FYAGFSAVRR TSFFDDVHDA HRPALSTAAT NDGQARDEDG GTELVRRLRP LTETEQQREL
1501 VSLVQSEVAA VLGHSSTDAV QPQRAFREIG FDSLTAVQLR NRLTATTGMR LPTTLVFDYP
1561 TTNGLAEYLR SELFGVSGAP ADLSVVRNAD EEDDPVVIVG MACRFPGGID TPEAFWKLLE
1621 AGGDVISELP ANRGWDMERL LNPDPEAKGT SATRYGGFLY DAGEFDAAFF GISPREALAM
1681 DPQQRLLLET VWELIESAGV APDSLHRSRT GTFIGSNGQF YAPLLWNSGG DLEGYQGVGN
1741 AGSVMSGRVA YSLGLEGPAV TVDTACSSSL VALHLAVQAL RRGECSLAIA GGVTVMSTPD
1801 SFVEFSRQQG LSEDGRCKAF ASTADGFGLA EGVSALLVER LSDARRLGHR VLAVVRGSAV
1861 NQDGASNGLT APNGPSQQRV IRAALADAGL APADVDVVEA HGTGTRLGDP IEAQALLATY
1921 GQGRAGGRPV VLGSVKSNIG HTQAAAGVAG VMKMVLALER GVVPKTLHVD EPSPHVDWSA
1981 GEVELAVEAV PWSRGGRVRR AGVSSFGISG TNAHVIVEEA PAEPEPEPGT RVVAAGDLVV
2041 PWVVSGRDAG ALREQAARLA AHVSSTGAGV VDVGWSLVAT RSVFEHRAVM VGSELDSMAE
2101 SLAGFAAGGV VPGVVSGVAP AEGRRVVFVF PGQGSQWVGM AAGLLDACPV FAEAVAECAA
2161 VLDPVTGWSL VEVLRGGGEA VLGRVDVVQP ALWAVMVSLA RTWRYYGVEP AAVVGHSQGE
2221 IAAACVAGGL SLADGARVVV LRSRAIARIA GGGGMVSVGL SAERVRTMLD TYGGRVSVAA
2281 VNGPSSTVVS GDVQALDELL AGCEREGVRA RRVPVDYASH SAQMDQLRDE LLEALADITP
2341 QHSSVPFFST VTADWLDTTA LDAGYWFTNL RETVRFQEAV EGLVAQGMGA FVECSPHPVL
2401 VPGIEQTLDA LDQNAAVLGS LRRDEGGLDR LLTSLAEAFV QGVPVDWTHA FEGMTPRTVD
2461 LPTYPFQRQH YWPKPAPAPG ANLGDVASVG LTAAGHPLLG AVVEMPDSDG LVLTGQISLR
2521 THPWLADHEV LGSVLLPGTA FVELAVQAAD RAGYDVLDEL TLEAPLVLPD RGGIQVRLAL
```

-continued

```
2581 GPSEADGRRS LQLHSRPEEA AGFHRWTRHA SGFVVPGGTG AARPTEPAGV WPPAGAEPVA

2641 LASDRYARLV ERGYTYGPSF QGLHTAWRHG DDVTAEVALP EGTPADGYAL HPALLDAAVQ

2701 AVGLGSFVED PGQVYLPFLW SDVTLHATGA TSLRVRVSPA GPDTVALALA DPAGAPVATV

2761 GALRLRTTSA AQLARARGSA EHAMFRVEWV EEGSAADRCR GGAGGTTYEG ERAAEAGAAA

2821 GTWAVLGPRV PAAVRTMGVD VVTALDTPDH PADPQSLADL AALGDTVPDV VVVTSLLSLA

2881 SGADSPLGNR PRPTAAEQDT AATVAGVHSA LHAALDLVQA WLADERHTAS RLVLVTRHAM

2941 TVAESDPEPD LLLAPVWGLV RSAQAENPGR FVLADIDGDE ASWDALPRAV ASAASEVAIR

3001 AGAVYVPRLA RATDEGLVVA DEAAGPWRLD VTEAGTLANL ALVPCPDASR PLGPDEVRIA

3061 VRAAGVNFRD VLLALGMYPD EGLMGAEAAG VVTEVGGGVT TLAPGDRVMG LVTGGFGPVA

3121 VTHHRMLVRM PRGWSFAEAA SVPVAFLTAY YALHDLAGLR GGESVLVHSA AGGVGMAAVQ

3181 LARHWDAEVF GTASKGKWDV LAAQGLDEEH IGSSRTTEFE QRFRATSGGR GIDVVLNALS

3241 GDFVDASARL LREGGRFVEM GKTDIRTDLG VVGADGVPDI RYVAFDLAEA GAERIGQMLD

3301 EIMALFDAGV LRLPPLRAWP VRRAHEALRF VSQARHVGKV VLTVPAALDA EGTVLITGAG

3361 TLGALVARHL VTEHDVRRLL LVSRSGVAPD LAAELGALGA EVTVAACDVA NRKALKALLE

3421 DIPPEHPVTG IVHTAGVLDD GVVSGLTPER VDTVLKSKVD AALTLESVIG ELDLDPALFV

3481 IFSSAASMLG GPGQGSYAAA NQFLDTLARH RARRGLTSVS LGWGLWHEAS GLTGGLADID

3541 RDRMSRAGIA PMPTDEALHL FDRATELGDP VLLPMRLNEA ALEDRAADGT LPPLLSGLVR

3601 VRHRPSARAG TATAAPATGP EAFARELAAA PDPRRALRDL VRGHVALVLG HSGPEAIDAE

3661 QAFRDIGFDS LTAVELRNRL NAETGLRLPG TLVFDYPNPS ALADHLLELL APATQPTAAP

3721 LLAELERVEQ LLSAAASPGG PASAVDEETR TLIATRLATL ASQWTHLPVG SPGNADNRSG

3781 PGESGQAQES GATGEHTAAW TSDDDLFAFL DKRLET
```

8,8a-deoxyoleandolide synthase 3: (SEQ ID NO:4)

```
8,8a-deoxyoleandolide synthase 3:
                                                              (SEQ ID NO:4)
   1 VAEAEKLREY LWRATTELKE VSDRLRETEE RAREPIAIVG MSCRFPGGGD ATVNTPEQFW

61 DLLNSGGDGI AGLPEDRGWD LGRLYDPDPD RAGTSYVREG GFLYDSGEFD AAFFGISPRE

121 ALAMDPQQRL LLETSWEAFE SAGIKRAALR GSDTGVYIGA WSTGYAGSPY RLVEGLEGQL

181 AIGTTLGAAS GRVAYTFGLE GPAVTVDTAC SSSLVALHLA VQGLRRGECS LALVGGVTVM

241 SSPVTLTTFS RQRGLSVDGR CKAFPASADG FGAAEGVGVL LVERLSDARR LGHRVLAVVR

301 GSAVNQDGAS NGLTAPNGPS QQRVIRAALA DAGLAPADVD VVEAHGTGTR LGDPIEAQAL

361 LATYGQGRAG GRPVWLGSVK SNIGHTQAAA GVAGVMKMVL ALGRGVVPKT LHVDEPSPHV

421 DWSAGAVELL TEERPWEPEA ERLRRAGISA FGVSGTNAHV IVEEAPAEPE PEPGTRVVAA

481 GDLVVPWVVS GRDARALRAQ AARLAAHVSG VSAVDVGWSL VATRSVFEHR AVAIGSELDS

541 MAGSLAGFAA GGVVPGVVSG VAPAEGRRVV FVFPGQGSQW VGMAAGLLDA CPVFAEAVAE

601 CAAVLDPVTG WSLVEVLQGR DATVLGRVDV VQPALWAVMV SLARTWRYYG VEPAAVVGHS

661 QGEIAAACVA GGLSLADGAR VVVLRSRAIA RIAGGGGMVS VSLPAGRVRT MLEEFDGRLS

721 VAAVNGPSST VVSGDVQALD ELLAGCEREG VRARRVPVDY ASHSAQMDQL RDELLEALAD

781 ITPQDSSVPF FSTVTADWLG TTALGAGYWF TNLRETVRFQ EAVEGLVAQG MGAFVECSPH

841 PVLVPGIEQT LDALDQNAAV FGSLRRDEGG LDRFLTSLAE AFVQGVPVDW SRAFEGVTPR
```

```
                             -continued
 901 TVDLPTYPFQ RQHYWLHAEE APVSQPPHSE NSFWSVVADA DAEAAAELLG VDVEAVEAVM
 961 PALSSWHRQS QLRAEVNQWR YDVAWKRLTT GALPEKPGNW LVVTPAGTDT TFAESLARTA
1021 AAELGVSVSF AQVDTAHPDR SQYAHALRQA LTGPENVDHL VSLLALDQAT DDLAAAPSCL
1081 AASLVLAQAL VDLGRVGEGP RLWLVTRGAV VAGPSDAGAV IDPVQAQVWG FGRVLGLEHP
1141 ELWGGLIDLP VGVDEEVCRR FVGVVASAGF EDQVAVRGSG VWVRRLVRAV VDGGGGGWRP
1201 RGTVLVTGGL GGLGAHTARW LVGGGADHVV LVSRRGGSAP GAGDLVRELE GLGGARVSVR
1261 ACDVADRVAL RALLSDLGEP VTAVFHAAGV PQSTPLAEIS VQEAADVMAA KVAGAVNLGE
1321 LVDPCGLEAF VLFSSNAGVW GSGGQAVYAA ANAFLDALAV RRRGVGLPAT SVAWGMWAGE
1381 GMASVGGAAR ELSRRGVRAM DPERAVAVMA DAVGRGEAFV AVADVDWERF VTGFASARPR
1441 PLISDLPEVR AVVEGQVQGR GQGLGLVGEE ESSGWLKRLS GLSRVRQEEE LVELVRAQAA
1501 VVLGHGSAQD VPAERAFKEL GFDSLTAVEL RNGLAAATGI RLPATMAFDH PNATAIARFL
1561 QSQLLPDAES ESAVPSSPED EVRQALASLS LDQLKGAGLL DPLLALTRLR EINSTVQNPE
1621 PTTESIDEMD GETCCAWRSA KSTAEPLTTG ADMPDPTAKY VEALRASLKE NERLRQQNHS
1681 LLAASREAIA ITAMSCRFGG GIDSPEDLWR FLAEGRDAVA GLPEDRGWDL DALYHPDPEN
1741 PGTTYVREGA FRYDAAQFDA GFFGISPREA LAMDPQQRLL LETSWELFER ADIDPYTVRG
1801 TATGIFIGAG HQGYGPDPKR APESVAGYLL TGTASAVLSG RISYTFGLEG PAVTVDTACS
1861 SSLVALHLAV QALRRGECSL AIAGGVAVMS TPDAFVEFSR QQGMARDGRC KAFAAAADGM
1921 GWGEGVSLLL LERLSDARRL GHRVLAVVRG SAVNQDGASN GLAAPNGPSQ QRVIRAALAD
1981 AGLAPADVDV VEAHGTGTRL GDPIEAQALL ATYGQGRAGG RPVWLGSVKS NIGHTQAAAG
2041 VAGVMKMVLA LGRGVVPKTL HVDEPSPHVD WSAGAVELLT EERPWEPEAE RLRRAGISAF
2101 GVSGTNAHVI VEEAPAEPEP EPGTRVVAAG DLVVPWVVSG RDVGALREQA ARLAAHVSST
2161 GAGVVDVGWS LVATRSVFEH RAVMVGTDLD SMAGSLAGFA AGGVVPGVVS GVAPAEGRRV
2221 VFVFPGQGSQ WVGMAAGLLD ACPVFAEAVA ECAAVLDPVT GWSLVEVLQG RDATVLGRVD
2281 VVQPALWAVM VSLARTWRYY GVEPAAVVGH SQGEIAAACV AGGLSLADGA RVVVLRSRAI
2341 ARIAGGGGMV SVSLPAGRVR TMLDTYGGRV SVAAVNGPSS TVVSGDVQAL DELLAGCERE
2401 GVRARRVPVD YASHSAQMDQ LRDELLEALA DITPQDSSVP FFSTVTADWL DTTALDAGYW
2461 FTNLRETVRF QEAVEGLVAQ GMGAFVECSP HPVLVPGIEQ TLDALDQNAA VLGSLRRDEG
2521 GLDRLLTSLA EAFVQGVPVD WTHAFEGVTP RTVDLPTYPF QRQRFWLDGS PASSANGVDG
2581 EADAMIWDAV EREDSVAVAE ELGIDAEALH TVLPALSSWR RRRVEHRRLQ DWRYRVEWKP
2641 FPAALDEVLG GGWLFVVPRG LADDGVVARV VAAVTARGGE VSVVELDPTR PDRRAYAEAV
2701 AGRGVSGVVS FLSWDDRRHS EHPVVPAGLA ASLVLAQALV DLGRVGEGPR LWLVTRDAVV
2761 AGPSDAGAVI DPVQAQVWGF GRVLGLEHPE LWGGLIDLPV EAPEPGSTCD HTYADLLATV
2821 VASAGFEDQV AVRGSGVWVR RLVRAVVDGG GGWRPRGTV LVTGGLGGLG AHTARWLVGG
2881 GADHVVLVSR RGGSAPGAGD LVRELEGLGG ARVSVRACDV ADRVALRALL SDLGEPVTAV
2941 FHAAGVPQST PLAEISVQEA ADVMAAKVAG AVNLGELVDP CGLEAFVLFS SNAGVWGSGG
3001 QAVYAAANAF LDALAVRRRG VGLPATSVAW GMWAGEGMAS VGGAARELSR RGVRAMDPER
3061 AVAVMADAVG RGEAFVAVAD VDWERFVTGF ASARPRPLIS DLPEVRTALR NQEQEQLHAP
3121 VPEDRSAQLL RRLSMLSPAG REAELVKLVR TEAAAVLGHG SAQDVPAERA FKELGFDSLT
3181 AVQLRNRLAA ATGTRLPASA VFDHPHAAAL ARWLLAGMRH ADGGHGGGHA GGPGPDADEG
3241 RSAGAGHSGM LADLYRRSAE LGRSREFIGL LADTAAFRPV FHGPADLDAP LEAVPLADGV
```

```
                             -continued
3301 RKPQLICCSG TAPVGGPHEF ARLASFFRGT RAVSALPLPG YLPGEQLPAD LDAVLAAQAE

3361 AVEKQTGGAP FVLVGYSAGG LMAHALACHL AGRGTPPSGE VLVDVYPPGR QEPVFGWQKE

3421 LTEGMFAQDF VPMDDTRLTA LGTYDRLMGE WRPAPSGLPT LLIRATEPMA EWTGAIDWRA

3481 SWEYDHTAVD MPGNHFTIMR EHAEDAARHI DVWLKGLTP
```

The recombinant DNA compounds of the invention that encode the oleandolide PKS proteins or portions thereof are useful in a variety of applications. While many of these applications relate to the heterologous expression of the oleandolide PKS or the construction of hybrid PKS enzymes, many useful applications involve the natural oleandomycin producer *Streptomyces antibioticus*.

For example, one can use the recombinant DNA compounds of the invention to disrupt the oleAI, oleAII, or oleAIII genes by homologous recombination in *Streptomyces antibioticus*. The resulting host cell is a preferred host cell for making polyketides modified by oxidation, hydroxylation, and glycosylation in a manner similar to oleandomycin, because the genes that encode the proteins that perform these reactions are present in the host cell. Such a host cell also does not naturally produce any oleandomycin that could interfere with production or purification of the polyketide of interest.

One illustrative recombinant host cell provided by the present invention expresses a recombinant oleandolide PKS in which the module 1 KS domain is inactivated by deletion or other mutation. In a preferred embodiment, the inactivation is mediated by a change in the KS domain that renders it incapable of binding substrate (the KS1° mutation). In a particularly preferred embodiment, this inactivation is rendered by a mutation in the codon for the active site cysteine that changes the codon to another codon, such as an alanine codon. Such constructs are especially useful when placed in translational reading frame with extender modules 1 and 2 of an oleandolide or the corresponding modules of another PKS. The utility of these constructs is that host cells expressing, or cell free extracts containing, a PKS comprising the protein encoded thereby can be fed or supplied with N-acylcysteamine thioesters of precursor molecules to prepare a polyketide of interest. See U.S. patent application Ser. No. 60/117,384, filed Jan. 27, 1999, and PCT patent publication No. US99/03986, both of which are incorporated herein by reference. Such KS1° constructs of the invention are useful in the production of 13-substituted-oleandomycin compounds in *Streptomyces antibioticus* host cells. Preferred compounds of the invention include those compounds in which the substituent at the 13-position is propyl, vinyl, propargyl, other lower alkyl, and substituted alkyl The compounds of the invention can also be used to construct recombinant host cells of the invention in which coding sequences for one or more domains or modules of the oleandolide PKS have been deleted by homologous recombination with the *Streptomyces antibioticus* chromosomal DNA. Those of skill in the art will appreciate that such compounds are characterized by their homology with the chromosomal DNA and not by encoding a functional protein due to their intended function of deleting or otherwise altering portions of chromosomal DNA. For this and a variety of other applications, the compounds of the present invention include not only those DNA compounds that encode functional proteins but also those DNA compounds that are complementary or identical to any portion of the oleandolide PKS genes.

Thus, the invention provides a variety of modified *Streptomyces antibioticus* host cells in which one or more of the genes in the oleandolide PKS gene cluster have been mutated or disrupted. These cells are especially useful when it is desired to replace the disrupted function with a gene product expressed by a recombinant DNA expression vector. While such expression vectors of the invention are described in more detail in the following Section, those of skill in the art will appreciate that the vectors have application to *S. antibioticus* as well. Such *S. antibioticus* host cells can be preferred host cells for expressing oleandolide derivatives of the invention. Particularly preferred host cells of this type include those in which the coding sequence for the loading module has been mutated or disrupted, those in which one or more of any of the PKS gene ORFs has been mutated or disrupted, and/or those in which the genes for one or more oleandolide modification enzymes (glycosylation, epoxidation) have been mutated or disrupted.

While the present invention provides many useful compounds having application to, and recombinant host cells derived from, *Streptomyces antibioticus*, many important applications of the present invention relate to the heterologous expression of all or a portion of the oleandolide PKS genes in cells other than *S. antibioticus*, as described in the following Section.

Section II: Heterologous Expression of the Oleandolide PKS

In one important embodiment, the invention provides methods for the heterologous expression of one or more of the oleandolide PKS genes and recombinant DNA expression vectors useful in the method. For purposes of the invention, any host cell other than *Streptomyces antibioticus* is a heterologous host cell. Thus, included within the scope of the invention in addition to isolated nucleic acids encoding domains, modules, or proteins of the oleandolide PKS, are recombinant expression vectors that include such nucleic acids. The term expression vector refers to a nucleic acid that can be introduced into a host cell or cell-free transcription and translation system. An expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which is translated into a polypeptide in the cell or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, are preferred and confer a selectable phenotype on transformed cells when the cells are grown in an appropriate selective medium.

The various components of an expression vector can vary widely, depending on the intended use of the vector and especially the host cell(s) in which the vector is intended to replicate or drive expression. Expression vector components suitable for the expression of genes and maintenance of vectors in *E. coli*, yeast, Streptomyces, and other commonly used cells are widely known and commercially available. For example, suitable promoters for inclusion in the expression vectors of the invention include those that function in eucaryotic or procaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used.

Thus, recombinant expression vectors contain at least one expression system, which, in turn, is composed of at least a portion of the oleandolide PKS coding sequences operably linked to a promoter and optionally termination sequences that operate to effect expression of the coding sequence in compatible host cells. The host cells are modified by transformation with the recombinant DNA expression vectors of the invention to contain the expression system sequences either as extrachromosomal elements or integrated into the chromosome. The resulting host cells of the invention are useful in methods to produce PKS and post-PKS tailoring (modification) enzymes as well as polyketides and antibiotics and other useful compounds derived therefrom.

Preferred host cells for purposes of selecting vector components for expression vectors of the present invention include fungal host cells such as yeast and procaryotic host cells such as *E. coli* and Streptomyces, but mammalian cell cultures can also be used. In hosts such as yeasts, plants, or mammalian cells that ordinarily do not produce modular polyketide synthase enzymes, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference. Particularly preferred host cells for purposes of the present invention are Streptomyces and Saccharopolyspora host cells, as discussed in greater detail below.

In a preferred embodiment, the expression vectors of the invention are used to construct a heterologous recombinant Streptomyces host cell that expresses a recombinant PKS of the invention. Streptomyces is a convenient host for expressing polyketides, because polyketides are naturally produced in certain Streptomyces species, and Streptomyces cells generally produce the precursors needed to form the desired polyketide. Those of skill in the art will recognize that, if a Streptomyces host cell produces any portion of a PKS enzyme or produces a polyketide-modifying enzyme, the recombinant vector need drive expression of only those genes constituting the remainder of the desired PKS enzyme or other polyketide-modifying enzymes. Thus, such a vector may comprise only a single ORF, with the desired remainder of the polypeptides constituting the PKS provided by the genes on the host cell chromosomal DNA. If a Streptomyces or other host cell ordinarily produces polyketides, it may be desirable to modify the host so as to prevent the production of endogenous polyketides prior to its use to express a recombinant PKS of the invention. Such modified hosts include *S. coelicolor* CH999 and similarly modified *S. lividans* described in U.S. Pat. No. 5,672,491, and PCT publication Nos. WO 95/08548 and WO 96/40968, incorporated herein by reference. In such hosts, it may not be necessary to provide enzymatic activities for all of the desired post-translational modifications of the enzymes that make up the recombinantly produced PKS, because the host naturally expresses such enzymes. In particular, these hosts generally contain holo-ACP synthases that provide the pantetheinyl residue needed for functionality of the PKS.

The invention provides a wide variety of expression vectors for use in Streptomyces. The replicating expression vectors of the present invention include, for example and without limitation, those that comprise an origin of replication from a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and pSG5(ts) (Muth et al., 1989, *Mol. Gen. Genet.* 219: 341–348, and Bierman et al., 1992, *Gene* 116: 43–49, each of which is incorporated herein by reference), or a high copy number vector, such as pIJ101 and pJV1 (see Katz et al., 1983, *J. Gen. Microbiol* 129: 2703–2714; Vara et al., 1989, *J. Bacteriol* 171: 5782–5781; and Servin-Gonzalez, 1993, *Plasmid* 30: 131–140, each of which is incorporated herein by reference). High copy number vectors are generally, however, not preferred for expression of large genes or multiple genes. For non-replicating and integrating vectors and generally for any vector, it is useful to include at least an *E. coli* origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSEb101 and pSE211, all of which integrate site-specifically in the chromosomal DNA of *S. lividans*, can be employed for purposes of the present invention.

The Streptomyces recombinant expression vectors of the invention typically comprise one or more selectable markers, including antibiotic resistance conferring genes selected from the group consisting of the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Alternatively, several polyketides are naturally colored, and this characteristic can provide a built-in marker for identifying cells.

Preferred Streptomyces host cell/vector combinations of the invention include *S. coelicolor* CH999 and *S. lividans* K4-114 and K4-155 host cells, which have been modified so as not to produce the polyketide actinorhodin, and expression vectors derived from the pRM1 and pRM5 vectors, as described in U.S. Pat. No. 5,830,750 and U.S. patent application Ser. Nos. 08/828,898, filed Mar. 31, 1997, now U.S. Pat. No. 6,022,731 and 09/181,833, filed Oct. 28, 1998, each of which is incorporated herein by reference. These vectors are particularly preferred in that they contain promoters compatible with numerous and diverse Streptomyces spp. Particularly useful promoters for Streptomyces host cells include those from PKS gene clusters that result in the production of polyketides as secondary metabolites, including promoters from aromatic (Type II) PKS gene clusters.

Examples of Type II PKS gene cluster promoters are act gene promoters and tcm gene promoters; examples of Type I PKS gene cluster promoter are the spiramycin PKS and DEBS genes promoter. The present invention also provides the oleandolide PKS gene promoter in recombinant form. The promoter for the oleA genes is located upstream of the oleAI gene on cosmid pKOS055-5 of the invention. This promoter is contained within an ~1 kb segment upstream of the oleAI coding sequence and can be used to drive expression of the oleandolide PKS or any other coding sequence of interest in host cells in which the promoter functions, particularly S. antibioticus and generally any Streptomyces species.

As described above, particularly useful control sequences are those that alone or together with suitable regulatory systems activate expression during transition from growth to stationary phase in the vegetative mycelium. The promoter contained in the aforementioned plasmid pRM5, i.e., the actI/actIII promoter pair and the actII-ORF4 activator gene, is particularly preferred. Other useful Streptomyces promoters include without limitation those from the ermE gene and the melCI gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to activate initiation of transcription at promoter sequences. Activator genes in addition to the actII-ORF4 gene described above include dnrI, redD, and ptpA genes (see U.S. patent application Ser. No. 09/181,833, supra).

To provide a preferred host cell and vector for purposes of the invention, the oleandolide PKS genes were placed on a recombinant expression vector that was transferred to the non-macrolide producing host Streptomyces lividans K4-114, as described in Example 4. Transformation of S. lividans K4-114 (strain K4-155 can also be used) with this expression vector resulted in a strain which produced detectable amounts of 8,8a-deoxyoleandolide as determined by analysis of extracts by LC/MS.

Moreover, and as noted in the preceding Section, the present invention also provides recombinant DNA compounds in which the encoded oleandolide module 1 KS domain is inactivated or absent altogether. Example 4 below describes the introduction into Streptomyces lividans of a recombinant expression vector of the invention that encodes an oleandolide PKS with a KS1° domain. The resulting host cells can be fed or supplied with N-acylcysteamine thioesters of precursor molecules to prepare oleandolide derivatives. Such cells of the invention are especially useful in the production of 13-substituted-6-deoxyerythronolide B compounds in recombinant host cells. Preferred compounds of the invention include those compounds in which the substituent at the 13-position is propyl, vinyl, propargyl, other lower alkyl, and substituted alkyl. The unmodified polyketides, called macrolide aglycones, produced in S. lividans K4-114 or K4-155 can be hydroxylated and glycosylated by adding them to the fermentation of a strain, such as, for example, S. antibioticus or Saccharopolyspora erythraea, that contains the requisite modification enzymes.

There are a wide variety of diverse organisms that can modify macrolide aglycones to provide compounds with, or that can be readily modified to have, useful activities. For example, Saccharopolyspora erythraea can convert 6-dEB and oleandolide to a variety of useful compounds. The erythronolide 6-dEB is converted by the eryF gene product to erythronolide B, which is, in turn, glycosylated by the eryB gene product to obtain 3-O-mycarosylerythronolide B, which contains L-mycarose at C-3. The enzyme eryC gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromycin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product.

The unmodified oleandolide compounds provided by the present invention, such as, for example, the oleandolide produced in Streptomyces lividans, can be provided to cultures of Saccharopolyspora erythraea and converted to the corresponding derivatives of erythromycins A, B, C, and D in accordance with the procedure provided in Example 6, below. To ensure that only the desired compound is produced, one can use an S. erythraea eryA mutant that is unable to produce 6-dEB but can still carry out the desired conversions (Weber et al., 1985, J. Bacteriol. 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, Streptomyces venezuelae, which produces picromycin, contains enzymes that can transfer a desosaminyl group to the C-5 hydroxyl and a hydroxyl group to the C-12 position. In addition, S. venezuelae contains a glucosylation activity that glucosylates the 2'-hydroxyl group of the desosamine sugar. This latter modification reduces antibiotic activity, but the glucosyl residue is removed by cellular enzymatic action. Another organism, S. narbonensis, contains the same modification enzymes as S. venezuelae, except the C-12 hydroxylase. Thus, the present invention provides the compounds produced by hydroxylation and glycosylation of the macrolide aglycones of the invention by action of the enzymes endogenous to S. narbonensis and S. venezuelae.

Other organisms suitable for making compounds of the invention include Streptomyces antibioticus (discussed in the preceding Section), Micromonospora megalomicea, S. fradiae, and S. thermotolerans. M. megalomicea produces megalomicin and contains enzymes that hydroxylate the C-6 and C-12 positions and glycosylate the C-3 hydroxyl with mycarose, the C-5 hydroxyl with desosamine, and the C-6 hydroxyl with megosamine (also known as rhodosamine), as well as acylating various positions. In addition to antibiotic activity, compounds of the invention produced by treatment with M. megalomicea enzymes can have antiparasitic activity as well. S. fradiae contains enzymes that glycosylate the C-5 hydroxyl with mycaminose and then the 4'-hydroxyl of mycaminose with mycarose, forming a disaccharide. S.

*thermotolerans* contains the same activities as well as acylation activities. Thus, the present invention provides the compounds produced by hydroxylation and glycosylation of the macrolide aglycones of the invention by action of the enzymes endogenous to *S. antibioticus, M. megalomicea, S. fradiae,* and *S. thermotolerans.*

The present invention also provides methods and genetic constructs for producing the glycosylated and/or hydroxylated compounds of the invention directly in the host cell of interest. Thus, the recombinant genes of the invention, which include recombinant oleAI, oleAII, and oleAIII genes with one or more deletions and/or insertions, including replacements of an oleA gene fragment with a gene fragment from a heterologous PKS gene (as discussed in the next Section), can be included on expression vectors suitable for expression of the encoded gene products in *Saccharopolyspora erythraea, Streptomyces antibioticus, S. venezuelae, S. narbonensis, Micromonospora megalomicea, S. fradiae,* and *S. thermotolerans.* A number of erythromycin high-producing strains of *S. erythraea* have been developed, and in a preferred embodiment, the oleandolide PKS genes are introduced into such strains (or erythromycin non-producing mutants thereof) to provide the corresponding modified oleandolide compounds in high yields.

Moreover, additional recombinant gene products can be expressed in the host cell to improve production of a desired polyketide. As but one non-limiting example, certain recombinant PKS proteins of the invention may produce a polyketide other than or in addition to the predicted polyketide, because the polyketide is cleaved from the PKS by the thioesterase (TE) domain in module 6 prior to processing by other domains on the PKS, in particular, any KR, DH, and/or ER domains in module 6. The production of the predicted polyketide can be increased in such instances by deleting the TE domain coding sequences from the gene and, optionally, expressing the TE domain as a separate protein. See Gokhale et al., February 1999, "Mechanism and specificity of the terminal thioesterase domain from the erythromycin polyketide synthase," *Chem. & Biol.* 6: 117–125, incorporated herein by reference.

Thus, in one important aspect, the present invention provides methods, expression vectors, and recombinant host cells that enable the production of oleandolide and hydroxylated and glycosylated derivatives of oleandolide in heterologous host cells. The present invention also provides methods for making a wide variety of polyketides derived in part from the oleandolide PKS, as described in the following Section.

Section III: Hybrid PKS Genes

The present invention provides recombinant DNA compounds encoding each of the domains of each of the modules of the oleandolide PKS. The availability of these compounds permits their use in recombinant procedures for production of desired portions of the oleandolide PKS fused to or expressed in conjunction with all or a portion of a heterologous PKS. The resulting hybrid PKS can then be expressed in a host cell to produce a desired polyketide.

Thus, in accordance with the methods of the invention, a portion of the oleandolide PKS coding sequence that encodes a particular activity can be isolated and manipulated, for example, to replace the corresponding region in a different modular PKS. In addition, coding sequences for individual modules of the PKS can be ligated into suitable expression systems and used to produce the portion of the protein encoded. The resulting protein can be isolated and purified or can may be employed in situ to effect polyketide synthesis. Depending on the host for the recombinant production of the domain, module, protein, or combination of proteins, suitable control sequences such as promoters, termination sequences, enhancers, and the like are ligated to the nucleotide sequence encoding the desired protein in the construction of the expression vector, as described in the preceding Section.

In one important embodiment, the invention thus provides hybrid PKS enzymes and the corresponding recombinant DNA compounds that encode those hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS. In one preferred embodiment, the first PKS is most but not all of the oleandolide PKS, and the second PKS is only a portion or all of a non-oleandolide PKS. An illustrative example of such a hybrid PKS includes an oleandolide PKS in which the oleandolide PKS loading module has been replaced with a loading module of another PKS. Another example of such a hybrid PKS is an oleandolide PKS in which the AT domain of extender module 3 is replaced with an AT domain that binds only malonyl CoA. In another preferred embodiment, the first PKS is most but not all of a non-oleandolide PKS, and the second PKS is only a portion or all of the oleandolide PKS. An illustrative example of such a hybrid PKS includes a rapamycin PKS in which an AT specific for malonyl CoA is replaced with the AT from the oleandolide PKS specific for methylmalonyl CoA. Other illustrative hybrid PKSs of the invention are described below.

Those of skill in the art will recognize that all or part of either the first or second PKS in a hybrid PKS of the invention need not be isolated from a naturally occurring source. For example, only a small portion of an AT domain determines its specificity. See PCT patent application No. WO US99/15047, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

With this general background regarding hybrid PKSs of the invention, one can better appreciate the benefit provided by the DNA compounds of the invention that encode the individual domains, modules, and proteins that comprise the oleandolide PKS. As described above, the oleandolide PKS is comprised of a loading module, six extender modules composed of a KS, AT, ACP, and KR, DH, and ER domains, and a thioesterase domain. The DNA compounds of the invention that encode these domains individually or in combination are useful in the construction of the hybrid PKS encoding DNA compounds of the invention.

The recombinant DNA compounds of the invention that encode the loading module of the oleandolide PKS and the corresponding polypeptides encoded thereby are useful for a variety of applications. In one embodiment, a DNA compound comprising a sequence that encodes the oleandolide PKS loading module is inserted into a DNA compound that comprises the coding sequence for a heterologous PKS protein or portion thereof The resulting construct, in which the coding sequence for the loading module of the heterologous PKS is replaced by that for the coding sequence of the oleandolide PKS loading module provides a novel PKS. Examples include the 6-deoxyerythronolide B, rapamycin, FK-506, FK-520, rifamycin, and avermectin PKS protein coding sequences. In another embodiment, a DNA compound comprising a sequence that encodes the oleandolide PKS loading module is inserted into a DNA compound that comprises the coding sequence for the oleandolide PKS or a recombinant oleandolide PKS that produces an oleandolide derivative.

In another embodiment, a portion of the loading module coding sequence is utilized in conjuction with a heterologous coding sequence. In this embodiment, the invention provides, for example, replacing the malonyl CoA (acetyl CoA) specific AT with a propionyl CoA (methylmalonyl), butyryl CoA (ethylmalonyl), or other CoA specific AT. In addition, the $KS^Q$ and/or ACP can be replaced by another inactivated KS and/or another ACP. Alternatively, the $KS^Q$ and AT of the loading module can be replaced by an AT of a loading module such as that of DEBS. The resulting heterologous loading module coding sequence can be utilized in conjunction with a coding sequence for a PKS that synthesizes oleandolide, an oleandolide derivative, or another polyketide.

The recombinant DNA compounds of the invention that encode the first extender module of the oleandolide PKS and the corresponding polypeptides encoded thereby are useful for a variety of applications. In one embodiment, a DNA compound comprising a sequence that encodes the oleandolide PKS first extender module is inserted into a DNA compound that comprises the coding sequence for a heterologous PKS. The resulting construct, in which the coding sequence for a module of the heterologous PKS is either replaced by that for the first extender module of the oleandolide PKS or the latter is merely added to coding sequences for modules of the heterologous PKS, provides a novel PKS coding sequence. In another embodiment, a DNA compound comprising a sequence that encodes the first extender module of the oleandolide PKS is inserted into a DNA compound that comprises coding sequences for the oleandolide PKS or a recombinant oleandolide PKS that produces an oleandolide derivative.

In another embodiment, a portion or all of the first extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (which includes inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS, from a gene for a PKS that produces a polyketide other than oleandolide, or from chemical synthesis. The resulting heterologous first extender module coding sequence can be utilized in conjunction with a coding sequence for a PKS that synthesizes oleandolide, an oleandolide derivative, or another polyketide.

Those of skill in the art will recognize, however, that deletion of the KR domain of module 1 or insertion of a DH domain or DH and KR domains into module 1 will prevent the typical cyclization of the polyketide at the hydroxyl group created by the KR if such hybrid module is employed as a first extender module in a hybrid PKS or is otherwise involved in producing a portion of the polyketide at which cyclization is to occur. Such deletions or insertions can be useful, however, to create linear molecules or to induce cyclization at another site in the molecule.

As noted above, the invention also provides recombinant PKSs and recombinant DNA compounds and vectors that encode a PKS protein in which the KS domain of the first extender module has been inactivated. Such constructs are especially useful when placed in translational reading frame with the remaining modules and domains of an oleandolide or oleandolide derivative PKS, a hybrid PKS, or a heterologous PKS. The utility of these constructs is that host cells expressing, or cell free extracts containing, the PKS encoded thereby can be fed or supplied with N-acylcysteamine thioesters of precursor molecules to prepare oleandolide derivative compounds. See U.S. patent application Ser. No. 60/117,384, filed Jan. 27, 1999, and PCT publication Nos. WO 99/03986 and 97/02358, each of which is incorporated herein by reference.

The recombinant DNA compounds of the invention that encode the second extender module of the oleandolide PKS and the corresponding polypeptides encoded thereby are usefull for a variety of applications. In one embodiment, a DNA compound comprising a sequence that encodes the oleandolide PKS second extender module is inserted into a DNA compound that comprises the coding sequence for a heterologous PKS. The resulting construct, in which the coding sequence for a module of the heterologous PKS is either replaced by that for the second extender module of the oleandolide PKS or the latter is merely added to coding sequences for the modules of the heterologous PKS, provides a novel PKS. In another embodiment, a DNA compound comprising a sequence that encodes the second extender module of the oleandolide PKS is inserted into a DNA compound that comprises the coding sequences for the oleandolide PKS or a recombinant oleandolide PKS that produces an oleandolide derivative.

In another embodiment, a portion or all of the second extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (or inactivating) the KR; replacing the KR with a KR, a KR and a DH, or a KR, DH, and ER; and/or inserting a DH or a DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS, from a coding sequence for a PKS that produces a polyketide other than oleandolide, or from chemical synthesis. The resulting heterologous second extender module coding sequence can be utilized in conjunction with a coding sequence from a PKS that synthesizes oleandolide, an oleandolide derivative, or another polyketide.

The recombinant DNA compounds of the invention that encode the third extender module of the oleandolide PKS and the corresponding polypeptides encoded thereby are useful for a variety of applications. In one embodiment, a DNA compound comprising a sequence that encodes the oleandolide PKS third extender module is inserted into a DNA compound that comprises the coding sequence for a heterologous PKS. The resulting construct, in which the coding sequence for a module of the heterologous PKS is either replaced by that for the third extender module of the oleandolide PKS or the latter is merely added to coding sequences for the modules of the heterologous PKS, provides a novel PKS. In another embodiment, a DNA compound comprising a sequence that encodes the third extender module of the oleandolide PKS is inserted into a DNA compound that comprises coding sequences for the oleandolide PKS or a recombinant oleandolide PKS that produces an oleandolide derivative.

In another embodiment, a portion or all of the third extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting the inactive KR; and/or replacing the KR with an active KR, or a KR and DH, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS, from a gene for a PKS that produces a polyketide other than oleandolide, or from chemical synthesis. The resulting heterologous third extender module coding sequence can be utilized in conjunction with a coding sequence for a PKS that synthesizes oleandolide, an oleandolide derivative, or another polyketide.

The recombinant DNA compounds of the invention that encode the fourth extender module of the oleandolide PKS and the corresponding polypeptides encoded thereby are useful for a variety of applications. In one embodiment, a DNA compound comprising a sequence that encodes the oleandolide PKS fourth extender module is inserted into a DNA compound that comprises the coding sequence for a heterologous PKS. The resulting construct, in which the coding sequence for a module of the heterologous PKS is either replaced by that for the fourth extender module of the oleandolide PKS or the latter is merely added to coding sequences for the modules of the heterologous PKS, provides a novel PKS. In another embodiment, a DNA compound comprising a sequence that encodes the fourth extender module of the oleandolide PKS is inserted into a DNA compound that comprises the coding sequences for the oleandolide PKS or a recombinant oleandolide PKS that produces an oleandolide derivative.

In another embodiment, a portion of the fourth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting or inactivating any one, two, or all three of the ER, DR, and KR; and/or replacing any one, two, or all three of the ER, DH, and KR with either a KR, a DH and KR, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS (except for the DH and ER domains), from a coding sequence for a PKS that produces a polyketide other than oleandolide, or from chemical synthesis. The resulting heterologous fourth extender module coding sequence can be utilized in conjunction with a coding sequence for a PKS that synthesizes oleandolide, an oleandolide derivative, or another polyketide.

The recombinant DNA compounds of the invention that encode the fifth extender module of the oleandolide PKS and the corresponding polypeptides encoded thereby are useful for a variety of applications. In one embodiment, a DNA compound comprising a sequence that encodes the oleandolide PKS fifth extender module is inserted into a DNA compound that comprises the coding sequence for a heterologous PKS. The resulting construct, in which the coding sequence for a module of the heterologous PKS is either replaced by that for the fifth extender module of the oleandolide PKS or the latter is merely added to coding sequences for the modules of the heterologous PKS, provides a novel PKS. In another embodiment, a DNA compound comprising a sequence that encodes the fifth extender module of the oleandolide PKS is inserted into a DNA compound that comprises the coding sequence for the oleandolide PKS or a recombinant oleandolide PKS that produces an oleandolide derivative.

In another embodiment, a portion or all of the fifth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (or inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS, from a coding sequence for a PKS that produces a polyketide other than oleandolide, or from chemical synthesis. The resulting heterologous fifth extender module coding sequence can be utilized in conjunction with a coding sequence for a PKS that synthesizes oleandolide, an oleandolide derivative, or another polyketide.

The recombinant DNA compounds of the invention that encode the sixth extender module of the oleandolide PKS and the corresponding polypeptides encoded thereby are useful for a variety of applications. In one embodiment, a DNA compound comprising a sequence that encodes the oleandolide PKS sixth extender module is inserted into a DNA compound that comprises the coding sequence for a heterologous PKS. The resulting construct, in which the coding sequence for a module of the heterologous PKS is either replaced by that for the sixth extender module of the oleandolide PKS or the latter is merely added to coding sequences for the modules of the heterologous PKS, provides a novel PKS. In another embodiment, a DNA compound comprising a sequence that encodes the sixth extender module of the oleandolide PKS is inserted into a DNA compound that comprises the coding sequences for the oleandolide PKS or a recombinant oleandolide PKS that produces an oleandolide derivative.

In another embodiment, a portion or all of the sixth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting or inactivating the KR or replacing the KR with another KR, a KR and DH, or a KR, DH, and an ER; and/or inserting a DH or a DH and ER. In addition, the KS and/or ACP can be replaced with another KS and/or ACP. In each of these replacements or insertions, the heterologous KS, AT, DH, KR, ER, or ACP coding sequence can originate from a coding sequence for another module of the oleandolide PKS, from a coding sequence for a PKS that produces a polyketide other than oleandolide, or from chemical synthesis. The resulting heterologous sixth extender module coding sequence can be utilized in conjunction with a coding sequence for a PKS that synthesizes oleandolide, an oleandolide derivative, or another polyketide.

The sixth extender module of the oleandolide PKS is followed by a thioesterase domain. This domain is important in the cyclization of the polyketide and its cleavage from the PKS. The present invention provides recombinant DNA compounds that encode hybrid PKS enzymes in which the oleandolide PKS is fused to a heterologous thioesterase or a heterologous PKS is fused to the oleandolide synthase thioesterase. Thus, for example, a thioesterase domain coding sequence from another PKS gene can be inserted at the end of the sixth (or other final) extender module coding sequence in recombinant DNA compounds of the invention or the oleandolide PKS thioesterase can be similarly fused to a heterologous PKS. Recombinant DNA compounds encoding this thioesterase domain are useful in constructing DNA compounds that encode the oleandolide PKS, a PKS that produces an oleandolide derivative, and a PKS that produces a polyketide other than oleandolide or an oleandolide derivative.

Thus, the hybrid modules of the invention are incorporated into a PKS to provide a hybrid PKS of the invention. A hybrid PKS of the invention can result not only:

(i) from fusions of heterologous domain (where heterologous means the domains in that module are from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more oleandolide PKS genes with one or more non-oleandolide PKS genes, including both naturally occurring and recombinant non-oleandolide PKS genes, and (iv) from combinations of the foregoing.

Various hybrid PKSs of the invention illustrating these various alternatives are described herein.

An example of a hybrid PKS comprising fused modules results from fusion of the loading module of either DEBS or the narbonolide PKS (see PCT patent application No. US99/11814, incorporated herein by reference) with extender modules 1 and 2 of the oleandolide PKS to produce a hybrid oleAI gene. Co-expression of either one of these two hybrid oleAI genes with the oleAII and oleAIII genes in suitable host cells, such as *Streptomcyes lividans,* results in expression of a hybrid PKS of the invention that produces 6-deoxyerythronolide B in recombinant host cells. Co-expression of either one of these two hybrid oleAI genes with the eryAII and eryAIII genes similarly results in the production of 6-dEB, while co-expression with the analogous narbonolide PKS genes (picAII and picAIII) results in the production of 3-keto-6-dEB.

Another example of a hybrid PKS comprising a hybrid module is prepared by co-expressing the oleAI and oleAII genes with an oleAIII hybrid gene encoding extender module 5 and the KS and AT of extender module 6 of the oleandolide PKS fused to the ACP of extender module 6 and the TE of the narbonolide PKS. The resulting hybrid PKS of the invention produces 3-deoxy-3-oxo-8,8a-deoxyoleandolide(3-keto-oleandolide). This compound is useful in the production of 14-desmethyl ketolides, compounds with potent anti-bacterial activity. This compound can also be prepared by a recombinant oleandolide derivative PKS of the invention in which the KR domain of module 6 of the oleandolide PKS has been deleted or replaced with an inactive KR domain. Moreover, the invention provides hybrid PKSs in which not only the above changes have been made but also the AT domain of module 6 has been replaced with a malonyl-specific AT. These hybrid PKSs produce 2-desmethyl-3-deoxy-3-oxo-8,8a-deoxyoleandolide, a useful intermediate in the preparation of 2,14-didesmethyl ketolides, compounds with potent antibiotic activity.

Another illustrative example of a hybrid PKS includes the hybrid PKS of the invention resulting only from the latter change in the hybrid PKS just described. Thus, co-expression of the oleAI and oleAII genes with a hybrid oleAIII gene in which the AT domain of module 6 has been replaced by a malonyl-specific AT results in the expression of a hybrid PKS that produces 2-desmethyl-8,8a-deoxyoleandolide in recombinant host cells. This compound is a useful intermediate for making 2,14-didesmethyl erythromycins in recombinant host cells of the invention.

While many of the hybrid PKSs described above are composed primarily of oleandolide PKS proteins, those of skill in the art recognize that the present invention provides many different hybrid PKSs, including those composed of only a small portion of the oleandolide PKS. For example, the present invention provides a hybrid PKS in which a hybrid oleAI gene that encodes the oleandolide loading module fused to extender modules 1 and 2 of DEBS is coexpressed with the eryAII and eryAIII genes. The resulting hybrid PKS produces 8,8a-deoxyoleandolide. When the construct is expressed in *Saccharopolyspora erythraea* host cells (either via chromosomal integration in the chromosome or via a vector that encodes the hybrid PKS), the resulting recombinant host cell of the invention produces 14-desmethyl erythromycins. Another illustrative example is the hybrid PKS of the invention composed of the oleAI and eryAII and eryAIII gene products. This construct is also useful in expressing 14-desmethyl erythromycins in *Saccharopolyspora erythraea* host cells, as described in Example 3, below. In a preferred embodiment, the *S. erythraea* host cells are eryAI mutants that do not produce 6-deoxyerythronolide B.

Another example is the hybrid PKS of the invention composed of the products of the picAI and picAII genes (the two proteins that comprise the loading module and extender modules 1–4, inclusive, of the narbonolide PKS) and the oleAIII gene. The resulting hybrid PKS produces the macrolide aglycone 3-hydroxy-narbonolide in *Streptomyces lividans* host cells and the corresponding erythromycins in *Saccharopolyspora erythraea* host cells. This hybrid PKS of the invention is described in Example 5, below.

Each of the foregoing hybrid PKS enzymes of the invention, and the hybrid PKS enzymes of the invention generally, can be expressed in a host cell that also expresses a functional oleP gene product. Such expression provides the compounds of the invention in which the C-8–C-8a epoxide is present.

The following Table lists references describing illustrative PKS genes and corresponding enzymes that can be utilized in the construction of the recombinant hybrid PKSs and the corresponding DNA compounds that encode them of the invention. Also presented are various references describing tailoring enzymes and corresponding genes that can be employed in accordance with the methods of the invention.
Avermectin
U.S. Pat. No. 5,252,474 to Merck.
MacNeil et al., 1993, *Industrial Microorganisms: Basic and Applied Molecular Genetics,* Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, *Gene* 115: 119–125, Complex Organization of the *Streptomyces avermitilis* genes encoding the avermectin polyketide synthase.
Candicidin (FR008)
Hu et al., 1994, *Mol. Microbiol.* 14: 163–172.
Epothilone
U.S. patent application Ser. No. 60/130,560, filed Apr. 22, 1999, and Ser. No. 60/122,620, filed Mar. 3, 1999.
Erythromycin
PCT Pub. No. 93/13663 to Abbott.
U.S. Pat. No. 5,824,513 to Abbott.
Donadio et al., 1991, *Science* 252:675–9.
Cortes et al., Nov. 8, 1990, *Nature* 348:176–8, An unusually large multifunctional polypeptide in the erythromycin producing polyketide synthase of *Saccharopolyspora erythraea.*
Glycosylation Enzymes
PCT Pat. App. Pub. No. 97/23630 to Abbott.
FK-506
Motamedi et al., 1998, The biosynthetic gene cluster for the macrolactone ring of the immunosuppressant FK506, *Eur. J biochem.* 256: 528–534.
Motamedi et al., 1997, Structural organization of a multifunctional polyketide synthase involved in the biosynthesis of the macrolide immunosuppressant FK506, *Eur. J. Biochem.* 244: 74–80.
Methyltransferase
U.S. Pat. No. 5,264,355, issued Nov. 23, 1993, Methylating enzyme from Streptomyces MA6858.31-O-desmethyl-FK506 methyltransferase.
Motamedi et al., 1996, Characterization of methyltransferase and hydroxylase genes involved in the biosynthesis of the immunosuppressants FK506 and FK520, *J. Bacteriol.* 178: 5243–5248.
FK-520
U.S. patent application Ser. No. 60/139,650, filed Jun. 17, 1999, and Ser. No. 60/123,810, filed Mar. 11, 1999. See also Nielsen et al., 1991, *Biochem.* 30:5789–96 (enzymology of pipecolate incorporation).
Lovastatin
U.S. Pat. No. 5,744,350 to Merck.
Narbomycin (and Picromycin)
PCT patent application No. WO US99/11814, filed May 28, 1999.
Nemadectin
MacNeil et al., 1993, supra.
Niddamycin
Kakavas et al., 1997, Identification and characterization of the niddamycin polyketide synthase genes from *Streptomyces caelestis, J. Bacteriol.* 179: 7515–7522.
Platenolide
EP Pat. App. Pub. No. 791,656 to Lilly.
Rapamycin
Schwecke et al., August 1995, The biosynthetic gene cluster for the polyketide rapamycin, *Proc. Natl. Acad. Sci. USA* 92:7839–7843.
Aparicio et al., 1996, Organization of the biosynthetic gene cluster for rapamycin in *Streptomyces hygroscopicus:* analysis of the enzymatic domains in the modular polyketide synthase, *Gene* 169: 9–16.
Rifamycin
August et al., Feb. 13, 1998, Biosynthesis of the ansamycin antibiotic rifamycin: deductions from the molecular analysis of the rifbiosynthetic gene cluster of *Amycolatopsis mediterranei* S669, *Chemistry & Biology,* 5(2): 69–79.
Soraphen
U.S. Pat. No. 5,716,849 to Novartis.
Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spiramycin
U.S. Pat. No. 5,098,837 to Lilly.
Activator Gene
U.S. Pat. No. 5,514,544 to Lilly.
Tylosin
EP Pub. No. 791,655 to Lilly.
Kuhstoss et al., 1996, *Gene* 183:231–6., Production of a novel polyketide through the construction of a hybrid polyketide synthase.
U.S. Pat. No. 5,876,991 to Lilly.
Tailoring enzymes
Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention. Methods for constructing hybrid PKS-encoding DNA compounds are described without reference to the oleandolide PKS in U.S. Pat. Nos. 5,672,491 and 5,712,146 and PCT publication No. 98/49315, each of which is incorporated herein by reference.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5): 1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, "Dissecting and Exploiting Intermodular Communication in Polyketide Synthases", *Science* 284: 482–485, incorporated herein by reference.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Thus, as one illustrative example, the invention provides a hybrid PKS that contains the naturally occurring loading module and thioesterase domain as well as extender modules one, two, four, and six of the oleandolide PKS and further contains hybrid or heterologous extender modules three and five. Hybrid or heterologous extender modules three and five contain AT domains specific for malonyl CoA and derived from, for example, the rapamycin PKS genes.

To construct a hybrid PKS or oleandolide PKS of the invention, one can employ a technique, described in PCT Pub. No. 98/27203 and U.S. provisional patent application Ser. No. 60/129,731, filed Apr. 16, 1999, incorporated herein by reference, in which the large oleandolide PKS gene cluster is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

The invention also provides libraries of PKS genes, PKS proteins, and ultimately, of polyketides, that are constructed by generating modifications in the oleandolide PKS so that the protein complexes produced have altered activities in one or more respects and thus produce polyketides other than the oleandolide natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on the polyketide, protein, and the encoding nucleotide sequence levels.

As described above, a modular PKS "derived from" the oleandolide or other naturally occurring PKS includes a modular PKS (or its corresponding encoding gene(s)) that retains the scaffolding of the utilized portion of the naturally occurring gene. Not all modules need be included in the constructs; the constructs can include a loading module and six, fewer than six, or more than six extender modules. On the constant scaffold, at least one enzymatic activity is mutated, deleted, replaced, or inserted so as to alter the activity of the resulting PKS relative to the original PKS. Alteration results when these activities are deleted or are replaced by a different version of the activity, or simply mutated in such a way that a polyketide other than the natural product results from these collective activities. This occurs because there has been a resulting alteration of the starter unit and/or extender unit, stereochemistry, chain length or cyclization, and/or reductive or dehydration cycle outcome at a corresponding position in the product polyketide. Where a deleted activity is replaced, the origin of the replacement activity may come from a corresponding activity in a different naturally occurring PKS or from a different region of the oleandolide PKS. Any or all of the oleandolide PKS genes may be included in the derivative or portions of any of these may be included, but the scaffolding of the PKS protein is retained in whatever derivative is constructed. The derivative preferably contains a thioesterase activity from the oleandolide or another PKS.

Thus, a PKS derived from the oleandolide PKS includes a PKS that contains the scaffolding of all or a portion of the oleandolide PKS. The derived PKS also contains at least two extender modules that are functional, preferably three extender modules, and more preferably four or more extender modules, and most preferably six extender modules. The derived PKS also contains mutations, deletions, insertions, or replacements of one or more of the activities of the functional modules of the oleandolide PKS so that the nature of the resulting polyketide is altered at both the protein and DNA sequence levels. Particular preferred embodiments include those wherein a KS, AT, or ACP domain has been deleted or replaced by a version of the activity from a different PKS or from another location within the same PKS. Also preferred are derivatives where at least one non-condensation cycle enzymatic activity (KR, DH, or ER) has been deleted or added or wherein any of these activities has been mutated so as to change the structure of the polyketide synthesized by the PKS.

Conversely, also included within the definition of a PKS derived from the oleandolide PKS are functional non-oleandolide PKS modules or their encoding genes wherein at least one portion, or two or more portions, of the oleandolide PKS activities have been inserted. Exemplary is the use of the oleandolide AT for extender module 2, which accepts a methylmalonyl CoA extender unit rather than malonyl CoA, to replace a malonyl specific AT in another PKS. Other examples include insertion of portions of non-condensation cycle enzymatic activities or other regions of oleandolide synthase activity into a heterologous PKS at both the DNA and protein levels.

Thus, there are at least five degrees of freedom for constructing a hybrid PKS in terms of the polyketide that will be produced. First, the polyketide chain length is determined by the number of modules in the PKS, and the present invention includes hybrid PKSs that contain a loading module and 6, as well as fewer or more than 6, extender modules. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit, such as propionyl, butyryl, and the like. As noted above and in the examples below, another method for varying loading module specificity involves inactivating the KS activity in extender module 1 (KS1) and providing alternative substrates, called diketides, that are chemically synthesized analogs of extender module 1 diketide products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the stereochemistry when there is a complete KR/DH/ER available.

Thus, the modular PKS systems generally and the oleandolide PKS system particularly permit a wide range of polyketides to be synthesized. As compared to the aromatic PKS systems, the modular PKS systems accept a wider range of starter units, including aliphatic monomers (acetyl, propionyl, butyryl, isovaleryl, etc.), aromatics (aminohydroxybenzoyl), alicyclics (cyclohexanoyl), and heterocyclics (thiazolyl). Certain modular PKSs have relaxed specificity for their starter units (Kao et al., 1994, *Science,* supra). Modular PKSs also exhibit considerable variety with regard to the choice of extender units in each condensation cycle. The degree of beta-ketoreduction following a condensation reaction has also been shown to be altered by genetic manipulation (Donadio et al., 1991, *Science,* supra; Donadio et al., 1993, *Proc. Natl. Acad Sci. USA* 90: 7119–7123). Likewise, the size of the polyketide product can be varied by designing mutants with the appropriate number of modules (Kao et al., 1994, *J. Am. Chem. Soc.* 116:11612–11613). Lastly, modular PKS enzymes are particularly well known for generating an impressive range of asymmetric centers in their products in a highly controlled manner. The polyketides, antibiotics, and other compounds produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular, such as the oleandolide, PKS scaffold is virtually unlimited.

While hybrid PKSs are most often produced by "mixing and matching" portions of PKS coding sequences, mutations in DNA encoding a PKS can also be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, *Proc. Natl. Acad. Sci. USA* 82: 448; Geisselsoder et al., 1987, *BioTechniques* 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, *Methods Enzymol.* 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, *Proc. Natl. Acad. Sci. USA* 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemical mutagens, transformed into *E. coli* and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER can correspond to a KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies. The invention provides a variety of recombinant DNA compounds in which the various coding sequences for the domains and modules of the oleandolide PKS are flanked by non-naturally occurring restriction enzyme recognition sites.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length enables the production of quite large libraries.

Methods for introducing the recombinant vectors of the invention into suitable hosts are known to those of skill in the art and typically include the use of $CaCl_2$ or agents such as other divalent cations, lipofection, DMSO, PEG, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) the proteins produced from the coding sequences; (3) the polyketides produced from the proteins assembled into a functional PKS; and (4) antibiotics or compounds with other desired activities derived from the polyketides. Combination libraries can also be constructed wherein members of a library derived, for example, from the oleandolide PKS can be considered as a part of the same library as those derived from, for example, the rapamycin PKS or DEBS.

Colonies in the library are induced to produce the relevant synthases and thus to produce the relevant polyketides to obtain a library of polyketides. Polyketides that are secreted into the media or have been otherwise isolated can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 137:167–173, incorporated herein by reference, and in Example 7, below.

The invention provides methods for the preparation of a large number of polyketides. These polyketides are useful intermediates in formation of compounds with antibiotic or other activity through hydroxylation and glycosylation reactions as described above. In general, the polyketide products of the PKS must be further modified, typically by hydroxylation and glycosylation, to exhibit antibiotic activity. Hydroxylation results in the novel polyketides of the invention that contain hydroxyl groups at C-6, which can be accomplished using the hydroxylase encoded by the eryF gene, and/or C-12, which can be accomplished using the hydroxylase encoded by the pick or eryK gene. Also, the present invention provides the oleP gene in recombinant form, which can be used to express the oleP gene product in any host cell. A host cell, such as a Streptomyces host cell or a *Saccharopolyspora erythraea* host cell modified to express the oleP gene thus can be used to produce polyketides comprising the C-8-C-8a epoxide present in oleandomycin. Thus the invention provides such modified polyketides. The presence of hydroxyl groups at these positions can enhance the antibiotic activity of the resulting compound relative to its unhydroxylated counterpart.

Methods for glycosylating the polyketides are generally known in the art; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosyl transferases. In addition, synthetic chemical methods may be employed.

The antibiotic modular polyketides may contain any of a number of different sugars, although D-desosamine, or a close analog thereof, is most common. Erythromycin, picromycin, narbomycin, and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides, thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea, Streptomyces venezuelae* or other host cells to make the conversion, preferably using mutants unable to synthesize macrolides, as discussed in the preceding Section.

Thus, a wide variety of polyketides can be produced by the hybrid PKS enzymes of the invention. These polyketides are useful as antibiotics and as intermediates in the synthesis of other useful compounds, as described in the following section.

Section IV: Compounds

The methods and recombinant DNA compounds of the invention are useful in the production of polyketides. In one important aspect, the invention provides methods for making antibiotic compounds related in structure to oleandomycin and erythromycin, both potent antibiotic compounds.

The invention also provides novel ketolide compounds, polyketide compounds with potent antibiotic activity of significant interest due to activity against antibiotic resistant strains of bacteria. See Griesgraber et al., 1996, *J. Antibiot.* 49: 465–477, incorporated herein by reference. Most if not all of the ketolides prepared to date are synthesized using erythromycin A, a derivative of 6-dEB, as an intermediate. While the invention provides hybrid PKSs that produce a polyketide different in structure from 6-dEB, the invention also provides methods for making intermediates useful in preparing traditional, 6-dEB- and erythromycin-derived ketolide compounds.

Because 6-dEB in part differs from oleandolide in that it comprises a 13-ethyl instead of a 13-methyl group, the novel hybrid PKS genes of the invention based on the oleandolide PKS provide many novel ketolides that differ from the known ketolides only in that they have a 13-methyl instead of 13-ethyl group. Thus, the invention provides the 13-methyl analogues of the ketolides and intermediates and precursor compounds described in, for example, Griesgraber et al., supra; Agouridas et al., 1998, *J. Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; 5,439,889; and PCT publication Nos. WO 98/09978 and 98/28316, each of which is incorporated herein by reference.

As noted above, the hybrid PKS genes of the invention can be expressed in a host cell that contains the desosamine biosynthetic genes and desosaminyl transferase gene as well as the required hydroxylase gene(s), which may be either picK (for the C-12 position) or eryK (for the C-12 position) and/or eryF (for the C-6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone.

The compounds of the invention are thus optionally glycosylated forms of the polyketide set forth in formula (1) below which are hydroxylated at either the C-6 or the C-12 or both. The compounds of formula (1) can be prepared using the loading and the six extender modules of a modular PKS, modified or prepared in hybrid form as herein described. These polyketides have the formula:

(1)

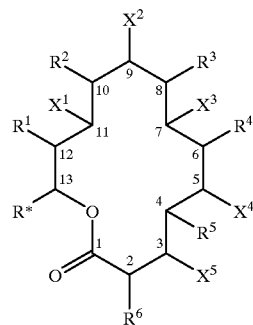

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ is independently two H, H and OH, or =O; or each of $X^1$–$X^5$ is independently H and the compound of formula (2) contains a double-bond in the ring adjacent to the position of said X at 2-3, 4-5, 6-7, 8-9 and/or 10-11;

with the proviso that:

at least two of $R^1$–$R^6$ are alkyl (1–4C).

Preferred compounds comprising formula 2 are those wherein at least three of $R^1$–$R^5$ are alkyl (1–4C), preferably methyl or ethyl; more preferably wherein at least four of $R^1$–$R^5$ are alkyl (1–4C), preferably methyl or ethyl. Also preferred are those wherein $X^2$ is two H, =O, or H and OH, and/or $X^3$ is H, and/or $X^1$ is OH and/or X4 is OH and/or $X^5$ is OH. Also preferred are compounds with variable R* when $R^1$–$R^5$ is methyl, $X^2$ is =O, and $X^1$, $X^4$ and $X^5$ are OH. The glycosylated forms of the foregoing are also preferred; glycoside residues can be attached at C-3, C-5, and/or C-6; the epoxidated forms are also included, i.e., and epoxide at C-8–C-8a.

As described above, there are a wide variety of diverse organisms that can modify compounds such as those described herein to provide compounds with or that can be readily modified to have useful activities. For example, *Saccharopolyspora erythraea* can convert oleandolide and 6-dEB to a variety of useful compounds. The compounds provided by the present invention can be provided to cultures of *Saccharopolyspora erythraea* and converted to the corresponding derivatives of erythromycins A, B, C, and D in accordance with the procedure provided in Example 6, below. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production. Each of the erythromycins A, B, C, and D has antibiotic activity, although erythromycin A has the highest antibiotic activity. Moreover, each of these compounds can form, under treatment with mild acid, a C-6 to C-9 hemiketal with motilide activity. For formation of hemiketals with motilide activity, erythromycins B, C, and D, are preferred, as the presence of a C-12 hydroxyl allows the formation of an inactive compound that has a hemiketal formed between C-9 and C-12.

Thus, the present invention provides the compounds produced by hydroxylation and glycosylation of the compounds of the invention by action of the enzymes endogenous to *Saccharopolyspora erythraea* and mutant strains of *S. erythraea*. Such compounds are useful as antibiotics or as motilides directly or after chemical modification. For use as antibiotics, the compounds of the invention can be used directly without further chemical modification. Erythromycins A, B, C, and D all have antibiotic activity, and the corresponding compounds of the invention that result from the compounds being modified by *Saccharopolyspora erythraea* also have antibiotic activity. These compounds can be chemically modified, however, to provide other compounds of the invention with potent antibiotic activity. For example, alkylation of erythromycin at the C-6 hydroxyl can be used to produce potent antibiotics (clarithromycin is C-6-O-methyl), and other useful modifications are described in, for example, Griesgraber et al., 1996, *J. Antibiot.* 49: 465–477, Agouridas et al., 1998, *J. Med Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; and 5,439,889; and PCT publication Nos. WO 98/09978 and 98/28316, each of which is incorporated herein by reference.

For use as motilides, the compounds of the invention can be used directly without further chemical modification. Erythromycin and certain erythromycin analogs are potent agonists of the motilin receptor that can be used clinically as prokinetic agents to induce phase III of migrating motor complexes, to increase esophageal peristalsis and LES pressure in patients with GERD, to accelerate gastric emptying in patients with gastric paresis, and to stimulate gall bladder contractions in patients after gallstone removal and in diabetics with autonomic neuropathy. See Peeters, 1999, Motilide Web Site, http://www.med.kuleuven. ac.be/med/gih/motilid.htm, and Omura et al., 1987, Macrolides with gastrointestinal motor stimulating activity, *J. Med. Chem.* 30: 1941–3). The corresponding compounds of the invention that result from the compounds of the invention being modified by *Saccharopolyspora erythraea* also have motilide activity, particularly after conversion, which can also occur in vivo, to the C-6 to C-9 hemiketal by treatment with mild acid. Compounds lacking the C-12 hydroxyl are especially preferred for use as motilin agonists. These compounds can also be further chemically modified, however, to provide other compounds of the invention with potent motilide activity.

Moreover, and also as noted above, there are other useful organisms that can be employed to hydroxylate and/or glycosylate the compounds of the invention. As described above, the organisms can be mutants unable to produce the polyketide normally produced in that organism the fermentation can be carried out on plates or in large fermentors, and the compounds produced can be chemically altered after fermentation. In addition to *Saccharopolyspora erythraea, Streptomyces venezuelae, S. narbonensis, S. antibioticus, Micromonospora megalomicea, S. fradiae,* and *S. thermotolerans* can also be used. In addition to antibiotic activity, compounds of the invention produced by treatment with *M. megalomicea* enzymes can have antiparasitic activity as well. Thus, the present invention provides the compounds produced by hydroxylation and glycosylation by action of the enzymes endogenous to *S. erythraea, S. venezuelae, S. narbonensis, S. antibioticus, M. megalomicea, S. fradiae,* and *S. thermotolerans.*

The present invention also provides methods and genetic constructs for producing the glycosylated and/or hydroxylated compounds of the invention directly in the host cell of interest. Thus, the recombinant genes of the invention, which include recombinant oleAI, oleAII, and oleAIII genes with one or more deletions and/or insertions, including replacements of an oleA gene fragment with a gene fragment from a heterologous PKS gene, can be included on expression vectors suitable for expression of the encoded gene products in *Saccharopolyspora erythraea, Micromonospora megalomicea, Streptomyces antibioticus, S. venezuelae, S. narbonensis, S. fradiae,* and *S. thermotolerans.*

Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The compounds of the invention can be produced by growing and fermenting the host cells of the invention under conditions known in the art for the production of other polyketides. The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings* XIX, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The compounds of the invention can be used as single therapeutic agents or in combination with other therapeutic agents. Drugs that can be usefully combined with compounds of the invention include one or more antibiotic or motilide agents.

A detailed description of the invention having been provided above, the following examples are given for the purpose of illustrating the invention and shall not be construed as being a limitation on the scope of the invention or claims.

EXAMPLE 1

General Methodology

Bacterial strains, plasmids, and culture conditions. *Streptomyces coelicolor* CH999 described in WO 95/08548, published Mar. 30, 1995, or *S. lividans* K4-114 or K4-155, described in Ziermann and Betlach, January 99, Recombinant Polyketide Synthesis in Streptomyces: Engineering of Improved Host Strains, *BioTechniques* 26: 106–110, incorporated herein by reference, was used as an expression host. DNA manipulations were performed in *Escherichia coli* XL1-Blue, available from Stratagene. *E. coli* MC1061 is also suitable for use as a host for plasmid manipulation. Plasmids were passaged through *E. coli* ET12567 (dam dcm hsdS Cm') (MacNeil, 1988, *J. Bacteriol*, 170: 5607, incorporated herein by reference) to generate unmethylated DNA prior to transformation of *S. coelicolor* or *Saccharopolyspora erythraea*. *E. coli* strains were grown under standard conditions. *S. coelicolor* strains were grown on R2YE agar plates (Hopwood et al, *Genetic manipulation of Streptomyces. A laboratory manual*. The John Innes Foundation: Norwich, 1985, incorporated herein by reference).

Many of the expression vectors of the invention illustrated in the examples are derived from plasmid pRM5, described in WO 95/08548, incorporated herein by reference. This plasmid includes a colEI replicon, an appropriately truncated SCP2* Streptomyces replicon, two act-promoters, the actI and actIII promoters, to allow for bidirectional cloning, the gene encoding the actII-ORF4 activator which induces transcription from act promoters during the transition from growth phase to stationary phase, and appropriate marker genes. Engineered restriction sites in the plasmid facilitate the combinatorial construction of PKS gene clusters starting from cassettes encoding individual domains of naturally occurring PKSs. When plasmid pRM5 is used for expression of a PKS, all relevant biosynthetic genes can be plasmid-borne and therefore amenable to facile manipulation and mutagenesis in *E. coli*. This plasmid is also suitable for use in Streptomyces host cells. Streptomyces is genetically and physiologically well characterized and expresses the ancillary activities required for in vivo production of most polyketides. Plasmid pRM5 utilizes the act promoter for PKS gene expression, so polyketides are produced in a secondary metabolite-like manner, thereby alleviating the toxic effects of synthesizing potentially bioactive compounds in vivo.

Manipulation of DNA and organisms. Polymerase chain reaction (PCR) was performed using Pfu polymerase (Stratagene; Taq polymerase from Perkin Elmer Cetus can also be used) under conditions recommended by the enzyme manufacturer. Standard in vitro techniques were used for DNA manipulations (Sambrook et al. *Molecular Cloning: A Laboratory Manual* (Current Edition)). *E. coli* was transformed using standard calcium chloride-based methods; a Bio-Rad *E. coli* pulsing apparatus and protocols provided by Bio-Rad could also be used. *S. coelicolor* was transformed by standard procedures (Hopwood et al. *Genetic manipulation of Streptomyces. A laboratory manual*. The John Innes Foundation: Norwich, 1985), and depending on what selectable marker was employed, transformants were selected using 1 mL of a 1.5 mg/mL thiostrepton overlay, 1 mL of a 2 mg/mL apramycin overlay, or both.

EXAMPLE 2

Cloning of the Oleandomycin Biosynthetic Gene Cluster from *Streptomyces antibioticus*

Genomic DNA (100 μg) was isolated from an oleandomycin producing strain of *Streptomyces antibioticus* (ATCC 11891) using standard procedures. The genomic DNA was partially digested with restriction enzyme Sau3A1 to generate fragments ~40 kbp in length, which were cloned into the commercially available Supercos™ cosmid vector that had been digested with restriction enzymes XbaI and BamHI to produce a genomic library. SuperCosI™ (Stratagene) DNA cosmid arms were prepared as directed by the manufacturer. A cosmid library was prepared by ligating 2.5 μg of the digested genomic DNA with 1.5 μg of cosmid arms in a 20 μL reaction. One microliter of the ligation mixture was propagated in *E. coli* XL1-Blue MR (Stratagene) using a GigapackIII XL packaging extract kit (Stratagene).

This library was then probed with a radioactively-labeled probe generated by PCR from *Streptomyces antibioticus* DNA using primers complementary to known sequences of KS domains hypothesized to originate from extender modules 5 and 6 of the oleandolide PKS. This probing identified about 30 different colonies, which were pooled, replated, and probed again, resulting in the identification of 9 cosmids. These latter cosmids were isolated and transformed into the commercially available *E. coli* strain XL-1 Blue. Plasmid DNA was isolated and analyzed by restriction enzyme digestion, which revealed that the entire PKS gene cluster was contained in overlapping segments on two of the cosmids identified. DNA sequence analysis using the T3 primer showed that the desired DNA had been isolated.

Further analysis of these cosmids and subdlones prepared from the cosmids facilitated the identification of the location of various oleandolide PKS ORFs, modules in those ORFs, and coding sequences for oleandomycin modification enzymes. The location of these genes and modules is shown on FIG. 1. FIG. 1 shows that the complete oleandolide PKS gene cluster is contained within the insert DNA of cosmids pKOS055-1 (insert size of ~43 kb) and pKOS055-5 (insert size of ~47 kb). Each of these cosmids has been deposited with the American Type Culture Collection in accordance with the terms of the Budapest Treaty (cosmid pKOS055-1 is available under accession no. ATCC 203798; cosmid pKOS055-5 is available under accession no. ATCC 203799). Various additional reagents of the invention can therefore be isolated from these cosmids. DNA sequence analysis was also performed on the various subdlones of the invention, as described above.

EXAMPLE 3

Expression of an Oleandolide/DEBS Hybrid PKS in *Saccharopoluspora erythraea*

Figure 3:
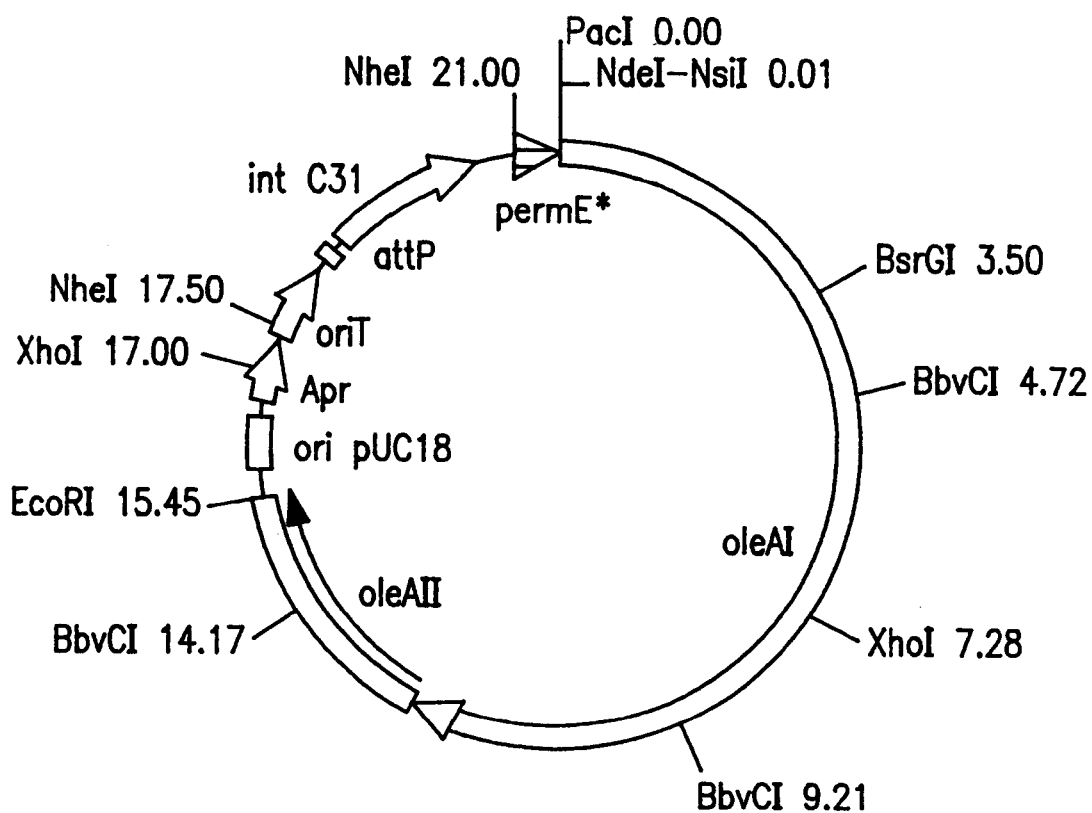
FIG. 3 shows a restriction site and function map of plasmid pKOS039-110, described in Example 3, below, which is an expression vector that can integrate (phiC31 based attachment and integration functions) into the chromosome of Streptomyces and other host cells and contains the ermE* promoter positioned to drive expression of the oleAI gene.

This Example describes the construction of an expression vector, plasmid pKOS039-1 10, that can integrate into the chromosome of *Saccharopolyspora erythraea* due to the phage phiC31 attachment and integration functions present on the plasmid and drive expression of the oleAI gene product under the control of the ermE* promoter. A restriction site and function map of plasmid pKOS039-110 is shown in FIG. 3 of the accompanying drawings. The expression of the oleAI gene product in a host cell that naturally produces the eryA gene products results in the formation of a functional hybrid PKS of the present invention composed of the oleAI, eryAII, and eryAIII gene products and the concomitant production of 13-methyl erythromycins. While the specific plasmids and vectors utilized in the construction are described herein, those of skill in the art will recognize that equivalent expression vectors of the invention can be readily constructed from publicly available materials and the oleA gene containing cosmids of the present invention deposited with the ATCC.

Plasmid pKOS039-98 is a cloning vector that contains convenient restriction sites that was constructed by inserting a polylinker oligonucleotide, containing a restriction enzyme recognition site for PacI, a Shine-Dalgarno sequence, and restriction enzyme recognition sites for NdeI, BglH, and HindIII, into a pUC19 derivative, called pKOS24-47. Plasmid pKOS039-98 (see PCT patent application No. WO US99/11814, incorporated herein by reference) was digested with restriction enzymes PacI and EcoRI and ligated to a polylinker composed of the oligonucleotides N39-51 and N39-52 having the following sequence:

N39-51: (SEQ ID NO:5)
5'-TAAGGAGGACCATATGCATCGCTCGAGTCTAGA CCTAGG-3'
N39-52: (SEQ ID NO:6)
5'-AATTCCTAGGTCTAGACTCGAGCGATGCATATG GTCCTCC-TTAAT-3', which thus includes the following restriction enzyme recognition sites in the order shown: NdeI-NsiI-XhoI-XbaI-EcoRI, to yield plasmid pKOS039-105.

Plasmid pKOS039-105 was digested with restriction enzymes NsiI and EcoRI, and the resulting large fragment ligated to the 15.2 kb NsiI-EcoRI restriction fragment of cosmid pKOS055-5 containing the oleAI gene to yield plasmid pKOS039-116. Plasmid pKOS039-116 was digested with restriction enzymes NdeI and EcoRI, and the resulting 15.2 kb fragment containing the oleAI gene was isolated and ligated to the 6 kb NdeI-EcoRI restriction fragment of plasmid pKOS039-134B to yield plasmid pKOS039-110 (FIG. 3).

Plasmid pKOS039-134B is a derivative of pKOS039-104 described in PCT patent application No. WO US99/11814, supra, prepared by digesting the latter with restriction enzyme BglII and ligating the ~10.5 kb fragment to get pKOS39-104B. Plasmid pKOS39-104B was digested with restriction enzyme PacI and partially digested with restriction enzyme XbaI. The ~7.4 kb fragment was ligated with PCR61A+62 fragment treated with restriction enzymes PacI and AvrII. The PCR61A+62 fragment was generated using the PCR primers:

N39-61A, (SEQ ID NO:7)
5'-TTCCTAGGCTAGCCCGACCCGAGCACGCGCCG GCA-3'; and
N39-62, (SEQ ID NO:8)
5'-CCTTAATTAAGGATCCTACCAACCGGCACGATT GTGCC-3', and the template was pWHM1104 (Tang et al., 1996, *Molecular Microbiology* 22(5): 801–813).

Plasmid pKOS039-110 DNA was passed through *E. coli* ET cells to obtain non-methylated DNA, which was then used to transform *Saccharopolyspora erythraea* cells, which contain a mutation in the eryAI coding sequence for the KS domain of module 1 of DEBS that renders the PKS non-functional. The resulting transformants produced detectable amounts of 14-desmethyl erythromycins.

EXAMPLE 4

Heterologous Expression of an Oleandolide PKS in *Stretomyces lividans*

Figure 4:
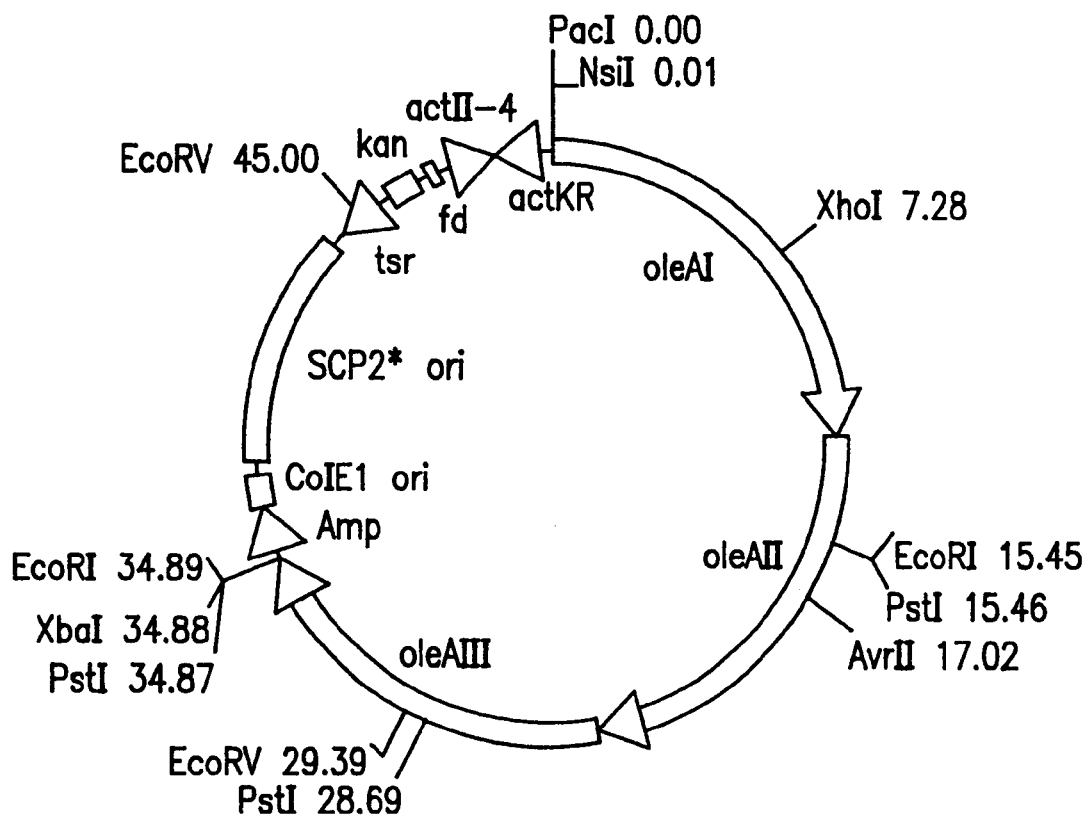
FIG. 4 shows a restriction site and function map of plasmid pKOS039-130, described in Example 4, below, which is an expression vector that replicates (SCP2* origin of replication) in Streptomyces host cells and contains the actI promoter and actII-ORF4 activator positioned to drive expression of the oleAI, oleAII, and oleAIII genes.

This Example describes the construction of an expression vector, plasmid pKOS039-130, that has an SCP2* origin of replication and so can replicate in Streptomyces host cells and drive expression of the oleAI, oleAII, and oleAIII gene products under the control of the actI promoter and actII-ORF4 activator. A restriction site and function map of plasmid pKOS039-130 is shown in FIG. 4 of the accompanying drawings. The expression of the oleA gene products in this host cell results in the formation of a functional oleandolide PKS composed of the oleAI, oleAII, and oleAIII gene products and the concomitant production of 8,8a-deoxyoleandolide. While the specific plasmids and vectors utilized in the construction are described herein, those of skill in the art will recognize that equivalent expression vectors of the invention can be readily constructed from publicly available materials and the oleA gene containing cosmids of the present invention deposited with the ATCC.

The 7.2 kb NsiI-XhoI restriction fragment of cosmid pKOS055-5 was cloned into pKOS39-105 to give plasmid pKOS039-106. The 8.0 kb XhoI-PstI restriction fragment of cosmid pKOS055-5 was cloned into commercially available plasmid pLitmus28 to yield plasmid pKOS039-107. The 14 kb EcoRI-EcoRV and 5.4 kb EcoRV-PstI restriction fragments of cosmid pKOS055-1 were ligated with pLitmus28 digested with EcoRI and PstI to yield plasmid pKOS039-115. The 19.5 kb SpeI-XbaI restriction fragment from plasmid pKOS039-115 was inserted into pKOS039-73, a derivative of plasmid pRM5, to yield plasmid pKOS039-129. The 15.2 kb PacI-EcoRI restriction fragment of plasmid pKOS039-110 was inserted into pKOS039-129 by replacing the 22 kb PacI-EcoRI restriction fragment to yield plasmid pKOS038-174. The 19 kb EcoRI restriction fragment from plasmid pKOS039-129 was then inserted into pKOS038-174 to yield plasmid pKOS039-130 (FIG. 4), which was used to transform *Streptomyces lividans* K4-114 (K4-155 could also be used). The resulting transformants produced 8,8a-deoxyoleandolide.

As noted above, the invention provides a recombinant oleAI gene in which the coding sequence for the KS domain of module 1 has been mutated to change the active site cysteine to another amino acid (the KS1° mutation). Recombinant PKS enzymes comprising this gene product do not produce a polyketide unless provided with diketide (or triketide) compounds that can bind to the KS2 or KS3 domain, where they are then processed to form a polyketide comprising the diketide (or triketide). This recombinant oleAI gene can be used together with the oleAII and oleAII genes to make a recombinant oleandolide PKS or can be used with modified forms of those genes or other naturally occurring or recombinant PKS genes to make a hybrid PKS.

To make the KS1° mutation in oleAI, the following primers were prepared:

N39-47, (SEQ ID NO:9)
5'-GCGAATTCCCGGGTGGCGTGACCTCT;
N39-48, (SEQ ID NO:10)
5'-GAGCTAGCCGCCGTGTCCACCGTGACC;
N39-49, (SEQ ID NO:11)
5'-CGGCTAGCTCGTCGCTGGTGGCACTGCAC; and
N39-50, (SEQ ID NO:12)
5'-CGAAGCTTGACCAGGAAAGACGAACACC.

These primers were used to amplify template DNA prepared from pKOS039-106. The amplification product of primers N39-47 and N39-48 was digested with restriction enzymes EcoRI and NheI, and the amplification product of primers N39-49 and N39-50 was digested with restriction enzymes NheI and HindIII, and the resulting restriction fragments were ligated to EcoRI and HindIII-digested plasmid pLitmus28 to yield plasmid pKOS038-179. The 1.5 kb BsrGI-BbvCI restriction fragment of plasmid pKOS038-179 was inserted into plasmid pKOS039-106 to yield pKOS098-2. The 7 kb NsiI-XhoI restriction fragment of plasmid pKOS098-2 and the 8 kb XhoI-EcoRI restriction fragments of plasmid pKOS039-107 are then used to replace the 15.2 kb NsiI-EcoRI restriction fragment of plasmid pKOS039-110 to yield the desired expression vector, pKOS039-110-KS1°, which comprises the oleAI KS1° gene under the control of the ermE* promoter.

To provide an expression vector of the invention that encodes the complete oleandolide PKS with the recombinant oleAI KS1° gene product, the oleAI KS1° gene can be isolated as a PacI-EcoRI restriction fragment from plasmid pKOS039-110-KS1°, which is then used to construct an expression vector analogous to the expression vector plasmid pKOS039-130 in the same manner in which the latter vector was constructed. The resulting expression vector can be used in *Streptomyces lividans, S. coelicolor*, and other compatible host cells to make polyketides by diketide feeding as described in PCT patent publication No. WO 99/03986, incorporated herein by reference.

EXAMPLE 5

Expression of an Oleandomycin/Picromycin Hybrid PKS

Figure 5:
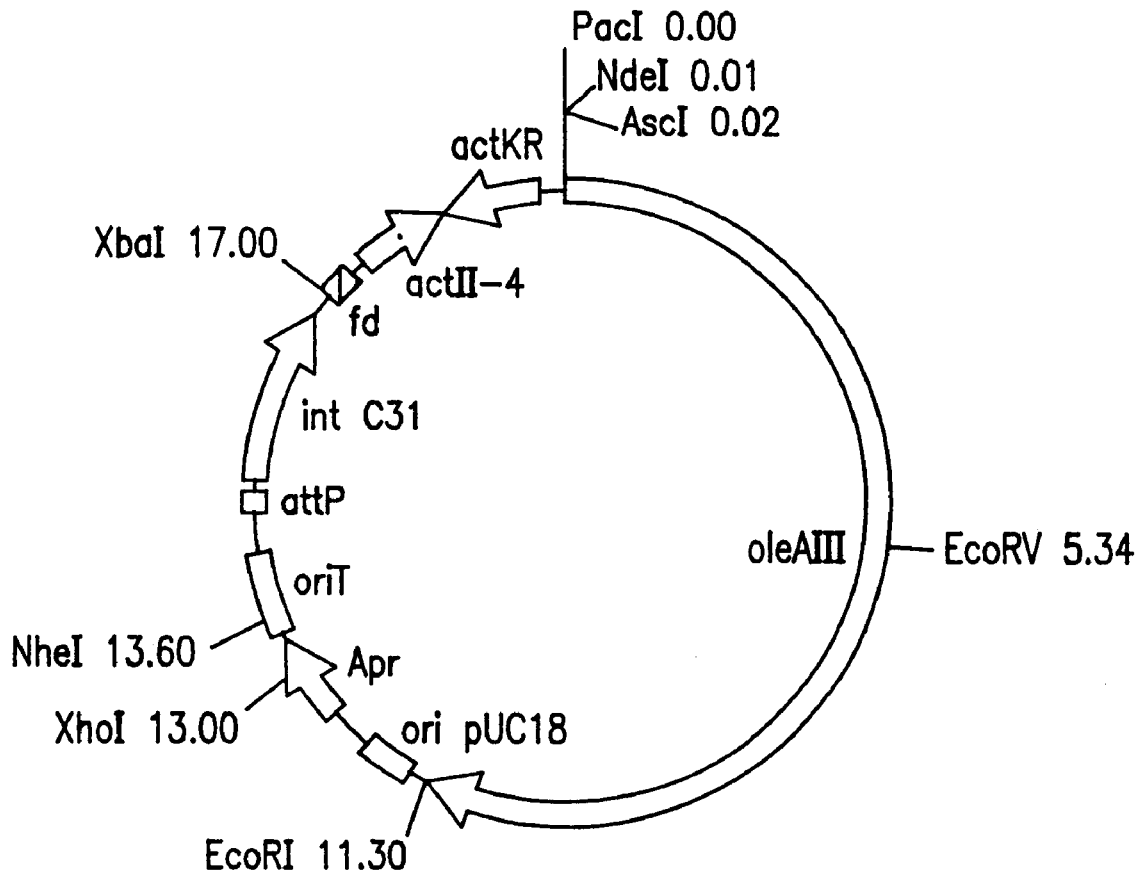
FIG. 5 shows a restriction site and function map of plasmid pKOS039-133, described in Example 5, below, which is an expression vector that can integrate (phiC31 based attachment and integration functions) into the chromosome of Streptomyces and other host cells and contains the actI promoter and actII-ORF4 activator positioned to drive expression of the oleAIII gene.

This Example describes the construction of an expression vector, plasmid pKOS039-133, that can integrate into the chromosome of Streptomyces due to the phage phiC31 attachment and integration functions present on the plasmid and drive expression of the oleAIII gene product under the control of the actI promoter and actII-ORF4 activator. A restriction site and function map of plasmid pKOS039-133 is shown in FIG. 5 of the accompanying drawings. This plasmid was introduced into *S. lividans* host cells together with a plasmid, pKOS039-83, that drives expression of the narbonolide PKS genes picAI and picAII (see PCT patent application No. WO US99/11814, supra). The expression of the oleAIII and picAI and picAII gene products in a host cell results in the formation of a functional hybrid PKS of the present invention composed of the oleAIII, picAI, and picAII gene products and the concomitant production of 3-hydroxy-narbonolide. While the specific plasmids and vectors utilized in the construction are described herein, those of skill in the art will recognize that equivalent expression vectors of the invention can be readily constructed from publicly available materials and the oleA gene containing cosmids of the present invention deposited with the ATCC.

Two oligonucleotides were prepared for the insertion of the oleAIII gene into pSET152 derivative plasmid pKOS039-42:

N39-59, (SEQ ID NO:13)
  5'-AATTCATATGGCTGAGGCGGAGAAGCTGCGCG
  AATACC-TGTGG;
and
N39-60, (SEQ ID NO:14)
  5'-CGCGCCACAGGTATTCGCGCAGCTTCTCCGCCT
  CAGCCATATG.

Plasmid pKOS039-115 was digested with restriction enzymes EcoRI and AscI to give the ~13.8 kb restriction fragment, which was inserted with the linker N39-59/N39-60 to yield plasmid pKOS039-132. Plasmid pKOS039-132 was digested with restriction enzymes NdeI and XbaI to give the ~10.8 kb restriction fragment, which was ligated to the ~9 kb NdeI-SpeI restriction fragment of plasmid pKOS039-42 to yield plasmid pKOS039-133 (FIG. 5). Plasmid pKOS039-133 and pKOS039-83 were co-transformed into *Streptomyces lividans* K4-114 (K4-155 can also be used; see Ziermann and Betlach, 1999, *Biotechniques* 26, 106–110, and U.S. patent application Ser. No. 09/181,833, filed Oct. 28, 1998, each of which is incorporated herein by reference). Protoplasts were transformed using standard procedures and transformants selected using overlays containing antibiotics. The strains were grown in liquid R5 medium (with 20 μg/mL thiostrepton, see Hopwood et al., *Genetic Manipulation of Streptomyces: A Laboratory Manual;* John Innes Foundation: Norwich, UK, 1985, incorporated herein by reference) for growth/seed and production cultures at 30° C. Analysis of extracts by LC/MS established the identity of the polyketide as the expected compound, 3--hydroxynarbonolide.

EXAMPLE 6

Conversion of Erythronolides to Erythromycins

A sample of an oleandolide (~50 to 100 mg) is dissolved in 0.6 mL of ethanol and diluted to 3 mL with sterile water. This solution is used to overlay a three day old culture of *Saccharopolyspora erythraea* WHM34 (an eryA mutant) grown on a 100 mm R2YE agar plate at 30° C. After drying, the plate is incubated at 30° C. for four days. The agar is chopped and then extracted three times with 100 mL portions of 1% triethylamine in ethyl acetate. The extracts are combined and evaporated. The crude product is purified by preparative HPLC (C-18 reversed phase, water-acetonitrile gradient containing 1% acetic acid). Fractions are analyzed by mass spectrometry, and those containing pure compound are pooled, neutralized with triethylamine, and evaporated to a syrup. The syrup is dissolved in water and extracted three times with equal volumes of ethyl acetate. The organic extracts are combined, washed once with saturated aqueous $NaHCO_3$, dried over $Na_2SO_4$, filtered, and evaporated to yield ~0.15 mg of product. The product is a glycosylated and hydroxylated oleandolide corresponding to erythromycin A, B, C, and D but differing therefrom as the oleandolide provided differed from 6-dEB.

EXAMPLE 7

Measurement of Antibacterial Activity

Antibacterial activity is determined using either disk diffusion assays with *Bacillus cereus* as the test organism or by measurement of minimum inhibitory concentrations (MIC) in liquid culture against sensitive and resistant strains of *Staphylococcus pneumoniae*.

The invention having now been described by way of written description and example, those of skill in the art will recognize that the invention can be practiced in a variety of embodiments and that the foregoing description and examples are for purposes of illustration and not limitation of the following claims.

What is claimed is:

1. An isolated recombinant DNA compound that comprises a coding sequence for a domain of a) a loading module or b) any one of extender modules one through four, which domain is of an oleandolide polyketide synthase (PKS) other than the acyl carrier protein domain of extender module four, wherein said extender modules are numbered as shown in FIG. 2, which domain is encoded by a coding sequence selected from the group consisting of nucleotides 5799–7055 of SEQ ID NO:1, nucleotides 7458–8563 of SEQ ID NO:1, nucleotides 8634–48873 of SEQ ID NO:1, nucleotides 8955–10205 of SEQ ID NO:1, nucleotides 10512–11549 of SEQ ID NO:1, nucleotides 12258–12818 of SEQ ID NO:1, nucleotides 13092–13349 of SEQ ED NO:1, nucleotides 13407–14690 of SEQ ID NO:1, nucleotides 14997–16031 of SEQ ID NO:1, nucleotides 16872–17423 of SEQ ID NO:1, nucleotides 17709–17996 of SEQ ID NO:1, nucleotides 18357–19643 of SEQ ID NO:1, nucleotides 19965–20999 of SEQ ID NO:1, nucleotides 21897–22449 of SEQ ID NO:1, nucleotides 22728–22985 of SEQ ID NO:1, nucleotides 23046–24329 of SEQ ID NO:1, nucleotides 24645–25682 of SEQ ID NO:1, nucleotides 25719–26256 of SEQ ID NO:1, nucleotides 27429–28301 of SEQ ID NO:1, and nucleotides 28314–28862 of SEQ ID NO:1, or a sequence that encodes an amino acid sequence identical to that encoded by any of the foregoing sequences.

2. The isolated recombinant DNA compound of claim 1 that comprises the coding sequence for the domains of the loading module and extender modules one and two of the oleandolide PKS.

3. The isolated recombinant DNA of claim 1 that comprises the coding sequence for the domains of the loading module and all six extender modules of the oleandolide PKS.

4. The isolated recombinant DNA of claim 1, further comprising a thioesterase domain.

5. The isolated recombinant DNA of claim 1 that is SEQ ID NO:1.

6. The isolated recombinant DNA compound of claim 1 that is cosmid pKOS055-1 (ATCC 203798).

7. The isolated recombinant DNA compound of claim 1 that is cosmid pKOS055-5 (ATCC 203799).

8. The isolated recombinant DNA compound of claim 1, wherein said coding sequence is operably linked to a promoter.

9. A recombinant DNA expression vector comprising the DNA compound of claim 8 and one of the following: (a) an origin of replication or (b) a segment of DNA that enables chromosomal integration.

10. The recombinant DNA expression vector of claim 9 that codes for expression of a PKS in Streptomyces host cells.

11. A recombinant host cell selected from the group consisting of Streptomyces host cells and Saccharopolyspora host cells that comprises a recombinant DNA expression vector of claim 9.

12. The recombinant DNA expression vector of claim 9 that encodes a hybrid modular PKS comprising at least a complete domain of oleandolide PKS and at least a portion of a second modular PKS other than oleandolide PKS.

13. The recombinant DNA expression vector of claim 12, wherein said second modular PKS is 6-deoxyerythronolide B synthase (DEBS).

14. The recombinant DNA expression vector of claim 13, wherein said hybrid modular PKS comprises the domains of the loading module of any one of extender modules one through four of oleandolide PKS, wherein said extender modules are numbered as shown in FIG. 2, and an extender module of DEBS.

15. The recombinant DNA expression vector of claim 12, wherein said hybrid modular PKS comprises the domains of the loading module and any one of extender modules one through four of oleandolide PKS, wherein said extender modules are numbered as shown in FIG. 2, and an extender module of narbonolide PKS.

16. A recombinant host cell, which in its untransformed state does not produce oleandolide, that comprises a recombinant DNA expression vector of claim 12 and expresses a holo-acyl carrier protein synthase and produces a polyketide synthesized by said hybrid modular PKS.

17. The recombinant host cell of claim 16 that is Streptomyces lividans.

18. The recombinant host cell of claim 16 that is Saccharopolyspora erythraea.

19. The recombinant DNA expression vector of claim 9, wherein extender module one contains a mutation that results in a non-functional ketosynthase domain.

20. A recombinant Streptomyces coelicolor or Streptomyces lividans host cell that comprises the recombinant DNA expression vector of claim 19.

21. A recombinant Saccharopolyspora erythraea host cell that comprises the recombinant DNA expression vector of claim 19.

22. A method for producing a polyketide in a cell, which method comprises transforming the cell with a recombinant expression vector that comprises a coding sequence for a domain of a) a loading module or b) any one of extender modules one through four, which domain is of an oleandolide polyketide synthase (PKS) other than the acyl carrier protein domain of extender module four, wherein said extender modules are numbered as shown in FIG. 2 and wherein the coding sequence is selected from the group consisting of nucleotides 5799–7055 of SEQ ID NO:1, nucleotides 7458–8563 of SEQ ID NO:1, nucleotides 8634–8873 of SEQ ID NO:1, nucleotides 8955–10205 of SEQ ID NO:1, nucleotides 10512–11549 of SEQ ID NO:1, nucleotides 12258–12818 of SEQ ID NO:1, nucleotides 13092–13349 of SEQ ID NO:1, nucleotides 13407–14690 of SEQ ID NO:1, nucleotides 14997–16031 of SEQ ID NO:1, nucleotides 16872–17423 of SEQ ID NO:1, nucleotides 17709–17996 of SEQ ID NO:1, nucleotides 18357–19643 of SEQ ID NO:1, nucleotides 19965–20999 of SEQ ID NO:1, nucleotides 21897–22449 of SEQ ID NO:1, nucleotides 22728–22985 of SEQ ID NO:1, nucleotides 23046–24329 of SEQ ID NO:1, nucleotides 24645–25682 of SEQ ID NO:1, nucleotides 25719–26256 of SEQ ID NO:1, nucleotidos 27429–28301 of SEQ ID NO:1, and nucleotides 28314–28862 of SEQ ID NO:1 or a sequence that encodes an amino acid sequence identical to that encoded by any of the foregoing sequences.

* * * * *